(12) United States Patent
Haynes

(10) Patent No.: US 8,920,812 B2
(45) Date of Patent: Dec. 30, 2014

(54) CHIMERIC RSV-F POLYPEPTIDE AND LENTIVIRUS OR ALPHA-RETROVIRUS GAG-BASED VLPS

(75) Inventor: Joel R. Haynes, Bozeman, MT (US)

(73) Assignee: Takeda Vaccines, Inc., Bozeman, MT (US)

( * ) Notice: Subject to any disclaimer, the term of this patent is extended or adjusted under 35 U.S.C. 154(b) by 134 days.

(21) Appl. No.: 13/505,250

(22) PCT Filed: Nov. 3, 2010

(86) PCT No.: PCT/US2010/055334
§ 371 (c)(1),
(2), (4) Date: Apr. 30, 2012

(87) PCT Pub. No.: WO2011/056899
PCT Pub. Date: May 12, 2011

(65) Prior Publication Data
US 2012/0213817 A1    Aug. 23, 2012

Related U.S. Application Data

(60) Provisional application No. 61/257,766, filed on Nov. 3, 2009.

(51) Int. Cl.
| | | |
|---|---|---|
| *A61K 39/295* | (2006.01) | |
| *A61K 39/155* | (2006.01) | |
| *A61K 39/21* | (2006.01) | |
| *C12N 7/00* | (2006.01) | |
| *C12N 15/45* | (2006.01) | |
| *C12N 15/49* | (2006.01) | |
| *C12N 15/48* | (2006.01) | |
| *A61K 39/12* | (2006.01) | |
| *C07K 16/08* | (2006.01) | |
| *C07K 14/005* | (2006.01) | |
| *C07K 16/10* | (2006.01) | |
| *A61K 39/00* | (2006.01) | |

(52) U.S. Cl.
CPC ..... *C07K 14/005* (2013.01); *C12N 2740/16023* (2013.01); *C12N 2760/00023* (2013.01); *C12N 2740/11023* (2013.01); *A61K 2039/5258* (2013.01); *A61K 39/12* (2013.01); *C07K 16/087* (2013.01); *C07K 2319/00* (2013.01); *C12N 2760/18522* (2013.01); *C12N 2740/16222* (2013.01); *C07K 16/1027* (2013.01); *C07K 2317/76* (2013.01)
USPC ............... 424/211.1; 424/207.1; 424/196.11; 435/235.1

(58) Field of Classification Search
None
See application file for complete search history.

(56) References Cited

U.S. PATENT DOCUMENTS

| | | | |
|---|---|---|---|
| 6,099,847 A | 8/2000 | Tobin et al. | |
| 6,818,216 B2 | 11/2004 | Young et al. | |
| 2003/0049607 A1 | 3/2003 | Greener et al. | |
| 2003/0198621 A1 | 10/2003 | Megede et al. | |
| 2004/0071661 A1 | 4/2004 | Klatzmann et al. | |
| 2005/0123563 A1 | 6/2005 | Doranz et al. | |
| 2006/0216702 A1 | 9/2006 | Compans et al. | |
| 2006/0263804 A1 | 11/2006 | Robinson et al. | |
| 2008/0233150 A1 | 9/2008 | Smith et al. | |
| 2010/0111989 A1* | 5/2010 | Grundwald et al. | ....... 424/185.1 |

FOREIGN PATENT DOCUMENTS

| | | | |
|---|---|---|---|
| JP | 2001-504702 A | 4/2001 | |
| JP | 2001-527091 A | 12/2001 | |
| JP | 2004-501647 A | 1/2004 | |
| JP | 2004-515218 A | 5/2004 | |
| JP | 2006-502704 A | 1/2006 | |
| JP | 2006-502979 A | 1/2006 | |
| JP | 2009-521850 A | 6/2009 | |
| WO | 98/23735 A1 | 6/1998 | |
| WO | 99/33868 A2 | 7/1999 | |
| WO | 02/00693 A2 | 1/2002 | |
| WO | 02/00885 A2 | 1/2002 | |
| WO | 03/097675 A1 | 11/2003 | |
| WO | 04/000351 A1 | 12/2003 | |
| WO | 2004/042001 A2 | 5/2004 | |
| WO | 2004/046176 A1 | 6/2004 | |
| WO | 2007/075741 A2 | 7/2007 | |
| WO | 2008/094197 A2 | 8/2008 | |
| WO | 2008/103819 A2 | 8/2008 | |
| WO | WO 2008/094200 * | 8/2008 | ............... A12Q 1/70 |
| WO | 2008/094200 A3 | 10/2008 | |

OTHER PUBLICATIONS

Georgescu et al (Expert Opinion on Biological Therapy 9: 139-147, 2009).*
International Preliminary Report on Patentability received for PCT Patent Application No. PCT/US2010/055334, mailed on May 18, 2012, 6 pages.
International Search Report and Written Opinion received for PCT Patent Application No. PCT/2010/055334, mailed on Jul. 28, 2011, 13 pages.
Anderson et al., "Indentification of Epitopes on Respiratory Syncytial Virus Proteins by Competitive Binding Immunoassy", Journal of Clinical Microbiology, vol. 23, No. 3, Mar. 1986, pp. 475-480.

(Continued)

*Primary Examiner* — Mary E Mosher
(74) *Attorney, Agent, or Firm* — Morrison & Foerster LLP

(57) ABSTRACT

The present invention relates to chimeric RSV-F polypeptide and lentivirus or alpha-retrovirus GAG-based virus-like particles (VLPs). The present invention also includes methods of making and using such chimeric VLPs. In certain embodiments, the GAG polypeptide of the chimeric VLPs comprises an HIV or ALV GAG polypeptide.

24 Claims, 44 Drawing Sheets

(56) References Cited

OTHER PUBLICATIONS

Anderson et al., "Neutralization of Respiratory Syncytial Virus by Individual and Mixtures of F and G Protein Monoclonal Antibodies", Journal of Virology, vol. 62, No. 11, Nov. 1988, pp. 4232-4238.
Beeler et al., "Neutralization Epitopes of the F Glycoprotein of Respiratory Syncytial Virus: Effect of Mutation upon Fusion Function", Journal of Virology, vol. 63, No. 7, Jul. 1989, pp. 2941-2950.
Chin et al., "Field Evaluation of a Respiratory Syncytial Virus Vaccine and a Trivalent Parainfluenza Virus Vaccine in a Pediatric Population", American Journal of Epidemiology, vol. 89, No. 4, 1969, pp. 449-463.
Garcia-Barreno et al., "Marked Differences in the Antigenic Structure of Human Respiratory Syncytial Virus F and G Glycoproteins", Journal of Virology, vol. 63, No. 2, Feb. 1989, pp. 925-932.
Hodes et al., "Genetic Alteration in a Temperature-Sensitive Mutant of Respiratory Syncytial Virus After Replication in Vivo (37972)", Proceedings of the Society for Experimental Biology and Medicine, vol. 145, No. 4, 1974, pp. 1158-1164.
Kapikian et al., "An Epidemiologic Study of Altered Clinical Reactivity to Respiratory Syncytial (RS) Virus Infection in Children Previously Vaccinated with an Inactivated RS Virus Vaccine", American Journal of Epidemiology, vol. 89, No. 4, 1969, pp. 405-421.
Kim et al., "Safety and Antigenicity of Temperature Sensitive (TS) Mutant Respiratory Syncytial Virus (RSV) in Infants and Children", Pediatrics, vol. 52, No. 1, Jul. 1973, pp. 56-63.
Taylor et al., "Monoclonal Antibodies Protect Against Respiratory Syncytial Virus Infection in Mice", Immunology, vol. 52, 1984, pp. 137-142.
Wright et al., "Evaluation of a Live, Attenuated Respiratory Syncytial Virus Vaccine in Infants", The Journal od Pediatrics, vol. 88, No. 6, Jun. 1976, pp. 931-936.
International Search Report and Written Opinion received for PCT Patent Application No. PCT/US2007/016938, mailed on Jul. 14, 2008, 8 pages.
Office Action received for Australian Patent Application No. 2007345682, mailed on Jun. 4, 2012, 3 pages.
Office Action received for Canadian Patent Application No. 2,657,955, mailed on May 13, 2013, 5 pages.
Office Action received for Chinese Patent Application No. 201080049907.7, issued on Jul. 31, 2013, 13 pages (6 pages of English Translation and 7 pages of Office Action).
Extended European Search Report (includes Supplementary European Search Report and Search Opinion) received for European Patent Application No. 07872588.4, mailed on Mar. 16, 2011, 11 pages.
Extended European Search Report (includes Supplementary European Search Report and Search Opinion) received for European Patent Application No. 10829045.3, mailed on Apr. 10, 2013, 9 pages.
Office Action received for European Patent Application No. 07872588.4, mailed on Dec. 17, 2012, 6 pages.
Office Action received for Japanese Patent Application No. 2009-521858, mailed on Aug. 7, 2012, 14 pages (8 pages of English Translation and 6 pages of Office Action).
Office Action received for Japanese Patent Application No. 2009-521858, mailed on Oct. 15, 2013, 13 pages (8 pages of English Translation and 5 pages of Office Action).
Non Final Office Action received for U.S. Appl. No. 12/375,281, mailed on Feb. 14, 2012, 19 pages.
Final Office Action received for U.S. Appl. No. 12/375,281, mailed on Aug. 7, 2012, 15 pages.
Non-Final Office Action received for U.S. Appl. No. 12/375,281, mailed on Jan. 30, 2014, 16 pages.
Alce et al., "APOBEC3G Is Incorporated into Virus-like Particles by a Direct Interaction with HIV-1 Gag Nucleocapsid Protein", The Journal of Biological Chemistry, vol. 279, No. 33, Aug. 13, 2004, pp. 34083-34086.
Bellier et al., "DNA Vaccines Encoding Retrovirus-Based Virus-Like Particles Induce Efficient Immune Responses without Adjuvant", Vaccine, vol. 24, 2006, pp. 2643-2655.
Bosch et al., "Inhibition of Release of Lentivirus Particles with Incorporated Human Influenza Virus Haemagglutinin by Binding to Sialic Acid-Containing Cellular Receptors", Journal of General Virology, vol. 82, 2001, pp. 2485-2494.
Breun et al., "Protection of MLV Vector Particles From Human Complement", Biochemical and Biophysical Research Communications, vol. 264, No. 1, 1999, pp. 1-5.
Briggs et al., "Do Lipid Rafts Mediate Virus Assembly and Pseudotyping", The Journal of General Virology, vol. 84, 2003, pp. 757-768.
Chunsheng, Mao, "Self-Assembly of Retrovirus GAG Protein", Foreign Medical Sciences, Section of Virology, vol. 3, No. 2, 1996, pp. 51-55 (See Statement Under 37 CFR § 1.98(a) (3)).
Douaisi et al., "HIV-1 and MLV Gag Proteins are Sufficient to Recruit APOBEC3G into Virus-Like Particles", Biochemical and Biophysical Research Communications, vol. 321, 2004, pp. 566-573.
Graham, Barney S., "Biological Challenges and Technological Opportunities for Respiratory Syncytial Virus Vaccine Development", Immunological Reviews, vol. 239, No. 1, Jan. 2011, pp. 149-166.
Guo et al., "Enhancement of Mucosal Immune Responses by Chimeric Influenza HA/SHIV Virus-Like Particles", Virology, vol. 313, 2003, pp. 502-513.
Harder et al., "Lipid Domain Structure of the Plasma Membrane Revealed by Patching of Membrane Components", The Journal of Cell Biology, vol. 141, No. 4, May 18, 1998, pp. 929-942.
Haynes, Joel R., "Influenza Virus-Like Particle Vaccines", Expert Review of Vaccines, vol. 8, No. 4, 2009, pp. 435-445.
Haynes et al., "Influenza-Pseudotyped Gag Virus-Like Particle Vaccines Provide Broad Protection against Highly Pathogenic Avian Influenza Challenge", Vaccine, vol. 27, 2009, pp. 530-541.
Krammer et al., "Alternative Influenza Vaccines Made by Insect Cells", Trends in Molecular Medicine, vol. 16, No. 7, 2010, pp. 313-320.
Metzner et al., "Rafts, Anchors and Viruses—A Role for Glycosylphosphatidylinositol Anchored Proteins in the Modification of Enveloped Viruses and Viral Vectors", Virology, vol. 382, 2008, pp. 125-131.
Pickl et al., "Lipid Rafts and Pseudotyping", Journal of Virology, vol. 75, No. 15, Aug. 2001, pp. 7175-7183.
Pillay et al., "Optimization of Chimeric HIV-1 Virus-like Particle Production in a Baculovirus-Insect Cell Expression System", Biotechnology Progress, vol. 25, No. 4, 2009, pp. 1153-1160.
Quan et al., "Viruslike Particle Vaccine Induces Protection Against Respiratory Syncytial Virus Infection in Mice", The Journal of Infectious Diseases, vol. 204, Oct. 1, 2011, pp. 987-995.
Simons et al., "Lipid Rafts and Signal Transduction", Nature Reviews Molecular Cell Biology, vol. 1, No. 1, Oct. 2000, pp. 31-39.
Wang et al., "Severe Acute Respiratory Syndrome Coronavirus Nucleocapsid Protein Confers Ability to Efficiently Produce Virus-Like Particles when Substituted for the Human Immunodeficiency Virus Nucleocapsid Domain", Journal of Biomedical Science, vol. 15, 2008, pp. 719-729.
Office Action Received for Canadian Patent Application No. 2,657,955, mailed on May 14, 2014, 3 pages.

* cited by examiner

922.104-Mouse Strain Study (A)

2⁰ Response-PostBoost (B)

RSV Plaque Reduction Assay

All micrographs have a 1000 nm scale bar.

CHIMERIC RSV-F POLYPEPTIDE AND LENTIVIRUS OR ALPHA-RETROVIRUS GAG-BASED VLPS

CROSS REFERENCE TO RELATED APPLICATIONS

This is a U.S. National Phase patent application of PCT/US2010/055334, filed Nov. 3, 2010, which claims priority to the U.S. Provisional Patent Application No. 61/257,766, filed Nov. 3, 2009, each of which is hereby incorporated by reference in the present disclosure in its entirety.

SUBMISSION OF SEQUENCE LISTING ON ASCII TEXT FILE The content of the following submission on ASCII text file is incorporated herein by reference in its entirety: a computer readable form (CRF) of the Sequence Listing (file name 606772000700SEQLIST.TXT, date recorded: Apr. 11, 2012, size: 119 KB).

FIELD

The present invention relates to the field of chimeric virus-like particles (VLPs) that include a respiratory syncytial virus (RSV) F polypeptide and a lentivirus or alpha-retrovirus GAG polypeptide. In preferred examples, the field includes chimeric VLPs and methods of producing chimeric VLPs. In certain embodiments, the chimeric VLPs comprise an avian leukosis virus (ALV), a rous sarcoma virus, a simian immunodeficiency virus (SIV), or a human immunodeficiency virus (HIV) Gag polypeptide and a respiratory syncytial virus F polypeptide.

BACKGROUND

Respiratory syncytial virus (RSV) is a leading cause of bronchiolitis and pneumonia among infants and children under 1 year of age (CDC National Center for Infectious Diseases (2004) Respiratory Syncytial Virus). RSV can also be a significant lower respiratory tract pathogen in immunocompromised adults and the elderly. Individuals can be infected multiple times as natural infection with RSV does not induce protective immunity.

RSV is a negative-sense, single-stranded RNA virus that belongs to the genus Pneumovirus of the family Paramyxoviridae. The RSV genome is surrounded by a helical nucleocapsid and encodes at least ten proteins: three transmembrane structural proteins (F, G, and SH), two matrix proteins (M and M2), three nucleocapsid proteins (N, P, and L), and two nonstructural proteins (NS1 and NS2) (Collins et al (1996) Respiratory syncytial virus, pp. 1313-1351, In B. N. Fields (ed.), Fields virology. Raven Press, New York, N.Y.). Neutralizing antibodies appear to be elicited only by the F and G proteins. RSV is divided into subgroups A and B based on the G protein, whereas F is more closely related between the subgroups. Monoclonal antibodies against the F protein have been shown to have neutralizing effects in vitro and prophylactic effects in vivo (e.g. Anderson et al. 1988. J. Virol. 62:4232-4238; Anderson et al. 1986. J. Clin. Micro. 23:475-480; Beeler and Coelingh 1989. J. Virol. 63:2941-50; Garcia-Barreno et al. 1989. J. Virol. 63:925-32; Taylor et al. 1984. Immunology 52: 137-142; and U.S. Pat. No. 6,818,216).

No safe and effective vaccine exists for RSV despite several decades of research. A formalin-inactivated virus vaccine tested in infants and children did not protect against infection and was associated with increased risk of severe symptoms during subsequent infections by wild-type RSV virus (Kapikian et al., 1969, Am. J. Epidemiol. 89:405-21; Chin et al., 1969, Am. J. Epidemiol. 89:449-63). Later attempts focused on developing live-attenuated temperature sensitive mutants also failed due to the inability to identify virus candidates at an appropriate level of attenuation and to the genetic instability of some candidates (I lodes et al. (1974) Proc. Soc. Exp. Biol. Med., 145, 1158-1164; Kim et al. (1973) Pediatrics, 52, 56-63; Wright et al (1976) J. Pediatrics, 88, 931-936).

Virus-like particles (VLPs) offer several advantages over conventional vaccine technology. An important advantage of VLPs for vaccine development is that they mimic native viruses in terms of three-dimensional structure and the ability to induce neutralizing antibody responses to both primary and conformational epitopes and therefore should prove more immunogenic than other vaccine formulations. Unlike viral vectored approaches, VLPs exhibit no problem with pre-existing immunity, thus allowing for recurrent use. VLPs containing RSV antigens have been generated by co-expression of RSV F protein with RSV matrix (M) protein or with a heterologous M protein in insect cells (US 2008/0233150). However, US 2008/02331050 does not teach actual expression of the RSV-F protein with a lentivirus or alpha-retrovirus GAG protein. In addition, the applicants in U.S. Ser. No. 61/115,780 teach expression of the RSV-F protein in the absence of an enveloped virus core forming polypeptides. However, the applicants found that the murine leukaemia virus (MLV—a gamma-retrovirus) GAG protein does not effectively form VLPs when co-expressed with the RSV-F protein. Thus, there is a need for VLPs that express RSV F protein on a core formed by a structural polypeptide other than the native RSV M protein.

SUMMARY

Various aspects of this disclosure meet this need by providing various methods and compositions as disclosed herein for methods of generating chimeric VLPs and compositions comprising chimeric VLPs. In preferred embodiments, the chimeric VLPs will comprise a lentivirus or alpha-retrovirus Gag polypeptide and a respiratory syncytial virus F polypeptide.

An aspect of the disclosed compositions includes chimeric virus-like particles comprising a lentivirus or alpha-retrovirus Gag polypeptide and a respiratory syncytial virus F polypeptide, which may have at least 80% sequence identity, at least 85% sequence identity, at least 90% sequence identity, at least 95% sequence identity, at least 97% sequence identity, or at least 99% sequence identity to any of the respiratory syncytial virus F polypeptide amino acid sequences disclosed in the examples herein. In some embodiments, the Gag polypeptide is from a human immunodeficiency virus, which may have at least 80% sequence identity, at least 85% sequence identity, at least 90% sequence identity, at least 95% sequence identity, at least 97% sequence identity, or at least 99% sequence identity to any of the human immunodeficiency virus Gag polypeptide amino acid sequences disclosed in the examples herein, or a simian immunodeficiency virus, which may have at least 80% sequence identity, at least 85% sequence identity, at least 90% sequence identity, at least 95% sequence identity, at least 97% sequence identity, or at least 99% sequence identity to the simian immunodeficiency virus Gag polypeptide amino acid sequences disclosed in the examples herein. In other embodiments, the Gag polypeptide is from an avian leukosis virus, which may have at least 80% sequence identity, at least 85% sequence identity, at least 90% sequence identity, at least 95% sequence identity, at least 97% sequence identity, or at least 99% sequence identity to any of the avian leukosis virus Gag polypeptide amino acid sequences disclosed in the examples herein. In another embodiment, the virus-like particle further comprises mammalian glycosylation.

In another embodiment that may be combined with any of the preceding embodiments or aspects, the preparation also includes an adjuvant in admixture with the virus-like particles. In another embodiment that may be combined with any of the preceding embodiments or aspects that include an adjuvant, the adjuvant may be located outside the virus-like particle or may be located inside the virus-like particle. In another embodiment that may be combined with any of the preceding embodiments or aspects that include an adjuvant, the adjuvant may be covalently linked to the respiratory syncytial virus F polypeptide to form a covalent linkage.

In another embodiment that may be combined with any of the preceding embodiments or aspects, a neutralizing anti-RSV-F antibody may bind to the respiratory syncytial virus F polypeptide (demonstrating that the RSV F polypeptide is in substantially a native conformation). In certain embodiments that may be combined with any of the preceding embodiments or aspects that include such a neutralizing antibody, the neutralizing anti-RSV-F antibody may be Palivizumab.

In another embodiment that may be combined with any of the preceding embodiments or aspects, the chimeric virus-like particles further comprise an additional VLP-associating antigen, or VLP-associating polypeptide linked to a second antigen.

Another aspect includes methods for producing a chimeric virus-like particle, comprising: (a) providing one or more expression vectors together which express a lentivirus or alpha-retrovirus Gag polypeptide and a respiratory syncytial virus F polypeptide, which may have at least 80% sequence identity, at least 85% sequence identity, at least 90% sequence identity, at least 95% sequence identity, at least 97% sequence identity, or at least 99% sequence identity to any of the respiratory syncytial virus F polypeptide nucleic acid sequences disclosed in the examples herein; (b) introducing the one or more expression vectors into a eukaryotic cell in a media; and (c) expressing the retroviral Gag polypeptide and the respiratory syncytial virus F polypeptide to produce the chimeric virus-like particle. In certain embodiments, the eukaryotic cell is a yeast cell or a mammalian cell. In certain embodiments, the eukaryotic cell is a mammalian cell. In some embodiments, the Gag polypeptide is from a human immunodeficiency virus, which may have at least 80% sequence identity, at least 85% sequence identity, at least 90% sequence identity, at least 95% sequence identity, at least 97% sequence identity, or at least 99% sequence identity to any of the human immunodeficiency Gag polypeptide nucleic acid sequences disclosed in the examples herein, or a simian immunodeficiency virus, which may have at least 80% sequence identity, at least 85% sequence identity, at least 90% sequence identity, at least 95% sequence identity, at least 97% sequence identity, or at least 99% sequence identity to the simian immunodeficiency virus Gag polypeptide amino acid sequences disclosed in the examples herein. In other embodiments, the Gag polypeptide is from an avian leukosis virus, which may have at least 80% sequence identity, at least 85% sequence identity, at least 90% sequence identity, at least 95% sequence identity, at least 97% sequence identity, or at least 99% sequence identity to any of the avian leukosis virus Gag polypeptide nucleic acid sequences disclosed in the examples herein. In another embodiment, the virus-like particle further comprises mammalian glycosylation.

In another embodiment which may be combined with the preceding aspect, the method further includes the step of recovering the virus-like particles from the media in which the eukaryotic cell is cultured.

In another embodiment which may be combined with the preceding embodiment and aspect, the expression vector may be a viral vector. In another embodiment which may be combined with the preceding embodiments and aspect, the viral vector may be selected from the group consisting of: an adenovirus, a herpesvirus, a poxvirus and a retrovirus. In another embodiment which may be combined with the preceding embodiments and aspect that include a viral vector, the viral vector further includes a transcriptional regulator that down-regulates expression of the respiratory syncytial virus F polypeptide when the viral vector is propagated in a helper cell or up-regulates expression of the respiratory syncytial virus F polypeptide in the eukaryotic cell. In certain embodiments, the transcriptional regulator may be a tet repressor or a metallothionine inducible enhancer. In another embodiment which may be combined with the preceding embodiment and aspect, the eukaryotic cell may be selected from the group consisting of a BHK cell, a VERO cell, an HT1080 cell, an MRC-5 cell, a WI 38 cell, an MDCK cell, an MDBK cell, a 293 cell, a 293T cell, an RD cell, a COS-7 cell, a CHO cell, a Jurkat cell, a HUT cell, a SUPT cell, a C8166 cell, a MOLT4/clone8 cell, an MT-2 cell, an MT-4 cell, an H9 cell, a PM1 cell, a CEM cell, a myeloma cell, SB20 cell, a LtK cell, a HeLa cell, a WI-38 cell, an L2 cell, a CMT-93, and a CEMX174 cell.

In another embodiment which may be combined with the preceding embodiment and aspect, a neutralizing anti-RSV-F antibody may bind to the expressed respiratory syncytial virus F polypeptide (demonstrating that the respiratory syncytial virus F polypeptide is substantially in a native fold). In another embodiment which may be combined with the preceding embodiments and aspect including a neutralizing antibody, the neutralizing anti-RSV-F antibody is Palivizumab.

Another aspect includes methods for treating or preventing respiratory syncytial virus infection comprising administering to a subject an immunogenic amount of the preparation of any of the preceding embodiments of that aspect or the population produced by the method or any of the preceding embodiments of that aspect. Another embodiment that may be combined with any of the embodiments of the preceding aspect, the administration induces a protective immunization response in the subject. Another embodiment that may be combined with any of the embodiments of the preceding aspect, the administration may be selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.

Another aspect includes pharmaceutical compositions comprising an immunogenic amount of the preparation of any of the preceding embodiments of that aspect or the population produced by the method or any of the preceding embodiments of that aspect. Another embodiment that may be combined with any of the embodiments of the preceding aspect, the pharmaceutical composition further includes a pharmaceutically acceptable carrier.

Another aspect includes methods for providing protection against respiratory syncytial virus infection comprising administering to a subject an immunogenic amount of the preparation of any of the preceding embodiments of that aspect or the population produced by the method or any of the preceding embodiments of that aspect. Another embodiment that may be combined with any of the embodiments of the preceding aspect, the administration may be selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.

The foregoing aspects and embodiments thereof may further be combined with any of the embodiments disclosed in the specification. Additional aspects of the compositions and methods disclosed herein may be found throughout the specification which may be included with any of foregoing embodiments and/or the additional embodiments disclosed in the specification.

SUMMARY OF THE FIGURES

FIG. 34 shows the plasmid map of pShuttle-CMV-TO.

DETAILED DESCRIPTION OF THE PREFERRED EMBODIMENTS

Figure 1:
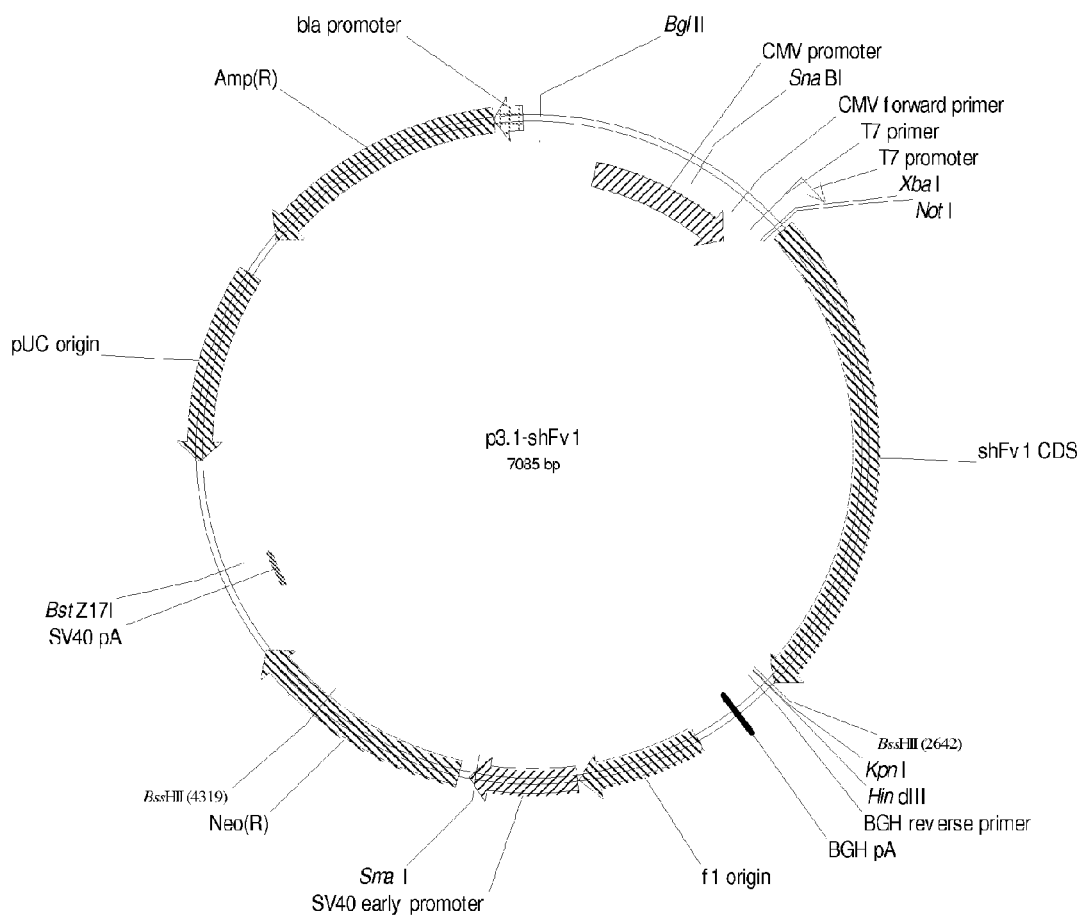
FIG. 1 shows the plasmid map of p3.1-shFv1.

Various aspects of the compositions and methods disclosed herein include, without limitation, chimeric VLPs that include at least an RSV-F polypeptide and a lentivirus or alpha-retrovirus GAG polypeptide; methods of expressing or generating such chimeric VLPs (which can be in a mammalian cell expression system); methods of further processing such VLPs into vaccine compositions and methods of using such vaccine compositions.

In certain embodiments, chimeric VLPs disclosed herein comprise a lentivirus or alpha-retrovirus Gag polypeptide and a respiratory syncytial virus F polypeptide.

Certain aspects and embodiments of the chimeric VLPs disclosed herein are based upon the surprising discovery that co-expression of an RSV-F polypeptide with a number of retroviral Gag proteins including the murine leukemia virus Gag protein, the Mason-Phizer monkey virus Gag protein, the bovine leukemia virus Gag protein, and the equine infectious anemia virus Gag protein result in markedly reduced amounts of VLPs which indicates that the RSV-F polypeptide interferes in some way with the budding function of the MLV Gag protein. This result does not depend upon interference between the cytoplasmic tail of the RSV-F polypeptide and the MLV gag, as constructs where the extracellular portion of the RSV-F polypeptide was anchored to the VLP via a GPI-anchor tag still interfered with VLP formation. In contrast, as demonstrated in the examples herein, the RSV-F polypeptide surprisingly does not interfere with VLP formation by rous sarcoma virus Gag protein, by avian leukosis virus Gag protein, by simian immunodeficiency virus Gag protein, or by human immunodeficiency virus Gag protein.

An exemplary method of generating the chimeric VLPs is by expression in eukaryotic cells, which in particular embodiments may be yeast, insect or mammalian cells, and which may include co-expression of additional polypeptide antigens.

The practice of the disclosed methods and protocols will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press.

DEFINITIONS

A "chimeric VLP" as used here refers to virus-like particles that are formed using a lentivirus or alpha-retrovirus Gag polypeptide that may be expressed simultaneously with a respiratory syncytial virus F polypeptide. Examples include, without limitation, VLPs comprising a respiratory syncytial virus F polypeptide substantially lacking the cytoplasmic portion of the respiratory syncytial virus F polypeptide or a respiratory syncytial virus F polypeptide substantially lacking the transmembrane domain and the cytoplasmic portion of respiratory syncytial virus F polypeptide and additionally linked to a GPI anchor signal.

"Mammalian glycosylation" refers to glycosylation patterns generated by mammalian cell expression systems. Such glycosylation patterns do not include glycosylation patterns produced by insect cells that have been modified to include mammalian glycosylation enzymes, so long as such modified insect cells only produce "mammalian-like" glycosylation rather than the glycosylation pattern that would be naturally produced by a mammal or a mammalian cell based expression system. Non-limiting examples of mammalian glycosylation patterns include glycosylation produced by expression in human (e.g., HEK 293, HeLa), Chinese hamster ovary (CHO), dog (e.g., MDCK), mouse (e.g., H9), rat (e.g., IE) and non-human primate (e.g., NCTC) cells.

A "Gag polypeptide" as used herein includes any retroviral Gag polypeptide that is from a lentivirus (but excluding EIAV) or alpha-retrovirus. Certain embodiments of the chimeric VLPs described herein are formed by ALV or HIV Gag polypeptides.

The genome of retroviruses codes for three major gene products: the gag gene coding for structural proteins, the pol gene coding for reverse transcriptase and associated proteolytic polypeptides, nuclease and integrase associated functions, and env whose encoded glycoprotein membrane proteins are detected on the surface of infected cells and also on the surface of mature released virus particles. The gag genes of all retroviruses have an overall structural similarity and within each group of retroviruses are conserved at the amino acid level. The gag gene gives rise to the core proteins excluding the reverse transcriptase.

For MLV the Gag precursor polyprotein is $Pr65^{Gag}$ and is cleaved into four proteins whose order on the precursor is $NH_2$-p15-pp12-p30-p10-COOH. These cleavages are mediated by a viral protease and may occur before or after viral release depending upon the virus. The MLV Gag protein exists in a glycosylated and a non-glycosylated form. The glycosylated forms are cleaved from $gPr80^{Gag}$ which is synthesized from a different inframe initiation codon located upstream from the AUG codon for the non-glycosylated $Pr65^{Gag}$. Deletion mutants of MLV that do not synthesize the glycosylated Gag are still infectious and the non-glycosylated Gag can still form virus-like particles, thus raising the question over the importance of the glycosylation events. The post translational cleavage of the HIV-1 Gag precursor of $pr55^{Gag}$ by the virus coded protease yields the N-myristoylated and internally phosphorylated p17 matrix protein (p17MA), the phosphorylated p24 capsid protein (p24CA), and the nucleocapsid protein p15 (p15NC), which is further cleaved into p9 and p6.

Structurally, the prototypical Gag polyprotein is divided into three main proteins that always occur in the same order in retroviral gag genes: the matrix protein (MA) (not to be confused with influenza matrix protein M1, which shares the name matrix but is a distinct protein from MA), the capsid protein (CA), and the nucleocapsid protein (NC). Processing of the Gag polyprotein into the mature proteins is catalyzed by the retroviral encoded protease and occurs as the newly budded viral particles mature. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. The form of the Gag protein that mediates assembly is the polyprotein. Thus, the assembly domains need not lie neatly within any of the cleavage products that form later. The state of the art is quite advanced regarding these important functional elements. See, e.g., Hansen et al. J. Virol 64, 5306-5316, 1990; Will et al., AIDS 5, 639-654, 1991; Wang et al. J. Virol. 72, 7950-7959, 1998; McDonnell et al., J. Mol. Biol. 279, 921-928, 1998; Schultz and Rein, J. Virol. 63, 2370-2372, 1989; Accola et al., J. Virol. 72, 2072-2078, 1998; Borsetti et al., J. Virol., 72, 9313-9317, 1998; Bowzard et al., J. Virol. 72, 9034-9044, 1998; Krishna et al., J. Virol. 72, 564-577, 1998; Wills et al., J. Virol. 68, 6605-6618, 1994; Xiang et al., J. Virol. 70, 5695-5700, 1996; Garnier et al., J. Virol. 73, 2309-2320, 1999.

Examples of retroviral sources for Gag polypeptides include alpha-retroviruses (such as the avian leukosis virus or the Rous sarcoma virus), or lentiviruses (human immunodeficiency virus type 1, HIV-2, simian immunodeficiency virus, feline immunodeficiency virus, and caprine arthritis encephalitis virus (but excluding the equine infectious anemia virus)).

Alpha-retroviruses such as avian leukosis virus contain their protease domain as part of the Gag polyprotein rather than the Pol polyprotein as is the case with most other retroviruses. For use in the compositions and methods as described herein, a Gag polypeptide may be substantially lacking a C-terminal protease domain.

The "lipid raft" as used herein refers to the cell membrane microdomain in which the gag polypeptide may concentrate during the viral particle assembly process and therefore may be used as a means to incorporate additional antigens that either naturally associated with lipid rafts or are linked to a lipid-raft associated polypeptide.

A "VLP-associated polypeptide" as used herein refers to any polypeptide that is directly or indirectly associated with a VLP excluding any enveloped virus core forming polypeptide that would interfere with the lentivirus or alpha-retrovirus Gag polypeptide. The particular VLP-associated polypeptide used in the compositions and methods disclosed herein will depend on the desired use of the VLP and the role of the VLP-associated polypeptide (e.g., attaching one or more additional antigens or adjuvants to the VLP).

The VLP-associated polypeptide can be an integral membrane protein or a lipid raft-associating portion, a protein or portion thereof directly associated with the VLP via a protein modification which causes association with the membrane such as lipid modification, or a polypeptide with an indirect association with the VLP via a lipid raft-associated polypeptide.

Many proteins with lipid anchors associate with lipid rafts. Often short fragments of such proteins are sufficient for lipid attachment making such fragments ideal for lipid raft association as the fragments can be readily attached to other proteins and polypeptide that may not themselves naturally associate with lipid rafts. Lipid anchors that couple polypeptides to lipid rafts include GPI anchors, myristoylation, palmitoylation, and double acetylation.

Many different types of polypeptides are associated with lipid rafts. Lipid rafts function as platforms for numerous biological activities including signal transduction, membrane trafficking, viral entry, viral assembly, and budding of assembled particles and are therefore associated with the various polypeptides involved in these processes.

The various types of polypeptides involved in signaling cascades are associated with lipid rafts that function as signaling platforms. One type of lipid raft which functions as signaling platform is called a caveolae. It is a flask shaped invagination of the plasma-membrane which contains polypeptides from the caveolin family (e.g., caveolin and/or flottillin).

Membrane trafficking polypeptides are associated with lipid rafts which function as membrane trafficking platforms. Examples include the proteins involved in endocytosis and excocytosis, such as syntaxin-1, syntaxin-4, synapsin I, adducin, VAMP2, VAMP/synaptobrevin, synaptobrevin II, SNARE proteins, SNAP-25, SNAP-23, synaptotagmin I, synaptotagmin II, and the like.

Viral receptors, receptor-coreceptor complexes, any other components which help modulate the entry process are associated with lipid rafts which function as specialized membrane trafficking platforms for viral entry. Examples of lipid raft-associated viral receptors include the decay accelerating factor (DAF or CD55), a GPI-anchored membrane glycoprotein that is a receptor for many enteroviruses; the receptor for group A rotaviruses, a complex containing multiple components including gangliosides, Hsc70 protein, alpha2-beta1 and alpha5-beta2 integrins; glycoproteins of several enveloped viruses like HIV, MLV, measles, and Ebola; and polypeptides involved in HIV entry like CD5, CCR5, and nef. See Chazal and Gerlier, 2003, Virus Entry, Assembly, Budding, and Membrane Rafts, Microbiol. & Mol. Bio. Rev. 67(2):226-237.

Polypeptides involved in viral particle assembly are associated with lipid rafts functioning as viral assembly platforms. So long as portions that are responsible for formation of the viral nucleocapsid, capsid or core are omitted, such polypeptides or portions thereof may be used as VLP-associated polypeptides. Examples of such polypeptides include the HA and NA influenza envelope glycoproteins, the H and mature F1-F2 fusion proteins from measles, and the gp160, gp41, and Pr55gag from HIV. See Chazal and Gerlier, 2003, Virus Entry, Assembly, Budding, and Membrane Rafts, Microbiol. And Mol. Bio. Rev. 67(2):226-237.

Polypeptides involved in budding of assembled virus are associated with lipid rafts that function as viral budding platforms. There is data suggesting that HIV-1 budding from the host cell occurs in membrane rafts. See Chazal and Gerlier, 2003, Virus Entry, Assembly, Budding, and Membrane Rafts, Microbiol. And Mol. Bio. Rev. 67(2):226-237. General information about polypeptides involved in viral budding can be found in Fields Virology (4th ed.) 2001.

Some VLP-associated polypeptides include viral polypeptides such as hemagglutinin polypeptide, neuraminidase polypeptide, fusion protein polypeptide, glycoprotein polypeptide, and envelope protein polypeptide. Each of these polypeptides can be from any type of virus; however, certain embodiments include envelope protein from HIV-1 virus, fusion protein from respiratory syncytial virus or measles virus, glycoprotein from respiratory syncytial virus, herpes simplex virus, or Ebola virus, and hemagglutinin protein from measles virus.

Certain non-viral pathogen VLP-associated polypeptides may be obtained from pathogenic protozoa, helminths, and other eukaryotic microbial pathogens including, but not limited to, *Plasmodium* such as *Plasmodium falciparum, Plasmodium malariae, Plasmodium ovale*, and *Plasmodium vivax; Toxoplasma gondii; Trypanosoma brucei, Trypanosoma cruzi; Schistosoma haematobium, Schistosoma mansoni, Schistosoma japonicum; Leishmania donovani; Giardia intestinalis; Cryptosporidium parvum*; and the like. Such non-viral VLP-associated polypeptides may be used without being linked to an antigen not naturally associated with a lipid-raft as the VLP-associated polypeptide itself will act as the antigen.

An example of a viral VLP-associated polypeptide that may be included with the chimeric VLPs is a hemagglutinin polypeptide. The "hemagglutinin polypeptide" as used herein is derived from the influenza virus protein that mediates binding of the virus to the cell to be infected. Hemagglutinin polypeptides may also be derived from the comparable measles virus protein. The protein is an antigenic glycoprotein found anchored to the surface of influenza viruses by a single membrane spanning domain. At least sixteen subtypes of the influenza hemagglutinin have been identified labeled H1 through H16. H1, H2, and H3, are found in human influenza viruses. Highly pathogenic avian flu viruses with H5 or H7 hemagglutinins have been found to infect humans at a low rate. It has been reported that single amino acid changes in the avian virus strain's type H5 hemagglutinin have been found in human patients that alters the receptor specificity to allow the H5 hemagglutinin to significantly alter receptor specificity of avian H5N1 viruses, providing them with an ability to bind to human receptors (109 and 110). This finding explains how an H5N1 virus that normally does not infect humans can mutate and become able to efficiently infect human cells.

Hemagglutinin is a homotrimeric integral membrane polypeptide. The membrane spanning domain naturally associates with the raft-lipid domains, which allows it to associate with the respiratory syncytial virus F polypeptides for incorporation into VLPs. It is shaped like a cylinder, and is approximately 135 Å long. The three identical monomers that constitute HA form a central coiled-coil and a spherical head that contains the sialic acid binding sites, which is exposed on the surface of the VLPs. HA monomers are synthesized as a single polypeptide precursor that is glycosylated and cleaved into two smaller polypeptides: the HA1 and HA2 subunits. The HA2 subunits form the trimeric coiled-coil that is anchored to the membrane and the HA1 subunits form the spherical head.

As used in certain VLPs disclosed herein as a VLP-associated polypeptide, the hemagglutinin polypeptide shall at a minimum include the membrane anchor domain. The hemagglutinin polypeptide may be derived from any influenza virus type, subtype, strain or substrain, which for example may be from the H1, H2, H3, H5, H7, and 1-19 hemagglutinins. In addition, the hemagglutinin polypeptide may be a chimera of different influenza hemagglutinins. The hemagglutinin polypeptide may include one or more additional antigens not naturally associated with a lipid raft that may be generated by splicing the coding sequence for the one or more additional polypeptides into the hemagglutinin polypeptide coding sequence. An exemplary site for insertion of additional polypeptides into the hemagglutinin polypeptide is the N-terminus.

Another example of a viral VLP-associated polypeptide is a neuraminidase polypeptide. The "neuraminidase polypeptide" as used herein is derived from the influenza virus protein that mediates release of the influenza virus from the cell by cleavage of terminal sialic acid residues from glycoproteins. The neuraminidase glycoprotein is expressed on the viral surface. The neuraminidase proteins are tetrameric and share a common structure consisting of a globular head with a beta-pinwheel structure, a thin stalk region, and a small hydrophobic region that anchors the protein in the virus membrane by a single membrane spanning domain. The active site for sialic acid residue cleavage includes a pocket on the surface of each subunit formed by fifteen charged amino acids, which are conserved in all influenza A viruses. At least nine subtypes of the influenza neuraminidase have been identified labeled N1 through N9.

As used in certain VLPs disclosed herein, the neuraminidase polypeptide shall at a minimum include the membrane anchor domain. The state of the art regarding functional regions is quite high. See, e.g., Varghese et al., Nature 303, 35-40, 1983; Colman et al., Nature 303, 41-44, 1983; Lentz et al., Biochem, 26, 5321-5385, 1987; Webster et al., Virol. 135, 30-42, 1984. The neuraminidase polypeptide may be derived from any influenza virus type, subtype strain or substrain, which may be from the N1 and N2 neuraminidases. In addition, the neuraminidase polypeptide may be a chimera of different influenza neuraminidase. The neuraminidase polypeptide may include one or more additional antigens that are not naturally associated with a lipid raft that may be generated by splicing the coding sequence for the one or more additional polypeptides into the hemagglutinin polypeptide. An exemplary site for insertion of additional polypeptides into the neuraminidase polypeptide coding sequence is the C-terminus.

Another example of a VLP-associated peptide is an insect derived adhesion protein termed fasciclin I (FasI). The "fasciclin I polypeptide" as used herein is derived from the insect protein that is involved in embryonic development. This non-viral protein can be expressed in an insect cell baculovirus expression system leading to lipid raft association of FasI (J. Virol. 77, 6265-6273, 2003). It therefore follows that attachment of a heterologous antigen to a fasciclin I polypeptide will lead to incorporation of the chimeric molecule into VLPs when co-expressed with respiratory syncytial F polypeptides. As used in the VLPs disclosed herein, the fasciclin I polypeptide shall at a minimum include the membrane anchor domain.

Another example of a VLP-associated peptide is a viral derived attachment protein from RSV named the G glycoprotein. The "G glycopolypeptide" as used herein is derived from the RSV G glycoprotein. Recent data has demonstrated that lipid raft domains are important for RSV particle budding as they are for influenza virus (Virol 327, 175-185, 2004; Arch. Virol. 149, 199-210, 2004; Virol. 300, 244-254, 2002). The G glycoprotein from RSV is a 32.5 kD integral membrane protein that serves as a viral attachment protein as well as a protective antigen for RSV infection. As with the hemagglutinin from influenza virus, its antigenicity may enhance the antigenicity of any non-lipid raft antigens attached to it. Any modifications to the G glycopolypeptide in the way of non-lipid raft foreign antigen attachment will result in chimeric VLPs capable of inducing significant immune responses to the foreign antigen.

Antigens

Certain aspects of the compositions and methods disclosed herein include additional antigens associated with the chimeric VLPs. Such additional antigens may be included in the same composition and may further be covalently or non-covalently associated with the VLPs. In certain embodiments, the Gag polypeptide is a readily adaptable platform for forming chimeric VLPs containing respiratory syncytial virus F polypeptide and/or other VLP-associated polypeptides. This section describes exemplary antigens for use with the disclosed VLPs.

Linkage Between Antigen and VLP-Associated Polypeptide

As a means for forming VLPs containing antigens not naturally associated with a VLP, a linkage may be formed between the respiratory syncytial virus F polypeptide and/or another VLP-associated polypeptide and the antigen. The VLP-associated polypeptide may be linked to a single antigen or to multiple antigens to increase immunogenicity of the VLP, to confer immunogenicity to various pathogens, or to confer immunogenicity to various strains of a particular pathogen.

The linkage between the antigen and a VLP-associated polypeptide can be any type of linkage sufficient to result in the antigen being incorporated into the VLP. The bond can be a covalent bond, an ionic interaction, a hydrogen bond, an ionic bond, a van der Waals force, a metal-ligand interaction, or an antibody-antigen interaction. In certain embodiments, the linkage is a covalent bond, such as a peptide bond, carbon-oxygen bond, a carbon-sulfur bond, a carbon-nitrogen bond, a carbon-carbon bond, or a disulfide bond.

The antigen may be produced recombinantly with an existing linkage to the VLP-associated polypeptide or it may be produced as an isolated substance and then linked at a later time to the VLP-associated polypeptide.

Antigen Types

The antigens as used herein can be any substance capable of eliciting an immune response and which does not naturally associate with a lipid raft. Antigens include, but are not limited to, proteins, polypeptides (including active proteins and individual polypeptide epitopes within proteins), glycopolypeptides, lipopolypeptides, peptides, polysaccharides, polysaccharide conjugates, peptide and non-peptide mimics of polysaccharides and other molecules, small molecules, lipids, glycolipids, and carbohydrates. If the antigen does not naturally associate either directly or indirectly with a VLP, it would not be expected to be incorporated into a VLP without linkage to a VLP-associated polypeptide. The antigen can be any antigen implicated in a disease or disorder, e.g., microbial antigens (e.g., viral antigens, bacterial antigens, fungal antigens, protozoan antigens, helminth antigens, yeast antigens, etc.), tumor antigens, allergens and the like.

Sources for Antigens

The antigens described herein may be synthesized chemically or enzymatically, produced recombinantly, isolated from a natural source, or a combination of the foregoing. The antigen may be purified, partially purified, or a crude extract.

Polypeptide antigens may be isolated from natural sources using standard methods of protein purification known in the art, including, but not limited to, liquid chromatography (e.g., high performance liquid chromatography, fast protein liquid chromatography, etc.), size exclusion chromatography, gel electrophoresis (including one-dimensional gel electrophoresis, two-dimensional gel electrophoresis), affinity chromatography, or other purification technique. In many embodiments, the antigen is a purified antigen, e.g., from about 50% to about 75% pure, from about 75% to about 85% pure, from about 85% to about 90% pure, from about 90% to about 95% pure, from about 95% to about 98% pure, from about 98% to about 99% pure, or greater than 99% pure.

One may employ solid phase peptide synthesis techniques, where such techniques are known to those of skill in the art. See Jones, The Chemical Synthesis of Peptides (Clarendon Press, Oxford) (1994). Generally, in such methods a peptide is produced through the sequential additional of activated monomeric units to a solid phase bound growing peptide chain.

Well-established recombinant DNA techniques can be employed for production of polypeptides either in the same vector as the lipid-raft associated polypeptide, where, e.g., an expression construct comprising a nucleotide sequence encoding a polypeptide is introduced into an appropriate host cell (e.g., a eukaryotic host cell grown as a unicellular entity in in vitro cell culture, e.g., a yeast cell, an insect cell, a mammalian cell, etc.) or a prokaryotic cell (e.g., grown in in vitro cell culture), generating a genetically modified host cell; under appropriate culture conditions, the protein is produced by the genetically modified host cell.

Viral Antigens

Suitable viral antigens include those associated with (e.g., synthesized by) viruses of one or more of the following groups: Retroviridae (e.g. human immunodeficiency viruses, such as HIV-1 (also referred to as HTLV-III, LAV or HTLV-III/LAV, or HIV-III); and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis, including Norwalk and related viruses); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); and astroviruses.

Norvirus Antigens

The VLPs disclosed herein may include various antigens from the Norovirus family. Noroviruses, also called "Norwalk-like viruses" represent one of four genera within the Caliciviridae virus family. Within the Norovirus genus there are two major genetic groups that have been designated Genogroup I and Genogroup II. Genogroup I Norovirus strains include Norwalk virus, Southampton virus, Desert Shield virus, and Chiba virus. Genogroup II Norovirus strains include Houston virus, Hawaii virus, Lordsdale virus, Grimsby virus, Mexico virus, and the Snow Mountain agent (Parker, T. D., et al. J. Virol. (2005) 79(12):7402-9; Hale, A. D., et al. J. Clin. Micro. (2000) 38(4):1656-1660). Norwalk virus (NV) is the prototype strain of a group of human caliciviruses responsible for the majority of epidemic outbreaks of acute viral gastroenteritis worldwide. The Norwalk virus capsid protein has two domains: the shell domain (S) and the protruding domain (P). The P domain (aa 226-530, Norwalk strain numbering) is divided into two subdomains, P1 and P2. The P2 domain is a 127 aa insertion (aa 279-405) in the P1 domain and is located at the most distal surface of the folded monomer. The P2 domain is the least conserved region of VP1 among norovirus strains, and the hypervariable region within P2 is thought to play an important role in receptor binding and immune reactivity. Given the external location of the P domain, it is an exemplary antigen or source of polypeptide epitopes for use as antigens for the VLP vaccines disclosed herein. The P2 domain is an exemplary antigen for Genogroup I or Genogroup II Norovirus strains. Yet another example is the mAb 61.21 epitope recently identified as lying in a region of the P2 domain conserved across a range of norovirus strains, as well as the mAb 54.6 epitope (Lochridge, V. P., et al. J. Gen. Virol. (2005) 86:2799-2806).

Influenza Antigens

The VLPs disclosed herein may include various antigens from influenza including, without limitation, hemagglutinin, neuraminidase, or an additional influenza antigen. An additional influenza antigen is the M2 polypeptide. The M2 polypeptide of influenza virus is a small 97 amino acid class III integral membrane protein encoded by RNA segment 7 (matrix segment) following a splicing event (80, 81). Very little M2 exists on virus particles but it can be found more abundantly on infected cells. M2 serves as a proton-selective ion channel that is necessary for viral entry (82, 83). It is minimally immunogenic during infection or conventional vaccination, explaining its conservation, but when presented in an alternative format it is more immunogenic and protective (84-86). This is consistent with observations that passive transfer of an M2 monoclonal antibody in vivo accelerates viral clearance and results in protection (87). When the M2 external domain epitope is linked to HBV core particles as a fusion protein it is protective in mice via both parenteral and intranasal inoculation and is most immunogenic when three tandem copies are fused to the N-terminus of the core protein (88-90). This is consistent with other carrier-hapten data showing that increased epitope density increases immunogenicity (91).

For intranasal delivery of an M2 vaccine an adjuvant is required to achieve good protection and good results have been achieved with LTR192G (88, 90) and CTA 1-DD (89). The peptide can also be chemically conjugated to a carrier such as KLH, or the outer membrane protein complex of *N. meningitides*, or human papilloma virus VLPs and is protective as a vaccine in mice and other animals (92, 93).

Insofar as the M2 protein is highly conserved it is not completely without sequence divergence. The M2 ectodomain epitopes of common strains A/PR/8/34 (1-11N1) and A/Aichi/68 ($H_3N_2$) were shown to be immunologically cross reactive with all other modern sequenced human strains except for A/Hong Kong/156/97 (H5N1)(92). Examination of influenza database sequences also shows similar divergence in the M2 sequence of other more recent pathogenic H5N1 human isolates such as A/Vietnam/1203/04. This finding demonstrates that a successful H5-specific pandemic vaccine incorporating M2 epitopes will need to reflect the M2 sequences that are unique to the pathogenic avian strains rather than M2 sequences currently circulating in human H1 and H3 isolates.

Additional proteins from influenza virus (other than HA, NA and M2) may be included in the VLP vaccine either by co-expression or via linkage of all or part of the additional antigen to the respiratory syncytial virus F polypeptide or other VLP-associated polypeptides. These additional antigens include PB2, PB1, PA, nucleoprotein, matrix (M1), NS1, and NS2. These latter antigens are not generally targets of neutralizing antibody responses but may contain important epitopes recognized by T cells. T cell responses induced by a VLP vaccine to such epitopes may prove beneficial in boosting protective immunity.

Other Pathogenic Antigens

Suitable bacterial antigens include antigens associated with (e.g., synthesized by and endogenous to) any of a variety of pathogenic bacteria, including, e.g., pathogenic gram positive bacteria such as pathogenic *Pasteurella* species, *Staphylococci* species, and *Streptococcus* species; and gram-negative pathogens such as those of the genera *Neisseria, Escherichia, Bordetella, Campylobacter, Legionella, Pseudomonas, Shigella, Vibrio, Yersinia, Salmonella, Haemophilus, Brucella, Francisella* and *Bacterioides*. See, e.g., Schaechter, M, H. Medoff, D. Schlesinger, Mechanisms of Microbial Disease. Williams and Wilkins, Baltimore (1989).

Suitable antigens associated with (e.g., synthesized by and endogenous to) infectious pathogenic fungi include antigens associated with infectious fungi including but not limited to: *Cryptococcus neoformans, Histoplasma capsulatum, Coccidioides immitis, Blastomyces dermatitidis*, and *Candida albicans, Candida glabrata, Aspergillus fumigata, Aspergillus flavus*, and *Sporothrix schenckii*.

Suitable antigens associated with (e.g., synthesized by and endogenous to) pathogenic protozoa, helminths, and other eukaryotic microbial pathogens include antigens associated with protozoa, helminths, and other eukaryotic microbial pathogens including, but not limited to, *Plasmodium* such as *Plasmodium falciparum, Plasmodium malariae, Plasmodium ovale*, and *Plasmodium vivax; Toxoplasma gondii; Trypanosoma brucei, Trypanosoma cruzi; Schistosoma haematobium, Schistosoma mansoni, Schistosoma japonicum; Leishmania donovani; Giardia intestinalis; Cryptosporidium parvum*; and the like.

Suitable antigens include antigens associated with (e.g., synthesized by and endogenous to) pathogenic microorganisms such as: *Helicobacter pyloris*, *Borelia burgdorferi*, *Legionella pneumophila*, *Mycobacteria* sps (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Chlamydia trachomatis*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*, pathogenic *Campylobacter* sp., *Enterococcus* sp., *Haemophilus influenzae*, *Bacillus anthracis*, *Corynebacterium diphtheriae*, *corynebacterium* sp., *Erysipelothrix rhusiopathiae*, *Clostridium perfringens*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israeli*. Non-limiting examples of pathogenic *E. coli* strains are: ATCC No. 31618, 23505, 43886, 43892, 35401, 43896, 33985, 31619 and 31617.

Any of a variety of polypeptides or other antigens associated with intracellular pathogens may be included in the VLPs. Polypeptides and peptide epitopes associated with intracellular pathogens are any polypeptide associated with (e.g., encoded by) an intracellular pathogen, fragments of which are displayed together with MHC Class I molecule on the surface of the infected cell such that they are recognized by, e.g., bound by a T-cell antigen receptor on the surface of, a $CD8^+$ lymphocyte. Polypeptides and peptide epitopes associated with intracellular pathogens are known in the art and include, but are not limited to, antigens associated with human immunodeficiency virus, e.g., HIV gp120, or an antigenic fragment thereof; cytomegalovirus antigens; *Mycobacterium* antigens (e.g., *Mycobacterium avium*, *Mycobacterium tuberculosis*, and the like); Pneumocystic carinii (PCP) antigens; malarial antigens, including, but not limited to, antigens associated with *Plasmodium falciparum* or any other malarial species, such as 41-3, AMA-1, CSP, PFEMP-1, GBP-130, MSP-1, PFS-16, SERP, etc.; fungal antigens; yeast antigens (e.g., an antigen of a *Candida* spp.); *toxoplasma* antigens, including, but not limited to, antigens associated with *Toxoplasma gondii*, *Toxoplasma* encephalitis, or any other *Toxoplasma* species; Epstein-Barr virus (EBV) antigens; *Plasmodium* antigens (e.g., gp190/MSP1, and the like); etc.

Another VLP vaccine may be directed against *Bacillus anthracis*. *Bacillus anthracis* are aerobic or facultative anaerobic Gram-positive, nonmotile rods measuring 1.0 μm wide by 3.0-5.0 μm long. Under adverse conditions, *B. anthracis* form highly resistant endospores, which can be found in soil at sites where infected animals previously died. An antigen for use in a VLP vaccine as disclosed herein is the protective antigen (PA), an 83 kDa protein that binds to receptors on mammalian cells and is critical to the ability of *B. anthracis* to cause disease. Another antigen is the C-terminal 140 amino acid fragment of *Bacillus anthracis* PA which may be used to induce protective immunity in a subject against *Bacillus anthracis*. Other exemplary antigens for use in a VLP vaccine against anthrax are antigens from the anthrax spore (e.g., BclA), antigens from the vegetative stage of the bacterium (e.g., a cell wall antigen, capsule antigen (e.g., poly-gamma-D-glutamic acid or PGA), secreted antigen (e.g., exotoxin such as protective antigen, lethal factor, or edema factor). Another antigen for use in a VLP vaccine is the tetra-saccharide containing anthrose, which is unique to *B. anthracis* (Daubenspeck J. M., et al. J. Biol. Chem. (2004), 279:30945). The tetra-saccharide may be coupled to a VLP-associated polypeptide allowing association of the antigen with the VLP vaccine.

Tumor-Associated Antigens

Any of a variety of known tumor-specific antigens or tumor-associated antigens (TAA) can be included in the VLPs. The entire TAA may be, but need not be, used. Instead, a portion of a TAA, e.g., an epitope, may be used. Tumor-associated antigens (or epitope-containing fragments thereof) which may be used in VLPs include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV18, MAN, alpha-feto protein (AFP), OFP, CA-125, CA-50, CA-19-9, renal tumor-associated antigen G250, EGP-40 (also known as EpCAM), 5100 (malignant melanoma-associated antigen), p53, and p21ras. A synthetic analog of any TAA (or epitope thereof), including any of the foregoing, may be used. Furthermore, combinations of one or more TAAs (or epitopes thereof) may be included in the composition.

Allergens

In one aspect, the antigen that is part of the VLP vaccine may be any of a variety of allergens. Allergen based vaccines may be used to induce tolerance in a subject to the allergen. Examples of an allergen vaccine involving co-precipitation with tyrosine may be found in U.S. Pat. Nos. 3,792,159, 4,070,455, and 6,440,426.

Any of a variety of allergens can be included in VLPs. Allergens include but are not limited to environmental aeroallergens; plant pollens such as ragweed/hayfever; weed pollen allergens; grass pollen allergens; Johnson grass; tree pollen allergens; ryegrass; arachnid allergens, such as house dust mite allergens (e.g., Der p I, Der f I, etc.); storage mite allergens; Japanese cedar pollen/hay fever; mold spore allergens; animal allergens (e.g., dog, guinea pig, hamster, gerbil, rat, mouse, etc., allergens); food allergens (e.g., allergens of crustaceans; nuts, such as peanuts; citrus fruits); insect allergens; venoms: (Hymenoptera, yellow jacket, honey bee, wasp, hornet, fire ant); other environmental insect allergens from cockroaches, fleas, mosquitoes, etc.; bacterial allergens such as streptococcal antigens; parasite allergens such as *Ascaris* antigen; viral antigens; fungal spores; drug allergens; antibiotics; penicillins and related compounds; other antibiotics; whole proteins such as hormones (insulin), enzymes (streptokinase); all drugs and their metabolites capable of acting as incomplete antigens or haptens; industrial chemicals and metabolites capable of acting as haptens and functioning as allergens (e.g., the acid anhydrides (such as trimellitic anhydride) and the isocyanates (such as toluene diisocyanate)); occupational allergens such as flour (e.g., allergens causing Baker's asthma), castor bean, coffee bean, and industrial chemicals described above; flea allergens; and human proteins in non-human animals.

Allergens include but are not limited to cells, cell extracts, proteins, polypeptides, peptides, polysaccharides, polysaccharide conjugates, peptide and non-peptide mimics of polysaccharides and other molecules, small molecules, lipids, glycolipids, and carbohydrates.

Examples of specific natural, animal and plant allergens include but are not limited to proteins specific to the following genera: Canine (*Canis familiaris*); *Dermatophagoides* (e.g. *Dermatophagoides farinae*); Felis (*Felis domesticus*); *Ambrosia* (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); Alder; *Alnus* (*Alnus gultinoas*); *Betula* (*Betula verrucosa*); *Quercus*

(*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poapratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherun elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

Exemplary Methods of Making Chimeric VLPs from Mammalian Cells

Chimeric VLPs may be made by any method available to one of skill in the art. Chimeric VLPs include a lentivirus or alpha-retrovirus Gag polypeptide which is responsible for the formation of the VLP with the RSV-F polypeptide. In addition, the chimeric VLP may include one or more additional polypeptides such as a membrane (including lipid-raft)-associated polypeptide to provide additional antigens (other than those present naturally or artificially as a part of the one or more polypeptides responsible for the formation of the VLP or the RSV-F polypeptide). In certain embodiments, the polypeptides may be co-expressed in any available protein expression system including, for example, a mammalian cell-based system that includes lipid raft domains in the plasma membrane.

Recombinant expression of the polypeptides for the VLPs involves expression vectors containing polynucleotides that encode one or more of the polypeptides. Once a polynucleotide encoding one or more of the polypeptides has been obtained, the vector for the production of the polypeptide may be produced by recombinant DNA technology using techniques well known in the art. Thus, methods for preparing a protein by expressing a polynucleotide containing any of the VLP polypeptide-encoding nucleotide sequences are described herein. Methods which are well known to those skilled in the art can be used to construct expression vectors containing the VLP polypeptide coding sequences and appropriate transcriptional and translational control signals. These methods include, for example, in vitro recombinant DNA techniques, synthetic techniques, and in vivo genetic recombination. The methods and compositions disclosed herein, thus, provides replicable vectors comprising a nucleotide sequence encoding a lentivirus or alpha-retrovirus Gag polypeptide and a nucleotide sequence encoding respiratory syncytial virus F polypeptide and optionally one or more additional VLP-associated polypeptides, all operably linked to one or more promoters.

Non-limiting examples of vectors that can be used to express sequences that assemble into VLPs as described herein include viral-based vectors (e.g., retrovirus, adenovirus, adeno-associated virus, lentivirus, pox viruses and baculovirus), plasmid vectors, non-viral vectors, mammalian vectors, mammalian artificial chromosomes (e.g., liposomes, particulate carriers, etc.) and combinations thereof.

The expression vector(s) typically contain(s) coding sequences and expression control elements which allow expression of the coding regions in a suitable host. The control elements generally include a promoter, enhancer, exon, intron, splicing sites translation initiation codon, and translation and transcription termination sequences, and an insertion site for introducing the insert into the vector. Translational control elements have been reviewed by M. Kozak (e.g., Kozak, M., Mamm. Genome 7(8):563-574, 1996; Kozak, M., Biochimie 76(9):815-821, 1994; Kozak, M., J Cell Biol 108 (2):229-241, 1989; Kozak, M., and Shatkin, A. J., Methods Enzymol 60:360-375, 1979).

For example, typical promoters used for mammalian cell expression include the SV40 early promoter, a CMV promoter such as the CMV immediate early promoter (a CMV promoter can include intron A), RSV, HIV-LTR, the mouse mammary tumor virus LTR promoter (MMLV-LTR), FIV-LTR, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. A sequence for optimization of initiation of translation, located 5' to the coding sequence, may also be present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs as described herein (Chapman et al., Nuc. Acids Res. (1991) 19:3979-3986).

Enhancer elements may also be used herein to increase expression levels of the constructs, for example in mammalian host cells. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence (Chapman et al., Nuc. Acids Res. (1991) 19:3979-3986).

It will be apparent that a vector may contain one or more sequences as described herein. For example, a single vector may carry sequences encoding all the proteins found in the VLP. Alternatively, multiple vectors may be used (e.g., multiple constructs, each encoding a single polypeptide-encoding sequence or multiple constructs, each encoding one or more polypeptide-encoding sequences). In embodiments in which a single vector comprises multiple polypeptide-encoding sequences, the sequences may be operably linked to the same or different transcriptional control elements (e.g., promoters) within the same vector.

In addition, one or more sequences encoding non-RSV proteins may be expressed and incorporated into the VLP, including, but not limited to, sequences comprising and/or encoding immunomodulatory molecules (e.g., adjuvants described below), for example, immunomodulating oligonucleotides (e.g., CpGs), cytokines, detoxified bacterial toxins and the like.

The expression vector may be transferred to a host cell by conventional techniques and the transfected cells are then cultured by conventional techniques to produce the VLP polypeptide(s). Thus, the compositions and methods disclosed herein include host cells containing a polynucleotide encoding one or more of the VLP polypeptides operably linked to a heterologous promoter. In certain embodiments for the generation of VLPs, vectors encoding the lentivirus or alpha-retrovirus Gag polypeptide and the respiratory syncytial virus F polypeptide and optionally an additional VLP-associating antigen or VLP-associated polypeptide linked to an additional antigen or adjuvant may be (co)expressed in the host cell for generation of the VLP, as detailed below.

The VLPs may be produced in eukaryotic cells, for example mammalian cells, following transfection, establishment of continuous cell lines (using standard protocols as known to one skilled in the art) and/or infection with DNA molecules that carry the RSV genes of interest. The level of expression of the proteins required for VLP formation is maximized by sequence optimization of the eukaryotic or viral promoters that drive transcription of the selected genes. The VLP is released into the culture medium from where the VLP may be purified and subsequently formulated as vaccine. The VLPs are not infectious vaccines and therefore vaccine inactivation is not required.

The ability of lentivirus or alpha-retrovirus Gag polypeptides expressed from sequences as described herein to self-assemble into VLPs with antigenic proteins presented on the surface allows these VLPs to be produced in any host cell by the co-introduction of the desired sequences. The sequence(s) (e.g., in one or more expression vectors) may be stably and/or transiently integrated in various combinations into a host cell.

Suitable host cells include, but are not limited to, bacterial, mammalian, insect, yeast, plant, and *Xenopus* cells.

For example, a number of mammalian cell lines are known in the art and include primary cells as well as immortalized cell lines available from the American Type Culture Collection (A.T.C.C.), such as, but not limited to, BHK, VERO, HT1080, MRC-5, WI 38, MDCK, MDBK, 293, 293T, RD, COS-7, CHO, Jurkat, HUT, SUPT, C8166, MOLT4/clone8, MT-2, MT-4, H9, PM1, CEM, myeloma cells (e.g., SB20 cells), LtK, HeLa, WI-38, L2, CMT-93, and CEMX174 (such cell lines are available, for example, from the A.T.C.C.).

Similarly, bacterial hosts such as *E. coli, Bacillus subtilis*, and *Streptococcus* spp. will find use with the present expression constructs.

Yeast hosts useful in the present disclosure include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Fungal hosts include, for example, *Aspergillus*.

Insect cells for use with baculovirus expression vectors include, inter alia, *Aedes aegypti, Bombyx mori, Drosophila melanogaster, Spodoptera frugiperda*, and *Trichoplusia ni*. See, Latham & Galarza (2001) J. Virol. 75(13):6154-6165; Galarza et al. (2005) Viral. Immunol. 18(1):244-51; and U.S. Patent Publications 200550186621 and 20060263804.

Cell lines expressing one or more of the sequences described above can readily be generated given the disclosure provided herein by stably integrating one or more sequences (expression vectors) encoding the respiratory syncytial virus F polypeptide of the VLP. The promoter regulating expression of the stably integrated respiratory syncytial virus F polypeptide sequences (s) may be constitutive or inducible.

The parent cell line from which a chimeric VLP-producer cell line is derived can be selected from any cell described above, including for example, mammalian, insect, yeast, bacterial cell lines. In certain embodiments, the cell line is a mammalian cell line (e.g., 293, RD, COS-7, CHO, BHK, VERO, MRC-5, HT1080, and myeloma cells). Production of chimeric VLPs using mammalian cells provides (i) VLP formation; (ii) correct myristylation, glycosylation and budding; (iii) absence of non-mammalian cell contaminants and (iv) ease of purification.

In addition to creating cell lines, lentivirus or alpha-retrovirus Gag- and RSV F-encoding sequences may also be transiently expressed in host cells, with or without an additional antigen or adjuvant. Suitable recombinant expression host cell systems include, but are not limited to, bacterial, mammalian, baculovirus/insect, vaccinia, Semliki Forest virus (SFV), adenovirus, Alphaviruses (such as, Sindbis, Venezuelan Equine Encephalitis (VEE)), mammalian, yeast and *Xenopus* expression systems, well known in the art. Exemplary expression systems are mammalian cell lines, vaccinia, Sindbis, insect and yeast systems.

Many suitable expression systems are commercially available, including, for example, the following: baculovirus expression (Reilly, P. R., et al., BACULOVIRUS EXPRESSION VECTORS: A LABORATORY MANUAL (1992); Beames, et al., Biotechniques 11:378 (1991); Pharmingen; Clontech, Palo Alto, Calif.), vaccinia expression systems (Earl, P. L., et al., "Expression of proteins in mammalian cells using vaccinia" In Current Protocols in Molecular Biology (F. M. Ausubel, et al. Eds.), Greene Publishing Associates & Wiley Interscience, New York (1991); Moss, B., et al., U.S. Pat. No. 5,135,855, issued Aug. 4, 1992), expression in bacteria (Ausubel, F. M., et al., CURRENT PROTOCOLS IN MOLECULAR BIOLOGY, John Wiley and Sons, Inc., Media Pa.; Clontech), expression in yeast (Rosenberg, S, and Tekamp-Olson, P., U.S. Pat. No. RE 35,749, issued, Mar. 17, 1998, herein incorporated by reference; Shuster, J. R., U.S. Pat. No. 5,629,203, issued May 13, 1997, herein incorporated by reference; Gellissen, G., et al., Antonie Van Leeuwenhoek, 62(1-2):79-93 (1992); Romanos, M. A., et al., Yeast 8(6):423-488 (1992); Goeddel, D. V., Methods in Enzymology 185 (1990); Guthrie, C., and G. R. Fink, Methods in Enzymology 194 (1991)), expression in mammalian cells (Clontech; Gibco-BRL, Ground Island, N.Y.; e.g., Chinese hamster ovary (CHO) cell lines (Haynes, J., et al., Nuc. Acid. Res. 11:687-706 (1983); 1983, Lau, Y. F., et al., Mol. Cell. Biol. 4:1469-1475 (1984); Kaufman, R. J., "Selection and coamplification of heterologous genes in mammalian cells," in Methods in Enzymology, vol. 185, pp 537-566. Academic Press, Inc., San Diego Calif. (1991)), and expression in plant cells (plant cloning vectors, Clontech Laboratories, Inc., Palo-Alto, Calif., and Pharmacia LKB Biotechnology, Inc., Pistcataway, N.J.; Hood, E., et al., J. Bacteriol. 168:1291-1301 (1986); Nagel, R., et al., FEMS Microbiol. Lett. 67:325 (1990); An, et al., "Binary Vectors", and others in Plant Molecular Biology Manual A3:1-19 (1988); Miki, B. L. A., et al., pp. 249-265, and others in Plant DNA Infectious Agents (Hohn, T., et al., eds.) Springer-Verlag, Wien, Austria, (1987); Plant Molecular Biology: Essential Techniques, P. G. Jones and J. M. Sutton, New York, J. Wiley, 1997; Miglani, Gurbachan Dictionary of Plant Genetics and Molecular Biology, New York, Food Products Press, 1998; Henry, R. J., Practical Applications of Plant Molecular Biology, New York, Chapman & Hall, (1997).

When expression vectors containing the altered genes that code for the proteins required for VLP formation are introduced into host cell(s) and subsequently expressed at the necessary level, the VLP assembles and is then released from the cell surface into the culture media.

Depending on the expression system and host selected, the VLPs are produced by growing host cells transformed by an expression vector under conditions whereby the particle-forming polypeptides are expressed and VLPs can be formed. The selection of the appropriate growth conditions is within the skill of the art.

The particles are then isolated (or substantially purified) using methods that preserve the integrity thereof, such as, by density gradient centrifugation, e.g., sucrose gradients, PEG-precipitation, pelleting, and the like (see, e.g., Kimbauer et al. J. Virol. (1993) 67:6929-6936), as well as standard purification techniques including, e.g., ion exchange and gel filtration chromatography.

Exemplary Methods of Inactivation of Infectious Agents in Chimeric VLPs

An exemplary method of inactivation is through electromagnetic radiation as electromagnetic radiation is capable of inactivating the infectious agents without substantially reducing the immunogenicity of the chimeric VLP. As all three exemplary modes of electromagnetic radiation (i.e., UV irradiation with photoreactive compounds, UV irradiation alone and gamma irradiation) have a long history of use for inactivation of pathogens in a wide variety of samples such as blood, food, vaccines, etc. there are a wide variety of commercially available apparatus for applying the inactivating electromagnetic radiation that may be used with little to no modification to practice the methods disclosed herein. Furthermore, optimizing wavelengths and dosages is routine in the art and therefore readily within the capabilities of one of ordinary skill in the art.

UV Irradiation with Photoreactive Compounds

An exemplary method of inactivation with electromagnetic radiation is a combination of ultraviolet irradiation, such as UV-A irradiation, in the presence of a photoreactive compound, such as one that will react with polynucleotides in the infectious agent.

Exemplary photoreactive compounds include: actinomycins, anthracyclinones, anthramycin, benzodipyrones, fluorenes, fluorenones, furocoumarins, mitomycin, monostral fast blue, norphillin A, phenanthridines, phenazathionium salts, phenazines, phenothiazines, phenylazides, quinolines, and thiaxanthenones. One species is furocoumarins which belong in one of two main categories. The first category is psoralens [7H-furo(3,2-g)-(1)-benzopyran-7-one, or delta-lactone of 6-hydroxy-5-benzofuranacrylic acid], which are linear and in which the two oxygen residues appended to the central aromatic moiety have a 1, 3 orientation, and further in which the furan ring moiety is linked to the 6 position of the two ring coumarin system. The second category is isopsoralens [2H-furo(2,3-h)-(1)-benzopyran-2-one, or delta-lactone of 4-hydroxy-5-benzofuranacrylic acid], which are angular and in which the two oxygen residues appended to the central aromatic moiety have a 1, 3 orientation, and further in which the furan ring moiety is linked to the 8 position of the two ring coumarin system. Psoralen derivatives may be generated by substitution of the linear furocoumarin at the 3, 4, 5, 8, 4', or 5' positions, while isopsoralen derivatives may be generated by substitution of the angular furocoumarin at the 3, 4, 5, 6, 4', or 5 positions. Psoralens can intercalate between the base pairs of double-stranded nucleic acids, forming covalent adducts to pyrimidine bases upon absorption of long wave ultraviolet light (UVA). See, e.g., G. D. Cimino et al., Ann. Rev. Biochem. 54:1151 (1985); Hearst et al., Quart. Rev. Biophys. 17:1 (1984).

Exemplary wavelengths of UV (or in some cases visible light) radiation will depend upon the wavelength at which photoadducts are generated which is dependent upon the chemistry of the photoreactive chemical. By way of example, UV radiation in the wavelengths between 320 and 380 nm are most effective for many psoralens with 330 to 360 nm having maximum effectiveness.

UV Irradiation Alone

In addition to UV irradiation in the presence of a photoreactive compound, infectious agents may be inactivated by UV irradiation alone. In certain embodiments, the radiation is UVC radiation having a wavelength between about 180 and 320 nm, or between about 225 and 290 nm, or about 254 nm (i.e., the maximal absorbance peak of polynucleotides). UVC radiation may be used because it is less detrimental to the components of the chimeric VLPs disclosed herein for both stability and immunogenicity such as the lipid bilayer forming the envelope while retaining sufficient energy to inactivate infectious agents. However, other types of UV radiation such as, for example, UVA and UVB may also be used.

Gamma Irradiation

Gamma irradiation (i.e., ionizing radiation) may also be used in the practice of the methods disclosed herein to generate the compositions. Gamma irradiation can inactivate infectious agents by introducing strand breaks in the polynucleotides encoding the genome of the infectious agent or by generating hydroxyl radicals that attack the polynucleotides.

Exemplary Methods of Using Chimeric VLPs

Formulations

An exemplary use of the chimeric VLPs described herein is as a vaccine preparation. Typically, such vaccines are prepared as injectables either as liquid solutions or suspensions; solid forms suitable for solution in, or suspension in, liquid prior to injection may also be prepared. Such preparations may also be emulsified or produced as a dry powder. The active immunogenic ingredient is often mixed with excipients which are pharmaceutically acceptable and compatible with the active ingredient. Suitable excipients are, for example, water, saline, dextrose, sucrose, glycerol, ethanol, or the like, and combinations thereof. In addition, if desired, the vaccine may contain auxiliary substances such as wetting or emulsifying agents, pH buffering agents, or adjuvants which enhance the effectiveness of the vaccines.

Vaccines may be conventionally administered parenterally, by injection, for example, either subcutaneously, intradermally, subdermally or intramuscularly. Additional formulations which are suitable for other modes of administration include suppositories and, in some cases, oral, intranasal, buccal, sublingual, intraperitoneal, intravaginal, anal and intracranial formulations. For suppositories, traditional binders and carriers may include, for example, polyalkalene glycols or triglycerides; such suppositories may be formed from mixtures containing the active ingredient in the range of 0.5% to 10%, or even 1-2%. In certain embodiments, a low melting wax, such as a mixture of fatty acid glycerides or cocoa butter is first melted and the chimeric VLPs described herein are dispersed homogeneously, for example, by stirring. The molten homogeneous mixture is then poured into conveniently sized molds, allowed to cool, and to solidify.

Formulations suitable for intranasal delivery include liquids (e.g., aqueous solution for administration as an aerosol or nasal drops) and dry powders (e.g. for rapid deposition within the nasal passage). Formulations include such normally employed excipients as, for example, pharmaceutical grades of mannitol, lactose, sucrose, trehalose, xylitol, and chitosan. Mucosadhesive agents such as chitosan can be used in either liquid or powder formulations to delay mucocilliary clearance of intranasally-administered formulations. Sugars such as mannitol and sucrose can be used as stability agents in liquid formulations and as stability, bulking, or powder flow and size agents in dry powder formulations. In addition, adjuvants such as monophosphoryl lipid A (MPL) or CpG oligonucleotides can be used in both liquid and dry powder formulations as an immunostimulatory adjuvant.

Formulations suitable for oral delivery include liquids, solids, semi-solids, gels, tablets, capsules, lozenges, and the like. Formulations suitable for oral delivery include tablets, lozenges, capsules, gels, liquids, food products, beverages, nutraceuticals, and the like. Formulations include such normally employed excipients as, for example, pharmaceutical grades of mannitol, lactose, starch, magnesium stearate, sodium saccharine, cellulose, magnesium carbonate, and the like. Other chimeric VLPs vaccine compositions may take the form of solutions, suspensions, pills, sustained release formulations or powders and contain 10-95% of active ingredient, or 25-70%. For oral formulations, cholera toxin is an interesting formulation partner (and also a possible conjugation partner).

The chimeric VLP vaccines when formulated for vaginal administration may be in the form of pessaries, tampons, creams, gels, pastes, foams or sprays. Any of the foregoing formulations may contain agents in addition to chimeric VLPs, such as carriers, known in the art to be appropriate.

In some embodiments, the chimeric VLP vaccine may be formulated for systemic or localized delivery. Such formulations are well known in the art. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Systemic and localized routes of administration include, e.g., intradermal, topical application, intravenous, intramuscular, etc.

The chimeric VLPs may be formulated into the vaccine including neutral or salt-based formulations. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines may be administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with an exemplary range from about 0.1 μg to 2000 μg (even though higher amounts in the 1-10 mg range are contemplated), such as in the range from about 0.5 μg to 1000 μg, or even in the range from 1 μg to 500 μg or in the range from about 10 μg to 100 μg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

Some of the vaccine formulations will be sufficiently immunogenic as a vaccine by themselves, but for some of the others the immune response will be enhanced if the vaccine further includes an adjuvant substance.

Delivery agents that improve mucoadhesion can also be used to improve delivery and immunogenicity especially for intranasal, oral or lung based delivery formulations. One such compound, chitosan, the N-deacetylated form of chitin, is used in many pharmaceutical formulations (32). It is an attractive mucoadhesive agent for intranasal vaccine delivery due to its ability to delay mucociliary clearance and allow more time for mucosal antigen uptake and processing (33, 34). In addition, it can transiently open tight junctions which may enhance transepithelial transport of antigen to the NALT. In a recent human trial, a trivalent inactivated influenza vaccine administered intranasally with chitosan but without any additional adjuvant yielded seroconversion and HI titers that were only marginally lower than those obtained following intramuscular inoculation (33).

Chitosan can also be formulated with adjuvants that function well intranasally such as the genetically detoxified *E. coli* heat-labile enterotoxin mutant LTK63. This adds an immunostimulatory effect on top of the delivery and adhesion benefits imparted by chitosan resulting in enhanced mucosal and systemic responses (35).

Finally, it should be noted that chitosan formulations can also be prepared in a dry powder format that has been shown to improve vaccine stability and result in a further delay in mucociliary clearance over liquid formulations (42). This was seen in a recent human clinical trial involving an intranasal dry powder diphtheria toxoid vaccine formulated with chitosan in which the intranasal route was as effective as the traditional intramuscular route with the added benefit of secretory IgA responses (43). The vaccine was also very well tolerated. Intranasal dry powdered vaccines for anthrax containing chitosan and MPL induce stronger responses in rabbits than intramuscular inoculation and are also protective against aerosol spore challenge (44).

Intranasal vaccines represent an exemplary formulation as they can affect the upper and lower respiratory tracts in contrast to parenterally administered vaccines which are better at affecting the lower respiratory tract. This can be beneficial for inducing tolerance to allergen-based vaccines and inducing immunity for pathogen-based vaccines.

In addition to providing protection in both the upper and lower respiratory tracts, intranasal vaccines avoid the complications of needle inoculations and provide a means of inducing both mucosal and systemic humoral and cellular responses via interaction of particulate and/or soluble antigens with nasopharyngeal-associated lymphoid tissues (NALT) (16-19). The intranasal route has been historically less effective than parenteral inoculation, but the use of chimeric VLPs, novel delivery formulations, and adjuvants are beginning to change the paradigm. Indeed, chimeric VLPs containing functional hemagglutinin polypeptides may be especially well suited for intranasal delivery due to the abundance of sialic acid-containing receptors in the nasal mucosa resulting in the potential for enhanced HA antigen binding and reduced mucociliary clearance.

Adjuvants

Various methods of achieving adjuvant effect for vaccines are known and may be used in conjunction with the chimeric VLPs disclosed herein. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9.

In some embodiments, a chimeric VLP vaccine includes the chimeric VLPs in admixture with at least one adjuvant, at a weight-based ratio of from about 10:1 to about $10^{10}$:1 chimeric VLP:adjuvant, e.g., from about 10:1 to about 100:1, from about 100:1 to about $10^3$:1, from about $10^3$:1 to about $10^4$:1, from about $10^4$:1 to about $10^5$:1, from about $10^5$:1 to about $10^6$:1, from about $10^6$:1 to about $10^7$:1, from about $10^7$:1 to about $10^8$:1, from about $10^8$:1 to about $10^9$:1, or from about $10^9$:1 to about $10^{10}$:1 chimeric VLP:adjuvant. One of skill in the art can readily determine the appropriate ratio through information regarding the adjuvant and routine experimentation to determine optimal ratios.

Exemplary examples of adjuvants may include, but are not limited to, toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, oil in water emulsions, virosomes, cochleates, poly (lactide-co-glycolides) (PLG) microparticles, poloxamer particles, microparticles, and liposomes. Preferably, the adjuvants are not bacterially-derived exotoxins. Preferred adjuvants are those which stimulate a Th1 type response such as 3DMPL, CpG oligonucleotides, or QS21.

Monophosphoryl Lipid A (MPL), a non-toxic derivative of lipid A from *Salmonella*, is a potent TLR-4 agonist that has been developed as a vaccine adjuvant (Evans et al. 2003). In pre-clinical murine studies intranasal MPL has been shown to enhance secretory, as well as systemic, humoral responses (Baldridge et al. 2000; Yang et al. 2002). It has also been proven to be safe and effective as a vaccine adjuvant in clinical studies of greater than 120,000 patients (Baldrick et al., 2002; 2004). MPL stimulates the induction of innate immunity through the TLR-4 receptor and is thus capable of eliciting nonspecific immune responses against a wide range of infectious pathogens, including both gram negative and gram positive bacteria, viruses, and parasites (Baldrick et al. 2004; Persing et al. 2002). Inclusion of MPL in intranasal formulations should provide rapid induction of innate responses, eliciting nonspecific immune responses from viral challenge while enhancing the specific responses generated by the antigenic components of the vaccine.

Accordingly, in one embodiment, the present invention provides a composition comprising monophosphoryl lipid A (MPL®) or 3 De-O-acylated monophosphoryl lipid A (3D-MPL®) as an enhancer of adaptive and innate immunity. Chemically 3D-MPL® is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA), which is incorporated herein by reference. In another embodiment, the present invention provides a composition comprising synthetic lipid A, lipid A mimetics or analogs, such as BioMira's PET Lipid A, or synthetic derivatives designed to function like TLR-4 agonists.

Exemplary examples of adjuvants are polypeptide adjuvants that may be readily added to the chimeric VLPs described herein by co-expression with the polypeptide components of the chimeric VLP or fusion with the polypeptide components to produce chimeric polypeptides. Bacterial flagellin, the major protein constituent of flagella, is an adjuvant which has received increasing attention as an adjuvant protein because of its recognition by the innate immune system by the toll-like receptor TLR5 (65). Flagellin signaling through TLR5 has effects on both innate and adaptive immune functions by inducing DC maturation and migration as well as activation of macrophages, neutrophils, and intestinal epithelial cells resulting in production of proinflammatory mediators (66-72).

TLR5 recognizes a conserved structure within flagellin monomers that is unique to this protein and is required for flagellar function, precluding its mutation in response to immunological pressure (73). The receptor is sensitive to a 100 fM concentration but does not recognize intact filaments. Flagellar disassembly into monomers is required for binding and stimulation.

As an adjuvant, flagellin has potent activity for induction of protective responses for heterologous antigens administered either parenterally or intranasally (66, 74-77) and adjuvant effects for DNA vaccines have also been reported (78). A Th2 bias is observed when flagellin is employed which would be appropriate for a respiratory virus such as influenza but no evidence for IgE induction in mice or monkeys has been observed. In addition, no local or systemic inflammatory responses have been reported following intranasal or systemic administration in monkeys (74). The Th2 character of responses elicited following use of flagellin is somewhat surprising since flagellin signals through TLR5 in a MyD88-dependent manner and all other MyD88-dependent signals through TLRs have been shown to result in a Th1 bias (67, 79). Importantly, pre-existing antibodies to flagellin have no appreciable effect on adjuvant efficacy (74) making it attractive as a multi-use adjuvant.

A common theme in many recent intranasal vaccine trials is the use of adjuvants and/or delivery systems to improve vaccine efficacy. In one such study an influenza 1-13 vaccine containing a genetically detoxified *E. coli* heat-labile enterotoxin adjuvant (LT R192G) resulted in heterosubtypic protection against H5 challenge but only following intranasal delivery. Protection was based on the induction of cross neutralizing antibodies and demonstrated important implications for the intranasal route in development of new vaccines (22).

Cytokines, colony-stimulating factors (e.g., GM-CSF, CSF, and the like); tumor necrosis factor; interleukin-2, -7, -12, interferons and other like growth factors, may also be used as adjuvants as they may be readily included in the chimeric VLP vaccine by admixing or fusion with the polypeptide component.

In some embodiments, the chimeric VLP vaccine compositions disclosed herein may include other adjuvants that act through a Toll-like receptor such as a nucleic acid TLR9 ligand comprising a 5'-TCG-3' sequence; an imidazoquinoline TLR7 ligand; a substituted guanine TLR7/8 ligand; other TLR7 ligands such as Loxoribine, 7-deazadeoxyguanosine, 7-thia-8-oxodeoxyguanosine, Imiquimod (R-837), and Resiquimod (R-848).

Certain adjuvants facilitate uptake of the vaccine molecules by APCs, such as dendritic cells, and activate these. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminum adjuvants; DNA adjuvants; MPL; and an encapsulating adjuvant.

Additional examples of adjuvants include agents such as aluminum salts such as hydroxide or phosphate (alum), commonly used as 0.05 to 0.1 percent solution in buffered saline (see, e.g., Nicklas (1992) Res. Immunol. 143:489-493), admixture with synthetic polymers of sugars (e.g. Carbopol®) used as 0.25 percent solution, aggregation of the protein in the vaccine by heat treatment with temperatures ranging between 70° to 101° C. for 30 second to 2 minute periods respectively and also aggregation by means of cross-linking agents are possible. Aggregation by reactivation with pepsin treated antibodies (Fab fragments) to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA may als be used.

DDA (dimethyldioctadecylammonium bromide) is an interesting candidate for an adjuvant, but also Freund's complete and incomplete adjuvants as well as quillaja saponins such as QuilA and QS21 are interesting. Further possibilities include poly[di(earboxylatophenoxy)phosphazene (PCPP) derivatives of lipopolysaccharides such as monophosphoryl lipid A (MPL®), muramyl dipeptide (MDP) and threonyl muramyl dipeptide (tMDP). The lipopolysaccharide based adjuvants may also be used for producing a predominantly Th1-type response including, for example, a combination of monophosphoryl lipid A, such as 3-de-O-acylated monophosphoryl lipid A, together with an aluminum salt. MPL® adjuvants are available from GlaxoSmithKline (see, for example, U.S. Pat. Nos. 4,436,727; 4,877,611; 4,866,034 and 4,912,094).

Liposome formulations are also known to confer adjuvant effects, and therefore liposome adjuvants may be used in conjunction with the chimeric VLPs.

Immunostimulating complex matrix type (ISCOM® matrix) adjuvants may also be used with the chimeric VLPs, especially since it has been shown that this type of adjuvants are capable of up-regulating MHC Class II expression by APCs. An ISCOM matrix consists of (optionally fractionated) saponins (triterpenoids) from Quillaja *saponaria*, cholesterol, and phospholipid. When admixed with the immunogenic protein such as in the VLPs, the resulting particulate formulation is what is known as an ISCOM particle where the saponin may constitute 60-70% w/w, the cholesterol and phospholipid 10-15% w/w, and the protein 10-15% w/w. Details relating to composition and use of immunostimulating complexes can for example be found in the above-mentioned text-books dealing with adjuvants, but also Morein B et al., 1995, Clin. Immunother. 3: 461-475 as well as Barr I G and Mitchell G F, 1996, Immunol. and Cell Biol. 74: 8-25 provide useful instructions for the preparation of complete immunostimulating complexes.

The saponins, whether or not in the form of iscoms, that may be used in the adjuvant combinations with the chimeric VLP vaccines disclosed herein include those derived from the bark of Quillaja *Saponaria* Molina, termed Quil A, and fractions thereof, described in U.S. Pat. No. 5,057,540 and "Saponins as vaccine adjuvants", Kensil, C. R., Crit. Rev Ther Drug Carrier Syst, 1996, 12 (1-2):1-55; and EP 0 362 279 B1. Exemplary fractions of Quil A are QS21, QS7, and QS17.

β-Escin is another haemolytic saponin for use in the adjuvant compositions of the chimeric VLPs. Escin is described in the Merck index (12th ed: entry 3737) as a mixture of saponins occurring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August; 44(8):1454-1464)). β-escin is also known as aescin.

Another haemolytic saponin for use in the chimeric VLPs is Digitonin. Digitonin is described in the Merck index (12$^{th}$ Edition, entry 3204) as a saponin, being derived from the seeds of Digitalis purpurea and purified according to the procedure described Gisvold et al., J. Am. Pharm. Assoc., 1934, 23, 664; and Ruhenstroth-Bauer, Physiol. Chem., 1955, 301, 621. Its use is described as being a clinical reagent for cholesterol determination.

Another interesting possibility of achieving adjuvant effect is to employ the technique described in Gosselin et al., 1992. In brief, the presentation of a relevant antigen such as an antigen in a chimeric VLP disclosed herein can be enhanced by conjugating the antigen to antibodies (or antigen binding antibody fragments) against the Fc receptors on monocytes/macrophages. Especially conjugates between antigen and anti-F$_C$RI have been demonstrated to enhance immunogenicity for the purposes of vaccination. The antibody may be conjugated to the chimeric VLP after generation or as a part of the generation including by expressing as a fusion to any one of the polypeptide components of the chimeric VLP.

Other possibilities involve the use of the targeting and immune modulating substances (i.e. cytokines). In addition, synthetic inducers of cytokines such as poly I:C may also be used.

Suitable mycobacterial derivatives may be selected from the group consisting of muramyl dipeptide, complete Freund's adjuvant, RIBI, (Ribi ImmunoChem Research Inc., Hamilton, Mont.) and a diester of trehalose such as TDM and TDE.

Examples of suitable immune targeting adjuvants include CD40 ligand and CD40 antibodies or specifically binding fragments thereof (cf. the discussion above), mannose, a Fab fragment, and CTLA-4.

Examples of suitable polymer adjuvants include a carbohydrate such as dextran, PEG, starch, mannan, and mannose; a plastic polymer; and latex such as latex beads.

Yet another interesting way of modulating an immune response is to include the immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. 12-15, 1998, Seascape Resort, Aptos, Calif."

Oligonucleotides may be used as adjuvants in conjunction with the chimeric VLP vaccines and may contain two or more dinucleotide CpG motifs separated by at least three or more or even at least six or more nucleotides. CpG-containing oligonucleotides (in which the CpG dinucleotide is unmethylated) induce a predominantly Th1 response. Such oligonucleotides are well known and are described, for example, in WO 96/02555, WO 99/33488 and U.S. Pat. Nos. 6,008,200 and 5,856,462.

Such oligonucleotide adjuvants may be deoxynucleotides. In certain embodiments, the nucleotide backbone in the oligonucleotide is phosphorodithioate, or a phosphorothioate bond, although phosphodiester and other nucleotide backbones such as PNA including oligonucleotides with mixed backbone linkages may also be used. Methods for producing phosphorothioate oligonucleotides or phosphorodithioate are described in U.S. Pat. No. 5,666,153, U.S. Pat. No. 5,278,302 and WO95/26204.

Exemplary oligonucleotides have the following sequences. The sequences may contain phosphorothioate modified nucleotide backbones.

```
OLIGO 1:
                                         (SEQ ID NO: 1)
TCC ATG ACG TTC CTG ACG TT (CpG 1826)

OLIGO 2:
                                         (SEQ ID NO: 2)
TCT CCC AGC GTG CGC CAT (CpG 1758)

OLIGO 3:
                                         (SEQ ID NO: 3)
ACC GAT GAC GTC GCC GGT GAC GGC ACC ACG

OLIGO 4:
                                         (SEQ ID NO: 4)
TCG TCG TTT TGT CGT TTT GTC GTT (CpG 2006)

OLIGO 5:
                                         (SEQ ID NO: 5)
TCC ATG ACG TTC CTG ATG CT (CpG 1668)
```

Alternative CpG oligonucleotides include the above sequences with inconsequential deletions or additions thereto. The CpG oligonucleotides as adjuvants may be synthesized by any method known in the art (e.g., EP 468520). For example, such oligonucleotides may be synthesized utilizing an automated synthesizer. Such oligonucleotide adjuvants may be between 10-50 bases in length. Another adjuvant system involves the combination of a CpG-containing oligonucleotide and a saponin derivative particularly the combination of CpG and QS21 is disclosed in WO 00/09159.

Many single or multiphase emulsion systems have been described. One of skill in the art may readily adapt such emulsion systems for use with chimeric VLPs so that the emulsion does not disrupt the chimeric VLP's structure. Oil in water emulsion adjuvants per se have been suggested to be useful as adjuvant compositions (EPO 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B).

The oil emulsion adjuvants for use with the chimeric VLP vaccines described herein may be natural or synthetic, and may be mineral or organic. Examples of mineral and organic oils will be readily apparent to the man skilled in the art.

In order for any oil in water composition to be suitable for human administration, the oil phase of the emulsion system may include a metabolizable oil. The meaning of the term metabolizable oil is well known in the art. Metabolizable can be defined as "being capable of being transformed by metabolism" (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and may be used with the chimeric VLPs. Squalene is a metabolizable oil virtue of the fact that it is an intermediate in the biosynthesis of cholesterol (Merck index, 10th Edition, entry no. 8619).

Exemplary oil emulsions are oil in water emulsions, and in particular squalene in water emulsions.

In addition, the oil emulsion adjuvants for use with the chimeric VLPs may include an antioxidant, such as the oil α-tocopherol (vitamin E, EP 0 382 271 B1).

WO 95/17210 and WO 99/11241 disclose emulsion adjuvants based on squalene, α-tocopherol, and TWEEN 80™, optionally formulated with the immunostimulants QS21 and/or 3D-MPL. WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilize the emulsion (WO 98/56414).

The size of the oil droplets found within the stable oil in water emulsion may be less than 1 micron, may be in the range of substantially 30-600 nm, substantially around 30-500 nm in diameter, or substantially 150-500 nm in diameter, and in particular about 150 nm in diameter as measured by photon correlation spectroscopy. In this regard, 80% of the oil droplets by number may be within these ranges, more than 90% or more than 95% of the oil droplets by number are within the defined size ranges. The amounts of the components present in oil emulsions are conventionally in the range of from 2 to 10% oil, such as squalene; and when present, from 2 to 10% alpha tocopherol; and from 0.3 to 3% surfactant, such as polyoxyethylene sorbitan monooleate. The ratio of oil:alpha tocopherol may be equal or less than 1 as this provides a more stable emulsion. SPAN 85™ may also be present at a level of about 1%. In some cases it may be advantageous that the chimeric VLP vaccines disclosed herein will further contain a stabilizer.

The method of producing oil in water emulsions is well known to the man skilled in the art. Commonly, the method includes the step of mixing the oil phase with a surfactant such as a PBS/TWEEN80® solution, followed by homogenization using a homogenizer, it would be clear to a man skilled in the art that a method comprising passing the mixture twice through a syringe needle would be suitable for homogenizing small volumes of liquid. Equally, the emulsification process in microfluidizer (M110S microfluidics machine, maximum of 50 passes, for a period of 2 minutes at maximum pressure input of 6 bar (output pressure of about 850 bar)) could be adapted by the man skilled in the art to produce smaller or larger volumes of emulsion. This adaptation could be achieved by routine experimentation comprising the measurement of the resultant emulsion until a preparation was achieved with oil droplets of the required diameter.

The chimeric VLP vaccine preparations disclosed herein may be used to protect or treat a mammal or bird susceptible to, or suffering from a viral infection, by means of administering the vaccine by intranasal, intramuscular, intraperitoneal, intradermal, transdermal, intravenous, or subcutaneous administration. Methods of systemic administration of the vaccine preparations may include conventional syringes and needles, or devices designed for ballistic delivery of solid vaccines (WO 99/27961), or needleless pressure liquid jet device (U.S. Pat. No. 4,596,556; U.S. Pat. No. 5,993,412), or transdermal patches (WO 97/48440; WO 98/28037). The chimeric VLP vaccines may also be applied to the skin (transdermal or transcutaneous delivery WO 98/20734; WO 98/28037). The chimeric VLP vaccines disclosed herein therefore includes a delivery device for systemic administration, pre-filled with the chimeric VLP vaccine or adjuvant compositions. Accordingly there is provided a method for inducing an immune response in an individual such as a mammal or bird, comprising the administration of a vaccine comprising any of the chimeric VLP compositions described herein and optionally including an adjuvant and/or a carrier, to the individual, wherein the vaccine is administered via the parenteral or systemic route.

The vaccine preparations of the chimeric VLPs may be used to protect or treat a mammal or bird susceptible to, or suffering from a viral infection, by means of administering the vaccine via a mucosal route, such as the oral/alimentary or nasal route. Alternative mucosal routes are intravaginal and intra-rectal. The mucosal route of administration may be via the nasal route, termed intranasal vaccination. Methods of intranasal vaccination are well known in the art, including the administration of a droplet, spray, or dry powdered form of the vaccine into the nasopharynx of the individual to be immunized. Nebulized or aerosolized vaccine formulations are potential forms of the chimeric VLP vaccines disclosed herein. Enteric formulations such as gastro resistant capsules and granules for oral administration, suppositories for rectal or vaginal administration are also formulations of the chimeric VLP vaccines disclosed herein.

The exemplary chimeric VLP vaccine compositions disclosed herein, represent a class of mucosal vaccines suitable for application in humans to replace systemic vaccination by mucosal vaccination.

The chimeric VLP vaccines may also be administered via the oral route. In such cases the pharmaceutically acceptable excipient may also include alkaline buffers, or enteric capsules or microgranules. The chimeric VLP vaccines may also be administered by the vaginal route. In such cases, the pharmaceutically acceptable excipients may also include emulsifiers, polymers such as CARBOPOL®, and other known stabilizers of vaginal creams and suppositories. The chimeric VLP vaccines may also be administered by the rectal route. In such cases the excipients may also include waxes and polymers known in the art for forming rectal suppositories.

Alternatively the chimeric VLP vaccines formulations may be combined with vaccine vehicles composed of chitosan (as described above) or other polycationic polymers, polylactide and polylactide-coglycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM.

Additional illustrative adjuvants for use in the pharmaceutical and vaccine compositions using the chimeric VLPs as described herein include SAF (Chiron, Calif., United States), MF-59 (Chiron, see, e.g., Granoff et al. (1997) Infect Immun. 65 (5):1710-1715), the SBAS series of adjuvants (e.g., SB-AS2 (SmithKline Beecham adjuvant system #2; an oil-in-water emulsion containing MPL and QS21); SBAS-4 (SmithKline Beecham adjuvant system #4; contains alum and MPL), available from SmithKline Beecham, Rixensart, Belgium), Detox (Enhanzyn®) (GlaxoSmithKline), RC-512, RC-522, RC-527, RC-529, RC-544, and RC-560 (GlaxoSmithKline) and other aminoalkyl glucosaminide 4-phosphates (AGPs), such as those described in pending U.S. patent application Ser. Nos. 08/853,826 and 09/074,720.

Other examples of adjuvants include, but are not limited to, Hunter's TiterMax® adjuvants (CytRx Corp., Norcross, Ga.); Gerbu adjuvants (Gerbu Biotechnik GmbH, Gaiberg, Germany); nitrocellulose (Nilsson and Larsson (1992) Res. Immunol. 143:553-557); alum (e.g., aluminum hydroxide, aluminum phosphate) emulsion based formulations including mineral oil, non-mineral oil, water-in-oil or oil-in-water emulsions, such as the Seppic ISA series of Montamide adjuvants (e.g., ISA-51, ISA-57, ISA-720, ISA-151, etc.; Seppic, Paris, France); and PROVAX® (IDEC Pharmaceuticals); OM-174 (a glucosamine disaccharide related to lipid A); *Leishmania* elongation factor; non-ionic block copolymers that form micelles such as CRL 1005; and Syntex Adjuvant Formulation. See, e.g., O'Hagan et al. (2001) Biomol Eng. 18(3):69-85; and "Vaccine Adjuvants: Preparation Methods and Research Protocols" D. O'Hagan, ed. (2000) Humana Press.

Other exemplary adjuvants include adjuvant molecules of the general formula $$HO(CH_2CH_2O)_n\text{-}A\text{-}R, \qquad (I)$$

wherein, n is 1-50, A is a bond or —C(O)—, R is $C_{1-50}$ alkyl or Phenyl $C_{1-50}$ alkyl.

One embodiment consists of a vaccine formulation comprising a polyoxyethylene ether of general formula (I), wherein n is between 1 and 50, 4-24, or 9; the R component is $C_{1-50}$, $C_4$-$C_{20}$ alkyl, or $C_{12}$ alkyl, and A is a bond. The concentration of the polyoxyethylene ethers should be in the range 0.1-20%, from 0.1-10%, or in the range 0.1-1%. Exemplary polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12$^{th}$ edition: entry 7717). These adjuvant molecules are described in WO 99/52549.

The polyoxyethylene ether according to the general formula (I) above may, if desired, be combined with another adjuvant. For example, an adjuvant combination may include the CpG as described above.

Further examples of suitable pharmaceutically acceptable excipients for use with the chimeric VLP vaccines disclosed herein include water, phosphate buffered saline, isotonic buffer solutions.

The disclosed compositions and methods will be better understood by reference to the following non-limiting Examples. As described herein, the invention includes chimeric VLPs which optionally comprise an additional VLP-associated polypeptide linked to an antigen or adjuvant. The following Examples describe a representative embodiment of the invention which includes chimeric VLPs.

Example 1

Attempted Pseudotyped MLV gag+RSV F VLPs

This example demonstrates that mammalian cell expression of a truncated version of the RSV fusion (F) glycoprotein lacking the cytoplasmic tail region or hybrid F proteins containing transmembrane and cytoplasmic tail regions derived from influenza hemagglutinin results in the formation of enveloped virus-like particles (VLPs) containing RSV F.

This example was designed such that the RSV F glycoprotein was expressed in mammalian cells with and without co-expression of the murine leukemia virus Gag gene product. The expectation was that the RSV F would be incorporated into enveloped Gag VLPs budding from the cells.

Figure 16:
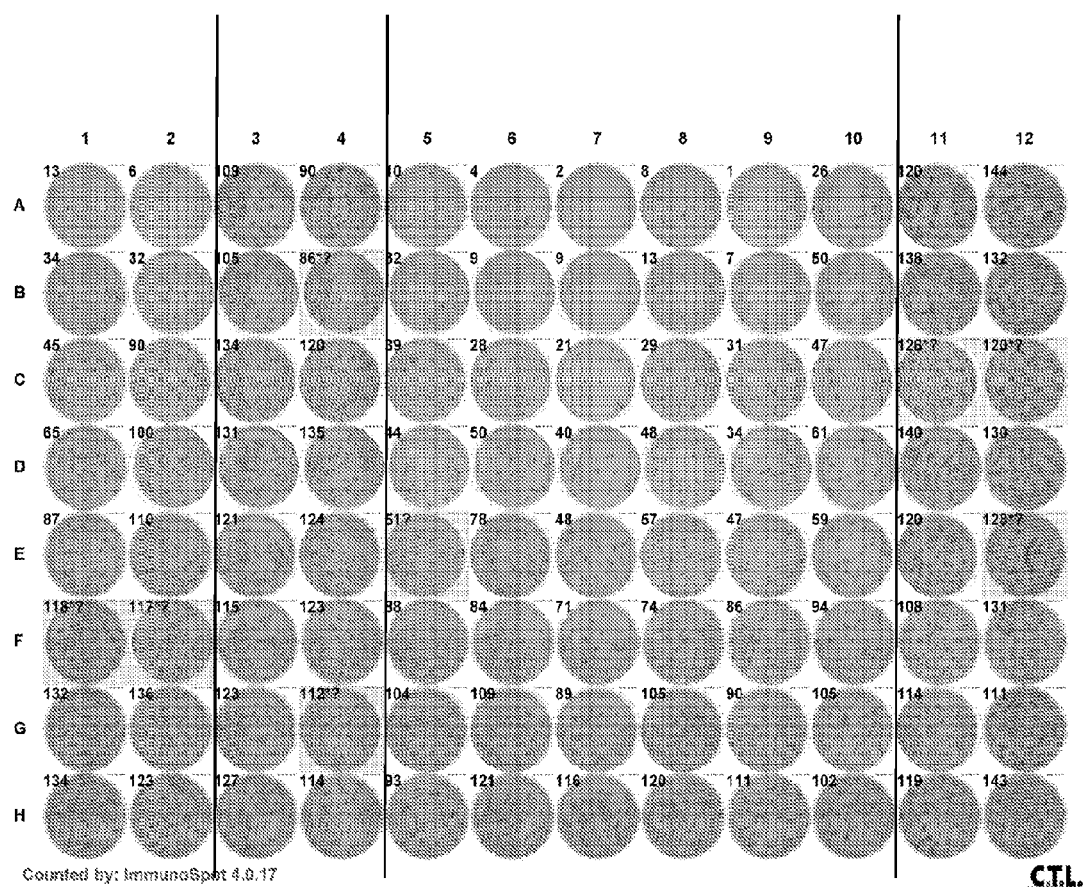
Figure 17:
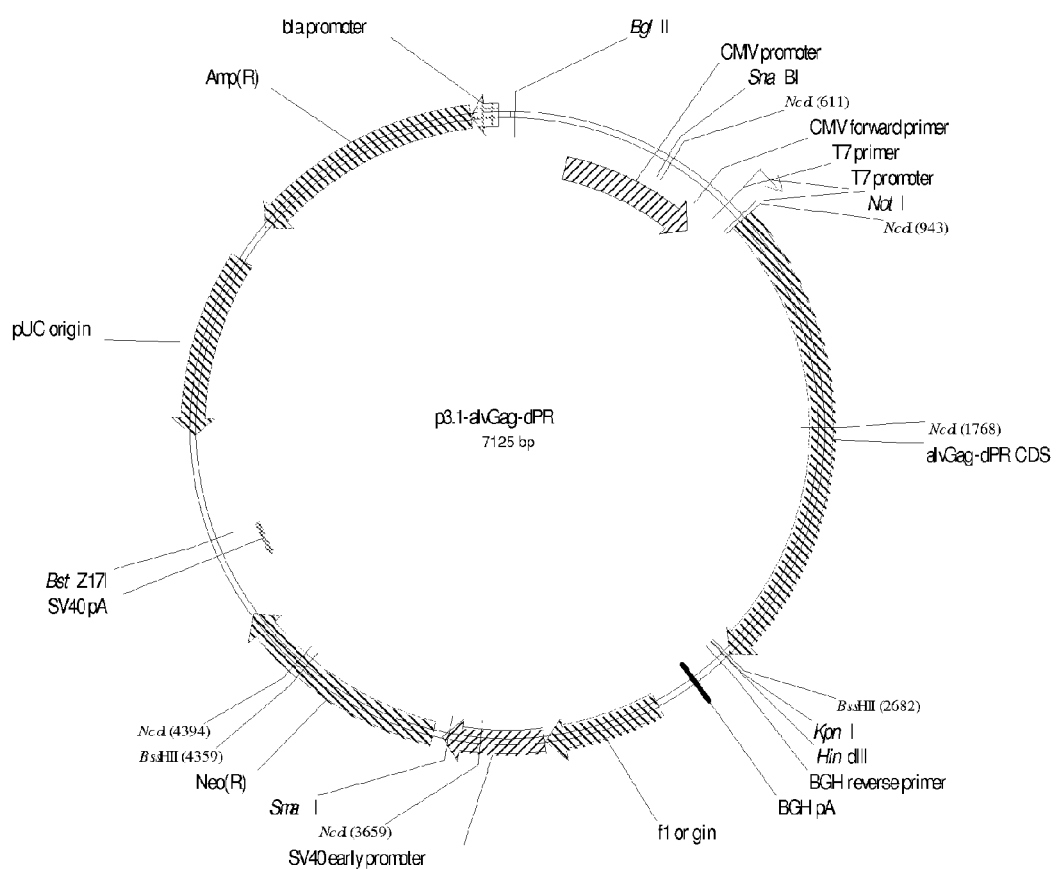

Plasmid p3.1-RSVFT encoded a truncated version of F (RSVFT) devoid of its cytoplasmic tail but containing the native transmembrane domain. A map of p3.1-RSVFT is shown in FIG. 16 and the coding sequence for RSVFT as follows:

(SEQ ID NO: 6)
atggaactgctgatcctgaaggctaacgctatcaccaccatcctgaccgc tgtcaccttctgcttcgcctccggccagaacatcaccgaggaattctacc agtccacctgctccgctgtctccaagggttacctgtccgctctgcgcacc ggctggtacacctccgtcatcaccatcgagctgtccaacatcaaggaaaa caagtgcaacggcaccgacgctaaggtcaagctgatcaagcaggaactgg acaagtacaagaacgctgtcaccgagctgcagctgctgatgcagtccacc cccgctaccaacaaccgcgctcgccgtgagctgccccgcttcatgaacta caccctgaacaacgccaagaaaaccaacgtcaccctgtccaagaagcgca agcgccgcttcctgggtttcctgctgggtgtcggttccgctatcgcttcc ggtgtcgctgtctctaaggtcctgcacctggaaggcgaggtcaacaagat caagtccgccctgctgtccaccaacaaggctgtcgtgtccctgtccaacg gtgtctccgtcctgacctccaaggtgctggacctgaagaactacatcgac aagcagctgctgcccatcgtcaacaagcagtcctgctccatctccaacat cgagactgtcatcgagttccagcagaagaacaaccgcctgctggaaatca cccgcgagttctccgtcaacgctggtgtcaccaccccctgtctccacctac atgctgaccaactccgagctgctgtccctgatcaacgacatgcccatcac caacgaccaaaagaaactgatgtccaacaacgtccagatcgtccgccagc agtcctactctatcatgagcatcatcaaggaagaggtcctggcttacgtc gtccagctgcccctgtacggtgtcatcgacaccccctgctggaagctgca cacctcccccctgtgcaccaccaacaccaaggaaggttccaacatctgcc tgacccgcaccgaccgcggctggttctgcgacaacgctggctctgtctcc ttcttcccccaagctgagacttgcaaggtccagtccaaccgcgtgttctg cgacaccatgaactccctgaccctgccctccgaggtcaacctgtgcaacg tcgacatcttcaaccccaagtacgactgcaagatcatgacctctaagacc gacgtgtcctcctctgtcatcacctccctgggtgctatcgtgtcctgcta cggcaagaccaagtgcaccgcttccaacaagaaccgcggtatcatcaaga ccttctccaacggttgcgactacgtgtccaacaagggcgtcgacaccgtg tccgtcggcaacaccctgtactacgtgaacaagcaggaaggcaagtccct gtacgtcaagggcgagcccatcatcaacttctacgacccccctggtgttcc cctccgacgagttcgacgcttccatcagccaggtcaacgagaagatcaac cagtccctggctttcatccgcaagtccgacgagctgctgcacaacgtgaa cgctggcaagtctaccaccaacatcatgatcaccactatcatcatcgtga tcatcgtcatcctgctgtctctgatcgctgtcggtctgctgctgtactaa The RSVFT coding sequence was synthesized as a custom synthetic DNA fragment and was not cloned from virus since the natural RSV F gene is from a paramyxovirus which replicates in the cytoplasm of cells and would therefore not be expected to be appropriately expression in the nucleus of a cell. The encoded amino acid sequence of RSVFT is as follows (with the signal peptide and transmembrane domains in capital letters):

(SEQ ID NO: 7)
MELLILKANAITTILTAVTFCfasgqniteefyqstcsavskgylsalrt gwytsvitielsnikenkcngtdakvklikqeldkyknavtelqllmqst patnnrarrelprfmnytlnnakktnvtlskkrkrrflgfllgvgsaias gvavskvlhlegevnkiksallstnkavvslsngvsvltskvldlknyid kqllpivnkqscsisnietviefqqknnrlleitrefsvnagvttpvsty mltnsellslindmpitndqkklmsnnvqivrqqsysimsiikeevlayv vqlplygvidtpcwklhtsplcttntkegsnicltrtdrgwfcdnagsvs ffpqaetckvqsnrvfcdtmnsltlpsevnlcnvdifnpkydckimtskt dvsssvitslgaivscygktkctasnknrgiiktfsngcdyvsnkgvdtv svgntlyyvnkqegkslyvkgepiinfydplvfpsdefdasisqvnekin qslafirksdellhnvnagksttnIMITTIIIVIIVILLSLIAVGLLLY Plasmid p3.1-shFv1 encoded a hybrid protein consisting of the ectodomain of RSV F fused to the transmembrane domain and cytoplasmic tail of an H5 hemagglutinin from influenza A. FIG. 1 shows a map of p3.1-shFv1 and the coding sequence for shFv1 is as follows:

(SEQ ID NO: 8)
atggaactgctgatcctgaaggctaacgctatcaccaccatcctgaccgc tgtgaccttctgcttcgcttccggccagaacatcaccgaggaattctacc agtccacctgctccgctgtgtccaagggttacctgtccgctctgcgtacc ggttggtacacctccgtgatcaccatcgagctgtccaacatcaaagagaa caagtgcaacggcaccgacgctaaggtcaagctgatcaagcaggaactgg acaagtacaagaacgctgtgaccgagctgcagctgctgatgcagtccacc cccgctaccaacaaccgtgctcgtcgtgagctgccccgtttcatgaacta caccctgaacaacgccaagaaaaccaacgtcaccctgtccaagaagcgta agcgtcgtttcctgggtttcctgctgggtgtgggtagcgctatcgcctcc ggtgtcgctgtctccaaggtgctgcacctcgagggcgaggtgaacaagat caagtccgccctgctgtccaccaacaaggctgtggtgtccctgtccaacg gtgtctccgttctgaccagcaaggtcttggacctgaagaactacatcgac aagcagctgctgcccatcgtgaacaagcagtcctgctccatctccaacat cgagactgtgatcgagttccagcagaagaacaaccgtctgctcgagatca cccgtgagttctccgtgaacgctggtgtcaccaccccgtgtccacctac atgctgaccaactccgagctgctgtccctgatcaacgacatgcccatcac caacgaccagaaaagctgatgtccaacaacgtgcagatcgtgcgtcagc agtcctactctatcatgagcatcatcaaagaggaagtcctggcttacgtg gtgcagctgcccctgtacggtgtcatcgacacccctgctggaagctgca cacctcccccctgtgcaccaccaacaccaaagagggttccaacatctgcc tgacccgtaccgatcgtggttggttctgtgacaacgctggttccgtgtcc ttcttcccccaagctgagacttgcaaggtgcagtccaaccgtgtgttctg

```
cgacaccatgaactccctgaccctgccctccgaggtgaacctgtgcaacg tggacatcttcaaccccaagtacgactgcaagatcatgacctctaagacc gacgtgtcctcctccgtcatcacctccctgggtgctatcgtgtcctgcta cggcaagaccaagtgcaccgcttccaacaagaaccgcggtatcatcaaga ccttctccaacggttgcgactacgtgtccaacaagggtgtcgataccgtg tccgtcggtaacaccctgtactacgtcaacaagcaggaaggcaagtctct gtacgtgaagggcgagcccatcatcaacttctacgacccctggtgttcc cctccgacgagttcgacgcttccatcagccaggtcaacgagaagatcaac cagtccctggctttcatccgtaagtccgacgagctgctgcacaacgtcaa cgctggcaagtccaccaccaacatcctgtccatctactccaccgtggctt cctccctggctctggctatcatgatggctggtctgtccctgtggatgtgc tccaacggctccctgcagtgccgtatctgcatctaataa
```

The amino acid sequence of shFv1 is as follows (with the signal peptide coding sequence and the HA transmembrane and cytoplasmic tail sequences shown in capital letters):

(SEQ ID NO: 9)
MELLILKANAITTILTAVTFcfasgqniteefyqstcsavskgylsalrt
gwytsvitielsnikenkcngtdakvklikqeldkyknavtelqllmqst
patnnrarrelprfmnytlnnakktnvtlskkrkrrflgfllgvgsaias
gvavskvlhlegevnkiksallstnkavvslsngvsvltskvldlknyid
kqllpivnkqscsisnietviefqqknnrlleitrefsvnagvttpvsty
mltnsellslindmpitndqkklmsnnvqivrqqsysimsiikeevlayv
vqlplygvidtpcwklhtsplcttntkegsnicltrtdrgwfcdnagsvs
ffpqaetckvqsnrvfcdtmnsltlpsevnlcnvdifnpkydckimtskt
dvsssvitslgaivscygktkctasnknrgiiiktfsngcdyvsnkgvdtv
svgntlyyvnkqegkslyvkgepiinfydplvfpsdefdasisqvnekin
gslafirksdellhnvnagksttnILSIYSTVASSLALAIMMAGLSLWMC
SNGSLQCRICI As with RSVFT, the shFv1 coding sequence was generated by DNA synthesis.

Figure 2:
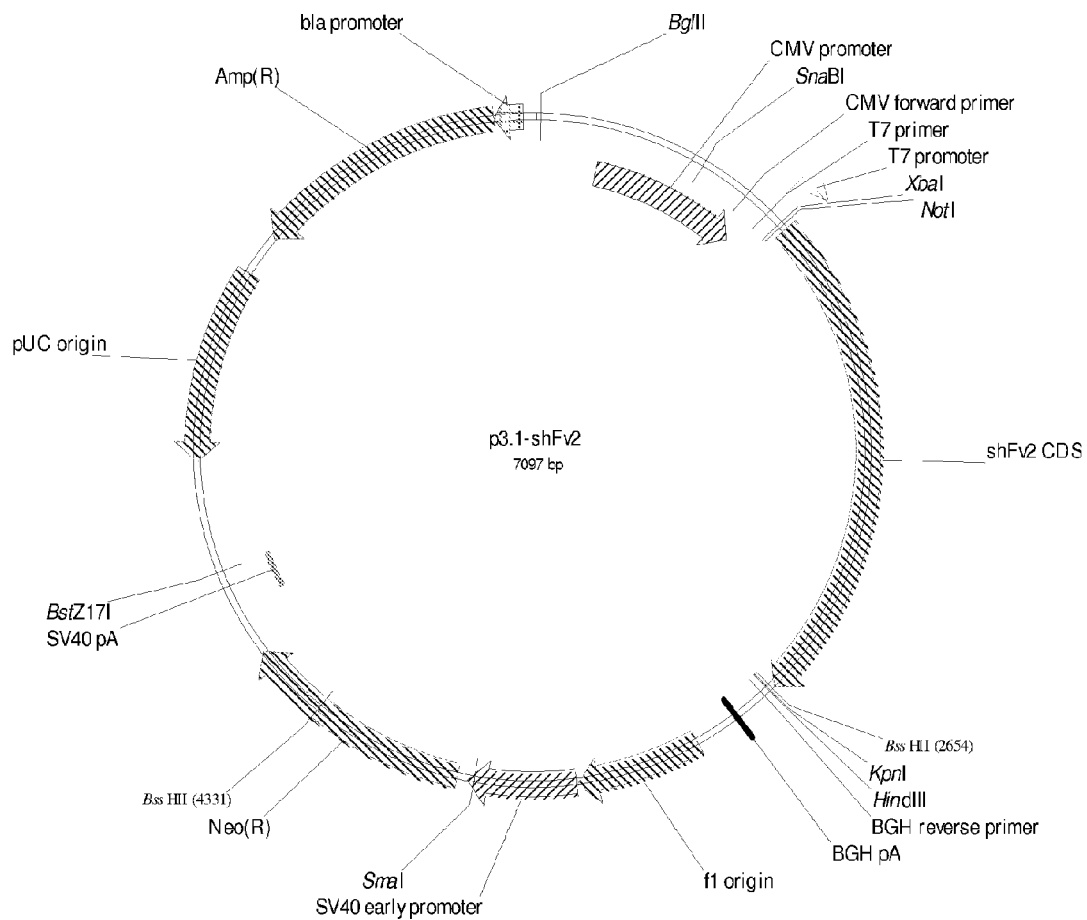
FIG. 2 shows the plasmid map of p3.1-shFv2.

Plasmid p3.1-shFv2 encoded a hybrid protein consisting of the ectodomain of RSV F fused to the transmembrane domain and cytoplasmic tail of an H5 hemagglutinin from influenza A. shFv2 differed from shFv1 in that the influenza HA-derived transmembrane and tail region is four amino acids longer. FIG. 2 shows a plasmid map of p3.1-shFv2. The coding sequence for shFv2 is as follows:

(SEQ ID NO: 10)
atggaactgctgatcctgaaggctaacgctatcaccaccatcctgaccgc tgtgaccttctgcttcgcttccggccagaacatcaccgaggaattctacc agtccacctgctccgctgtgtccaaggggtacctgtccgctctgcgtacc ggttggtacacctccgtgatcaccatcgagctgtccaacatcaaagagaa caagtgcaacggcaccgacgctaaggtcaagctgatcaagcaggaactgg acaagtacaagaacgctgtgaccgagctgcagctgctgatgcagtccacc cccgctaccaacaaccgtgctcgtcgtgagctgccccgtttcatgaacta caccctgaacaacgccaagaaaaccaacgtcaccctgtccaagaagcgta agcgtcgtttcctgggtttcctgctgggtgtgggtagcgctatcgcctcc ggtgtcgctgtctccaaggtgctgcacctcgagggcgaggtgaacaagat caagtccgccctgctgtccaccaacaaggctgtggtgtccctgtccaacg gtgtctccgttctgaccagcaaggtcttggacctgaagaactacatcgac aagcagctgctgcccatcgtgaacaagcagtcctgctccatctccaacat cgagactgtgatcgagttccagcagaagaacaaccgtctgctcgagatca cccgtgagttctccgtgaacgctggtgtcaccacccccgtgtccacctac atgctgaccaactccgagctgctgtccctgatcaacgacatgcccatcac caacgaccagaaaaagctgatgtccaacaacgtgcagatcgtgcgtcagc agtcctactctatcatgagcatcatcaaagaggaagtcctggcttacgtg gtgcagctgcccctgtacggtgtcatcgacacccctgctggaagctgca cacctcccccctgtgcaccaccaacaccaaagagggttccaacatctgcc tgacccgtaccgatcgtggttggttctgtgacaacgctggttccgtgtcc ttcttcccccaagctgagacttgcaaggtgcagtccaaccgtgtgttctg cgacaccatgaactccctgaccctgccctccgaggtgaacctgtgcaacg tggacatcttcaaccccaagtacgactgcaagatcatgacctctaagacc gacgtgtcctcctccgtcatcacctccctgggtgctatcgtgtcctgcta cggcaagaccaagtgcaccgcttccaacaagaaccgcggtatcatcaaga ccttctccaacggttgcgactacgtgtccaacaagggtgtcgataccgtg tccgtcggtaacaccctgtactacgtcaacaagcaggaaggcaagtctct gtacgtgaagggcgagcccatcatcaacttctacgacccctggtgttcc cctccgacgagttcgacgcttccatcagccaggtcaacgagaagatcaac cagtccctggctttcatccgtaagtccgacgagctgctgcacaacgtcaa cgctggcaagtccaccaccaacggcacctaccagatcctgtccatctact ccaccgtggcttcctccctggctctggctatcatgatggctggtctgtcc ctgtggatgtgctccaacggctccctgcagtgccgtatctgcatctaata
a
```

The amino acid sequence of shFv2 is as follows (with the signal peptide coding sequence and the HA transmembrane and cytoplasmic tail sequences shown in capital letters):

(SEQ ID NO: 11)
MELLILKANAITTILTAVTFcfasgqniteefyqstcsavskgylsalrt
gwytsvitielsnikenkcngtdakvklikqeldkyknavtelqllmqst
patnnrarrelprfmnytlnnakktnvtlskkrkrrflgfllgvgsaias
gvavskvlhlegevnkiksallstnkavvslsngvsvltskvldlknyid
kqllpivnkqscsisnietviefqqknnrlleitrefsvnagvttpvsty
mltnsellslindmpitndqkklmsnnvqivrqqsysimsiikeevlayv vqlplygvidtpcwklhtsplcttntkegsnicltrtdrgwfcdnagsys ffpqaetckvqsnrvfcdtmnsltlpsevnlcnvdifnpkydckimtskt dvsssvitslgaivscygktkctasnknrgiiktfsngcdyvsnkgvdtv svgntlyyvnkqegkslyvkgepiinfydplvfpsdefdasisqvnekin qslafirksdellhnvnagksttnGTYQILSIYSTVASSLALAIMMAGLS

LWMCSNGSLQCRICI

The shFv2 coding sequence was generated by DNA synthesis.

Figure 3:
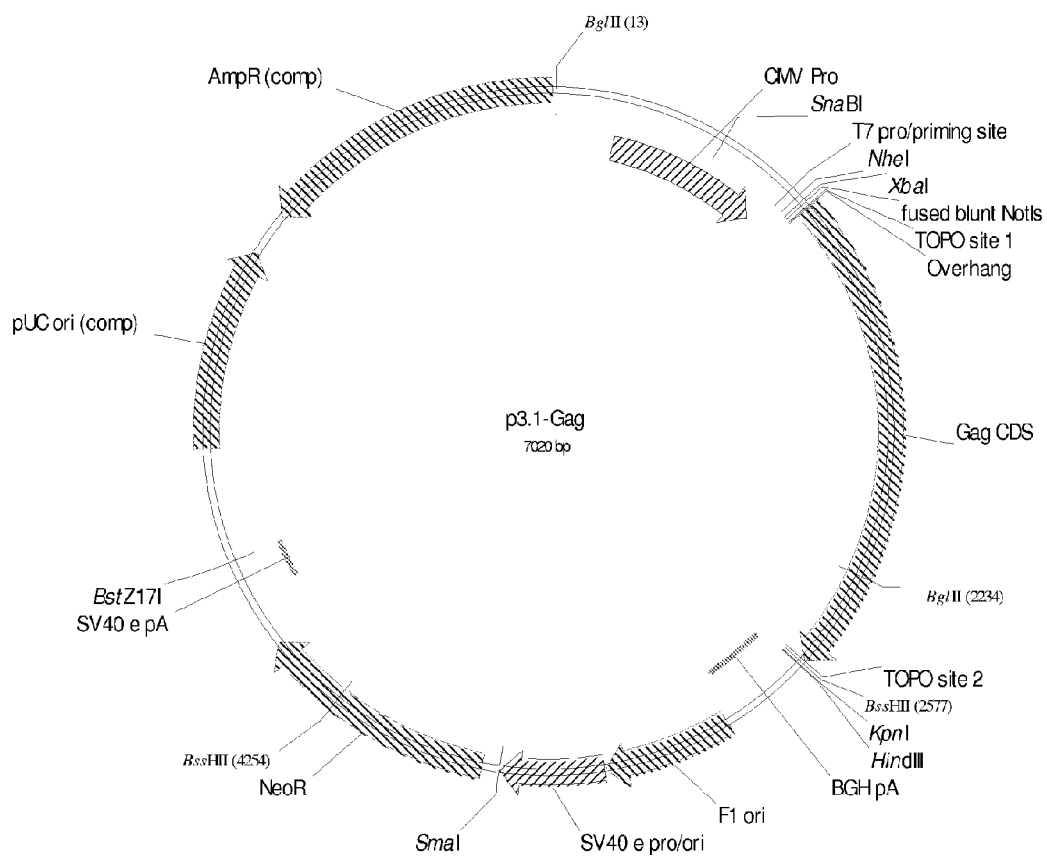
FIG. 3 shows the plasmid map for p3.1-Gag.

Plasmid p3.1-Gag encoded the Gag gene product from murine leukemia virus. FIG. 3 shows a plasmid map of p3.1 Gag. The coding sequence for Gag from plasmid p3.1-Gag is as follows:

(SEQ ID NO: 12)
atgggccagactgttaccactcccttaagtttgaccttaggtcactggaa agatgtcgagcggatcgctcacaaccagtcggtagatgtcaagaagagac gttgggttaccttctgctctgcagaatggccaacctttaacgtcggatgg ccgcgagacggcacctttaaccgagacctcatcacccaggttaagatcaa ggtcttttcacctggcccgcatggacacccagaccaggtcccctacatcg tgacctgggaagccttggcttttgaccccctccctgggtcaagcccttt gtacaccctaagcctccgcctcctcttcctccatccgcccgtctctccc ccttgaacctcctcgttcgacccgcctcgatcctcccttatccagccc tcactccttctctaggcgccaaacctaaacctcaagttctttctgacagt ggggggccgctcatcgacctacttacagaagacccccgccttataggga cccaagaccaccccttccgacagggacggaaatggtggagaagcgaccc ctgcgggagaggcaccggacccctcccaatggcatctcgcctacgtggg agacgggagcccctgtggccgactccactacctcgcaggcattcccct ccgcgcaggaggaaacggacagcttcaatactggccgttctcctcttctg acctttacaactggaaaaataataaccottctttttctgaagatccaggt aaactgacagctctgatcgagtctgttctcatcacccatcagcccacctg ggacgactgtcagcagctgttggggactctgctgaccggagaagaaaaac aacgggtgctcttagaggctagaaaggcggtgcggggcgatgatgggcgc cccactcaactgcccaatgaagtcgatgccgcttttcccctcgagcgcc agactgggattacaccacccaggcaggtaggaaccacctagtccactatc gccagttgctcctagcgggtctccaaaacgcgggcagaagcccaccaat ttggccaaggtaaaggaataacacaagggcccaatgagtctccctcggc cttcctagagagacttaaggaagcctatcgcaggtacactccttatgacc ctgaggacccaggggcaagaaactaatgtgtctatgtctttcatttggcag tctgccccagacattgggagaaagttagagaggttagaagatttaaaaaa caagacgcttggagatttggttagagaggcagaaaagatctttaataaac gagaaccccggaagaaagaggaacgtatcaggagagaaacagaggaa aaagaagaacgccgtaggacagaggatgagcagaaagagaaagaagaga tcgtaggagacatagagagatgagcaagctattggccactgtcgttagtg gacagaaacaggatagacagggaggagaacgaaggaggtcccaactcgat cgcgaccagtgtgcctactgcaaagaaaaggggcactgggctaaagattg tcccaagaaaccacgaggacctcggggaccaagaccccagacctccctcc tgaccctagatgactagtag The amino acid sequence for MLV Gag is as follows:

(SEQ ID NO: 13)
Mgqtvttplsltlghwkdveriahnqsvdvkkrrwvtfcsaewptfnvgw prdgtfnrdlitqvkikvfspgphghpdqvpyivtwealafdpppwvkpf vhpkppplppsapslplepprstpprsslypaltpslgakpkpqvlsds ggplidlltedpppyrdprpppsdrdgnggeatpageapdpspmasrlrg rreppvadsttsqafplraggngqlqywpfsssdlynwknnnpsfsedpg kltaliesvlithqptwddcqqllgtlltgeekqrvllearkavrgddgr ptqlpnevdaafplerpdwdyttqagrnhlvhyrqlllaglqnagrsptn lakvkgitqgpnespsaflerlkeayrrytpydpedpgqetnvsmsfiwq sapdigrklerledlknktlgdlvreaekifnkretpeereerirretee keerrrtedeqkekerdrrrhremskllatvvsgqkqdrqggerrrsqld rdqcayckekghwakdcpkkprgprgprpqtslltldd The Gag gene represented a natural clone from the genome of MLV found in plasmid pAMS (ATCC).

Figure 4:
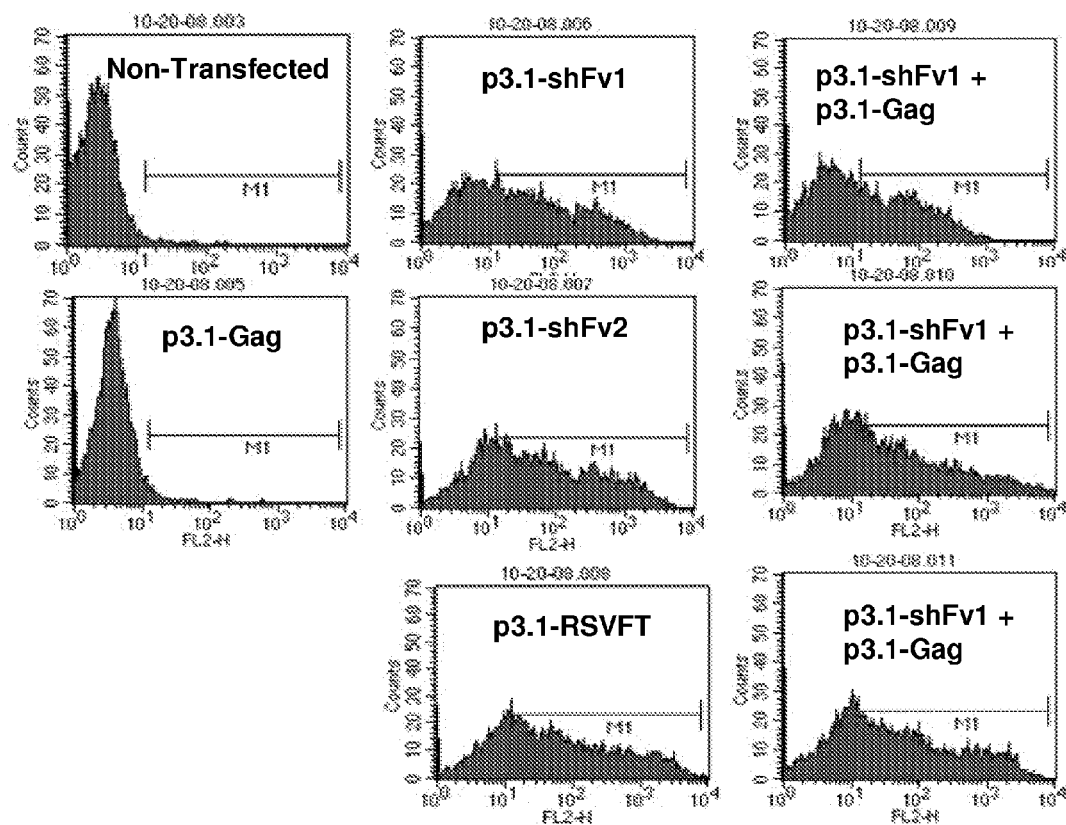
FIG. 4 shows cytometric analysis of surface expression of RSV F on cells transfected with RSV F and Gag expression vectors. Non-transfected cells and cells transfected with p3.1-Gag alone exhibit background fluorescence levels. Cells transfected with RSV F expression vectors, with and without p3.1-Gag, show significant levels of fluorescence as a result of F detection by the 9C5 monoclonal antibody and fluorescent secondary antibody.
Figure 5:
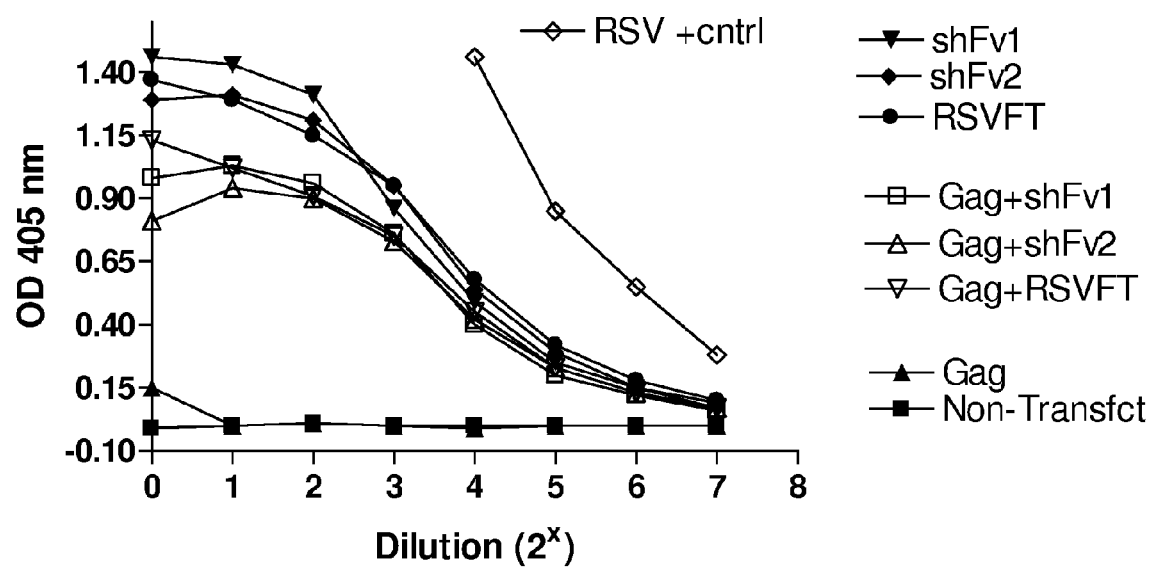
FIG. 5 shows detection of RSV F antigenic activity in the 100,000×g pellets from the medium of cells transfected with RSV F genes with and without co-transfection with a Gag gene.
Figure 6:
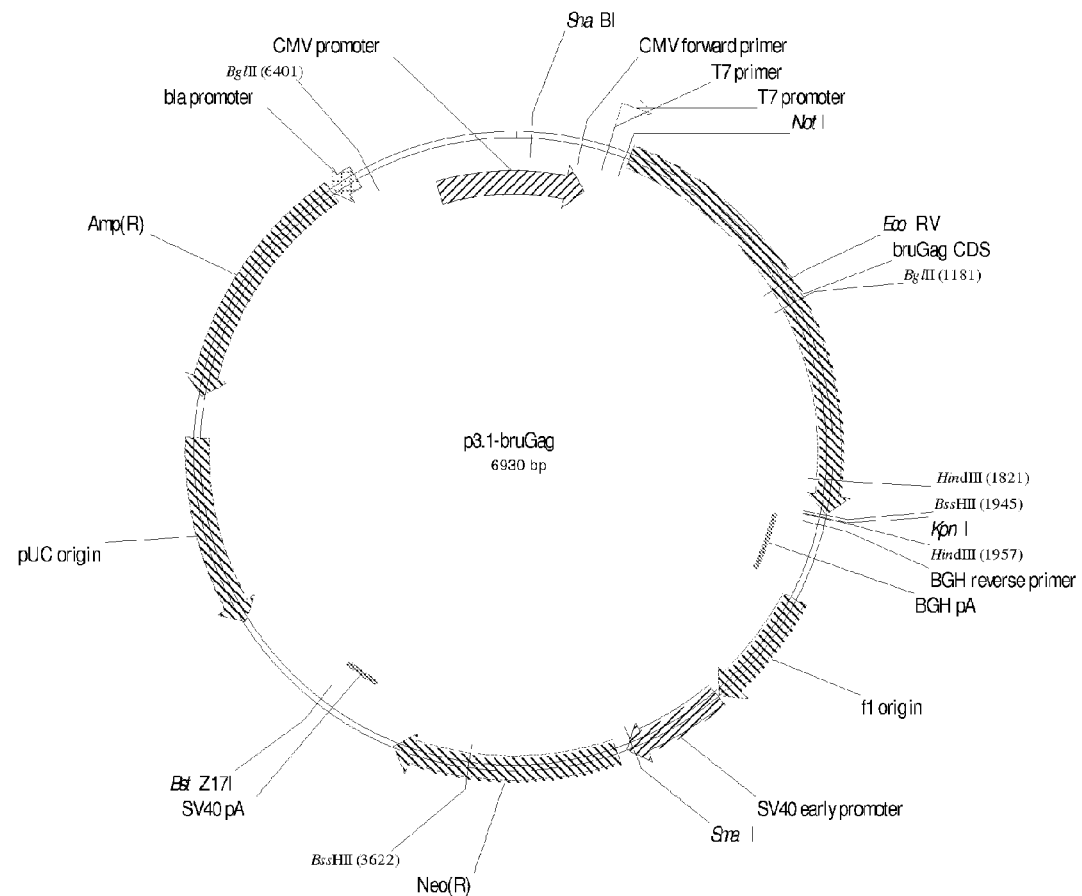
FIG. 6 shows the plasmid map of p3.1-bruGag.

Eight 10 cm² tissue culture dishes were seeded with 293-F cells cultured in Dulbecco's Modified Eagle's medium supplemented with 10% fetal bovine serum. When the cells reached approximately 95% confluence (monolayer culture), each well was transfected with a total of 4 µg of plasmid DNA as follows:
1. No DNA
2. 4 µg p3.1-Gag
3. 4 µg p3.1-RSVFT
4. 4 µg p3.1-shFv1
5. 4 µg p3.1-shFv2
6. 2 µg p3.1-RSVFT+2 µg p3.1-Gag
7. 2 µg p3.1-shFv1+2 µg p3.1-Gag
8. 2 µg p3.1-shFv2+2 µg p3.1-Gag Plasmid DNA was transfected using LIPOFECTAMINE™ 2000 (Invitrogen) according to the manufacture's recommendations. Eight hours post-transfection, the transfection medium was replaced with CD293 serum-free medium and culture was continued. At forty-eight hours post-transfection all dishes containing cells transfected with any of the RSV F expression vectors exhibited significant levels of syncytia (fused cells) consistent with surface expression of correctly folded F. At forty-eight hours post-transfection cells were detached by pipetting and cells and medium were harvested. The expression of RSV F antigenic activity on the surface of cells was further demonstrated by flow cytometry after staining cells with a mouse monoclonal antibody (9C5) that recognizes the correctly folded F antigen in its membrane integrated state. Cells were further reacted with a goat-anti-mouse secondary antibody conjugated to phycoerythrin for fluorescent detection of F-positive cells. FIG. 4 shows the histograms from the flow cytometric runs demonstrating significant levels of surface expression of F on cells transfected with any of the F expression vectors with and without the Gag vector. These data are consistent with the presence of syncytia in transfected cell populations and demonstrate the presence of correctly folded F antigen on the cell surface.

The growth medium harvested from the transfected cells was centrifuged at 2000 rpm for 5 minutes to remove syncytia and any cellular debris and the supernatant from this step was centrifuged over a 30% sucrose cushion in tris-buffered saline at 100,000×g for 1 hour to collect any VLPs that may have been released into the medium as a result of Gag and/or F gene expression. 100,000×g pellets from this step were resuspended in tris-buffered saline for additional analyses.

Resuspended pellets from the ultracentrifuge step were subjected to Western blot analysis to detect the presence of the Gag product as an indication of VLP formation. Unexpectedly, a significant amount of the Gag product was detected in the sample from cells transfected with the p3.1-Gag vector alone, but markedly reduced amounts of Gag were found in pellets from cells transfected with p3.1-Gag in combination with any of the F gene vectors. The results are consistent with expression of the F gene product interfering in some manner with the budding functions of the Gag product.

The presence of the F antigen in resuspended ultracentrifuge pellets was subsequently examined by ELISA as follows: Each resuspended ultracentrifuge pellet sample was loaded into a single well in row A of a Nunc MAXISORP™ flat bottom 96-well ELISA plate and each sample was serially diluted two-fold down each column of the plate. After coating overnight at 4° C., the plate was washed 3 times with PBS containing 0.05% TWEEN 20™ (PBS-T) and then blocked with STARTING BLOCK™ (PBS) (Pierce, Biotechnology). After blocking, 100 μl of 1:1000 diluted monoclonal antibody 9C5 in STARTING BLOCK T20™ (Pierce) was loaded into each well and the plate was incubated at room temperature for 3 hours. The plate was washed again and 100 μl of goat anti-mouse HRP conjugate antibody (Southern Biotech) diluted 1:1000 in STARTING BLOCK T20™ was added to each well and incubated at room temperature for 1.5 hours. Following a final wash (3×) with PBS-T, the plate was developed by the addition of 100 μl ABTS reagent (Pierce) and incubated at room temperature for 45 minutes.

FIG. 5 shows the results of this ELISA in which it can be observed that significant levels of RSV F antigen were detected in the 100,000×g pellets from both F gene alone and F gene+Gag gene transfections. Importantly and unexpectedly, greater amounts of RSV F antigenic activity were observed in the pellets from cells transfected with the RSV F genes alone. These data demonstrates that expression of the F gene alone, in the absence of Gag expression, results in the formation of VLPs carrying the F antigen. This is also consistent with the above observation that co-expression of F and Gag results in a suppression of Gag budding, possibly due to interference of Gag budding by F.

Example 2—Pseudotyped HIV-1 Gag+RSV F VLPs

This example demonstrates the production of HIV-1 Gag VLPs pseudotyped with the GPI-anchored version of the RSV F glycoprotein.

Materials and Methods

Plasmid p3.1-bruGag contains a synthetic sequence that encodes the HIV-Gag product from the bru strain of HIV-1. This plasmid employs the CMV immediate early promoter and is suitable for transient transfection expression studies. FIG. 6 shows the map of p3.1-bruGag. The coding sequence for the bruGag is as follows:

```
                                        (SEQ ID NO: 14)
atgggagccagagccagcgtgctgtctggcggcgagctggacagatggga
gaagatccggctgcggccaggcggcaagaagaagtacaagctgaagcaca
tcgtgtgggctagccgggagctggaaagattcgccgtgaaccccggactg
ctggaaaccagcgagggctgcagacagatcctgggccagctgcagccatc
tctgcagaccggcagcgaggaactgcggagcctgtacaacaccgtggcca
ccctgtactgcgtgcaccagcggatcgagatcaaggacaccaaagaggcc
ctggacaagatcgaggaagaacagaacaagtccaagaagaaggcccagca
ggccgctgccgataccggccacagcagccaggtgtcccagaactacccca
tcgtgcagaacatccagggccagatggtgcaccaggccatctctcccaga
accctgaacgcctgggtgaaagtggtggaggaaaaggccttcagccccga
agtgatccccatgttcagcgccctgagcgaaggcgccacccccccaggacc
tgaacaccatgctgaacaccgtgggaggacaccaggccgccatgcagatg
ctgaaagagacaatcaacgaagaggccgccgagtgggacagagtgcaccc
tgtgcacgccggacctatcgcccctggccagatgagagagcccagaggca
gcgatatcgccggcaccacaagcaccctgcaggaacagatcggctggatg
acaaacaacccccccatccccgtgggcgagatctacaagcggtggatcat
cctgggcctgaacaagatcgtgcggatgtacagccccacctccatcctgg
acatccggcagggccccaaagagcccttccgggactacgtggaccggttc
tacaagaccctgcgggccgagcaggccagccaggaagtgaagaactggat
gaccgagacactgctggtgcagaacgccaaccccgactgcaagaccatcc
tgaaggccctgggaccagccgccaccctggaagagatgatgaccgcctgt
cagggcgtgggcggacctggacacaaagccagagtgctggccgaggccat
gagccaggtgaccaacagcgccaccatcatgatgcagcggggcaacttcc
ggaaccagcggaagatcgtgaagtgcttcaactgcggcaaggaaggccac
attgcccggaactgcagagcccccagaaagaaaggctgctggaagtgcgg
gaaagaggggcaccagatgaaggactgcaccgagcggcaggccaacttcc
tcggcaaaatctggcccagctacaagggcagacccggcaacttcctgcag
agcagacccgagcctaccgcccctcccttcctgcagtccaggcctgaacc
taccgctcccccgaggaaagcttcagatccggcgtggagacaaccaccc
ctagccagaagcaggaacccatcgacaaagagctgtacccccctgaccagc
ctgagaagcctgttcggcaacgaccccagcagccagtga
```

The amino acid sequence encoded by p3.1-bruGag is as follows:

```
                                        (SEQ ID NO: 15)
mgarasvlsggeldrwekirlrpggkkkyklkhivwasrelerfavnpgl
letsegcrqilgqlqpslqtgseelrslyntvatlycvhgrieikdtkea
ldkieeeqnkskkkaqqaaadtghssqvsqnypivqniqgqmvhqaispr
tlnawvkvveekafspevipmfsalsegatpqdlntmlntvgghqaamqm
lketineeaaewdrvhpvhagpiapgqmreprgsdiagttstlqeqigwm
tnnppipvgeiykrwiilglnkivrmysptsildirqgpkepfrdyvdrf
```

-continued yktlraegasqevknwmtetllvqnanpdcktilkalgpaatleemmtac qgvggpghkarvlaeamsqvtnsatimmqrgnfrnqrkivkcfncgkegh iarncraprkkgcwkcgkeghqmkdcterqanflgkiwpsykgrpgnflq srpeptappflqsrpeptappeesfrsgvettpsqkqepidkelyplts lrslfgndpssq*

Figure 7:
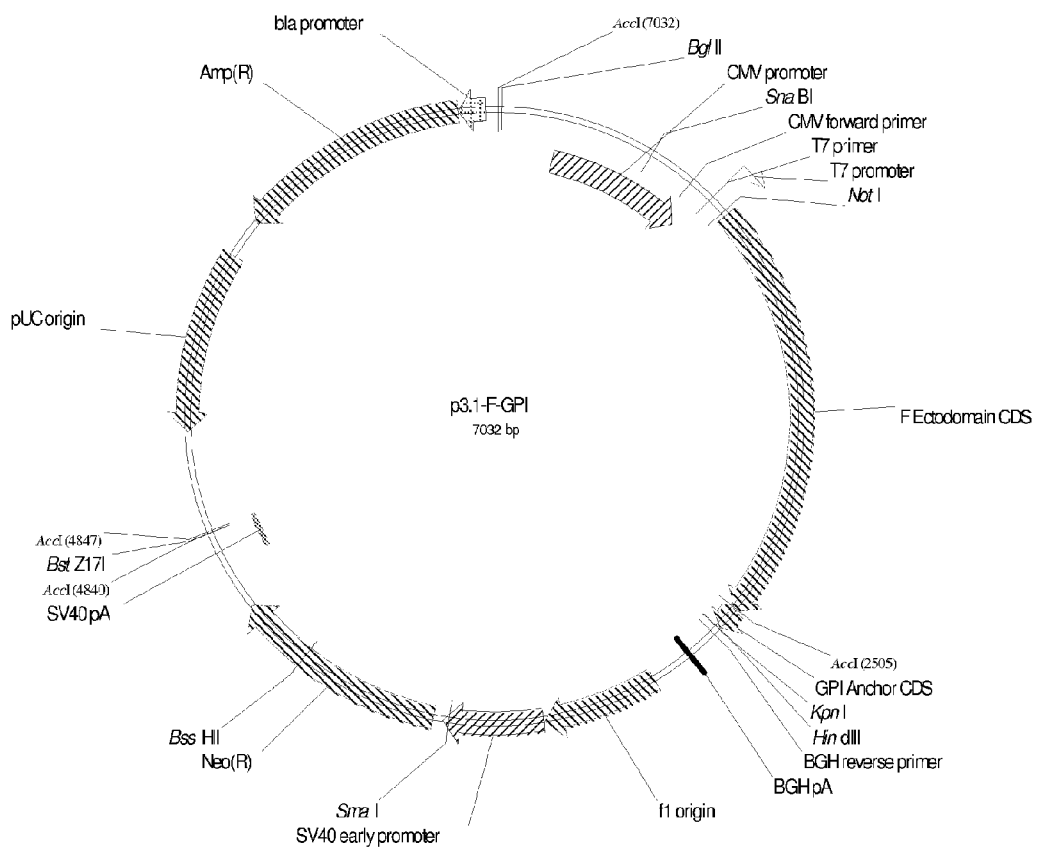
FIG. 7 shows the plasmid map of p3.1-F-GPI.

Plasmid p3.1-F-GPI contains a synthetic sequence that encodes a GPI-anchored version of the RSV F glycoprotein from RSV strain A2. This plasmid was constructed by deleting the F gene sequences encoding the transmembrane and cytoplasmic tail domains and replacing them with sequences encoding the GPI anchor signal from human carboxypeptidase M. FIG. 7 shows a map of p3.1-F-GPI. The F-GPI coding sequence is as follows:

(SEQ ID NO: 16)
atggagctgctgatcctgaaggccaacgccatcaccaccatcctgaccgc cgtgaccttctgcttcgcctccggccagaacatcaccgaggagttctacc agtccacctgctccgccgtgtccaagggctacctgtccgccctgcggacc ggctggtacacctccgtgatcaccatcgagctgtccaacatcaaagaaaa caagtgcaacggcaccgacgccaaggtgaagctgatcaagcaggagctgg acaagtacaagaacgccgtgaccgagctgcagctgctgatgcagtccacc cctgccaccaacaacgggccaggcgggagctgcctcggttcatgaacta cacctgaacaacgccaagaaaaccaacgtcaccctgtccaagaagcgga agcggcggttcctgggcttcctgctgggcgtgggctccgctatcgcctct ggcgtggccgtgtctaaggtgctgcacctggagggcgaggtgaacaagat caagtctgccctgctgtccaccaacaaggccgtggtgtccctgtccaacg gcgtgtccgtgctgacctccaaggtgctggatctgaagaactacatcgac aagcagctgctgcctatcgtgaacaagcagtcctgctccatctccaacat cgagacagtgatcgagttccagcagaagaacaaccggctgctggaaatca caagagagttctccgtcaacgctggtgtgaccactcctgtctctacttat atgctgaccaactccgagctgctgtccctgatcaacgacatgcctatcac caacgaccagaaaaagctgatgtccaacaacgtgcagatcgtgcggcagc agtcctactctatcatgagcatcatcaaggaggaggtcctggcctacgtg gtgcagctgcctctgtacggcgtgatcgacaccccttgctggaagctgca cacctccccctgtgcaccaccaacaccaaggagggctccaacatctgcc tgacccggaccgaccggggctggttctgcgacaacgccggctccgtgtcc ttctttccacaggccgagacatgcaaggtgcagtccaaccgggtgttctg cgataccatgaactccctgaccctgccttccgaggtgaacctgtgcaacg tggacatcttcaaccctaagtacgactgcaagatcatgacctctaagacc gacgtgtcctcctctgtgatcacctccctgggcgccatcgtgtcctgcta cggcaagaccaagtgcaccgcctccaacaagaacggggaatcatcaaga ccttctccaacggctgcgactacgtgtccaataagggcgtggacaccgtg tccgtgggcaacacactgtactacgtgaataagcaggagggcaagtctct gtacgtgaagggcgagcctatcatcaacttctacgaccctctggtgttcc cttccgacgagttcgacgcctccatcagccaggtgaacgagaagatcaac cagtccctggccttcatccggaagtccgacgagctgctgcacaacgtgaa cgctggcaagtctaccaccaacccgaccactccgccgccaccaagccct ccctgttcctgttcctggtgtccctgctgcacatcttcttcaagtgataa The amino acid sequence encoded by p3.1-F-GPI is as follows:

(SEQ ID NO: 17)
mellilkanaittiltavtfcfasgqniteefyqstcsavskgylsalrt gwytsvitielsnikenkcngtdakvklikqeldkyknavtelqllmqst patnnrarrelprfmnytlnnakktnvtlskkrkrrflgfllgvgsaias gvavskvlhlegevnkiksallstnkavvslsngvsvltskvldlknyid kqllpivnkqscsisnietviefqqknnrlleitrefsvnagvttpvsty mltnsellslindmpitndqkklmsnnvqivrqqsysimsiikeevlayv vqlplygvidtpcwklhtsplcttntkegsnicltrtdrgwfcdnagsvs ffpqaetckvqsnrvfcdtmnsltlpsevnlcnvdifnpkydckimtskt dvsssvitslgaivscygktkctasnknrgiiktfsngcdyvsnkgvdtv svgntlyyvnkqegkslyvkgepiinfydplvfpsdefdasisqvnekin qslafirksdellhnvnagksttnpdhsaatkpslflflvsllhiffk*

Plasmids p3.1-bruGag and p3.1-F-GPI were transfected into 293F cells either alone or in combination with one another at various ratios (1:1, 3:1, and 9:1 Gag-to-F). Each transfection employed a T75 culture flask of 293F cells growing as a monolayer. Transfections employed LIPOFECTAMINE™ 2000 as described by the manufacturer. Approximately 6 hours post-transfection, the DMEM+10% FBS growth medium was replaced with serum-free CD293 medium. At forty-eight hours post-transfection, the growth medium was harvested and clarified of debris by low speed centrifugation, after which, VLPs in the medium were collected by centrifugation at 100,000×g through a 20% sucrose cushion in tris-buffered saline (TBS). Pelleted material was resuspended in TBS and subjected to Western blot analysis using antibodies specific for HIV-1 Gag and RSV antigens.

Results

Figure 8:
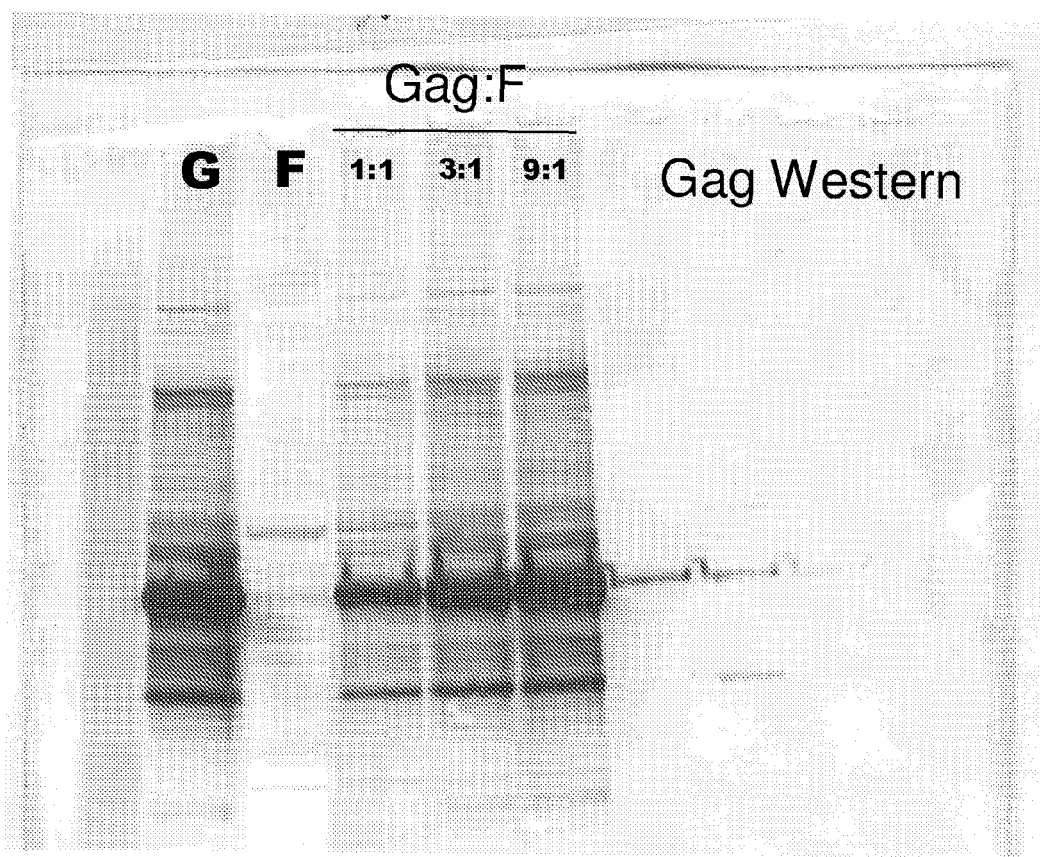
FIG. 8 shows the HIV-1 Gag Western blot of VLPs derived from p3.1-bruGag plus p3.1-F-GPI transfection. "G" indicates bruGag only exp Table 1), C (Transfection #314-85, see Table 1); standard; D (Transfection #314-91, see Table 1), E (Transfection #314-91, see Table 1), F (Transfection #314-91, see Table 1), and G (Transfection #314-91, see Table 1). Panel (A) shows the western blot using an anti-HSVgD monoclonal antibody, and (B) shows the western blot using anti-P27 alvGAG polyclonal antibodies.
Figure 9:
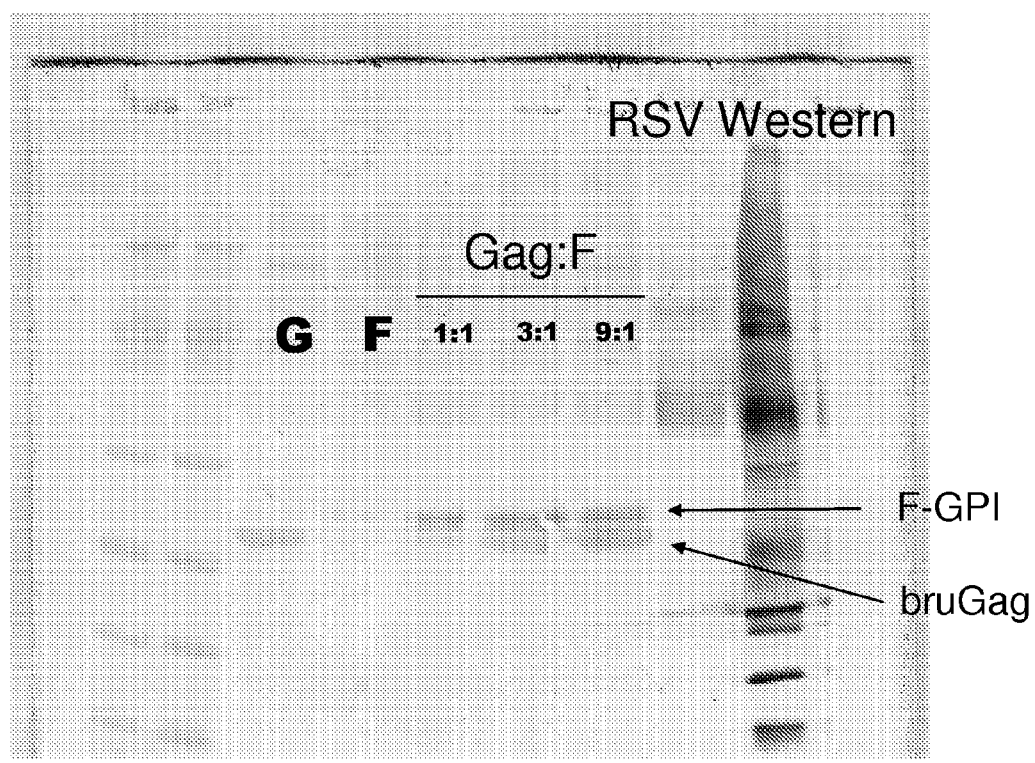

FIG. 8 shows the Gag Western blot and FIG. 9 shows the RSV Western blot. The Gag Western blot (FIG. 8) shows that abundant amounts of the Gag product were present in all cultures whether transfected with the Gag vector alone or in combination with the F vector. There was some reduction in the yield of the Gag gene product in the 1:1 ratio culture but HIV Gag gene expression and VLP budding was not shut down by RSV F expression as was the case for MLV Gag. The RSV F antigen was detected in the pelleted samples as shown in FIG. 9 and the amount of F antigen found in the samples was markedly increased in those cultures in which HIV-1 Gag was expressed along with RSV F. This increase in high molecular weight F antigen release in the presence of Gag co-expression was evidence for the pseudotyping of the F antigen onto HIV-1 Gag VLPs. It should be noted that the Gag product showed up as a background band in the RSV Western blot, and this was likely due to some low level cross-reactivity that the secondary conjugated antibody exhibited for the Gag product.

Example 3

Scaled-Up Pseudotyped HIV-1 Gag+RSV F (GPI) VLPs

This example describes larger scale production of HIV-1 Gag VLPs pseudotyped with the GPI-anchored version of the RSV F glycoprotein.

Materials and Methods

Six T175 flasks of 293F cells were transfected with p3.1-bruGag and p3.1-F-GPI at a ratio of 3:1 (Gag-to-F) using LIPOFECTAMINE™ 2000. Approximately 8 hours post-transfection the transfection medium (DMEM+10% FBS) was replaced with CD293 medium. Forty-eight hours post-transfection the growth medium was collected, clarified of debris, and centrifuged at 100,000×g for 1 hour at 10° C. through a 20% sucrose cushion to pellet VLPs. The VLP pellet was resuspended in TBS, layered onto a 20-60% sucrose step gradient, and centrifuged at 100,000×g for 1 hour at 10° C. Gradient fractions were analyzed by SDS-PAGE to identify Gag-containing fractions. Peak Gag-containing fractions were pooled, sucrose was diluted by three-fold with TBS, and VLPs were concentrated by centrifugation once again at 100,000×g for 1 hour at 10° C. Samples were then resuspended in TBS for analysis by SDS-PAGE, Western blotting, and ELISA.

Results

Figure 10:
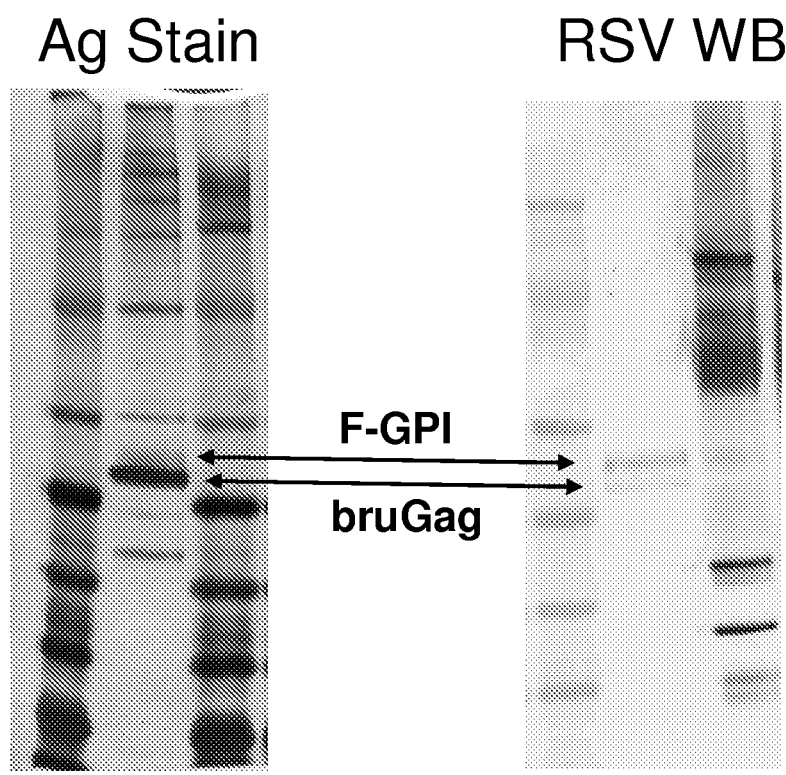
Figure 11:
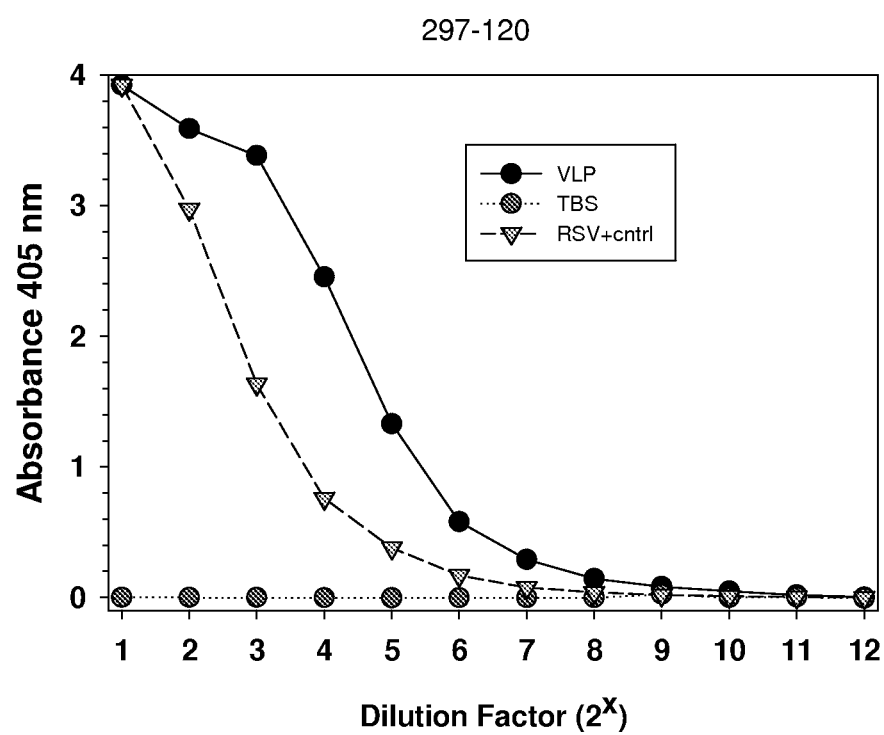

FIG. 10 shows a silver-stained SDS-PAGE gel (left panel) revealing a prominent bruGag band (~57 Kd) and a lighter band consistent with the GPI-anchored F (~61 Kd). The identity of the F band was confirmed by Western blotting (FIG. 10, right panel). Further evidence for the presence of the F antigen was obtained by ELISA in which a sample of the VLPs was serially diluted on an ELISA plate and was reacted with the Synagis RSV F-specific neutralizing monoclonal antibody (MedImmune). ELISA data are shown in FIG. 11 in which the sucrose-banded VLPs elicited a signal similar to that of live RSV virus in their reactivity to the Synagis antibody.

Example 4

Scaled-Up Pseudotyped HIV-1 Gag+RSV F (trunc) VLPs

This example describes larger scale production of HIV-1 Gag VLPs pseudotyped with the RSV F glycoprotein containing the cytoplasmic tail truncation.

Materials and Methods

Figure 12:
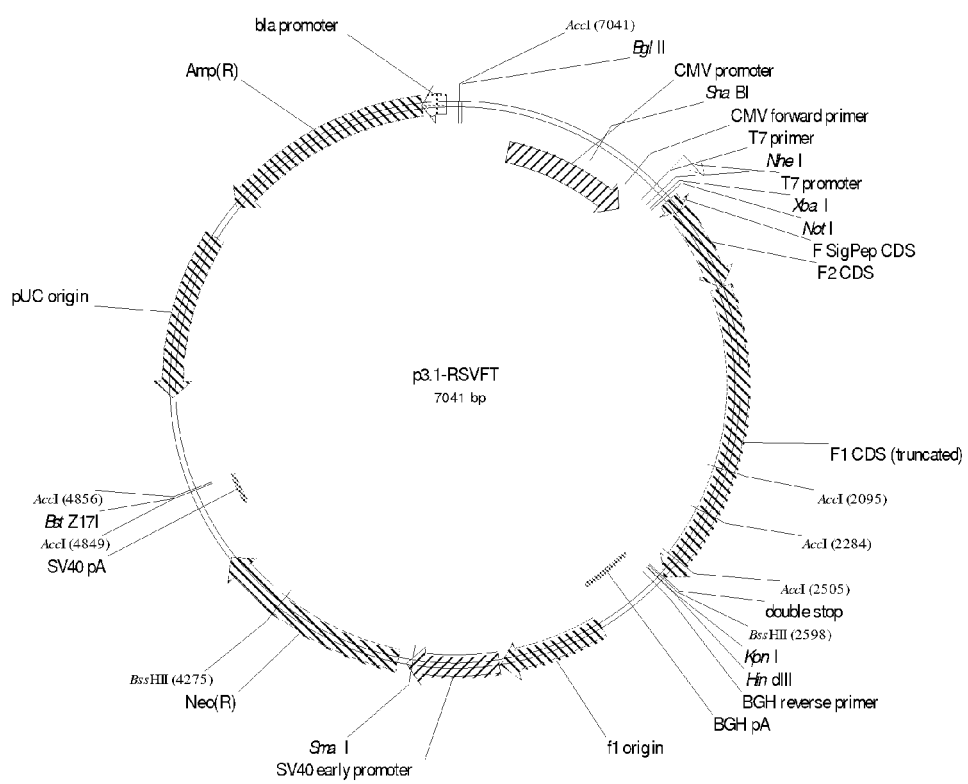

Eight T175 flasks of 293F cells were transfected with p3.1-bruGag and p3.1-RSVFT at a ratio of 3:1 (Gag-to-F) using LIPOFECTAMINE™ 2000. Plasmid p3.1-FT contains a synthetic fragment that encodes a cytoplasmic tail-truncated version of the RSV F glycoprotein. FIG. 12 shows a map of p3.1-RSVFT. The F coding sequence is as follows:

```
                                       (SEQ ID NO: 18)
atggaactgctgatcctgaaggctaacgctatcaccaccatcctgaccgc tgtcaccttctgcttcgcctccggccagaacatcaccgaggaattctacc agtccacctgctccgctgtctccaagggttacctgtccgctctgcgcacc ggctggtacacctccgtcatcaccatcgagctgtccaacatcaaggaaaa caagtgcaacggcaccgacgctaaggtcaagctgatcaagcaggaactgg acaagtacaagaacgctgtcaccgagctgcagctgctgatgcagtccacc cccgctaccaacaaccgcgctcgccgtgagctgccccgcttcatgaacta caccctgaacaacgccaagaaaaccaacgtcaccctgtccaagaagcgca agcgccgcttcctgggctttcctgctgggtgtcggttccgctatcgcttcc ggtgtcgctgtctctaaggtcctgcacctggaaggcgaggtcaacaagat caagtccgccctgctgtccaccaacaaggctgtcgtgtccctgtccaacg gtgtctccgtcctgacctccaaggtgctggacctgaagaactacatcgac aagcagctgctgcccatcgtcaacaagcagtcctgctccatctccaacat cgagactgtcatcgagttccagcagaagaacaaccgcctgctggaaatca cccgcgagttctccgtcaacgctggtgtcaccaccctgtctccacctac atgctgaccaactccgagctgctgtccctgatcaacgacatgcccatcac caacgaccaaaagaaactgatgtccaacaacgtccagatcgtccgccagc agtcctactctatcatgagcatcatcaaggaagaggtcctggcttacgtc gtccagctgccccctgtacggtgtcatcgacacccctgctggaagctgca cacctccccctgtgcaccaccaacaccaaggaaggttccaacatctgcc tgacccgcaccgaccgcggctggttctgcgacaacgctggctctgtctcc ttcttccccaagctgagacttgcaaggtccagtccaaccgcgtgttctg cgacaccatgaactccctgaccctgccctccgaggtcaacctgtgcaacg tcgacatcttcaaccccaagtacgactgcaagatcatgacctctaagacc gacgtgtcctcctctgtcatcacctccctgggtgctatcgtgtcctgcta cggcaagaccaagtgcaccgcttccaacaagaaccgcggtatcatcaaga ccttctccaacggttgcgactacgtgtccaacaagggcgtcgacaccgtg tccgtcggcaacaccctgtactacgtgaacaagcaggaaggcaagtccct gtacgtcaagggcgagcccatcatcaacttctacgaccccctggtgttcc cctccgacgagttcgacgcttccatcagccaggtcaacgagaagatcaac cagtccctggctttcatccgcaagtccgacgagctgctgcacaacgtgaa cgctggcaagtctaccaccaacatcatgatcaccactatcatcatcgtga tcatcgtcatcctgctgtctctgatcgctgtcggtctgctgctgtactaa
```

The encoded F amino acid sequence is as follows (the N-terminal signal peptide and the C-terminal transmembrane domain are underlined:

```
                                       (SEQ ID NO: 19)
mellilkanaittiltavtfcfasgqniteefyqstcsavskgylsalrt gwytsvitielsnikenkcngtdakvklikqeldkyknavtelqllmqst patnnrarrelprfmnytlnnakktnvtlskkrkrrflgfllgvgsaias gvavskvlhlegevnkiksallstnkavvslsngvsvltskvldlknyid kqllpivnkqscsisnietviefqqknnrlleitrefsvnagvttpvsty mltnsellslindmpitndqkklmsnnvqivrqqsysimsiikeevlayv vqlplygvidtpcwklhtsplcttntkegsnicltrtdrgwfcdnagsvs ffpqaetckvqsnrvfcdtmnsltlpsevnlcnvdifnpkydckimtskt dvsssvitslgaivscygktkctasnknrgiiktfsngcdyvsnkgvdtv
```

-continued svgntlyyvnkqegkslyvkgepiinfydplvfpsdefdasisqvnekin qslafirksdellhnvnagksttn<u>imittiiiviivillsliavqllly</u>*

Approximately 8 hours post-transfection, the transfection medium (DMEM+10% FBS) was replaced with CD293 medium. Forty-eight hours post-transfection the growth medium was collected, clarified of debris, and centrifuged at 100,000×g for 1 hour at 10° C. through a 20% sucrose cushion to pellet VLPs. The VLP pellet was resuspended in TBS, layered onto a 20-60% sucrose step gradient, and centrifuged at 100,000×g for 1 hour at 10° C. Gradient fractions were analyzed by SDS-PAGE to identify Gag-containing fractions. Peak Gag-containing fractions were pooled, sucrose was diluted by three-fold with TBS, and VLPs were concentrated by centrifugation once again at 100,000×g for 1 hour at 10° C. The samples were then resuspended in TBS for analysis by SDS-PAGE, Western blotting, and ELISA.

Results

Figure 13:
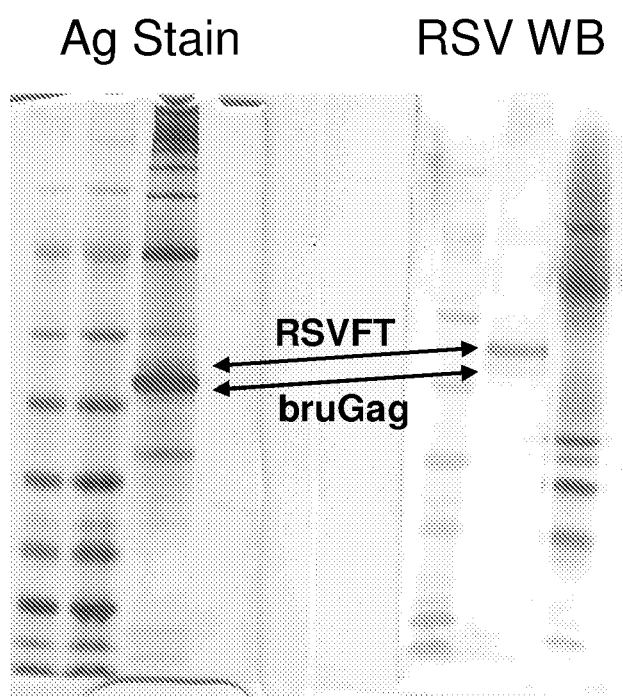
Figure 14:
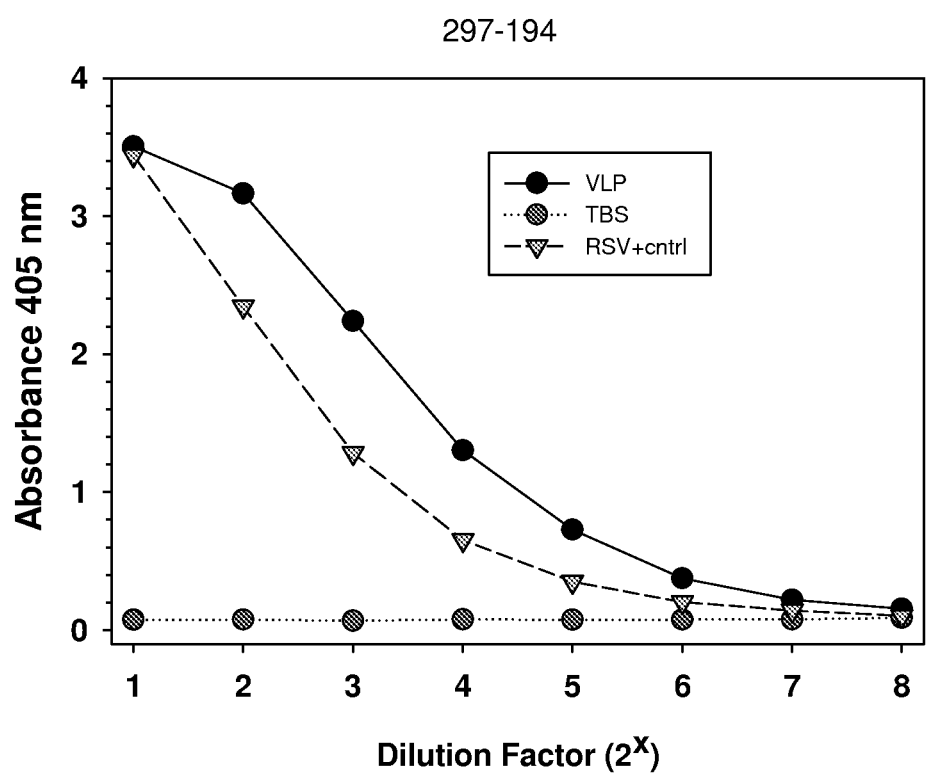

FIG. 13 shows a silver-stained SDS-PAGE gel (left panel) revealing a prominent bruGag band (~57 Kd) and a lighter band consistent with the truncated F (~61 Kd). The identity of the F band was confirmed by Western blotting (FIG. 13, right panel). Further evidence for the presence of the F antigen was obtained by ELISA in which a sample of the VLPs was serially diluted on an ELISA plate and was reacted with the Synagis RSV F-specific neutralizing monoclonal antibody (MedImmune). ELISA data are shown in FIG. 14 in which the sucrose-banded VLPs elicited a signal similar to that of live RSV virus in their reactivity to the Synagis antibody.

Figure 15:
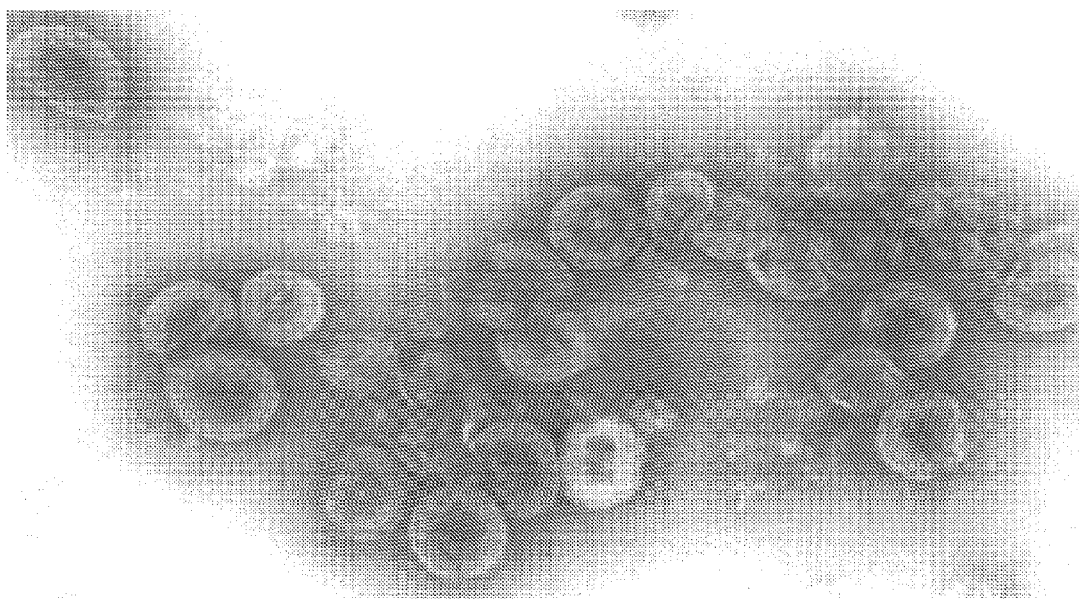

A sample of the sucrose-banded VLPs was also subjected to electron microscopy via negative staining. A representative micrograph is shown in FIG. 15 revealing the presence of uniform enveloped particles containing an immature (unprocessed) Gag core as would be expected from use of the HIV-1 Gag polyprotein precursor as the VLP budding engine.

Example 5

Immunogenicity of Pseudotyped HIV-1 Gag+RSV F VLPs

This example demonstrates the induction of neutralizing antibody responses in mice by RSV F-pseudotyped HIV Gag VLPs.

Materials and Methods

RSV F-GPI pseudotyped HIV-1 Gag VLPs were prepared as described in Example 3 and used to immunize mice. Mice received two immunizations each, spaced 4 weeks apart, in which each immunization consisted of VLPs in TBS that contained approximately 0.5 μg of the F antigen. Two weeks following the second immunization serum samples were collected for use in an RSV plaque reduction (virus neutralizing) assay. Live RSV aliquots consisting of an average of 125 plaque forming units (pfu) of virus were treated with serial dilutions of RSV neutralizing control antibodies or sera from immunized mice or control mice. The antibody-treated virus inocula were then added to individual wells of a 96-well plate of Vero cells, and the plate was incubated for 48 hours at 37° C. to allow non-neutralized virus to infect cells. After 48 hours plaques of RSV growth were identified by fixing the cells and allowing them to react with a goat polyclonal RSV-specific antibody.

Results

Data from this experiment are shown in FIG. 16 in which columns 1 and 2 show RSV neutralizing activity exhibited by Synagis and goat anti-RSV control antibodies, respectively. Columns 3 and 4 represent negative control mouse sera in which no neutralizing activity was seen. Columns 5-10 represent VLP-immunized mouse sera in which significant neutralizing activity was observed in six of six immunized mice. Finally, columns 11 and 12 represent untreated RSV inocula in which no neutralizing activity was expected nor observed. These data demonstrated that pseudotyped VLPs containing the RSV F antigen can induce significant RSV-specific neutralizing antibody responses.

Example 6

Pseudotyped ALV Gag+RSV F (trunc) VLPs

This example demonstrates the production of RSV F-pseudotyped ALV Gag VLPs. In addition to HIV-1 Gag (lentivirus), a vector encoding the Gag product of avian leukosis virus (ALV, an alpharetrovirus) was also constructed. While it is recognized that HIV virions bud from lipid raft domains and that HIV-1 Gag is capable of targeting to lipid rafts, similar data regarding the ALV Gag product are lacking.

Materials and Methods

To determine if the RSV F glycoprotein could be pseudotyped onto alpharetroviral particles such as ALV Gag, a vector encoding ALV Gag was produced. Plasmid p3.1-alvGag-dPR contains a synthetic sequence encoding the ALV Gag gene product devoid of its C-terminal protease domain. Alpha retroviruses such as ALV contain their protease domain as part of the Gag polyprotein rather than the Pol polyprotein as is the case with most other retroviruses. Because the protease domain is dispensable for VLP budding, it was not included in the final vector. FIG. 17 shows a map of p3.1-alvGag-dPR. The nucleotide coding sequence is as follows:

```
                                     (SEQ ID NO: 20)
atggaagctgtgatcaaggtcatctcctccgcttgcaagacctactgcgg caagacctccccctccaagaaagaaatcggtgctatgctgtccctgctgc agaaagagggcctgctgatgtccccctccgacctgtactcccccggttcc tgggaccctatcaccgctgctctgtcccagcgtgctatgatcctgggcaa gtccggcgaactcaagacctggggcctggtgctgggtgctctgaaggctg ctcgcgaggaacaagtgacctccgagcaggctaagttctggctgggtctg ggtggtggtcgtgtgtccccccctggtcccgagtgcatcgagaagcccgc taccgagcgtcgtatcgacaagggcgaggaagtgggcgagactaccgtgc agcgtgacgctaagatggctcccgaggaaaccgctacccccaagaccgtg ggcacctcctgctaccactgcggcaccgctatcggttgcaactgcgctac cgcttccgctcccccccctccttacgtgggctccggcctgtacccttccc tggctggtgtcggcgagcagcaaggacagggtggagacacccctcccggt gctgaacagtcccgtgccgagcctggtcacgctggtcaagctcccggtcc cgctctgactgactgggctcgtgtgcgtgaggaactggcttccaccggtc cccctgtggtggctatgcccgtggtcatcaagaccgagggtcccgcttgg acccccctggaacccaagctgatcacccgtctggctgacaccgtgcgtac caagggcctgcgttccccaatcaccatggctgaggtggaggctctgatgt cctcccccctgctgcctcacgacgtgaccaacctgatgcgtgtgatcctg
```

-continued

```
ggtcccgctccctacgctctgtggatggacgcttggggcgtgcagctgca gaccgtgatcgctgctgctacccgtgaccccgtcaccctgctaacggac agggtcgtggcgagcgtaccaacctgaaccgtctgaagggcctggctgac ggcatggtcggcaaccctcagggacaggctgctctgctgcgtcctggcga gctggtcgctatcaccgccagcgctctgcaggcttttccgtgaggtggccc gtttggccgaaccagctggtccctgggctgacatcatgcagggcccctcc gagtccttcgtggacttcgctaaccgtctgatcaaggctgtggagggctc cgacctccctccttccgctcgtgctcccgtgatcatcgactgcttccgtc agaagtcccagcccgacatccagcagctgatccgtaccgctccctccacc ctgactacccctggcgagatcatcaagtacgtgctggaccgtcaaaagac cgctcccctgaccgaccaaggtatcgctgccgctatgtcctccgctatcc agcccctgatcatggctgtcgtgaaccgcgagagggacggacagaccggt tccggtggtcgtgctcgtggcctgtgctacacttgcggttccccggtca ctaccaggctcagtgccccaagaagcgcaagtccggaaactcccgcgagc gctgccagctctgcaacggcatgggtcacaacgccaagcagtgccgcaag cgcgacggaaaccagggccagcgtcccggaaagggactgtcctccggtcc ttggcctggtcctgagcccctgctgtgtcctaa
```

The encoded amino acid sequence is as follows:

(SEQ ID NO: 21)
```
meavikvissacktycgktspskkeigamlsllqkegllmspsdlyspgs wdpitaalsqramilgksgelktwglvlgalkaareeqvtseqakfwlgl gggrvsppgpeciekpaterridkgeevgettvqrdakmapeetatpktv gtscyhcgtaigcncatasappppyvgsglypslagvgeqqgqggdtppg aeqsraepghagqapgpaltdwarvreelastgppvvampvviktegpaw tplepklitrladtvrtkglrspitmaevealmsspllphdvtnlmrvil gpapyalwmdawgvqlqtviaaatrdprhpangqgrgertnlnrlkglad gmvgnpqgqaallrpgelvaitasalqafrevarlaepagpwadimqgps esfvdfanrlikavegsdlppsarapviidcfrqksqpdiqqlirtapst lttpgeiikyvldrqktapltdqgiaaamssaiqplimavvnrerdgqtg sggrarglcytcgspghyqaqcpkkrksgnsrercqlcngmghnakqcrk rdgnqgqrpgkglssgpwpgpeppavs*
```

Plasmids p3.1-alvGag-dPR and p3.1-RSVFT were transfected into 293F cells individually or together at ratios of 1:1, 3:1 and 9:1 (Gag-to-F). Forty-eight hours post-transfection the medium was harvested, clarified of debris, and VLPs were pelleted at 100,000×g for 1 hour at 10° C. Resuspended pellets were analyzed for RSV F antigenic activity via an ELISA using the Synagis monoclonal antibody as described above.

Results

Figure 18:
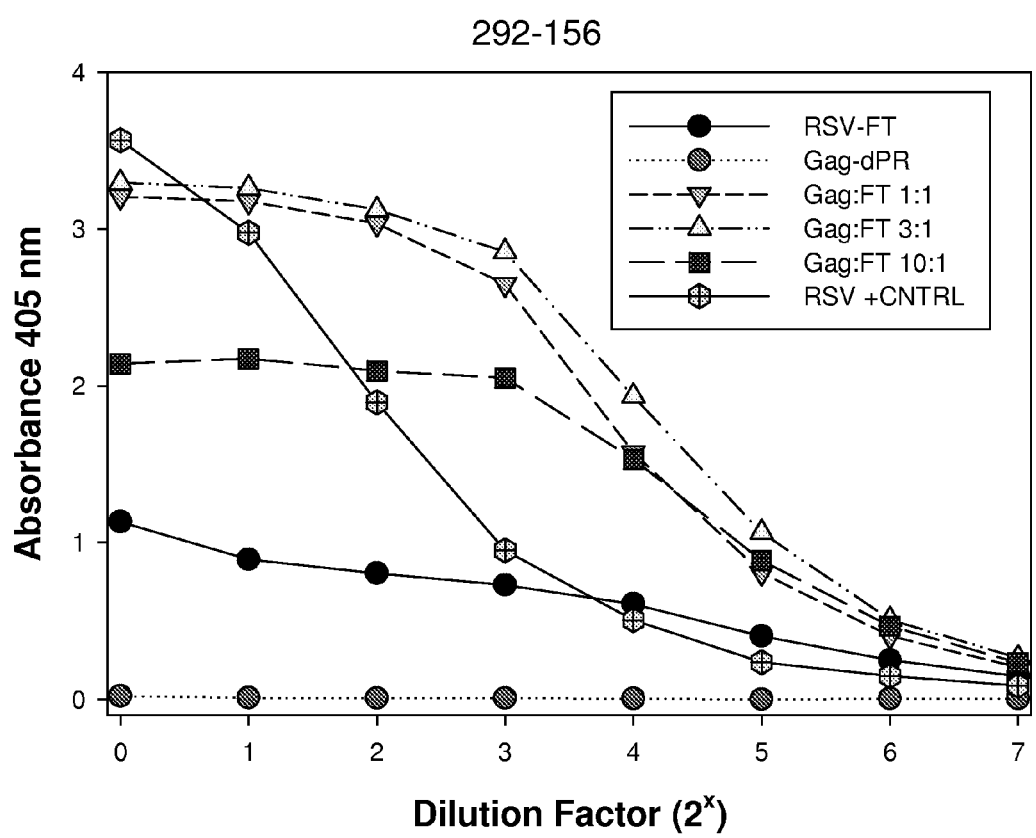

The data shown in FIG. 18 demonstrates that the combination of p3.1-alvGag-dPR plus p3.1-RSVFT resulted in the release of considerably more Synagis-reactive VLPs than seen with the expression of p3.1-RSVFT alone. Therefore, the RSV F antigen, while demonstrating some VLP budding activity on its own can be pseudotyped onto Gag products from both lentiviruses and alpharetroviruses.

Example 7

Comparison of RSV F Pseudotyped VLP Production Between Vectors Encoding HIV-1 Gag and alvGag-dPR This example compares the productions of pseudotyped HIV-1 Gag+RSV F VLP with the production of alvGag-dPR+RSV F VLP.

Materials and Methods

Plasmid p3.1-alvGag-dPR was co-transfected into 293F cells along with p3.1-RSVFT at ratios of 1:1 and 3:1. In addition, plasmid p3.1-bruGag was co-transfected into 293F cells with p3.1-RSVFT at a ratio of 3:1. Seventy-two hours post-transfection the medium was harvested, clarified of debris and VLPs were pelleted at 100,000×g for 1 hour at 10° C. Resuspended pellets were analyzed for RSV F antigenic activity via an ELISA using the Synagis monoclonal antibody as described above.

Results

Figure 19:
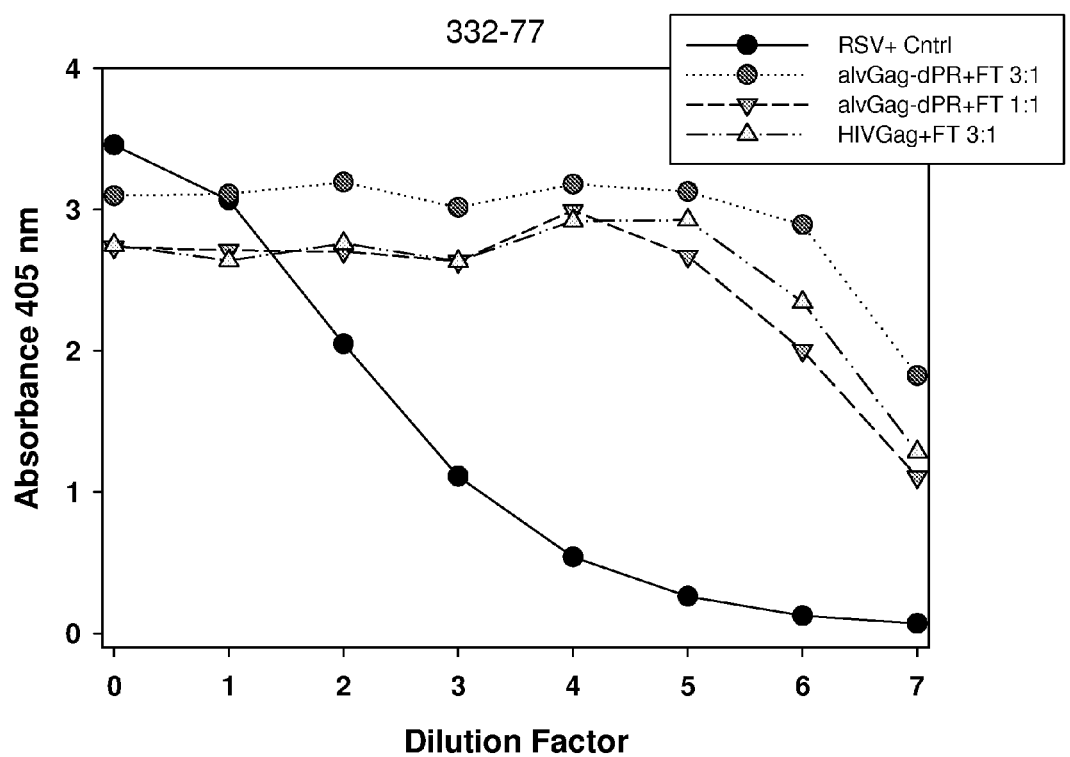

These data are shown in FIG. 19 which shows that similar amounts of Synagis reactive VLPs were detected in all three transfections demonstrating that the alvGag-dPR expression vector is equally effective as the HIV Gag expression vector in terms of producing RSV F-pseudotyped VLPs.

Example 8

Attempted Pseudotyping of RSV F with MPMV-Gag, BVL-Gag, and EIAV-Gag

This example attempts to determine if Gag proteins from other retroviruses were effective for the production of RSV F-pseudotyped VLPs.

Materials and Methods

Vectors encoding the Gag products of Mason Pfizer Monkey virus (MPMV, betaretrovirus), Bovine Leukemia virus (BLV, deltaretrovirus), and Equine Infectious Anemia virus (EIAV, lentivirus) were constructed using custom synthesized Gag coding sequence fragments that were confirmed by DNA sequence analysis. These vectors were co-transfected into 293F cells along with the F-encoding vector p3.1-RSVFT at a ratio of 3:1 (Gag:F). Seventy-two hours post-transfection the medium was harvested, clarified of debris and VLPs were pelleted at 100,000×g for 1 hour at 10° C. Resuspended pellets were analyzed for RSV F antigenic activity via an ELISA using the Synagis monoclonal antibody as described above.

Results

Figure 20:
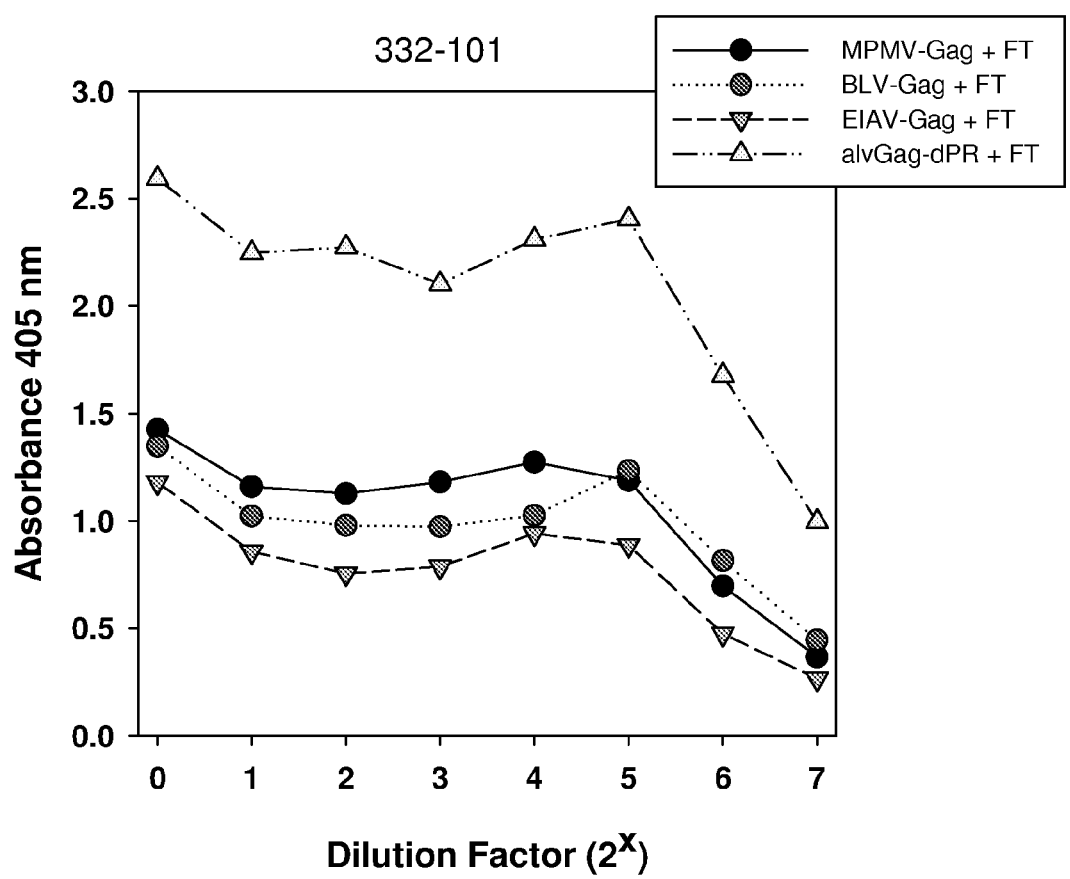

The data are shown in FIG. 20, in which it is demonstrated that vectors encoding the three alternative Gag products do not function like alvGag in terms of the release of RSV F-pseudotyped VLPs as determined by an ELISA assay employing an F-specific monoclonal antibody. The weaker F ELISA signals obtained with vectors encoding MPMV Gag, BLV Gag, and EIAV Gag were similar to signals typically obtained following expression of RSV F alone in which F protein self-budding (Gag-independent) activity us usually detected. The inability of MPMV, BLV, and EIVA Gags to significantly augment F particle release is similar to results with MLV Gag in which this latter Gag product was shown not form pseudotypes with RSV F and therefore does not increase the release of RSV F-containing particles when co-expressed with F. Moreover, data indicate that expression of MLV, MPMV, BLV, and EIAV Gags in the presence of RSV F expression is suppressed showing an incompatibility between VLP production by these latter Gags and RSV F expression.

Example 9

Comparison of alvGag with Intact Protease to alvGag-dPR

Figure 21:
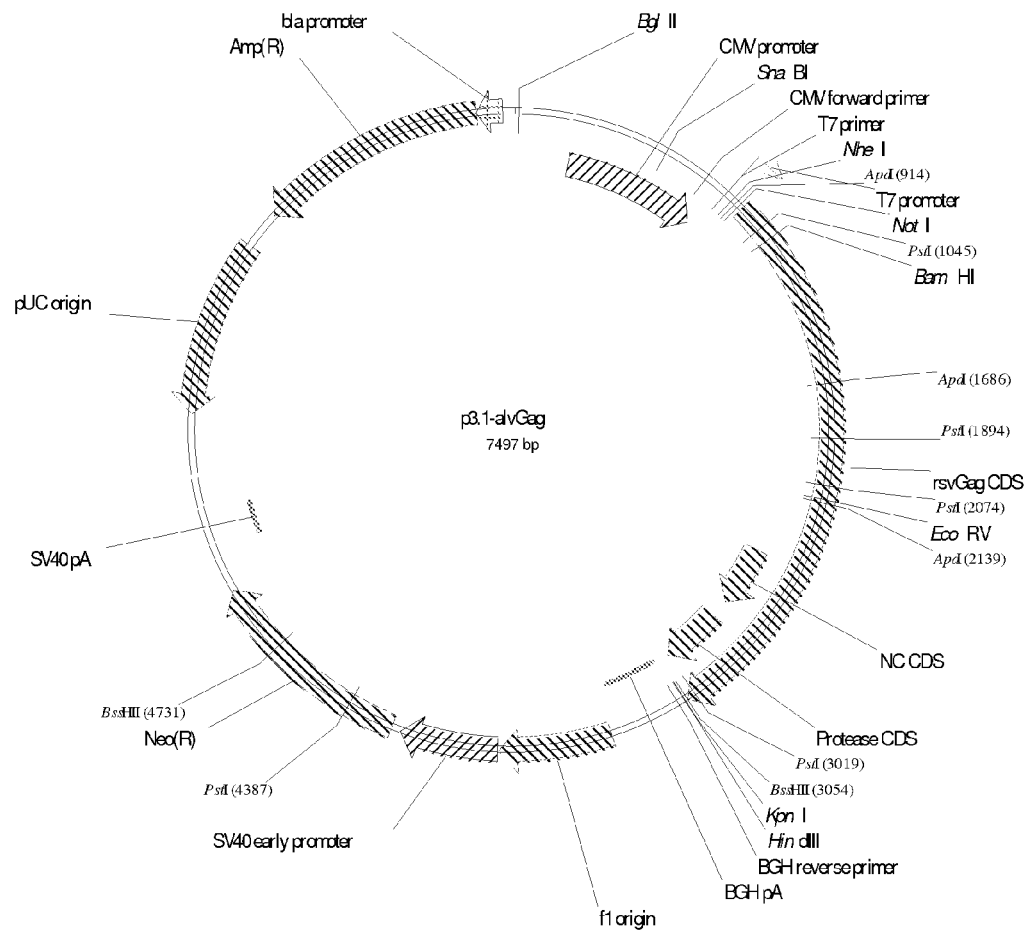

In addition to alvGag-dPR, the complete alvGag with its C-terminal protease activity intact can also form pseudotyped VLPs with the RSV F protein. This was demonstrated in a transfection experiment comparing the release of VLPs following transfection with p3.1-alvGag-dPR (plus FL or FT) versus transfection with p3.1-alvGag (plus FL or FT) versus transfection of a mixture of p3.1-alvGag-dPR and p3.1-alvGag (plus FL or FT). FIG. 21 shows a map of plasmid p3.1-alvGag encoding the complete alvGag polyprotein with intact retroviral protease activity. The nucleotide coding sequence is as follows:

(SEQ ID NO: 22)
atggaagccgtgatcaaagtgatcagcagcgcctgcaagacctactgcgg caagaccagcccagcaagaaagaaattggcgccatgctgtctctgctgc agaaggaaggcctgctgatgagccccagcgacctgtacagcccggcagc tgggatcctatcacagctgccctgagccagagagccatgatcctgggcaa gagcggcgagctgaaaacctggggcctggtgctgggagccctgaaggccg ccagagaagaacaggtcaccagcgagcaggccaagttttggctgggcctg ggcggaggaagagtgtctcccctggccccgagtgtatcgagaagcccgc caccgagcggagaatcgacaagggcgaggaagtgggcgagacaaccgtgc agcgggacgccaagatggcccctgaggaaaccgccacccccaagaccgtg ggcaccagctgctaccactgtggcaccgccatcggctgcaattgtgccac cgccagcgccctccacctccttacgtgggcagcggcctctatccttcac tggccggcgtgggcgaacagcagggacagggcggcgatacacctcctggc gccgagcagagcagagccgaacctggacatgccggacaggcccctggacc tgctctgaccgattgggccagagtgcgggaggaactggcctctaccggac cccctgtggtggctatgcccgtggtgattaagacagagggccctgcctgg accctctggaacccaagctgatcaccggctggccgatacagtgcggac caagggcctgagaagcccatcaccatggccgaggtggaggccctgatga gcagcccctgctgcccacgacgtgaccaacctgatgagagtgatcctg ggaccgctccctacgccctgtggatggatgcctggggcgtgcagctgca gacagtgatcgccgctgccaccagagatcccagacacccgccaatggcc agggcagaggcgagagaaccaacctgaaccggctgaagggcctggccgac ggcatggtcggcaatcctcagggacaggccgctctgctgaggcctggcga actggtggccatcacagccagcgcctgcaggccttcagagaagtggcta gactggccgaacctgccggcccttgggccgatatcatgcagggcccagc gagagcttcgtggacttcgccaaccggctgatcaaggccgtggagggcag cgatctgcctcctagcgccagagcccccgtgatcatcgactgcttccggc agaagtcccagcccgacatccagcagctgatcagaaccgccccagcacc ctgaccaccctggcgagatcatcaaatacgtgctggaccggcagaaaac cgcccctctgaccgatcagggcattgccgccgctatgagcagcgccatcc agcccctgattatggccgtggtgaaccgggagagggatggccagacagga agcggcggcagagctagaggactgtgctacacctgtggcagccctggcca ctaccaggctcagtgccccaagaagcggaagtccggcaacagccgggaga gatgccagctgtgcaacggcatgggccacaacgccaagcagtgcagaaag agggacggcaatcagggccagaggcccggcaaaggcctgtctagcggacc ttggcctggacctgagcctcctgccgtgagcctggccatgaccatggaac acaaggaccggcccctggtccgcgtgatcctgaccaacaccggcagccac cccgtgaagcagcggagcgtgtacatcaccgccctgctggactctggcgc cgacatcaccatcatcagcgaagaggactggcccaccgactggcctgtga tggaagccgccaacccccagatccacggcatcggcggaggcatccccatg cggaagtccagagacatgatcgagctgggcgtgatcaaccgggacggcag cctggaaagacccctgctgctgttcccagctgtggccatggtccggggca gcatcctgggcagagactgtctgcagggactgggcctgcggctgaccaat ctgtgatga The encoded amino acid sequence is as follows:

(SEQ ID NO: 23)
meavikvissacktycgktspskkeigamlsllqkegllmspsdlyspgs wdpitaalsqramilgksgelktwglvlgalkaareeqvtseqakfwlgl gggrvsppgpeciekpaterridkgeevgettvqrdakmapeetatpktv gtscyhcgtaigcncatasappppyvgsglypslagvgeqqgqggdtppg aeqsraepghagqapgpaltdwarvreelastgppvvampvviktegpaw tplepklitrladtvrtkglrspitmaevealmsspllphdvtnlmrvil gpapyalwmdawgvqlqtviaaatrdprhpangqgrgertnlnrlkglad gmvgnpqgqaallrpgelvaitasalqafrevarlaepagpwadimqgps esfvdfanrlikavegsdlppsarapviidcfrqksqpdiqqlirtapst lttpgeiikyvldrqktapltdqgiaaamssaiqplimavvnrerdgqtg sggrarglcytcgspghyqaqcpkkrksgnsrercqlcngmghnakqcrk rdgnqgqrpgkglssgpwpgpeppavslamtmehkdrplvrviltntgsh pvkqrsvyitalldsgaditiiseedwptdwpvmeaanpqihgigggipm rksrdmielgvinrdgslerplllfpavamvrgsilgrdclqglglrltn l*

Figure 22:
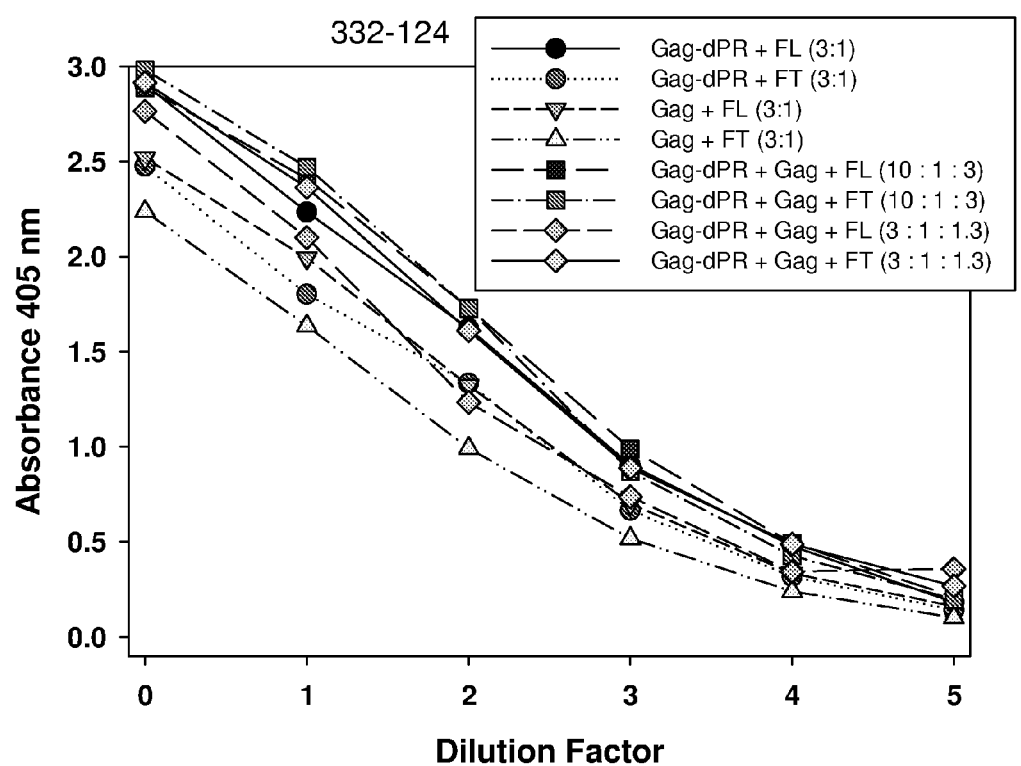
Figure 23:
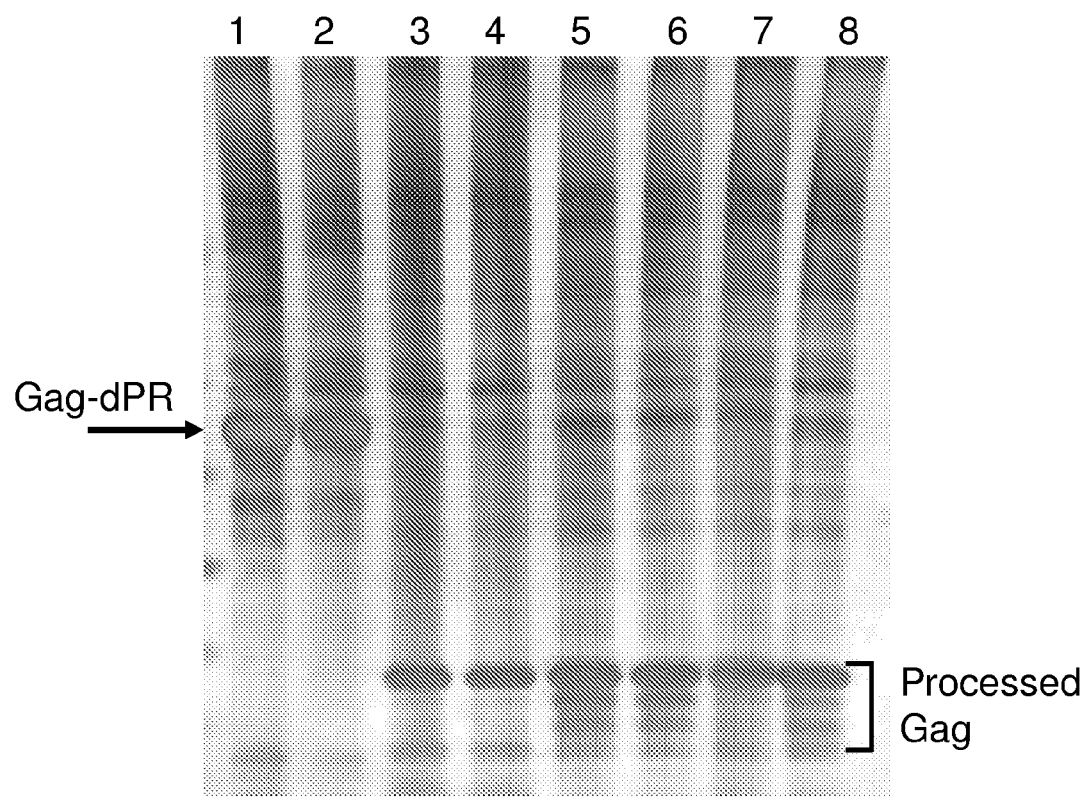

Following transfection, medium supernatants were clarified of debris and VLPs were pelleted through a 30% sucrose cushion. Quantification of the amount of F antigen released on VLPs was performed by an ELISA assay using a 0.2 micron filter-bottom ELISA plate in which VLPs were trapped on the filter then reacted with an RSV-specific antibody and developed using a secondary antibody conjugated to horse radish peroxidase. Results of the assay are shown in FIG. 22 in which shows that plasmids p3.1-alvGag-dPR and p3.1-alvGag performed similarly in terms the amount of high molecular weight RSV F antigenic activity released into the medium following co-transfection with F-encoding plasmids. Also, similar amounts of RSV F antigenic activity were released into the medium when 10:1 or 3:1 ratios of p3.1-alvGag-dPR and p3.1-alvGag were employed. FIG. 23 shows the status of the ALV Gag protein in each of these transfections. As expected, transfection with p3.1-alvGag-dPR resulted in a prominent 61 kD band consistent with expression of the intact Gag-dPR polyprotein (lanes 1 and 2). The remaining lanes representing transfection with p3.1-alvGag or combinations of p3.1-alv-Gag and p3.1-alvGag-dPR resulted in a prominent 27 kD band consistent with Gag processing due to the presence of the retroviral protease activity.

Figure 24:
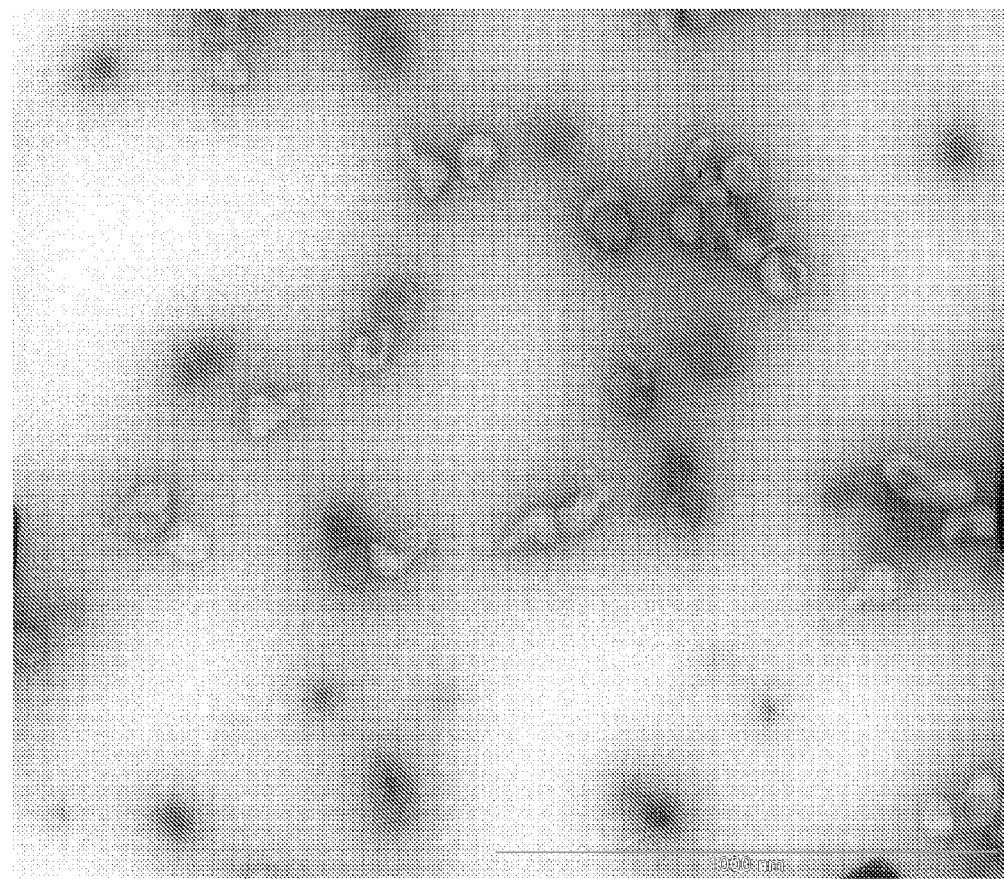

Final confirmation of VLP production in cells co-transfected with p3.1-RSVFT along with a combination of p3.1-alvGag-dPR and p3.1-alvGag (10:1:3 alvGag-dPR-to-alv-Gag-to-RSVFT) is shown in FIG. 24 in which VLPs from such a transfection were purified by banding between 30% and 60% sucrose layers in tris-buffered saline at 100,000×g for 1 hour. VLPs were applied to nitrocellulose-coated, 300 mesh copper grids and negatively stained with 2% w/v uranyl acetate for analysis by electron microscopy. The micrograph in FIG. 24 shows the presence of enveloped VLPs.

Example 10

RSV F-Pseudotyped ALV Gag VLPs Induce Neutralizing Antibody Responses in Mice

Figure 25:
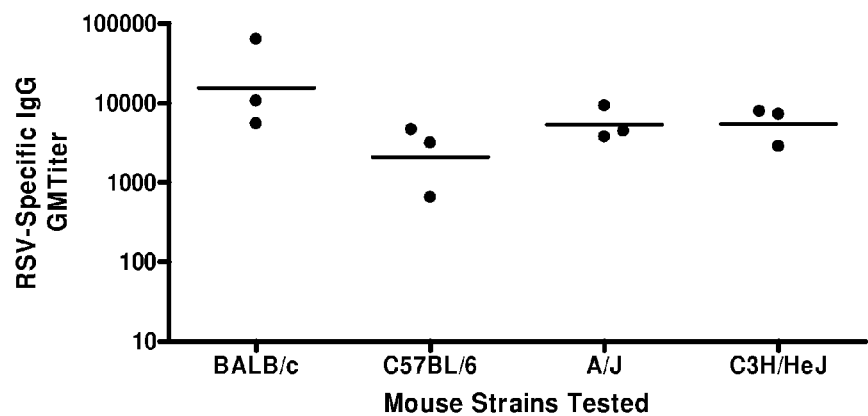
Figure 25:
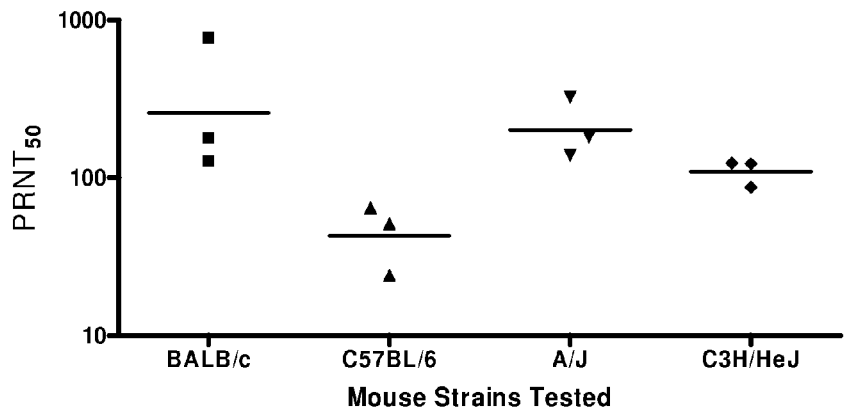

ALV Gag VLPs containing RSV "FT" or "FL" were prepared from HEK293 cells following transfection of cells with p3.1-alvGag-dPR along with p3.1-RSVFT or p3.1-RSVFL. The "Gag" to "F" plasmid DNA transfection ratio was 3:1. VLPs containing F antigen were pelleted from the growth medium harvested on day 3 by centrifugation at 100,000×g through a 30% sucrose cushion then banded on 20-60% discontinuous sucrose gradients. Aliquots of VLPs containing less that 1 µg F antigen were used for immunization of various strains of mice in which each mouse received priming and booster vaccinations spaced 21 days apart. Each vaccine inoculum contained both "FT" and "FL" VLPs. Two weeks following the booster immunization sera were collected and used to measure RSV-specific antibody responses. These data are shown in FIG. 25 in which the top panel shows ELISA titer data in which sera were tested for reactivity in a traditional ELISA employing RSV virus particles immobilized on an ELISA plate. The bottom panel shows levels of virus-neutralizing antibodies measured using a plaque reduction assay as described in Example 5 above.

Example 11

Attempted Pseudotyping of HSV gD+ALV Gag

Other enveloped viruses produce surface glycoproteins that are analogous to the F protein of RSV; these glycoproteins can function in adhesion and interaction with host cell receptors and play critical roles in viral pathogenesis. One such example from Herpes Simplex Virus (HSV) is glycoprotein D (gD), which interacts with more than one host receptor during viral entry (reviewed in J. C. Whitbeck, et al. The major neutralizing antigenic site on Herpes Simplex Virus glycoprotein D overlaps a receptor-binding domain. 1999. J Virol 73(12):9879-9890). HSV gD subunit vaccine formulations have been tested in clinical trials for the prevention of HSV infections (D. I. Bernstein, et al., Safety and immunogenicity of glycoprotein D-adjuvant genital herpes vaccine. 2005. Clin Inf Disease 40:1271-1281).

To compare pseudotyping of an alternative viral glycoprotein onto ALV Gag-based VLPs, the HSV gD gene was utilized in co-expression studies with p3.1-alvGag-dPR.

Materials and Methods

Figure 26:
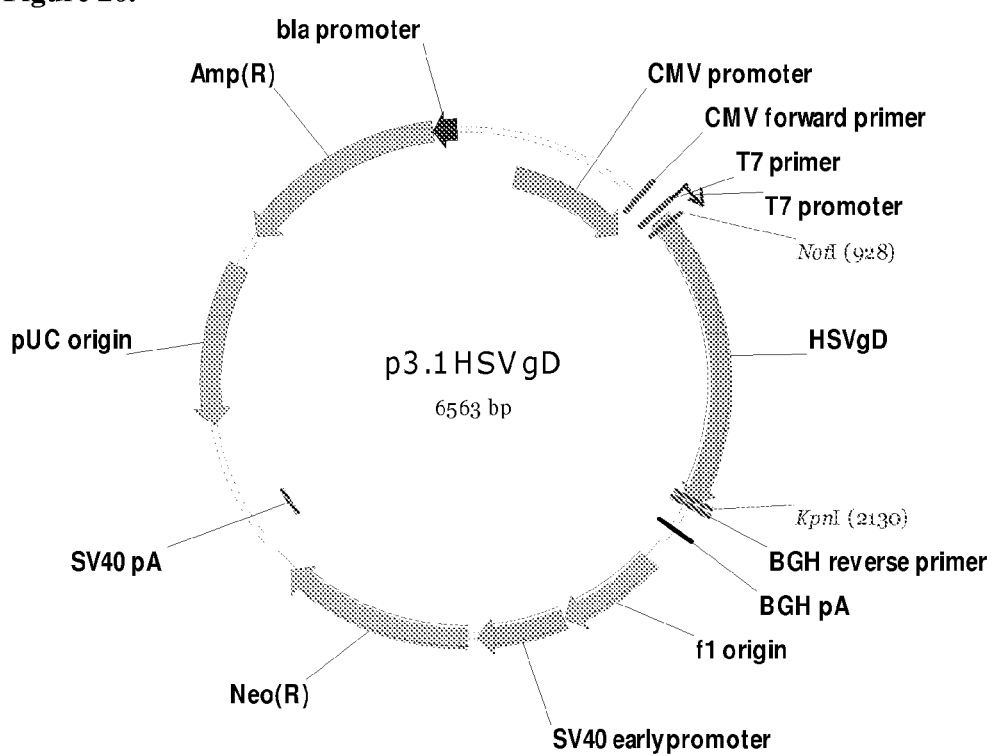

A human INV type 2 gD gene (GeneBank GeneID: 1487358) was synthesized and cloned into the pcDNA3.1(−) vector (Invitrogen) to construct plasmid p3.1-HSVgD. The plasmid map is shown in FIG. 26. The nucleic acid coding sequence is as follows:

(SEQ ID NO: 24)
atgggtagactgacttccggagtgggcaccgccgctctgctggtcgtggc tgtgggcctgcgcgtcgtgtgcgccaagtacgcactggccgatccctccc tgaagatggccgacccgaaccgcttccgcggcaagaacctccccgtgctg gaccagctgaccgaccccctggcgtgaagcgcgtgtaccacatccagcc ttccctggaagatcccttccagccccctccatccccatcaccgtgtact acgcagtgctggaacgcgcctgccgctccgtgctgctgcatgctccctcc gaggcccctcagatcgtgcgcggagcctccgacgaggcccgcaagcacac ctacaacctgactatcgcctggtacaggatgggcgacaactgcgccatcc ctatcactgtgatggaatacaccgagtgcccctacaacaagtccctgggc gtgtgccccatccgcacccagccccgctggtcctactacgactccttctc cgccgtgtccgaggacaacctgggcttcctgatgcacgccctgccttcg aaaccgccggcacctacctgaggctggtcaagatcaacgactggaccgag atcacccagttcatcctggaacaccgcgccagggcctcttgcaagtacgc tctgcccctgcgcatcccccctgccgcctgcctgacctctaaggcctacc agcagggcgtgaccgtggactccatcggcatgctgcctcgcttcatcccc gagaaccagcgcaccgtggccctgtacagcctgaagatcgccggctggca cggccccaagccaccctacacctccaccctgctgccccccgagctgtccg acaccaccaacgccacccagcccgagctggtgcccgaggaccctgaggac tccgccctgctcgaagatcccgccggaaccgtgtcctcccagatcccccc caactggcacatcccttccatccaggacgtggcccccaccacgctccag ccgcaccttccaacccaggcctgatcatcggagccctggccggctccacc ctggccgtcctggtcatcggcggaatcgctttctgggtcaggagaagggc ccagatggctccaaagcgcctgcgcctgccccacatccgcgacgacgacg cccctccctctcaccagccctgttctac The encoded amino acid sequence is as follows:

(SEQ ID NO: 25)
Mgrltsgvgtaallvvavglrvvcakyaladpslkmadpnrfrgknlpvl dqltdppgvkrvyhiqpsledpfqppsipitvyyavleracrsvllhaps eapqivrgasdearkhtynltiawyrmgdncaipitvmeytecpynkslg vcpirtqprwsyydsfsavsednlgflmhapafetagtylrlvkindwte itqfilehrarasckyalplrippaacltskayqqgvtvdsigmlprfip enqrtvalyslkiagwhgpkppytstllppelsdttnatqpelvpedped salledpagtvssqippnwhipsiqdvaphhapaapsnpgliigalagst lavlviggiafwvrrraqmapkrlrlphirdddappshqplfy Plasmids p3.1-HSVgD and p3.1-alvGag-dPR were transfected into 293F cells either alone or in combination ratios of 1:1, 5.6:1, and 2.3:1 HSVgD-to-ALVGag. HEK 293F monolayers in T75 flasks were transfected with the above DNAs using LIPOFECTAMINE™ 2000, incubated 8 hours and switched to fresh serum-free medium for 48 hours. The culture supernatants were harvested, centrifuged to pellet cells (3 min at 500×g) and to pellet cell debris (10 min at 4000×g) to produce clarified culture supernatant fluids. These samples were utilized directly in ELISA screening or overlaid onto a 30% sucrose-TBS cushion for ultracentrifugation (10° C., 100,000×g, 1 hour) to pellet VLPs and multimeric protein complexes. Ultracentrifuge pelleted material (i.e., UC pellet) was suspended in sterile TBS and electrophoresed on 4-12% SDS-PAGE (NuPAGE Bis-Tris Gels, Invitrogen) and transferred to polyvinylidene fluoride membranes for Western blot analysis. Expression of the HSVgD and ALV Gag proteins was tracked with specific antibody reagents: anti-HSVgD monoclonal antibody (GeneTex) and a goat anti-p27 alvGAG polyclonal antibody (Synbiotics).

Direct ELISAs

ELISAs were performed by coating Immunon II microtiter plate wells with test or control samples (25-100 µL of culture supernatant), rinsed in TBS and blocked in fresh milk block (5% w/v skim milk and 1% w/v BSA in TBS containing 0.1% v/v Tween 20) for 1 hour at room temperature, rinsed in TBS and incubated in primary antibody (anti-HSVgD mAb at 1 µg/mL block, anti-ALV Gag Ab at 1:1000 dilution in block) overnight at 4° C. Plates were washed (3×TBS+0.1% Tween 20 plus 3×TBS), incubated in appropriate secondary antibodies (HRP-conjugated anti-mouse or anti-goat antibodies diluted 1:2000 in block) for 1 hour at room temperature, washed and o-phenylenediamine substrate in citrate buffer was added. Color development was stopped with 10% sulfuric acid and plates read at 490 nm.

Immunoblot Assay

Western blot assay steps were as follows: polyvinylidene fluoride (PVDF) blots were blocked 1 hour at room temperature in fresh milk block (same as above) and incubated in primary antibodies (anti-HSVgD mAb at 1 µg/mL and 1:2000 dilution of anti-ALV Gag pAb) overnight at 4° C. Blots were washed 3×15 min in fresh block and incubated in AP-conjugated anti-mouse or anti-goat antibodies diluted 1:2000 in block for 1 hour at room temperature. Blots were washed 3×15 min in Tris-NaCl—MgCl$_2$ pH 9.5 buffer and immersed in NBT-BCIP substrate for color development. The reaction was stopped in 2 mM Na$_2$EDTA pH 8.0 buffer and blots dried between fresh 3 MM filter paper sheets.

Electron Microscopy

UC pelleted material from the HSVgD plus alvGag-dPR transfections of HEK 293F cells were applied to nitrocellulose-coated, 300 mesh copper grids and negatively stained with 2% w/v uranyl acetate for analysis by electron microscopy. Particle images were captured as 8-bit data files with embedded scale bars, using the SIS Soft-Imaging Systems software interface.

Results

Figure 27:
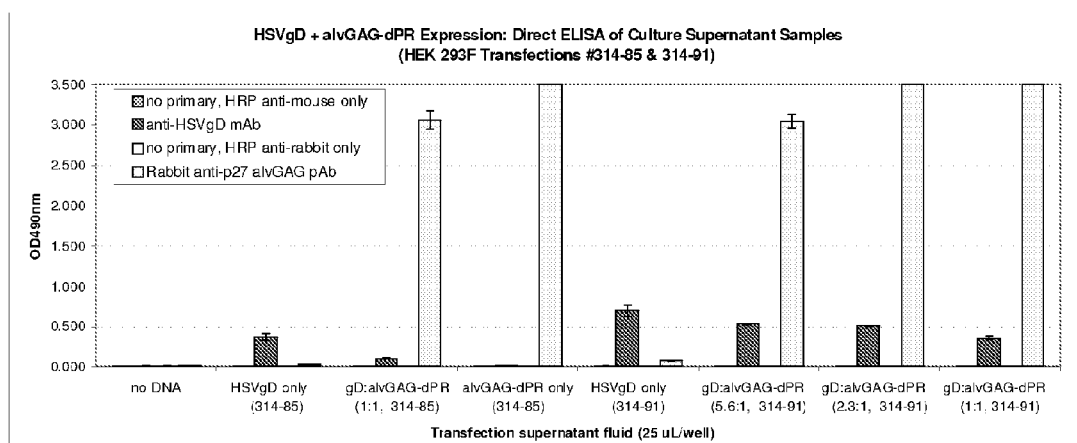

ELISA data for screening of HSVgD and alvGag-dPR transfection supernatant fluids is shown in FIG. 27. HSVgD protein was detected in supernatant samples from cells transfected with the p3.1-HSVgD construct in a dose-dependent fashion. All transfectants receiving the p3.1-alvGAG-dPR construct showed substantial levels of the ALV Gag protein in supernatant fluids. Despite coating microtiter wells directly with only 25 µL of a T75 transfectant supernatant volume, even the lowest alvGAG-dPR DNA level (1.5 µg/flask) in the 5.6:1 gD:GAG ratio transfection produced strong signals with the polyclonal detection reagent. Because the HSVgD detection antibody is a monoclonal and the ALV Gag is a polyclonal antibody, direct comparison of expression levels was not performed.

Figure 28:
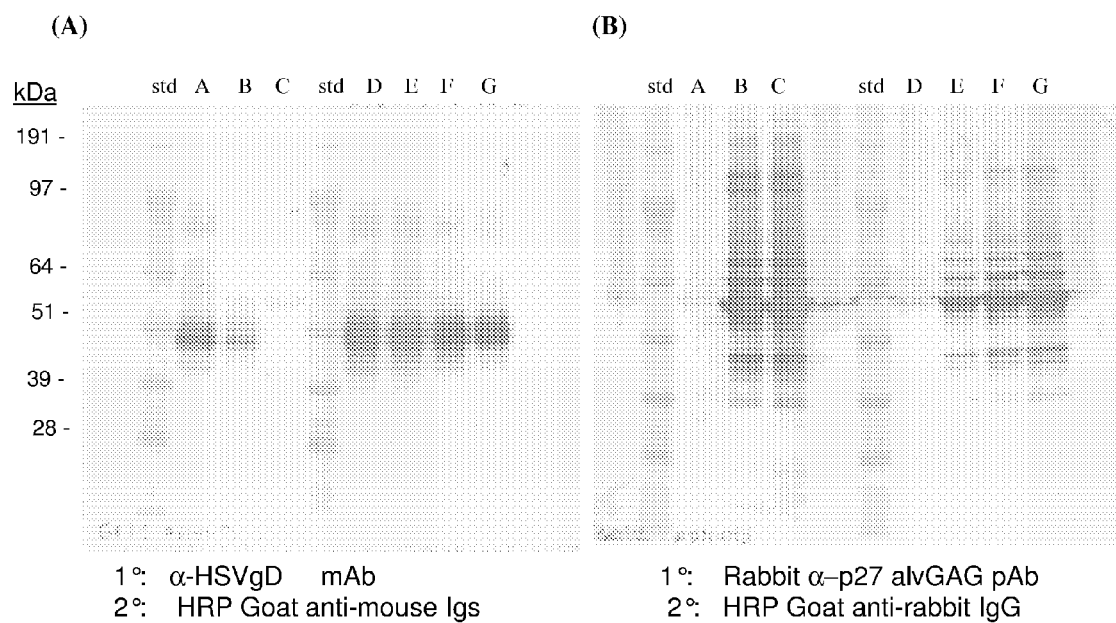

FIG. 28 shows the Western blot results of two HEK 293F transfection studies at the T75-flask size. Table 1 below lists the flask labels A-G, the micrograms of DNA added per T75 flask, and the resulting ratio of HSVgD and alvGAG-dPR constructs. UC pellet samples representing approximately 10% of the T75 harvest were loaded in duplicate gels, blotted, and probed with the anti-HSVgD and anti-p27 alvGAG antibody reagents. The data demonstrate DNA dose-dependent expression of the both the HSVgD and ALV Gag proteins in the mammalian host cells. As noted in the ELISA results above, expression of the ALV Gag protein was strong even at low DNA levels (Sample E with 1.5 µg input). The mass of expressed HSVgD is in the expected range, as discussed above. The ALV Gag (-dPR) would be expected to electrophorese at approximately 60 kDa, which was one of heavier signal bands in the blot profile in FIG. 28 (panel (B)). The smaller bands are likely degradation products, and the larger bands may be multimers or complexes with other proteins not fully denatured or reduced in the NuPAGE gel system; similar Gag banding patterns have been presented for other Gag cores (e.g., FIG. 8 blot of HIV-Gag). The ELISA and Western blot data demonstrate that HSVgD and ALV Gag are co-expressed in the HEK 293F transfection system.

TABLE 1

| | HEK293F | | | | | | |
|---|---|---|---|---|---|---|---|
| | Micrograms DNA of HSVgD to alvGAG-pPR in transfections | | | | | | |
| Constructs | A | B | C | D | E | F | G |
| HSVgD | 10 | 5 | 0 | 10 | 8.5 | 7 | 5 |
| alvGAG-dPR | 0 | 5 | 10 | 0 | 1.5 | 3 | 5 |
| Ratio gD:GAG | | 1:1 | | | 5.6:1 | 2.3:1 | 1:1 |

Transfection #314-85 = samples A, B, and C
Transfection #314-91 = samples D, E, F, and G Unlike the results observed above with co-expression of ALV-Gag and RSV F, co-expression of ALV-Gag with gD did not result in an increase in the release of high molecular weight gD in cell supernatants as would be expected if the ALV Gag was forming virus-like-particle pseudotypes with gD. Data from the ELISA and Western blot indicate that the gD protein was able to exit from cells in a manner independent of ALV Gag particle budding.

To determine whether VLPs could be visualized in these samples, aliquots were subjected to electron microscopy: p3.1-alvGAG-dPR alone (Sample C), p3.1-HSVgD alone (Sample D), and the 2.3:1 ratio gD:alvGAG-dPR transfection (Sample F). Results are shown in FIGS. 29, 30 and 31, containing two or more photomicrographs captured from each aliquot.

Figure 29:
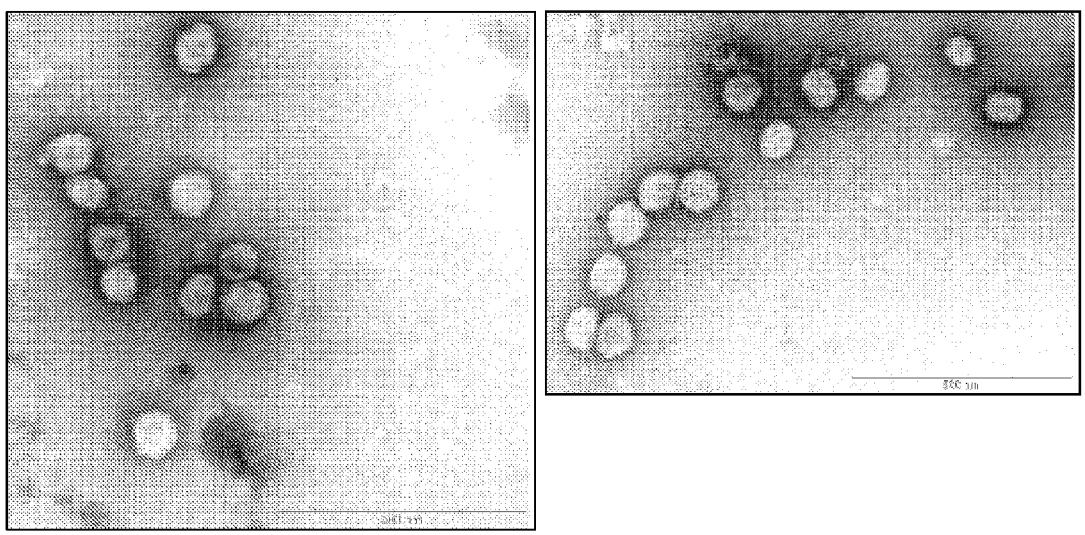
FIG. 29 shows two electron micrographs of sample C: p3.1-alvGAG-dPR only transfected HEK 293F Ultracentrifuge (UC) pelleted material. Both micrographs have a 500 nm scale bar.

FIG. 29 shows typical retroviral particles formed by ALV Gag (-dPR) transfectants in Sample C. Measurements (n=3, separate fields of view) taken with the imaging software indicated an average VLP size of 71.7±2.6 nm.

Figure 30:
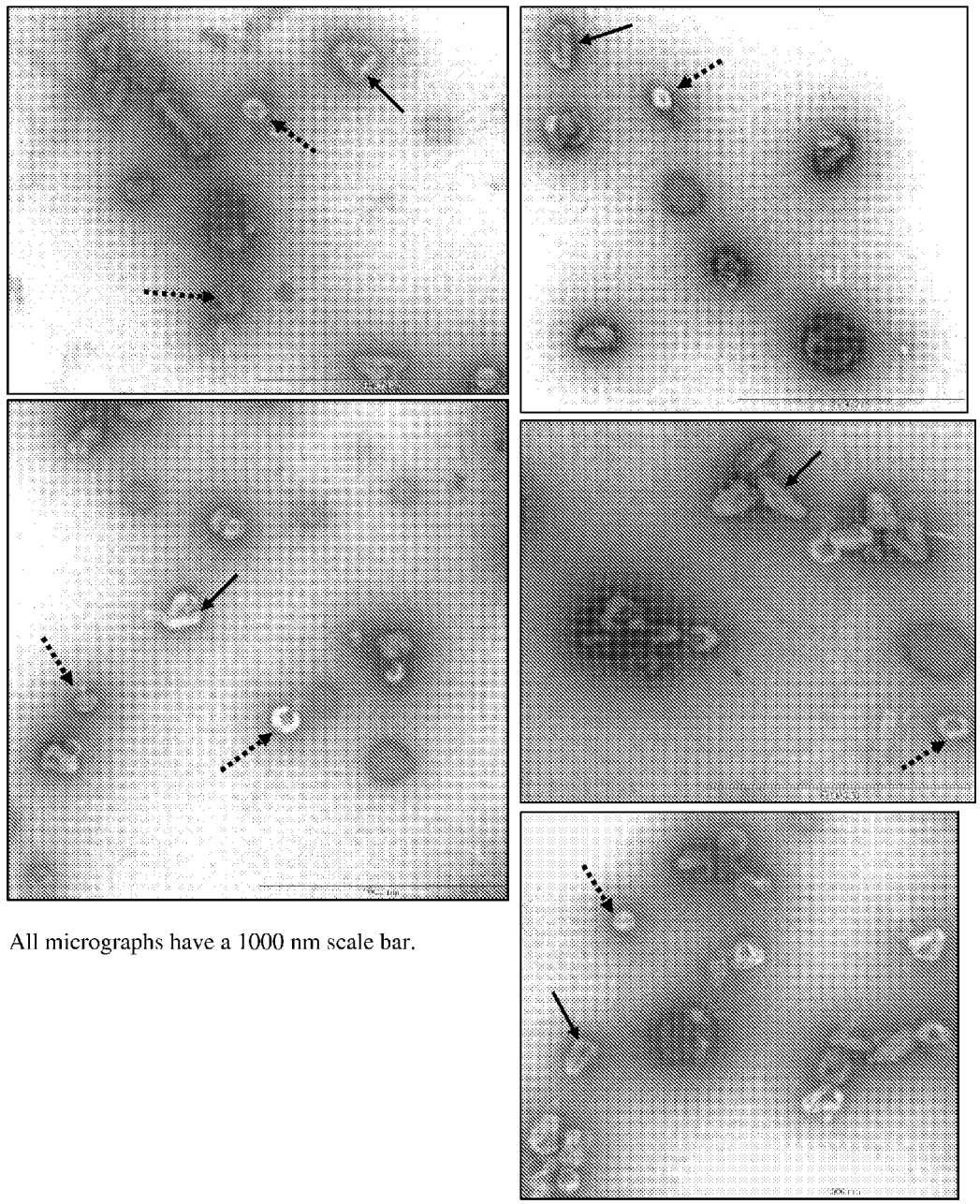
FIG. 30 shows five electron micrographs of Sample D: p3.1-HSVgD only transfected HEK 293F Ultracentrifuge (UC) pelleted material. All five micrographs have a 1000 nm scale bar. The solid line arrows point to large triangular or folded particles ~150-200 nm. The dashed line arrows point to smaller oval to round particles ~90-120 nm.

FIG. 30 reveals polymorphic, heterogeneously-sized particles formed by HSVgD transfectants in Sample D. Particle sizes for some of the shapes were as follows: large triangular or folded particles were 150 200 nm (black line arrows); smaller oval to round particles were 90-120 nm (black dotted line arrows). The finding of self-budded HSVgD glycoprotein particles shows behavior similar to results obtained with RSV F alone expression yielding polymorphic self-budded VLPs.

Figure 31:
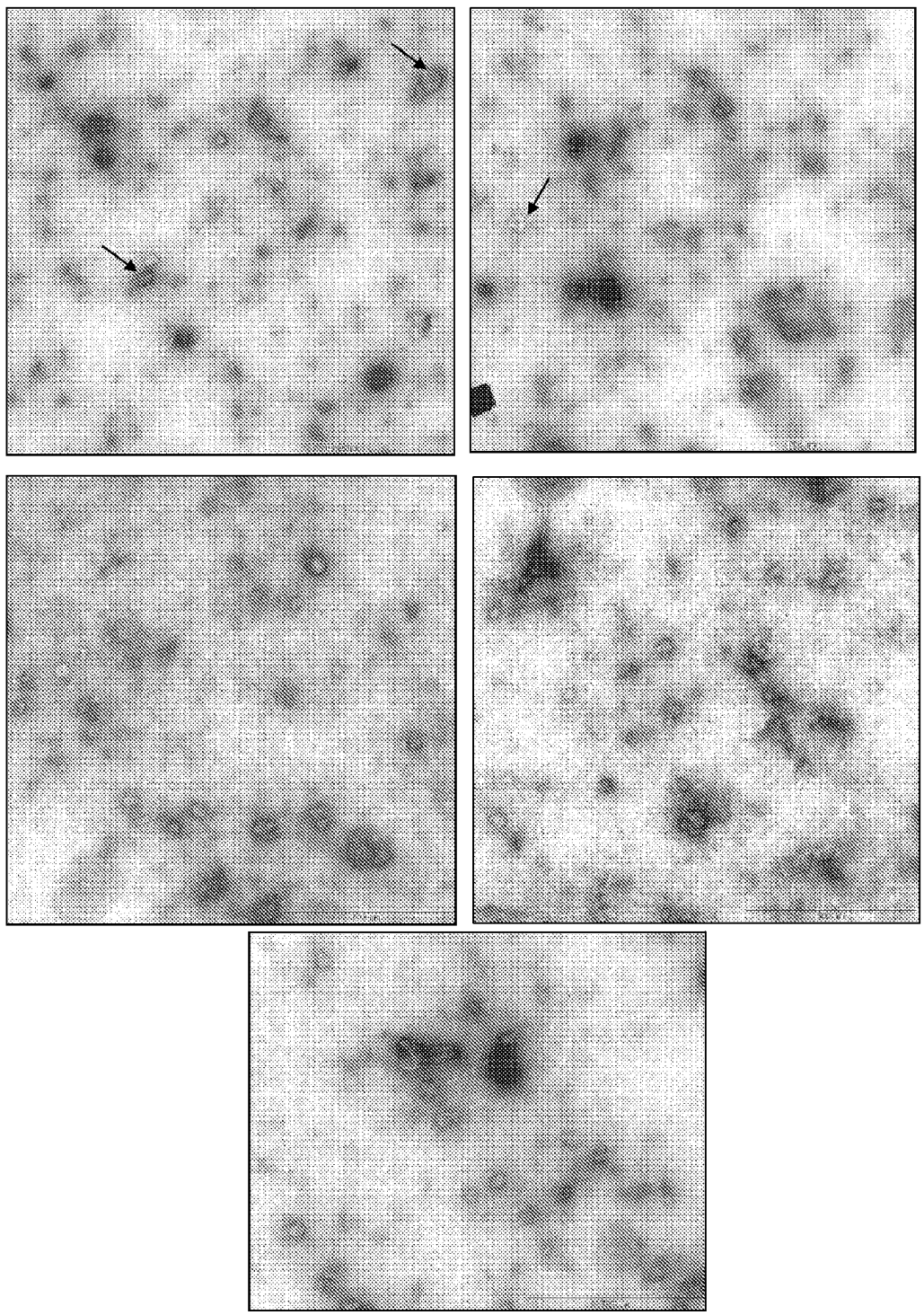
FIG. 31 shows five electron micrographs of Sample F: p3.1-HSVgD and p3.1-alvGAG-dPR (2.3:1) transfected HEK 293F Ultracentrifuge (UC) pelleted material. Top two micrographs have a 1000 scale bar.

FIG. 31 shows multiple photomicrographs from the Sample F transfection with HSVgD in combination with ALV Gag-dPR. Observation of particles showing a more-organized, rounded structure of even 30-50 nm (black arrows in top two micrographs containing the 1000 nm scale bar) was rare in Sample F. Most of the protein structures appeared disorganized and heterogeneous in sizes smaller than 30 nm. None of the material in Sample F was similar to VLPs observed in the ALV Gag alone or the HSVgD alone samples, despite viewing over 20 EM fields of view during sample screening.

The lack of VLP production in Sample F was not expected from at least two perspectives. First, the fact that neither HSVgD nor ALV Gag continued to make their independent VLP structures when the proteins were expressed together in the same host cell is counter-intuitive, especially when ELISA and Western blot data indicate substantial expression of each protein in sedimented material. Second, one might anticipate that the self-budding behavior of HSVgD alone would categorize it with RSV F, and that pseudotyping HSVgD onto ALV GAG-dPR VLPs would be as successful as with RSV F in mammalian host cells as presented in the above examples. These data illustrate the complexities and unexpected incompatibilities in pseudotyping viral glycoproteins onto retroviral Gag cores.

Example 12

Pseudotyped SIV Gag+RSV F VLPs

This example demonstrates that a vector encoding the Gag gene product of simian immunodeficiency virus (African green monkey) (SIVagm) substituted for HIV Gag for the formation of chimeric VLPs containing RSV F. SIVagm is also a member of the lentivirus family.

Materials and Methods

Figure 32:
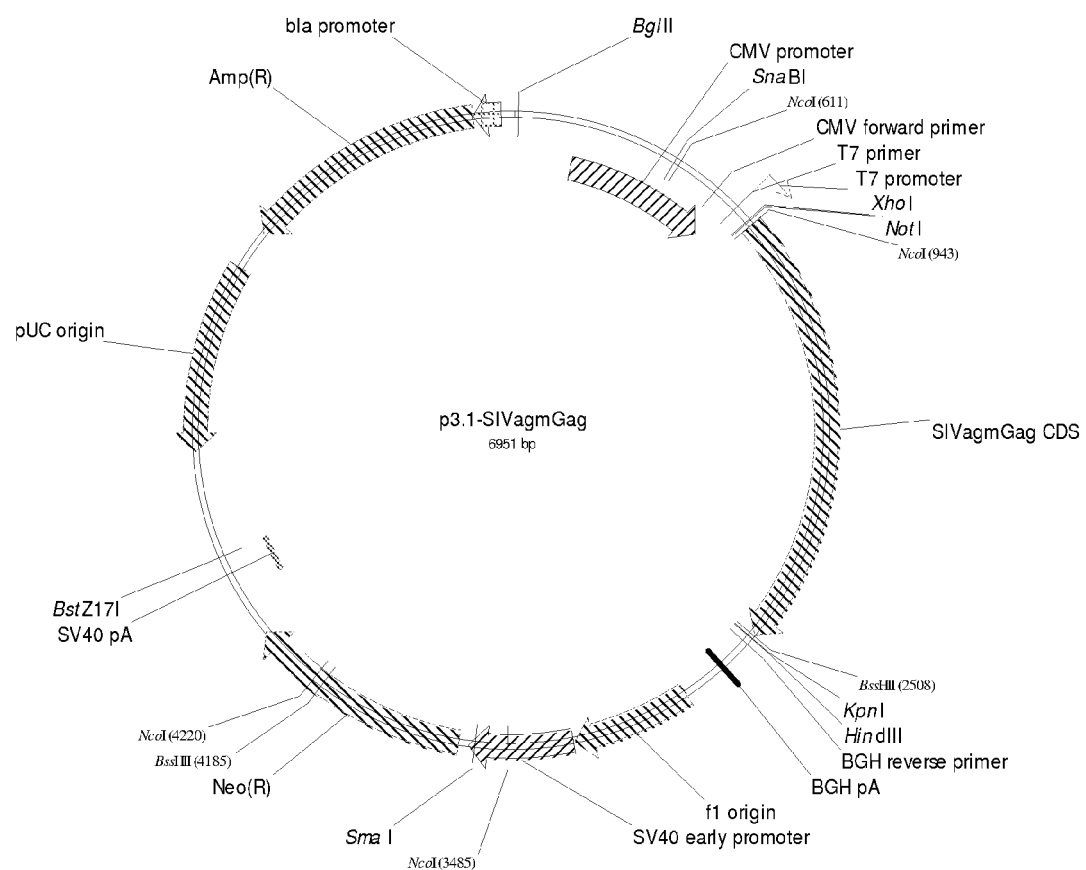
FIG. 32 shows the map of p3.1-SIVagmGag.

FIG. 32 shows a map of the plasmid p3.1-SIVagmGag. The synthetic coding sequence for SIVagm Gag is as follows:

```
                                          (SEQ ID NO: 26)
atgggtgctgctacctccgctctgaaccgtcgtcagctggaccagttcga gaagatccgtctgcgtcccaacggcaagaagaagtaccagatcaagcacc tgatctgggctggcaaggaaatggaacgtttcggtctgcacgagcgtctg ctggaaaccgaggaaggttgcaagcgtatcatcgaggtgctgtaccccct ggaacccaccggttccgagggcctgaagtccctgttcaacctcgtgtgcg tgctgtactgcctgcacaaggaacagaaggtcaaggacaccgaggaagct gtggctaccgtccgtcagcactgccacctggtggagaaggaaaagtccgc taccgagacttcctccggccagaagaagaacgacaagggtatcgctgctc ccctggtggttcccagaacttccccgcccagcagcagggaaacgcttgg gtgcacgtgcctctgtcccccgtactctgaacgcctgggtcaaggctgt ggaggaaaagaagttcggcgctgagatcgtgcccatgttccaggctctgt ccgagggttgcactccctacgacatcaaccagatgctgaacgtgctgggt gaccaccagggtgctctgcagatcgtgaaggaaatcatcaacgaagaggc tgctcagtgggacgtgacccaccctctgcctgctggtcctctgccagccg gccagctgcgtgaccctcgtggttccgacatcgctggcaccacctcttcc gtgcaagagcagctggaatggatctacaccgctaaccccgtgtggacgt gggcgctatctaccgtcgttggatcatcctgggtctgcaaaagtgcgtga agatgtacaaccctgtgtccgtgctggacatccgtcagggtcccaaggaa cccttcaaggactacgtggaccgcttctacaaggctatccgtgccgagca ggcttccggcgaggtcaagcagtggatgaccgagtccctgctgatccaga acgctaaccccgactgcaaggtcatcctgaagggcctgggcatgcacccc accctggaagagatgctgaccgcttgccagggtgtcggtggtccctccta caaggccaaggtcatggctgagatgatgcagaccatgcagaaccagaaca tggtgcagcagggtggtcccaagcgtcagcgtcccctctgcgttgctac aactgcggcaagttcggtcacatgcagcgccagtgccctgagcctcgcaa gaccaagtgcctgaagtgcggaaagctgggtcacctggctaaggactgcc gtggtcaagtgaacttcctggggttacggtcgttggatgggtgccaagccc cgtaacttccctgctgctaccctgggtgccgagccttctgctcccctcc ccctccggtactaccccctacgacccgctaagaagctgctccagcagt acgctgagaagggcaagcagctgcgcgagcagaagcgtaaccccctgct atgaaccctgactggaccgaggtacagcctgaactctctgttcggcga ggaccagtaa
```

The amino acid sequence of SIVagmGag encoded by p3.1-SIVagmGag is as follows:

```
                                          (SEQ ID NO: 27)
mgaatsalnrrqldqfekirlrpngkkkyqikhliwagkemerfglherl leteegckriievlypleptgseglkslfnlvcvlyclhkeqkvkdteea vatvrqhchlvekeksatetssgqkkndkgiaappggsqnfpaqqqgnaw vhvplsprtlnawvkaveekkfgaeivpmfqalsegctpydinqmlnvlg dnqgalqivkeiineeaaqwdvthplpagplpagqlrdprgsdiagttss vqeqlewiytanprvdvgaiyrrwiilglqkcvkmynpvsvldirqgpke pfkdyvdrfykairaeqasgevkqwmteslliqnanpdckvilkglgmhp tleemltacqgvggpsykakvmaemmqtmqnqnmvqqggpkrqrpplrcy ncgkfghmqrqcpeprktkclkcgklghlakdcrgqvnflgygrwmgakp rnfpaatlgaepsappppsgttpydpakkllqqyaekgkqlreqkrnppa mnpdwtegyslnslfgedq*
```

Eight T175 flasks of 293F cells were transfected with p3.1-SIVagmGag and p3.1-RSVFT at a ratio of 3:1 (Gag-to-F) using LIPOFECTAMINE™ 2000. Approximately 8 hours post-transfection the transfection medium (DMEM+10% FBS) was replaced with CD293 medium. Seventy-two hours post-transfection the growth medium was collected, clarified of debris and centrifuged at 100,000×g for 1 hour at 10° C. through a 20% sucrose cushion to pellet VLPs. The VLP pellet was resuspended in TBS then layered onto a 20-60% sucrose step gradient and centrifuged at 100,000×g for 1 hour at 10° C. Gradient fractions were analyzed by SDS-PAGE to identify Gag-containing fractions. Peak Gag-containing fractions were pooled, sucrose was diluted two-fold with TBS, and VLPs were concentrated by centrifugation once again at 100,000×g for 1 hour at 10° C. then resuspended in TBS for analysis by ELISA using the Synagis monoclonal antibody (Palivizumab).

Results

Figure 33:
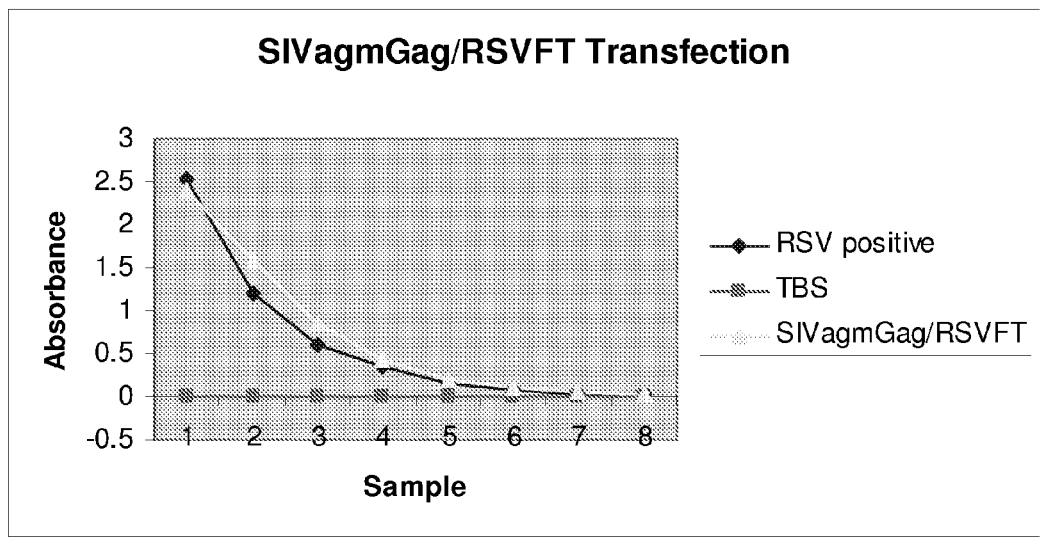
FIG. 33 shows ELISA detection of F antigen in VLPs released from 293 F cells following transfection with plasmids encoding SIVagmGag and RSVFT.

ELISA data are shown in FIG. 33 in which the sucrose-banded VLPs elicited a signal similar to that of live RSV virus in their reactivity to the Synagis antibody. These data are similar to the example above employing the p3.1-HIVGag expression vector demonstrating the SIVagm Gag can substitute for HIV Gag for the generation of F-containing chimeric VLPs.

Example 13

Pseudotyped RSV F+ALV Gag VLP Production via Adenovirus Vector Transduction

The preparation of RSV F-pseudotyped VLPs via plasmid transfection of HEK293 cells does not result in large yields of VLPs which is likely due to the inability to achieve the delivery of a sufficient number of plasmid DNA copies into a sufficient number of cells to induce robust Gag and F expression and subsequent VLP formation. To correct this deficiency, in this example, the ALV Gag and RSV F genes were inserted into a replication-defective, recombinant adenovirus vector in order to achieve the high efficiency transduction of Gag and F coding sequences into an appropriate VLP production cell line such as Vero cells. The derivation of the recombinant adenovirus vector is summarized below.

Because expression of the RSV F gene product in tissue culture cells is toxic, the inventors reasoned that the propagation of an RSV F-expressing recombinant adenovirus vector in an HEK293 helper cell line would be problematic in that F-induced toxicity would interfere with adenovirus vector propagation resulting in low virus yields. Similarly, the inventors also reasoned that if F gene expression was inhibited in the cell line used to propagate the adenovirus vector, then sufficient quantities of the viral vector could be produced to allow for subsequent transduction of a suitable cell line for VLP production.

Materials and Methods

Figure 34:
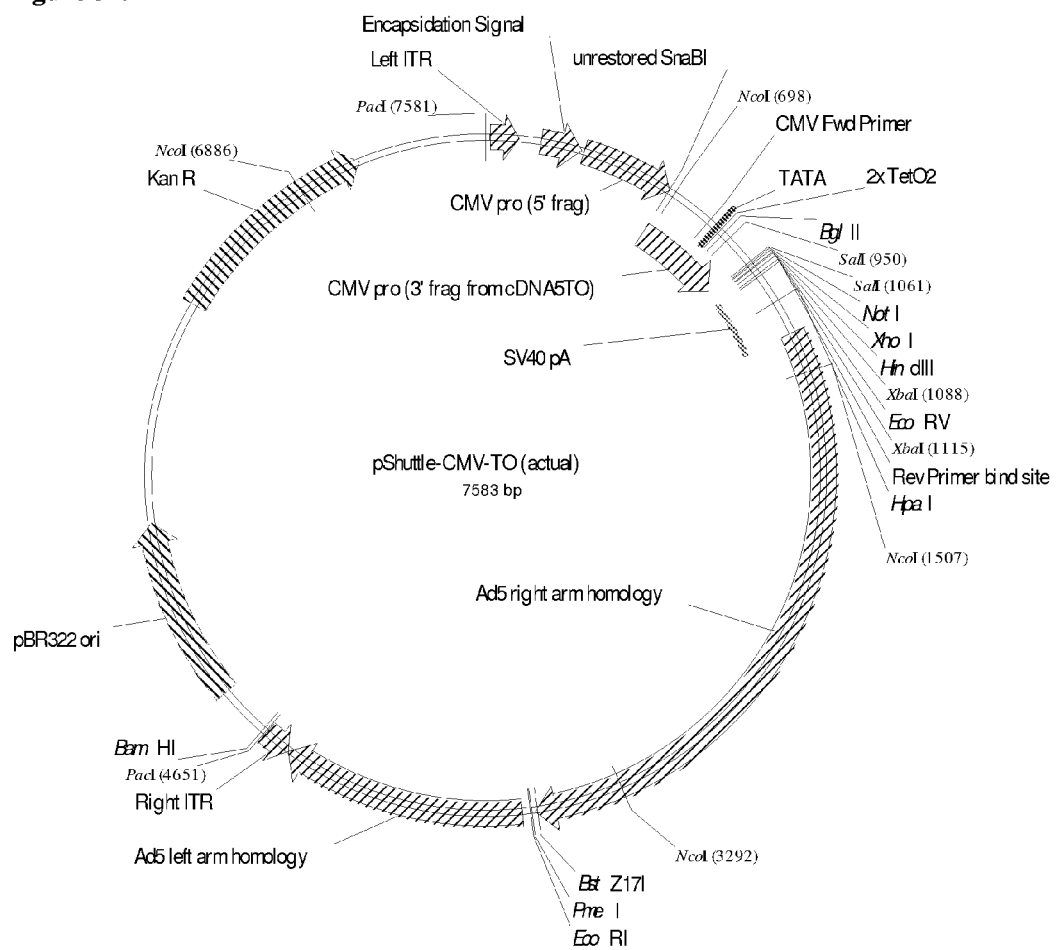

To achieve the inhibition of RSV F expression in an adenovirus vector during vector propagation, the adenovirus shuttle vector pShuttle-CMV, which is used to derive replication-defective adenovirus vectors, was modified by insertion of two copies of the tetracycline operator sequence into its CMV promoter. This strategy was designed to cause the inhibition of F expression when an F-containing adenovirus vector is propagated on an HEK293-based helper cell line expressing the tetracycline repressor. The modified shuttle vector was named pShuttle-CMV-TO and the functional map of this vector is shown in FIG. 34 and the sequence of this vector is as follows:

(SEQ ID NO: 28)
catcatcaataatataccttatttttggattgaagccaatatgataatgag ggggtggagtttgtgacgtggcgcggggcgtgggaacggggcgggtgacg tagtagtgtggcggaagtgtgatgttgcaagtgtggcggaacacatgtaa gcgacggatgtggcaaaagtgacgttttggtgtgcgccggtgtacacag gaagtgacaattttcgcgcggttttaggcggatgttgtagtaaatttggg cgtaaccgagtaagatttggccattttcgcgggaaaactgaataagagga -continued agtgaaatctgaataattttgtgttactcatagcgcgtaatactgtaata gtaatcaattacggggtcattagttcatagcccatatatggagttccgcg ttacataacttacggtaaatggcccgcctggctgaccgcccaacgacccc cgcccattgacgtcaataatgacgtatgttcccatagtaacgccaatagg gactttccattgacgtcaatgggtggagtatttacggtaaactgcccact tggcagtacatcaagtgtatcatatgccaagtacgcccctattgacgtc aatgacggtaaatggcccgcctggcattatgcccagtacatgaccttatg ggactttcctacttggcagtacatctagtattagtcatcgctattaccat ggtgatgcggttttggcagtacatcaatgggcgtggatagcggtttgact cacggggattttccaagtctccaccccattgacgtcaatgggagtttgttt tggcaccaaaatcaacgggactttccaaaatgtcgtaacaactccgcccc attgacgcaaatgggcggtaggcgtgtacggtgggaggtctatataagca gagctctccctatcagtgatagagatctccctatcagtgatagagatcgt cgacgagctcgtttagtgaaccgtcagatcgcctggagacgccatccacg ctgttttgacctccatagaagacaccgggaccgatccagcctccggactc tagcgtttcgtcgacgcggccgctcgagcctaagcttctagataagatat ccgatccaccggatctagataactgatcataatcagccataccacatttg tagaggttttacttgctttaaaaaacctcccacacctcccctgaacctg aaacataaaatgaatgcaattgttgttgttaacttgtttattgcagctta taatggttacaaataaagcaatagcatcacaaatttcacaaataaagcat ttttttcactgcattctagttgtggtttgtccaaactcatcaatgtatct taacgcggatctgggcgtggttaagggtgggaaagaatatataaggtggg ggtcttatgtagttttgtatctgttttgcagcagccgccgccgccatgag caccaactcgtttgatggaagcattgtgagctcatatttgacaacgcgca tgccccatgggcgggggtgcgtcagaatgtgatgggctccagcattgat ggtcgccccgtcctgcccgcaaactctactaccttgacctacgagaccgt gtctggaacgccgttggagactgcagcctccgccgccgcttcagccgctg cagccaccgcccgcgggattgtgactgactttgctttcctgagcccgctt gcaagcagtgcagcttccgttcatccgcccgcgatgacaagttgacggc tcttttggcacaattggattcttttgacccgggaacttaatgtcgtttctc agcagctgttggatctgcgccagcaggtttctgccctgaaggcttcctcc cctcccaatgcggtttaaaacataaataaaaaaccagactctgtttggat ttggatcaagcaagtgtcttgctgtctttatttaggggttttgcgcgcgc ggtaggcccgggaccagcggtctcggtcgttgagggtcctgtgtattttt tccaggacgtggtaaaggtgactctggatgttcagatacatgggcataag cccgtctctggggtggaggtagcaccactgcagagcttcatgctgcgggg tggtgttgtagatgatccagtcgtagcaggagcgctgggcgtggtgccta aaaatgtctttcagtagcaagctgattgccaggggcaggcccttggtgta agtgtttacaaagcggttaagctgggatgggtgcatacgtggggatatga gatgcatcttggactgtattttaggttggctatgttcccagccatatcc -continued

```
ctccggggattcatgttgtgcagaaccaccagcacagtgtatccggtgca
cttgggaaatttgtcatgtagcttagaaggaaatgcgtggaagaacttgg
agacgcccttgtgacctccaagattttccatgcattcgtccataatgatg
gcaatgggcccacgggcggcggcctgggcgaagatatttctgggatcact
aacgtcatagttgtgttccaggatgagatcgtcataggccattttacaa
agcgcgggcggagggtgccagactgcggtataatggttccatccggccca
ggggcgtagttaccctcacagatttgcatttcccacgctttgagttcaga
tggggggatcatgtctacctgcggggcgatgaagaaaacggtttccgggg
taggggagatcagctgggaagaaagcaggttcctgagcagctgcgactta
ccgcagccggtgggcccgtaaatcacacctattaccggctgcaactggta
gttaagagagctgcagctgccgtcatccctgagcaggggggccacttcgt
taagcatgtccctgactcgcatgttttccctgaccaaatccgccagaagg
cgctcgccgcccagcgatagcagttcttgcaaggaagcaaagttttcaa
cggtttgagaccgtccgccgtaggcatgcttttgagcgtttgaccaagca
gttccaggcggtcccacagctcggtcacctgctctacggcatctcgatcc
agcatatctcctcgtttcgcggtttggggcggctttcgctgtacggcagt
agtcggtgctcgtccagacgggccagggtcatgtctttccacgggcgcag
ggtcctcgtcagcgtagtctgggtcacggtgaaggggtgcgctccgggct
gcgcgctggccagggtgcgcttgaggctggtcctgctggtgctgaagcgc
tgccggtcttcgccctgcgcgtcggccaggtagcatttgaccatggtgtc
atagtccagcccctccgcgcgtggcccttggcgcgcagcttgcccttgg
aggaggcgccgcacgagggcagtgcagacttttgagggcgtagagcttg
ggcgcgagaaataccgattccggggagtaggcatccgcgccgcaggcccc
gcagacggtctcgcattccacgagccaggtgagctctggccgttcggggt
caaaaaccaggtttcccccatgcttttgatgcgtttcttacctctggtt
tccatgagccggtgtccacgctcggtgacgaaaaggctgtccgtgtcccc
gtatacagacttgagagggagtttaaacgaattcaatagcttgttgcatg
ggcggcgatataaaatgcaaggtgctgctcaaaaaatcaggcaaagcctc
gcgcaaaaagaaagcacatcgtagtcatgctcatgcagataaaggcagg
taagctccggaaccaccacagaaaaagacaccatttttctctcaaacatg
tctgcgggtttctgcataaacacaaataaaataacaaaaaacatttaa
acattagaagcctgtcttacaacaggaaaaacaacccttataagcataag
acggactacggccatgccggcgtgaccgtaaaaaaactggtcaccgtgat
taaaaagcaccaccgacagctcctcggtcatgtccggagtcataatgtaa
gactcggtaaacacatcaggttgattcacatcggtcagtgctaaaaagcg
accgaaatagcccggggaatacatacccgcaggcgtagagacaacatta
cagcccccataggaggtataacaaaattaataggagagaaaaacataa
acacctgaaaaaccctcctgcctaggcaaaatagcacccttcccgctccag
aacaacatacagcgcttccacagcggcagccataacagtcagccttacca
gtaaaaagaaaacctattaaaaaaacaccactcgacacggcaccagctc
```

-continued

```
aatcagtcacagtgtaaaaaagggccaagtgcagagcgagtatatatagg
actaaaaaatgacgtaacggttaaagtccacaaaaaacacccagaaaacc
gcacgcgaacctacgcccagaaacgaaagccaaaaaacccacaacttcct
caaatcgtcacttccgttttcccacgttacgtcacttccatttttaagaa
aactacaattcccaacacatacaagttactccgccctaaaacctacgtca
cccgcccgttcccacgccccgcgccacgtcacaaactccaccccctcat
tatcatattggcttcaatccaaaataaggtatattattgatgatgttaat
taacatgcatggatccatatgcggtgtgaaataccgcacagatgcgtaag
gagaaaataccgcatcaggcgctcttccgcttcctcgctcactgactcgc
tgcgctcggtcgttcggctgcggcgagcggtatcagctcactcaaaggcg
gtaatacggttatccacagaatcagggggataacgcaggaaagaacatgtg
agcaaaaggccagcaaaaggccaggaaccgtaaaaaggccgcgttgctgg
cgttttccataggctccgcccccctgacgagcatcacaaaaatcgacgc
tcaagtcagaggtggcgaaacccgacaggactataaagataccaggcgtt
tccccctggaagctccctcgtgcgctctcctgttccgaccctgccgctta
ccggatacctgtccgcctttctcccttcgggaagcgtggcgctttctcat
agctcacgctgtaggtatctcagttcggtgtaggtcgttcgctccaagct
gggctgtgtgcacgaaccccccgttcagcccgaccgctgcgccttatccg
gtaactatcgtcttgagtccaacccggtaagacacgacttatcgccactg
gcagcagccactggtaacaggattagcagagcgaggtatgtaggcggtgc
tacagagttcttgaagtggtggcctaactacggctacactagaaggacag
tatttggtatctgcgctctgctgaagccagttaccttcggaaaaagagtt
ggtagctcttgatccggcaaacaaaccaccgctggtagcggtggttttttt
tgtttgcaagcagcagattacgcgcagaaaaaaaggatctcaagaagatc
ctttgatcttttctacggggtctgacgctcagtggaacgaaaactcacgt
taagggattttggtcatgagattatcaaaaaggatcttcacctagatcct
tttaaattaaaaatgaagttttaaatcaatctaaagtatatatgagtaaa
cttggtctgacagttaccaatgcttaatcagtgaggcacctatctcagcg
atctgtctatttcgttcatccatagttgcctgactccccgtcgtgtagat
aactacgatacgggagggcttaccatctggccccagtgctgcaatgatac
cgcgagacccacgctcaccggctccagatttatcagcaataaaccagcca
gccggaagggccgagcgcagaagtggtcctgcaactttatccgcctccat
ccagtctattaattgttgccgggaagctagagtaagtagttcgccagtta
atagtttgcgcaacgttgttgccattgctgcagccatgagattatcaaaa
aggatcttcacctagatccttttcacgtagaaagccagtccgcagaaacg
gtgctgaccccggatgaatgtcagctactgggctatctggacaaggaaa
acgcaagcgcaaagagaaagcaggtagcttgcagtgggcttacatggcga
tagctagactgggcggttttatggacagcaagcgaaccggaattgccagc
tggggcgccctctggtaaggttgggaagccctgcaaagtaaactggatgg
cttttcttgccgccaaggatctgatggcgcaggggatcaagctctgatcaa
```

```
gagacaggatgaggatcgtttcgcatgattgaacaagatggattgcacgc
aggttctccggccgcttgggtggagaggctattcggctatgactgggcac
aacagacaatcggctgctctgatgccgccgtgttccggctgtcagcgcag
gggcgcccggttcttttttgtcaagaccgacctgtccggtgccctgaatga
actgcaagacgaggcagcgcggctatcgtggctggccacgacgggcgttc
cttgcgcagctgtgctcgacgttgtcactgaagcgggaagggactggctg
ctattgggcgaagtgccggggcaggatctcctgtcatctcaccttgctcc
tgccgagaaagtatccatcatggctgatgcaatcggcggctgcatacgc
ttgatccggctacctgcccattcgaccaccaagcgaaacatcgcatcgag
cgagcacgtactcggatggaagccggtcttgtcgatcaggatgatctgga
cgaagagcatcaggggctcgcgccagccgaactgttcgccaggctcaagg
cgagcatgcccgacggcgaggatctcgtcgtgacccatggcgatgcctgc
ttgccgaatatcatggtggaaaatggccgcttttctggattcatcgactg
tggccggctgggtgtggcgaccgctatcaggacatagcgttggctaccc
gtgatattgctgaagagcttggcggcgaatgggctgaccgcttcctcgtg
ctttacggtatcgccgctcccgattcgcagcgcatcgccttctatcgcct
tcttgacgagttcttctgaattttgttaaaattttgttaaatcagctca
tttttaaccaataggccgaaatcggcaccatcccttataaatcaaaaga
atagaccgagatagggttgagtgttgttccagtttggaacaagagtccac
tattaaagaacgtggactccaacgtcaaagggcgaaaaaccgtctatcag
ggcgatggcccactacgtgaaccatcaccctaatcaagttttttgtggtc
gaggtgccgtaaagcactaaatcggaaccctaaagggagccccgattta
gagcttgacggggaaagccggcgaacgtggcgagaaaggaagggaagaaa
gcgaaaggagcgggcgctagggcgctggcaagtgtagcggtcacgctgcg
cgtaaccaccacacccgcgcgcttaatgcgccgctacagggcgcgtccat
tcgccattcaggatcgaattaattcttaattaa
```

Figure 35:
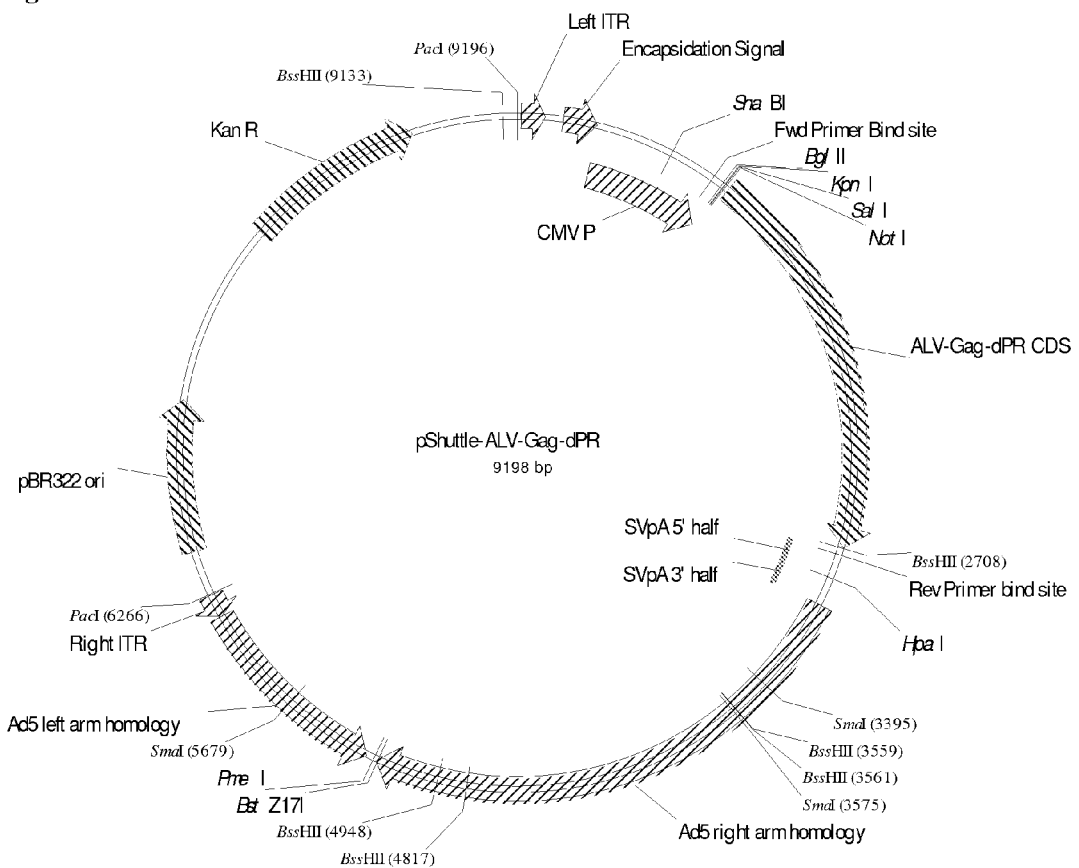
FIG. 35 shows the plasmid map of pShuttle-ALV-Gag-dPR.

To develop a replication-defective, recombinant adenovirus vector containing both Gag and F, the protease-deleted version of the ALV Gag gene was first inserted into pShuttle-CMV and the RSV F gene was inserted into pShuttle-CMV-TO resulting in the new plasmids pShuttle-ALV Gag-dPR and pShuttle-TO-FL, respectively. The plasmid map of pShuttle-ALV-Gag-dPR is shown in FIG. 35 and its sequence is as follows:

(SEQ ID NO: 29)
```
catcatcaataatataccttatttggattgaagccaatatgataatgag
ggggtggagtttgtgacgtggcgcggggcgtgggaacggggcgggtgacg
tagtagtgtggcggaagtgtgatgttgcaagtgtggcggaacacatgtaa
gcgacggatgtggcaaaagtgacgttttggtgtgcgccggtgtacacag
gaagtgacaattttcgcgcggttttaggcggatgttgtagtaaatttggg
cgtaaccgagtaagatttggccattttcgcgggaaaactgaataagagga
agtgaaatctgaataattttgtgttactcatagcgcgtaatactgtaata
gtaatcaattacgggtcattagttcatagcccatatatggagttccgcg
ttacataacttacggtaaatggcccgcctggctgaccgcccaacgaccc
cgcccattgacgtcaataatgacgtatgttcccatagtaacgccaatagg
gactttccattgacgtcaatgggtggagtatttacggtaaactgcccact
tggcagtacatcaagtgtatcatatgccaagtacgccccctattgacgtc
aatgacggtaaatggcccgcctggcattatgcccagtacatgaccttatg
ggactttcctacttggcagtacatctacgtattagtcatcgctattacca
tggtgatgcggttttggcagtacatcaatgggcgtggatagcggtttgac
tcacggggatttccaagtctccacccattgacgtcaatgggagtttgtt
ttggcaccaaaatcaacgggactttccaaaatgtcgtaacaactccgccc
cattgacgcaaatgggcggtaggcgtgtacggtgggaggtctatataagc
agagctggtttagtgaaccgtcagatccgctagagatctggtaccgtcga
cgcggccgccccctccaccatggaagctgtgatcaaggtcatctcctccg
cttgcaagacctactgcgcgcaagacctccccctccaagaaagaaatcgt
gctatgctgtccctgctgcagaaagagggcctgctgatgtcccctccga
cctgtactcccccggttcctgggaccctatcaccgctgctctgtcccagc
gtgctatgatcctgggcaagtccggcgaactcaagacctggggcctggtg
ctgggctctgaaggctgctcgcgaggaacaagtgacctccgagcaggc
taagttctggctgggtctgggtggtggtcgtgtgtccccccctggtcccg
agtgcatcgagaagcccgctaccgagcgtcgtatcgacaagggcgaggaa
gtgggcgagactaccgtgcagcgtgacgctaagatggctcccgaggaaac
cgctaccccaagaccgtgggccacctcctgctaccactgcggcaccgcta
tcggttgcaactgcgctaccgcttccgctccccccctccttacgtgggc
tccggcctgtaccttccctggctggtgtcggcgagcagcaaggacaggg
tggagacacccctcccggtgctgaacagtcccgtgccgagcctggtcacg
ctggtcaagctcccggtcccgctctgactgactgggctcgtgtgcgtgag
gaactggcttccaccggtcccctgtggtggctatgcccgtggtcatcaa
gaccgagggtcccgcttggacccccctggaacccaagctgatcaccgtc
tggctgacaccgtgcgtaccaagggcctgcgttcccaatcaccatggct
gaggtggaggctctgatgtcctccccctgctgcctcacgacgtgaccaa
cctgatgcgtgtgatcctgggtcccgctccctacgctctgtggatggacg
cttggggcgtgcagctgcagaccgtgatcgctgctgctaccgtgacccc
cgtcacctgctaacggacagggtcgtggcgagcgtaccaacctgaaccg
tctgaagggcctggctgacggcatggtcggcaaccctcagggacaggctg
ctctgctgcgtcctggcgagctggtcgctatcaccgccagcgctctgcag
gctttccgtgaggtggcccgtttggccgaaccagctggtccctgggctga
catcatgcagggccccccgagtccttcgtggacttcgctaaccgtctga
tcaaggctgtggagggctccgacctccctccttccgctcgtgctcccgtg
atcatcgactgcttccgtcagaagtcccagcccgacatccagcagctgat
ccgtaccgctccctccaccctgactacccctggcgagatcatcaagtacg
```

-continued

```
tgctggaccgtcaaaagaccgctcccctgaccgaccaaggtatcgctgcc
gctatgtcctccgctatccagcccctgatcatggctgtcgtgaaccgcga
gagggacggacagaccggttccggtggtcgtgctcgtggcctgtgctaca
cttgcggttccccggtcactaccaggctcagtgccccaagaagcgcaag
tccggaaactcccgcgagcgctgccagctctgcaacggcatgggtcacaa
cgccaagcagtgccgcaagcgcgacggaaaccagggccagcgtcccggaa
agggactgtcctccggtccttggcctggtcctgagcccctgctgtgtcc
taataagcgcgcgatccgatccaccggatctagataactgatcataatca
gccataccacatttgtagaggttttacttgctttaaaaaacctcccacac
ctccccctgaacctgaaacataaaatgaatgcaattgttgttgttaactt
gtttattgcagcttataatggttacaaataaagcaatagcatcacaaatt
tcacaaataaagcatttttttcactgcattctagttgtggtttgtccaaa
ctcatcaatgtatcttaacgcggatctgggcgtggttaagggtgggaaag
aatatataaggtgggggtcttatgtagttttgtatctgttttgcagcagc
cgccgccgccatgagcaccaactcgtttgatggaagcattgtgagctcat
atttgacaacgcgcatgccccatgggccggggtgcgtcagaatgtgatg
ggctccagcattgatggtcgccccgtcctgcccgcaaactctactacctt
gacctacgagaccgtgtctggaacgccgttggagactgcagcctccgccg
ccgcttcagccgctgcagccaccgcccgcgggattgtgactgactttgct
ttcctgagcccgcttgcaagcagtgcagcttcccgttcatccgcccgcga
tgacaagttgacggctcttttggcacaattggattctttgacccgggaac
ttaatgtcgtttctcagcagctgttggatctgcgccagcaggtttctgcc
ctgaaggcttcctcccctcccaatgcggtttaaaacataaataaaaaacc
agactctgtttggatttggatcaagcaagtgtcttgctgtctttatttag
gggttttgcgcgcgcggtaggcccgggaccagcggtctcggtcgttgagg
gtcctgtgtattttttccaggacgtggtaaaggtgactctggatgttcag
atacatgggcataagcccgtctctggggtggaggtagcaccactgcagag
cttcatgctgcggggtggtgttgtagatgatccagtcgtagcaggagcgc
tgggcgtggtgcctaaaaatgtctttcagtagcaagctgattgccagggg
caggcccttggtgtaagtgtttacaaagcggttaagctgggatgggtgca
tacgtggggatatgagatgcatcttggactgtatttttaggttggctatg
ttcccagccatatccctccggggattcatgttgtgcagaaccaccagcac
agtgtatccggtgcacttgggaaatttgtcatgtagcttagaaggaaatg
cgtggaagaacttggagacgcccttgtgacctccaagattttccatgcat
tcgtccataatgatggcaatgggcccacgggcggcggcctgggcgaagat
atttctgggatcactaacgtcatagttgtgttccaggatgagatcgtcat
aggccatttttacaaagcgcgggcggagggtgccagactgcggtataatg
gttccatccggcccaggggcgtagttaccctcacagatttgcatttccca
cgctttgagttcagatggggggatcatgtctacctgcggggcgatgaaga
aaacggtttccggggtaggggagatcagctgggaagaaagcaggttcctg
```

```
agcagctgcgacttaccgcagccggtgggcccgtaaatcacacctattac
cggctgcaactggtagttaagagagctgcagctgccgtcatccctgagca
gggggggccacttcgttaagcatgtccctgactcgcatgttttccctgacc
aaatccgccagaaggcgctcgccgcccagcgatagcagttcttgcaagga
agcaaagttttttcaacggtttgagaccgtccgccgtaggcatgcttttga
gcgtttgaccaagcagttccaggcggtcccacagctcggtcacctgctct
acggcatctcgatccagcatatctcctcgtttcgcggggttggggcggctt
tcgctgtacggcagtagtcggtgctcgtccagacgggccagggtcatgtc
tttccacgggcgcagggtcctcgtcagcgtagtctgggtcacggtgaagg
ggtgcgctccgggctgcgcgctggccagggtgcgcttgaggctggtcctg
ctggtgctgaagcgctgccggtcttcgccctgcgcgtcggccaggtagca
tttgaccatggtgtcatagtccagccccctccgcggcgtggcccttggcgc
gcagcttgcccttggaggaggcgccgcacgaggggcagtgcagacttttg
agggcgtagagcttgggcgcgagaaataccgattccggggagtaggcatc
cgcgccgcaggccccgcagacggtctcgcattccacgagccaggtgagct
ctggccgttcggggtcaaaaaccaggtttcccccatgctttttgatgcgt
ttcttacctctggtttccatgagccggtgtccacgctcggtgacgaaaag
gctgtccgtgtccccgtatacagacttgagagggagtttaaacgaattca
atagcttgttgcatgggcggcgatataaaatgcaaggtgctgctcaaaaa
atcaggcaaagcctcgcgcaaaaaagaaagcacatcgtagtcatgctcat
gcagataaaggcaggtaagctccggaaccaccacagaaaaagacaccatt
ttttctctcaaacatgtctgcgggtttctgcataaacacaaaataaaataa
caaaaaaacatttaaacattagaagcctgtcttacaacaggaaaaacaac
ccttataagcataagacggactacggccatgccggcgtgaccgtaaaaaa
actggtcaccgtgattaaaaagcaccaccgacagctcctcggtcatgtcc
ggagtcataatgtaagactcggtaaacacatcaggttgattcacatcggt
cagtgctaaaaagcgaccgaaatagcccgggggaatacatacccgcaggc
gtagagacaacattacagcccccataggaggtataacaaaattaatagga
gagaaaaacacataaacacctgaaaaaccctcctgcctaggcaaaatagc
accctcccgctccagaacaacatacagcgcttccacagcggcagccataa
cagtcagccttaccagtaaaaagaaaacctattaaaaaaacaccactcg
acacggcaccagctcaatcagtcacagtgtaaaaaagggccaagtgcaga
gcgagtatatataggactaaaaaatgacgtaacggttaaagtccacaaaa
aacacccagaaaaccgcacgcgaacctacgcccagaaacgaaagccaaaa
aacccacaacttcctcaaatcgtcacttccgttttcccacgttacgtcac
ttcccattttaagaaaactacaattcccaacacatacaagttactccgcc
ctaaaacctacgtcacccgccccgttcccacgccccgcgccacgtcacaa
actccaccccctcattatcatattggcttcaatccaaaataaggtatatt
attgatgatgttaattaacatgcatggatccatatgcggtgtgaaatacc
gcacagatgcgtaaggagaaaataccgcatcaggcgctcttccgcttcct
```

-continued

```
cgctcactgactcgctgcgctcggtcgttcggctgcggcagcggtatca gctcactcaaaggcggtaatacggttatccacagaatcagggataacgc aggaaagaacatgtgagcaaaaggccagcaaaaggccaggaaccgtaaaa aggccgcgttgctggcgtttttccataggctccgcccccctgacgagcat cacaaaaatcgacgctcaagtcagaggtggcgaaacccgacaggactata aagataccaggcgtttccccctggaagctccctcgtgcgctctcctgttc cgaccctgccgcttaccggatacctgtccgcctttctcccttcgggaagc gtggcgctttctcatagctcacgctgtaggtatctcagttcggtgtaggt cgttcgctccaagctgggctgtgtgcacgaaccccccgttcagcccgacc gctgcgccttatccggtaactatcgtcttgagtccaacccggtaagacac gacttatcgccactggcagcagccactggtaacaggattagcagagcgag gtatgtaggcggtgctacagagttcttgaagtggtggcctaactacggct acactagaaggacagtatttggtatctgcgctctgctgaagccagttacc ttcggaaaaagagttggtagctcttgatccggcaaacaaaccaccgctgg tagcggtggtttttttgtttgcaagcagcagattacgcgcagaaaaaag gatctcaagaagatcctttgatcttttctacggggtctgacgctcagtgg aacgaaaactcacgttaagggattttggtcatgagattatcaaaaggat cttcacctagatccttttaaattaaaaatgaagttttaaatcaatctaaa gtatatatgagtaaacttggtctgacagttaccaatgcttaatcagtgag gcacctatctcagcgatctgtctatttcgttcatccatagttgcctgact ccccgtcgtgtagataactacgatacgggagggcttaccatctggcccca gtgctgcaatgataccgcgagacccacgctcaccggctccagatttatca gcaataaaccagccagccggaagggccgagcgcagaagtggtcctgcaac tttatccgcctccatccagtctattaattgttgccgggaagctagagtaa gtagttcgccagttaatagtttgcgcaacgttgttgccattgctgcagcc atgagattatcaaaaggatcttcacctagatccttttcacgtagaaagc cagtccgcagaaacggtgctgaccccggatgaatgtcagctactgggcta tctggacaagggaaaacgcaagcgcaaagagaaagcaggtagcttgcagt gggcttacatggcgatagctagactgggcggttttatggacagcaagcga accggaattgccagctggggcgccctctggtaaggttgggaagccctgca aagtaaactggatgctttcttgccgccaaggatctgatggcgcaggga tcaagctctgatcaagagacaggatgaggatcgtttcgcatgattgaaca agatggattgcacgcaggttctccggccgcttgggtggagaggctattcg gctatgactgggcacaacagacaatcggctgctctgatgccgccgtgttc cggctgtcagcgcaggggcgcccggttcttttgtcaagaccgacctgtc cggtgccctgaatgaactgcaagacgaggcagcgcggctatcgtggctgg ccacgacgggcgttccttgcgcagctgtgctcgacgttgtcactgaagcg ggaagggactggctgctattgggcgaagtgccggggcaggatctcctgtc atctcaccttgctcctgccgagaaagtatccatcatggctgatgcaatgc ggcggctgcatacgcttgatccggctacctgcccattcgaccaccaagcg aaacatcgcatcgagcgagcacgtactcggatggaagccggtcttgtcga tcaggatgatctggacgaagagcatcaggggctcgcgccagccgaactgt tcgccaggctcaaggcgagcatgcccgacggcgaggatctcgtcgtgacc catggcgatgcctgcttgccgaatatcatggtggaaaatggccgctttc tggattcatcgactgtggccggctgggtgtggcggaccgctatcaggaca tagcgttggctacccgtgatattgctgaagagcttggcggcgaatgggct gaccgcttcctcgtgctttacggtatcgccgctcccgattcgcagcgcat cgccttctatcgccttcttgacgagttcttctgaattttgttaaaatttt tgttaaatcagctcatttttttaaccaataggccgaaatcggcaccatccc ttataaatcaaaagaatagaccgagatagggttgagtgttgttccagttt ggaacaagagtccactattaaagaacgtggactccaacgtcaaagggcga aaaaccgtctatcagggcgatggcccactacgtgaaccatcaccctaatc aagttttttgtggtcgaggtgccgtaaagcactaaatcggaaccctaaag ggagcccccgatttagagcttgacggggaaagccggcgaacgtggcgaga aaggaagggaagaaagcgaaaggagcgggcgctagggcgctggcaagtgt agcggtcacgctgcgcgtaaccaccacacccgcgcgcttaatgcgccgct acagggcgcgtccattcgccattcaggatcgaattaattcttaattaa
```

Figure 36:
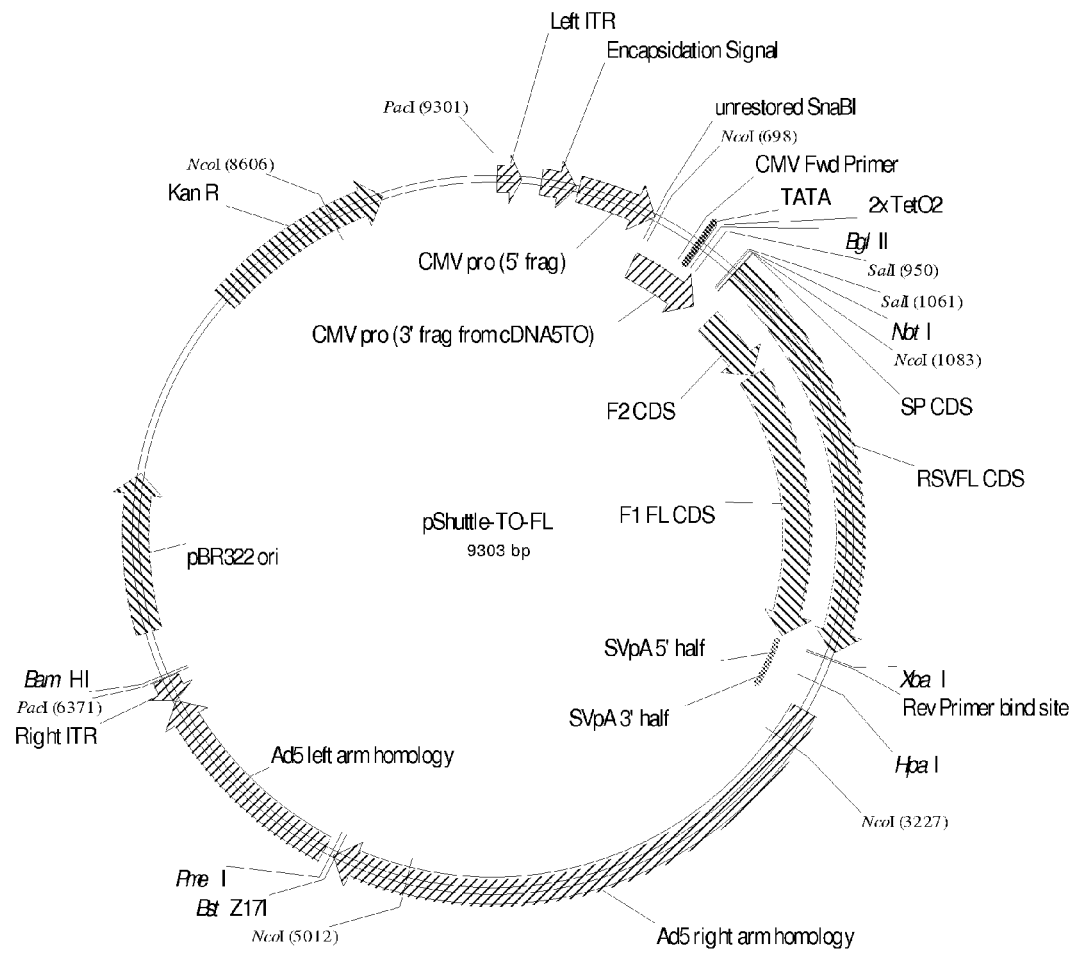
FIG. 36 shows the plasmid map of pShuttle-TO-FL.

The plasmid map of pShuttle-TO-FL is shown in FIG. 36 and its sequence is as follows:

```
                                   (SEQ ID NO: 30)
catcatcaataatataccttatttggattgaagccaatatgataatgag ggggtggagtttgtgacgtggcgcggggcgtgggaacggggcgggtgacg tagtagtgtggcggaagtgtgatgttgcaagtgtggcggaacacatgtaa gcgacggatgtggcaaaagtgacgttttggtgtgcgccggtgtacacag gaagtgacaattttcgcgcggttttaggcggatgttgtagtaaatttggg cgtaaccgagtaagatttggccatttcgcgggaaaactgaataagagga agtgaaatctgaataattttgtgttactcatagcgcgtaatactgtaata gtaatcaattacggggtcattagttcatagcccatatatggagttccgcg ttacataacttacggtaaatggcccgcctggctgaccgcccaacgacccc cgcccattgacgtcaataatgacgtatgttcccatagtaacgccaatagg gactttccattgacgtcaatgggtggagtatttacggtaaactgcccact tggcagtacatcaagtgtatcatatgccaagtacgccccctattgacgtc aatgacggtaaatggcccgcctggcattatgcccagtacatgaccttatg ggactttcctacttggcagtacatctagtattagtcatcgctattaccat ggtgatgcggttttggcagtacatcaatgggcgtggatagcggtttgact cacggggatttccaagtctccaccccattgacgtcaatgggagtttgttt tggcaccaaaatcaacgggactttccaaaatgtcgtaacaactccgcccc attgacgcaaatgggcggtaggcgtgtacggtgggaggtctatataagca gagctctccctatcagtgatagagatctccctatcagtgatagagatcgt cgacgagctcgtttagtgaaccgtcagatcgcctggagacgccatccacg
```

-continued ctgttttgacctccatagaagacaccgggaccgatccagcctccggactc
tagcgtttcgtcgacgcggccgccccttcaccatggagctgctgatcct
gaaggccaacgccatcaccaccatcctgaccgccgtgaccttctgcttcg
cctccggccagaacatcaccgaggagttctaccagtccacctgctccgcc
gtgtccaagggctacctgtccgccctgcggaccggctggtacacctccgt
gatcaccatcgagctgtccaacatcaaagaaaacaagtgcaacggcaccg
acgccaaggtgaagctgatcaagcaggagctggacaagtacaagaacgcc
gtgaccgagctgcagctgctgatgcagtccacccctgccaccaacaaccg
ggccaggcgggagctgcctcggttcatgaactacaccctgaacaacgcca
agaaaaccaacgtcaccctgtccaagaagcggaagcggcggttcctgggc
ttcctgctgggcgtgggctccgctatcgcctctggcgtggccgtgtctaa
ggtgctgcacctggagggcgaggtgaacaagatcaagtctgccctgctgt
ccaccaacaaggccgtggtgtccctgtccaacggcgtgtccgtgctgacc
tccaaggtgctggatctgaagaactacatcgacaagcagctgctgcctat
cgtgaacaagcagtcctgctccatctccaacatcgagacagtgatcgagt
ccagcagaagaacaaccggctgctggaaatcacaagagagttctccgtc
aacgctggtgtgaccactcctgtctctacttatatgctgaccaactccga
gctgctgtccctgatcaacgacatgcctatcaccaacgaccagaaaaagc
tgatgtccaacaacgtgcagatcgtgcggcagcagtcctactctatcatg
agcatcatcaaggaggaggtcctggcctacgtggtgcagctgcctctgta
cggcgtgatcgacacccctgctggaagctgcacacctccccctgtgca
ccaccaacaccaaggaggggctccaacatctgcctgacccggaccgaccgg
ggctggttctgcgacaacgccggctccgtgtccttctttccacaggccga
gacatgcaaggtgcagtccaaccgggtgttctgcgataccatgaactccc
tgaccctgccttccgaggtgaacctgtgcaacgtggacatcttcaaccct
aagtacgactgcaagatcatgacctctaagaccgacgtgtcctcctctgt
gatcaccctccctgggcgccatcgtgtcctgctacggcaagaccaagtgca
ccgcctccaacaagaaccggggaatcatcaagaccttctccaacggctgc
gactacgtgtccaataagggcgtggacaccgtgtccgtgggcaacacact
gtactacgtgaataagcaggagggcaagtctctgtacgtgaagggcgagc
ctatcatcaacttctacgaccctctggtgttcccttccgacgagttcgac
gcctccatcagccaggtgaacgagaagatcaaccagtccctggccttcat
ccggaagtccgacgagctgctgcacaacgtgaacgctggcaagtctacca
ccaacatcatgatcaccacaatcatcattgtcatcatcgtcatcctgctg
tctctgatcgccgtgggcctgctgctgtactgcaaggcccggtccaccc
cgtgaccctgagcaaggaccagctgtccggcatcaacaatatcgccttca
gcaactgatgagcgcgcgatccgatccaccggatctagataactgatcat
aatcagccataccacatttgtagaggttttacttgctttaaaaaacctcc
cacacctcccctgaacctgaaacataaaatgaatgcaattgttgttgtt
aacttgtttattgcagcttataatggttacaaataaagcaatagcatcac aaatttcacaaataaagcattttttttcactgcattctagttgtggtttgt
ccaaactcatcaatgtatcttaacgcggatctgggcgtggttaagggtgg
gaaagaatatataaggtgggggtcttatgtagttttgtatctgttttgca
gcagccgccgcgccatgagcaccaactcgtttgatggaagcattgtgag
ctcatatttgacaacgcgcatgccccatgggccggggtgcgtcagaatg
tgatgggctccagcattgatggtcgcccgtcctgcccgcaaactctact
accttgacctacgagaccgtgtctggaacgccgttggagactgcagcctc
cgccgcgcttcagccgctgcagccaccgcccgcggattgtgactgact
ttgctttcctgagcccgcttgcaagcagtgcagcttcccgttcatccgcc
cgcgatgacaagttgacggctcttttggcacaattggattctttgacccg
ggaacttaatgtcgtttctcagcagctgttggatctgcgccagcaggttt
ctgccctgaaggcttcctcccctcccaatgcggtttaaaacataaataaa
aaaccagactctgtttggatttggatcaagcaagtgtcttgctgtcttta
tttaggggttttgcgcgcgcggtaggcccgggaccagcggtctcggtcgt
tgagggtcctgtgtatttttttccaggacgtggtaaaggtgactctggatg
ttcagatacatgggcataagcccgtctctgggtggaggtagcaccactg
cagagcttcatgctgcggggtggtgttgtagatgatccagtcgtagcagg
agcgctgggcgtggtgcctaaaaatgtctttcagtagcaagctgattgcc
aggggcaggcccttggtgtaagtgtttacaaagcggttaagctgggatgg
gtgcatacgtggggatatgagatgcatcttggactgtatttttaggttgg
ctatgttcccagccatatccctccggggattcatgttgtgcagaaccacc
agcacagtgtatccggtgcacttgggaaatttgtcatgtagcttagaagg
aaatgcgtggaagaacttggagacgcccttgtgacctccaagattttcca
tgcattcgtccataatgatggcaatgggcccacgggcggcggcctgggcg
aagatatttctgggatcactaacgtcatagttgtgttccaggatgagatc
gtcataggccatttttacaaagcgcgggcggagggtgccagactgcggta
taatggttccatccggcccaggggcgtagttaccctcacagatttgcatt
tcccacgctttgagttcagatggggggatcatgtctacctgcggggcgat
gaagaaaacggtttccggggtaggggagatcagctgggaagaaagcaggt
tcctgagcagctgcgacttaccgcagccggtgggcccgtaaatcacacct
attaccggctgcaactggtagttaagagagctgcagctgccgtcatccct
gagcaggggggccacttcgttaagcatgtccctgactcgcatgttttccc
tgaccaaatccgccagaaggcgctcgccgcccagcgatagcagttcttgc
aaggaagcaaagttttttcaacggtttgagaccgtccgccgtaggcatgct
tttgagcgtttgaccaagcagttccaggcggtcccacagctcggtcacct
gctctacggcatctcgatccagcatatcctcgtttcgcgggttgggc
ggctttcgctgtacggcagtagtcggtgctcgtccagacgggccagggtc
atgtctttccacgggcgcagggtcctcgtcagcgtagtctgggtcacggt
gaagggtgcgctccgggctgcgcgctggccagggtgcgcttgaggctgg
tcctgctggtgctgaagcgctgccggtcttcgccctgcgcgtcggccagg

Figure 37:
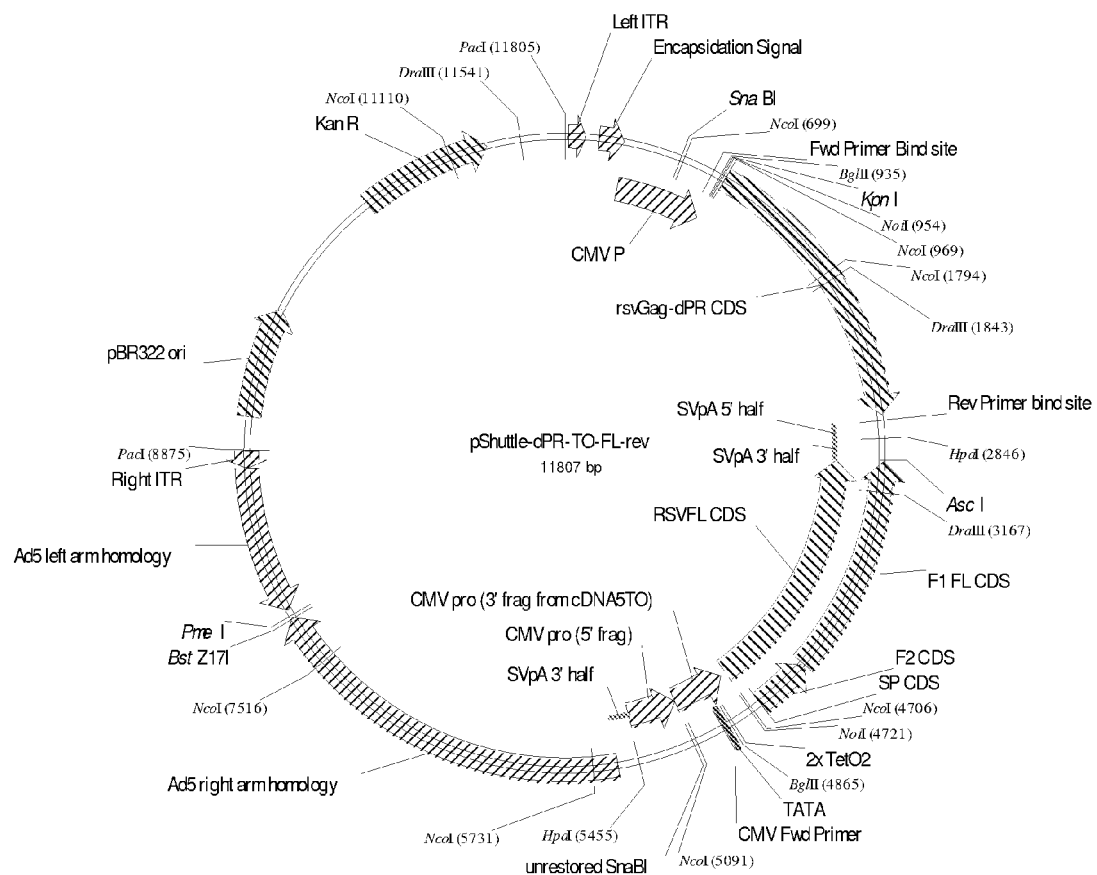
FIG. 37 shows the plasmid map of pShuttle-dPR-TO-FL-rev.
Figure 38:
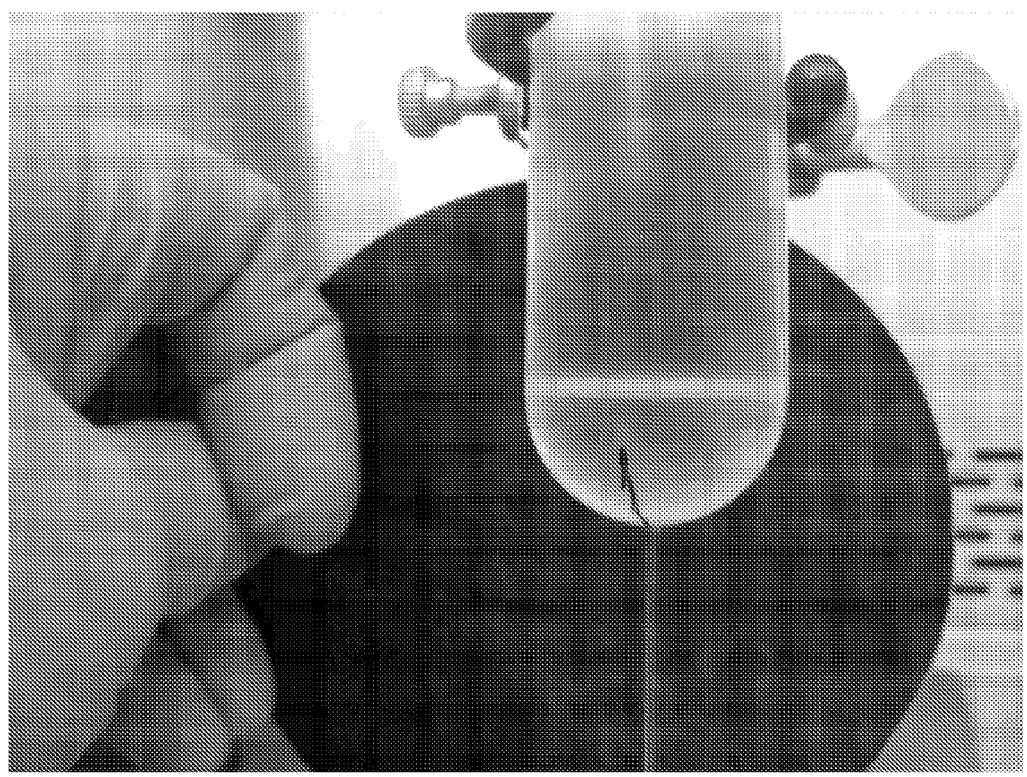
FIG. 38 shows (a) the visible band of RSV F-pseudotyped VLPs collected between the 30% and 60% steps of a sucrose step gradient and (b) SDS-PAGE analysis of purified RSV F-pseudotyped VLPs produced via adenovirus vector transduction of Vero cells.
Figure 38:
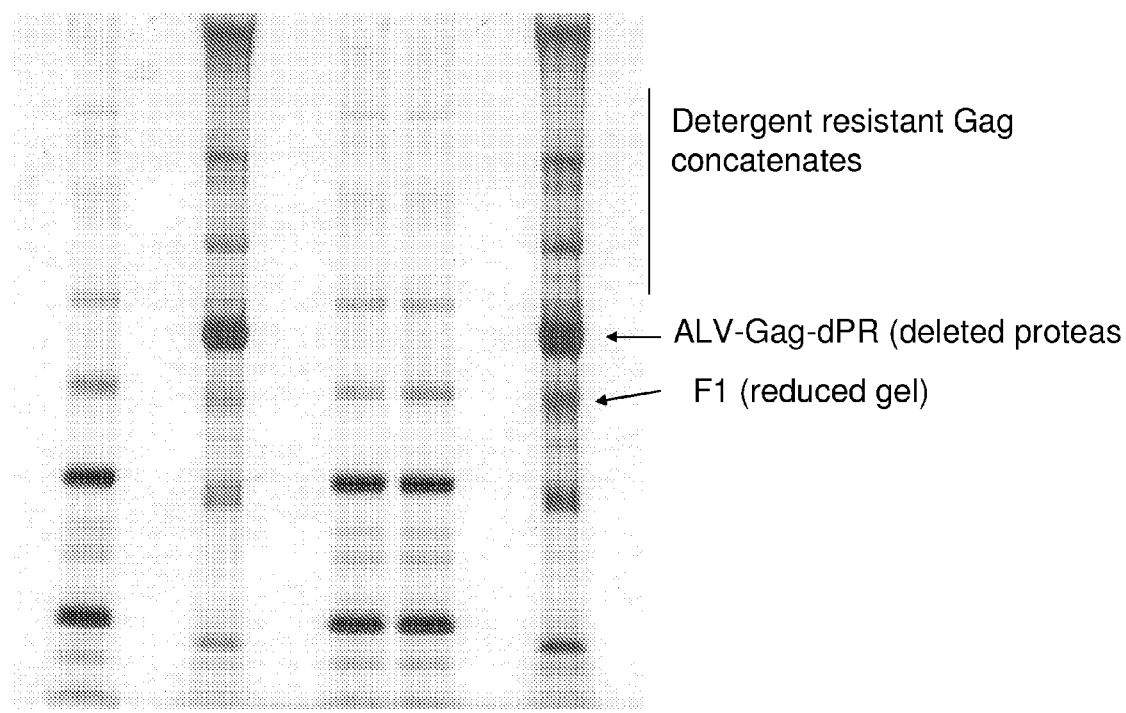
Figure 39:
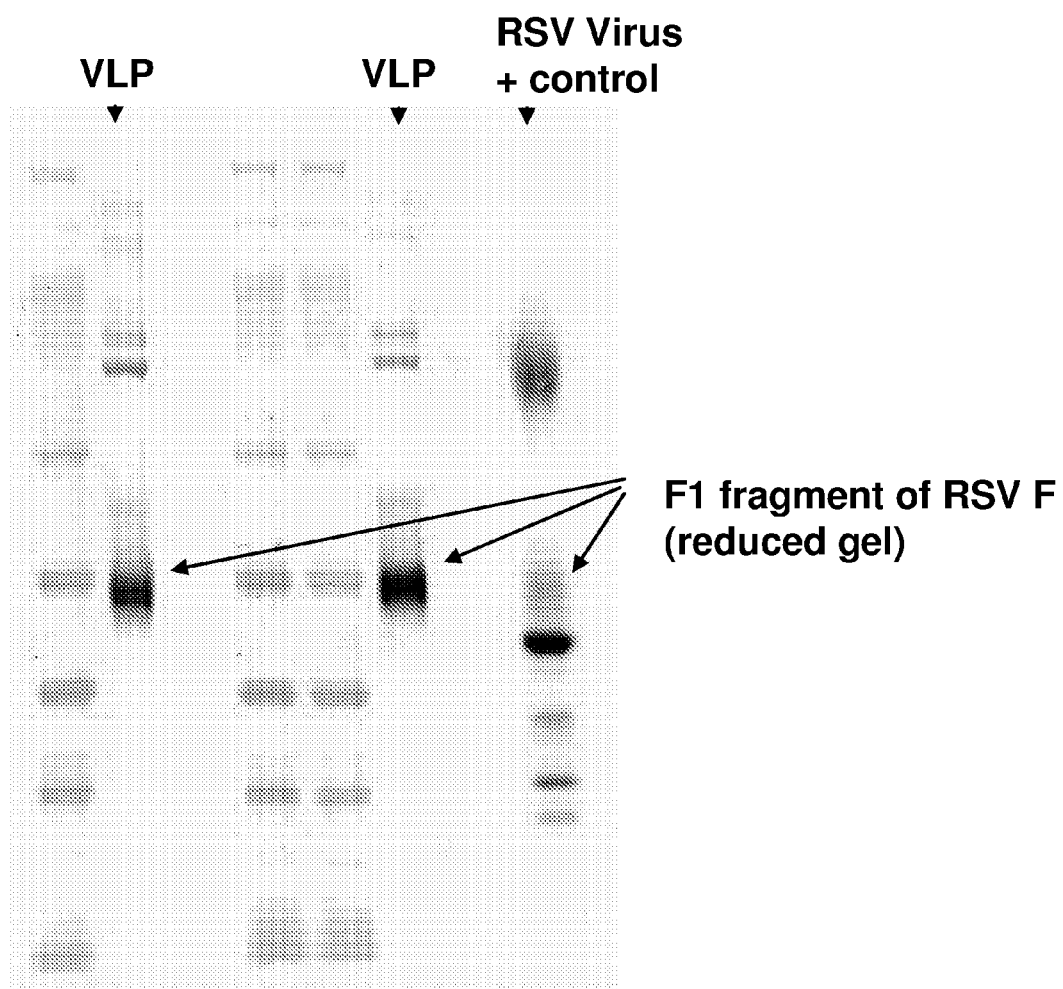
FIG. 39 shows the Western blot of VLPs showing presence of F antigen.
Figure 40:
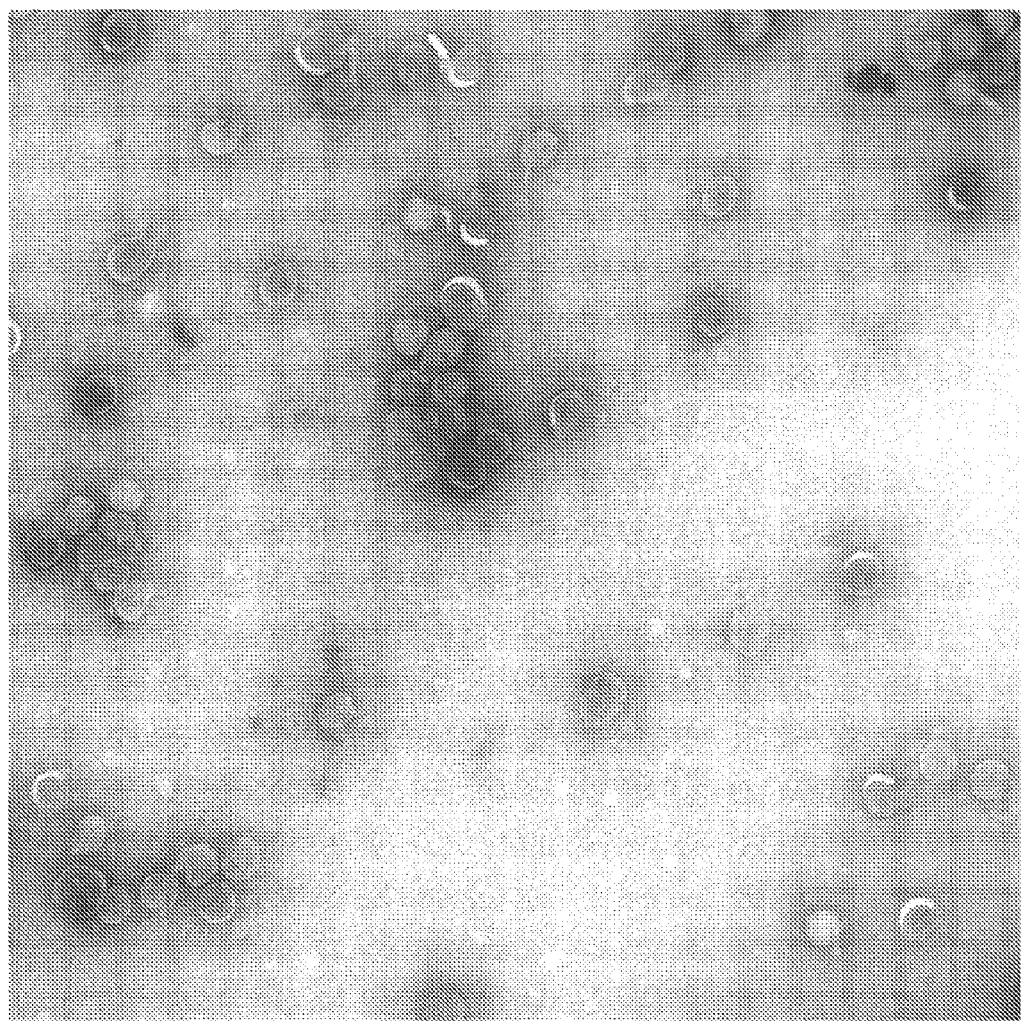
FIG. 40 shows an electron micrograph of RSV F-pseudotyped VLPs in the final VLP preparation derived from adenovirus vector-transduced Vero cells.

```
tagcatttgaccatggtgtcatagtccagccctccgcggcgtggccctt
ggcgcgcagcttgcccttggaggaggcgccgcacgaggggcagtgcagac
ttttgagggcgtagagcttgggcgcgagaaataccgattccggggagtag
gcatccgcgccgcaggccccgcagacggtctcgcattccacgagccaggt
gagctctggccgttcggggtcaaaaaccaggtttcccccatgcttttga
tgcgtttcttacctctggtttccatgagccggtgtccacgctcggtgacg
aaaaggctgtccgtgtcccgtatacagacttgagagggagtttaaacga
attcaatagcttgttgcatgggcggcgatataaaatgcaaggtgctgctc
aaaaaatcaggcaaagcctcgcgcaaaaaagaaagcacatcgtagtcatg
ctcatgcagataaaggcaggtaagctccggaaccaccacagaaaaagaca
ccatttttctctcaaacatgtctgcgggtttctgcataaacacaaaataa
aataacaaaaaaacatttaaacattagaagcctgtcttacaacaggaaaa
acaacccttataagcataagacggactacggccatgccggcgtgaccgta
aaaaaactggtcaccgtgattaaaaagcaccaccgacagctcctcggtca
tgtccggagtcataatgtaagactcggtaaacacatcaggttgattcaca
tcggtcagtgctaaaaagcgaccgaaatagcccgggggaatacatacccg
caggcgtagagacaacattacagcccccataggaggtataacaaaattaa
taggagagaaaacacataaacacctgaaaaaccctcctgcctaggcaaa
atagcaccctcccgctccagaacaacatacagcgcttccacagcggcagc
cataacagtcagccttaccagtaaaaaagaaaacctattaaaaaaacacc
actcgacacggcaccagctcaatcagtcacagtgtaaaaaagggccaagt
gcagagcgagtatatataggactaaaaaatgacgtaacggttaaagtcca
caaaaaacacccagaaaaccgcacgcgaacctacgcccagaaacgaaagc
caaaaaacccacaacttcctcaaatcgtcacttccgttttcccacgttac
gtcacttcccattttaagaaaactacaattcccaacacatacaagttact
ccgccctaaaacctacgtcacccgccccgttcccacgccccgcgccacgt
cacaaactccaccccctcattatcatattggcttcaatccaaaataaggt
atattattgatgatgttaattaacatgcatggatccatatgcggtgtgaa
ataccgcacagatgcgtaaggagaaaataccgcatcaggcgctcttccgc
ttcctcgctcactgactcgctgcgctcggtcgttcggctgcggcgagcgg
tatcagctcactcaaaggcggtaatacggttatccacagaatcagggat
aacgcaggaaagaacatgtgagcaaaaggccagcaaaaggccaggaaccg
taaaaaggccgcgttgctggcgtttttccataggctccgcccccctgacg
agcatcacaaaaatcgacgctcaagtcagaggtggcgaaacccgacagga
ctataaagataccaggcgtttccccctggaagctccctcgtgcgctctcc
tgttccgaccctgccgcttaccggatacctgtccgcctttctcccttcgg
gaagcgtggcgctttctcatagctcacgctgtaggtatctcagttcggtg
taggtcgttcgctccaagctgggctgtgtgcacgaaccccccgttcagcc
cgaccgctgcgccttatccggtaactatcgtcttgagtccaacccggtaa
gacacgacttatcgccactggcagcagccactggtaacaggattagcaga
gcgaggtatgtaggcggtgctacagagttcttgaagtggtggcctaacta
cggctacactagaaggacagtatttggtatctgcgctctgctgaagccag
ttaccttcggaaaaagagttggtagctcttgatccggcaaacaaaccacc
gctggtagcggtggttttttgtttgcaagcagcagattacgcgcagaaa
aaaaggatctcaagaagatcctttgatctttctacggggtctgacgctc
agtggaacgaaaactcacgttaagggattttggtcatgagattatcaaaa
aggatcttcacctagatccttttaaattaaaaatgaagttttaaatcaat
ctaaagtatatatgagtaaacttggtctgacagttaccaatgcttaatca
gtgaggcacctatctcagcgatctgtctatttcgttcatccatagttgcc
tgactccccgtcgtgtagataactacgatacgggagggcttaccatctgg
ccccagtgctgcaatgataccgcgagacccacgctcaccggctccagatt
tatcagcaataaaccagccagccggaagggccgagcgcagaagtggtcct
gcaactttatccgcctccatccagtctattaattgttgccgggaagctag
agtaagtagttcgccagttaatagtttgcgcaacgttgttgccattgctg
cagccatgagattatcaaaaaggatcttcacctagatccttttcacgtag
aaagccagtccgcagaaacggtgctgaccccggatgaatgtcagctactg
ggctatctggacaagggaaaacgcaagcgcaaagagaaagcaggtagctt
gcagtgggcttacatggcgatagctagactgggcggttttatggacagca
agcgaaccggaattgccagctggggcgccctctggtaaggttgggaagcc
ctgcaaagtaaactggatggctttcttgccgccaaggatctgatggcgca
ggggatcaagctctgatcaagagacaggatgaggatcgtttcgcatgatt
gaacagatggattgcacgcaggttctccggccgcttgggtggagaggct
attcggctatgactgggcacaacagacaatcggctgctctgatgccgccg
tgttccggctgtcagcgcaggggcgcccggttctttttgtcaagaccgac
ctgtccggtgccctgaatgaactgcaagacgaggcagcgcggctatcgtg
gctggccacgacgggcgttccttgcgcagctgtgctcgacgttgtcactg
aagcgggaagggactggctgctattgggcgaagtgccggggcaggatctc
ctgtcatctcaccttgctcctgccgagaaagtatccatcatggctgatgc
aatgcggcggctgcatacgcttgatccggctacctgcccattcgaccacc
aagcgaaacatcgcatcgagcgagcacgtactcggatggaagccggtctt
gtcgatcaggatgatctggacgaagagcatcaggggctcgcgccagccga
actgttcgccaggctcaaggcgagcatgcccgacggcgaggatctcgtcg
tgacccatggcgatgcctgcttgccgaatatcatggtggaaaatggccgc
ttttctggattcatcgactgtggccggctgggtgtggcggaccgctatca
ggacatagcgttggctacccgtgatattgctgaagagcttggcggcgaat
gggctgaccgcttcctcgtgctttacggtatcgccgctcccgattcgcag
cgcatcgccttctatcgccttcttgacgagttcttctgaattttgttaaa
atttttgttaaatcagctcatttttttaaccaataggccgaaatcggcacc
atccctataaatcaaaagaatagaccgagatagggttgagtgttgttcc
agtttggaacaagagtccactattaaagaacgtggactccaacgtcaaag
``` ggcgaaaaaccgtctatcagggcgatggcccactacgtgaaccatcaccc taatcaagttttttgtggtcgaggtgccgtaaagcactaaatcggaaccc taaagggagcccccgatttagagcttgacggggaaagccggcgaacgtgg cgagaaaggaagggaagaaagcgaaaggagcgggcgctagggcgctggca agtgtagcggtcacgctgcgcgtaaccaccacacccgcgcgcttaatgcg ccgctacagggcgcgtccattcgccattcaggatcgaattaattcttaat taa After completion of the individual Gag and F shuttle vectors a combined Gag plus F shuttle vector was derived from them. Using PCR techniques DNA fragments containing the modified promoter and F coding sequences from pShuttle-TO-FL, as well as SV40 polyadenylation sequences, were generated and inserted into the HpaI site of pShuttle-ALV-Gag-dPR. This resulted in construction of a double shuttle vector in which the two genes (Gag+F) were transcriptionally opposed sharing a single SV40 polyadenylation region fragment between them. The plasmid map for the new double shuttle vector, pShuttle-dPR-TO-FL-rev, is shown in FIG. 37 and its nucleotide sequence is as follows:

(SEQ ID NO: 31)
catcatcaataatatacccttattttggattgaagccaatatgataatgag ggggtggagtttgtgacgtggcgcggggcgtgggaacggggcgggtgacg tagtagtgtggcggaagtgtgatgttgcaagtgtggcggaacacatgtaa gcgacggatgtggcaaaagtgacgttttggtgtgcgccggtgtacacag gaagtgacaattttcgcgcggttttaggcggatgttgtagtaaatttggg cgtaaccgagtaagatttggccattttcgcgggaaaactgaataagagga agtgaaatctgaataattttgtgttactcatagcgcgtaatactgtaata gtaatcaattacggggtcattagttcatagcccatatatggagttccgcg ttacataacttacggtaaatggcccgcctggctgaccgcccaacgacccc cgcccattgacgtcaataatgacgtatgttcccatagtaacgccaatagg gactttccattgacgtcaatgggtggagtatttacggtaaactgcccact tggcagtacatcaagtgtatcatatgccaagtacgccccctattgacgtc aatgacggtaaatggcccgcctggcattatgcccagtacatgaccttatg ggactttcctacttggcagtacatctacgtattagtcatcgctattacca tggtgatgcggttttggcagtacatcaatgggcgtggatagcggtttgac tcacggggatttccaagtctccaccccattgacgtcaatgggagtttgtt ttggcaccaaaatcaacgggactttccaaaatgtcgtaacaactccgccc cattgacgcaaatgggcggtaggcgtgtacggtgggaggtctatataagc agagctggtttagtgaaccgtcagatccgctagagatctggtaccgtcga cgcggccgccccttcaccatggaagctgtgatcaaggtcatctcctccg cttgcaagacctactgcgggcaagacctcccctcaagaaagaaatcggt gctatgctgtccctgctgcagaaagagggcctgctgatgtccctccga cctgtactccccggttcctgggaccctatcaccgctgctctgtcccagc gtgctatgatcctgggcaagtccggcgaactcaagacctggggcctggtg ctgggtgctctgaaggctgctcgcgaggaacaagtgacctccgagcaggc taagttctggctgggtctgggtggtggtcgtgtgtccccccctggtcccg agtgcatcgagaagcccgctaccgagcgtcgtatcgacaagggcgaggaa gtgggcgagactaccgtgcagcgtgacgctaagatggctcccgaggaaac cgctaccccaagaccgtgggcacctcctgctaccactgcggcaccgcta tcggttgcaactgcgctaccgcttccgctcccccccctccttacgtgggc tccggcctgtacccttccctggctggtgtcggcgagcagcaaggacaggg tggagacacccctcccggtgctgaacagtcccgtgccgagcctggtcacg ctggtcaagctcccggtcccgctctgactgactgggctcgtgtgcgtgag gaactggcttccaccggtcccctgtggtggctatgcccgtggtcatcaa gaccgagggtcccgcttggaccccctggaacccaagctgatcacccgtc tggctgacaccgtgcgtaccaagggcctgcgttcccaatcaccatggct gaggtggaggctctgatgtcctccccctgctgcctcacgacgtgaccaa cctgatgcgtgtgatcctgggtcccgctccctacgtctgtggatggacg cttggggcgtgcagctgcagaccgtgatcgctgctgctaccgtgacccc cgtcaccctgctaacggacagggtcgtggcgagcgtaccaacctgaaccg tctgaagggcctggctgacggcatggtcggcaaccctcagggacaggctg ctctgctgcgtcctggcgagctggtcgctatcaccgccagcgctctgcag gctttccgtgaggtggcccgtttggccgaaccagctggtccctgggctga catcatgcagggcccctccgagtcctcgtggacttcgctaaccgtctga tcaaggctgtggagggctccgacctccctccttccgctcgtgctcccgtg atcatcgactgcttccgtcagaagtcccagcccgacatccagcagctgat ccgtaccgctccctccaccctgactaccctggcgagatcatcaagtacg tgctggaccgtcaaaagaccgctcccctgaccgaccaaggtatcgctgcc gctatgtcctccgctatccagcccctgatcatggctgtcgtgaaccgcga gagggacggacagaccggttccggtggtcgtgctcgtggcctgtgctaca cttgcggttccccggtcactaccaggctcagtgccccaagaagcgcaag tccggaaactcccgcgagcgctgccagctctgcaacggcatgggtcacaa cgccaagcagtgccgcaagcgcgacgaaaccagggccagcgtcccggaa agggactgtcctccggtccttggcctggtcctgagcccctgctgtgtcc taataagcgcgcgatccgatccaccggatctagataactgatcataatca gccataccacatttgtagaggttttacttgctttaaaaaacctcccacac ctcccccctgaacctgaaacataaaatgaatgcaattgttgttgttaacttt gtttattgcagcttataatggttacaaataaagcaatagcatcacaaatt tcacaaataaagcattttttttcactgcattctagttgtggtttgtccaaa ctcatcaatgtatcttaacgcggcgcgccctcatcagttgctgaaggcga tattgttgatgccggacagctggtccttgctcagggtcacggggtggac cgggccttgcagtacagcagcaggcccacggcgatcagagacagcaggat gacgatgatgacaatgatgattgtggtgatcatgatgttggtggtagact tgccagcgttcacgttgtgcagcagctcgtcggacttccggatgaaggcc agggactggttgatcttctcgttcacctggctgatggaggcgtcgaactc
gtcggaagggaacaccagagggtcgtagaagttgatgataggctcgccct
tcacgtacagagacttgccctcctgcttattcacgtagtacagtgtgttg
cccacggacacggtgtccacgcccttattggacacgtagtcgcagccgtt
ggagaaggtcttgatgattccccggttcttgttggaggcggtgcacttgg
tcttgccgtagcaggacacgatggcgcccaggagggtgatcacagaggag
gacacgtcggtcttagaggtcatgatcttgcagtcgtacttagggttgaa
gatgtccacgttgcacaggttcacctcggaaggcagggtcagggagttca
tggtatcgcagaacacccggttggactgcaccttgcatgtctcggcctgt
ggaaagaaggacacggagccggcgttgtcgcagaaccagccccggtcggt
ccgggtcaggcagatgttggagccctccttggtgttggtggtgcacaggg
gggaggtgtgcagcttccagcaaggggtgtcgatcacgccgtacagaggc
agctgcaccacgtaggccaggacctcctccttgatgatgctcatgataga
gtaggactgctgccgcacgatctgcacgttgttggacatcagcttttttct
ggtcgttggtgataggcatgtcgttgatcagggacagcagctcggagttg
gtcagcatataagtagagacaggagtggtcacaccagcgttgacggagaa
ctctcttgtgatttccagcagccggttgttcttctgctggaactcgatca
ctgtctcgatgttggagatggagcaggactgcttgttcacgataggcagc
agctgcttgtcgatgtagttcttcagatccagcaccttggaggtcagcac
ggacacgccgttggacagggacaccacggccttgttggtggacagcaggg
cagacttgatcttgttcacctcgccctccaggtgcagcaccttagacacg
gccacgccagaggcgatagcggagcccacgcccagcaggaagcccaggaa
ccgccgcttccgcttcttggacagggtgacgttggttttcttggcgttgt
tcagggtgtagttcatgaaccgaggcagctcccgcctggccggttgttg
gtggcaggggtggactgcatcagcagctgcagctcggtcacggcgttctt
gtacttgtccagctcctgcttgatcagcttcaccttggcgtcggtgccgt
tgcacttgttttctttgatgttggacagctcgatggtgatcacggaggtg
taccagccggtccgcagggcggacaggtagcccttggacacggcggagca
ggtggactggtagaactcctcggtgatgttctggccggaggcgaagcaga
aggtcacggcggtcaggatggtggtgatggcgttggccttcaggatcagc
agctccatggtgaaggggcggccgcgtcgacgaaacgctagagtccgga
ggctggatcggtcccggtgtcttctatggaggtcaaaacagcgtggatgg
cgtctccaggcgatctgacggttcactaaacgagctcgtcgacgatctct
atcactgataggagatctctatcactgatagggagagctctgcttatat
agacctccaccgtacacgcctaccgcccatttgcgtcaatggggcggag
ttgttacgacattttggaaagtcccgttgattttggtgccaaaacaaact
cccattgacgtcaatggggtggagacttggaaatccccgtgagtcaaacc
gctatccacgcccattgatgtactgccaaaaccgcatcaccatggtaata
gcgatgactaatactagatgtactgccaagtaggaaagtcccataaggtc
atgtactgggcataatgccaggcgggccatttaccgtcattgacgtcaat aggggggcgtacttggcatatgatacacttgatgtactgccaagtgggcag
tttaccgtaaatactccacccattgacgtcaatggaaagtccctattggc
gttactatgggaacatacgtcattattgacgtcaatgggcgggggtcgtt
gggcggtcagccaggcgggccatttaccgtaagttatgtaacgcggaact
ccatatatgggctatgaactaatgaccccgtaattgattactattacagt
agttaacttgtttattgcagcttataatggttacaaataaagcaatagca
tcacaaatttcacaaataaagcatttttttcactgcattctagttgtggt
ttgtccaaactcatcaatgtatcttaacgcggatctgggcgtggttaagg
gtgggaaagaatatataaggtgggggtcttatgtagttttgtatctgttt
tgcagcagccgccgccgccatgagcaccaactcgtttgatggaagcattg
tgagctcatatttgacaacgcgcatgccccatgggccggggtgcgtcag
aatgtgatgggctccagcattgatggtcgccccgtcctgcccgcaaactc
tactaccttgacctacgagaccgtgtctggaacgccgttggagactgcag
cctccgccgccgcttcagccgctgcagccaccgcccgcgggattgtgact
gactttgctttcctgagcccgcttgcaagcagtgcagcttcccgttcatc
cgcccgcgatgacaagttgacggctcttttggcacaattggattctttga
cccgggaacttaatgtcgtttctcagcagctgttggatctgcgccagcag
gtttctgccctgaaggcttcctcccctcccaatgcggtttaaaacataaa
taaaaaaccagactctgtttggatttggatcaagcaagtgtcttgctgtc
tttatttaggggttttgcgcgcgcggtaggcccgggaccagcggtctcgg
tcgttgagggtcctgtgtatttttccaggacgtggtaaaggtgactctg
gatgttcagatacatgggcataagcccgtctctggggtggaggtagcacc
actgcagagcttcatgctgcggggtggtgttgtagatgatccagtcgtag
caggagcgctgggcgtggtgcctaaaaatgtctttcagtagcaagctgat
tgccaggggcaggcccttggtgtaagtgtttacaaagcggttaagctggg
atgggtgcatacgtggggatatgagatgcatcttggactgtattttagg
ttggctatgttcccagccatatccctccggggattcatgttgtgcagaac
caccagcacagtgtatccggtgcacttgggaaatttgtcatgtagcttag
aaggaaatgcgtggaagaacttggagacgcccttgtgacctccaagatt
tccatgcattcgtccataatgatggcaatgggcccacgggcggcggcctg
ggcgaagatatttctgggatcactaacgtcatagttgtgttccaggatga
gatcgtcataggccatttttacaaagcgcgggcggagggtgccagactgc
ggtataatggttccatccggcccaggggcgtagttaccctcacagatttg
catttcccacgctttgagttcagatgggggggatcatgtctacctgcgggg
cgatgaagaaaacggtttccggggtaggggagatcagctgggaagaaagc
aggttcctgagcagctgcgacttaccgcagccggtgggcccgtaaatcac
acctattaccggctgcaactggtagttaagagagctgcagctgccgtcat
ccctgagcagggggggccacttcgttaagcatgtccctgactcgcatgttt
tccctgaccaaatccgccagaaggcgctcgccgcccagcgatagcagttc
ttgcaaggaagcaaagttttttcaacggtttgagaccgtccgccgtaggca -continued tgcttttgagcgtttgaccaagcagttccaggcggtcccacagctcggtc
acctgctctacggcatctcgatccagcatatctcctcgtttcgcgggttg
gggcggctttcgctgtacggcagtagtcggtgctcgtccagacgggccag
ggtcatgtctttccacgggcgcagggtcctcgtcagcgtagtctgggtca
cggtgaaggggtgcgctccgggctgcgcgctggccagggtgcgcttgagg
ctggtcctgctggtgctgaagcgctgccggtcttcgccctgcgcgtcggc
caggtagcatttgaccatggtgtcatagtccagcccctccgcggcgtggc
ccttggcgcgcagcttgcccttggaggaggcgccgcacgaggggcagtgc
agacttttgagggcgtagagcttgggcgcgagaaataccgattccgggga
gtaggcatccgcgccgcaggccccgcagacggtctcgcattccacgagcc
aggtgagctctggccgttcggggtcaaaaaccaggtttcccccatgctttt
ttgatgcgtttcttacctctggtttccatgagccggtgtccacgctcggt
gacgaaaaggctgtccgtgtccccgtatacagacttgagagggagtttaa
acgaattcaatagcttgttgcatgggcggcgatataaaatgcaaggtgct
gctcaaaaaatcaggcaaagcctcgcgcaaaaaagaaagcacatcgtagt
catgctcatgcagataaaggcaggtaagctccggaaccaccacagaaaaa
gacaccattttttctctcaaacatgtctgcgggtttctgcataaacacaaa
ataaaataacaaaaaaacatttaaacattagaagcctgtcttacaacagg
aaaaacaacccttataagcataagacggactacggccatgccggcgtgac
cgtaaaaaaactggtcaccgtgattaaaaagcaccaccgacagctcctcg
gtcatgtccggagtcataatgtaagactcggtaaacacatcaggttgatt
cacatcggtcagtgctaaaagcgaccgaaatagcccggggaatacata
cccgcaggcgtagagacaacattacagcccccataggaggtataacaaaa
ttaataggagagaaaaacataaacacctgaaaaaccctcctgcctagg
caaaatagcaccctcccgctccagaacaacatacagcgcttccacagcgg
cagccataacagtcagccttaccagtaaaaaagaaaacctattaaaaaaa
caccactcgacacggcaccagctcaatcagtcacagtgtaaaaaagggcc
aagtgcagagcgagtatatataggactaaaaaatgacgtaacggttaaag
tccacaaaaaacacccagaaaaccgcacgcgaacctacgcccagaaacga
aagccaaaaaacccacaacttcctcaaatcgtcacttccgttttcccacg
ttacgtcacttcccatttttaagaaaactacaattcccaacacatacaagt
tactccgccctaaaacctacgtcaccgccccgttcccacgcccgcgcc
acgtcacaaactccacccccctcattatcatattggcttcaatccaaaata
aggtatattattgatgatgttaattaacatgcatggatccatatgcggtg
tgaaataccgcacagatgcgtaaggagaaaataccgcatcaggcgctctt
ccgcttcctcgctcactgactcgctgcgctcggtcgttcggctgcggcga
gcggtatcagctcactcaaaggcggtaatacggttatccacagaatcagg
ggataacgcaggaaagaacatgtgagcaaaaggccagcaaaaggccagga
accgtaaaaaggccgcgttgctggcgtttttccataggctccgcccccct
gacgagcatcacaaaaatcgacgctcaagtcagaggtggcgaaacccgac aggactataaagataccaggcgtttccccctggaagctccctcgtgcgct
ctcctgttccgaccctgccgcttaccggatacctgtccgcctttctccct
tcgggaagcgtggcgctttctcatagctcacgctgtaggtatctcagttc
ggtgtaggtcgttcgctccaagctgggctgtgtgcacgaaccccccgttc
agcccgaccgctgcgccttatccggtaactatcgtcttgagtccaacccg
gtaagacacgacttatcgccactggcagcagccactggtaacaggattag
cagagcgaggtatgtaggcggtgctacagagttcttgaagtggtggccta
actacggctacactagaaggacagtatttggtatctgcgctctgctgaag
ccagttaccttcggaaaaagagttggtagctcttgatccggcaaacaaac
caccgctggtagcggtggtttttttgtttgcaagcagcagattacgcgca
gaaaaaaggatctcaagaagatcctttgatcttttctacggggtctgac
gctcagtggaacgaaaactcacgttaagggattttggtcatgagattatc
aaaaaggatcttcacctagatccttttaaattaaaaatgaagttttaaat
caatctaaagtatatatgagtaaacttggtctgacagttaccaatgctta
atcagtgaggcacctatctcagcgatctgtctatttcgttcatccatagt
tgcctgactccccgtcgtgtagataactacgatacgggagggcttaccat
ctggccccagtgctgcaatgataccgcgagacccacgctcaccggctcca
gatttatcagcaataaaccagccagccggaagggccgagcgcagaagtgg
tcctgcaactttatccgcctccatccagtctattaattgttgccgggaag
ctagagtaagtagttcgccagttaatagtttgcgcaacgttgttgccatt
gctgcagccatgagattatcaaaaaggatcttcacctagatccttttcac
gtagaaagccagtccgcagaaacggtgctgaccccggatgaatgtcagct
actgggctatctggacaagggaaaacgcaagcgcaaagagaaagcaggta
gcttgcagtgggcttacatggcgatagctagactgggcggttttatggac
agcaagcgaaccggaattgccagctggggcgccctctggtaaggttggga
agccctgcaaagtaaactggatggctttcttgccgccaaggatctgatgg
cgcaggggatcaagctctgatcaagagacaggatgaggatcgtttcgcat
gattgaacaagatggattgcacgcaggttctccggccgcttgggtggaga
ggctattcggctatgactgggcacaacagacaatcggctgctctgatgcc
gccgtgttccggctgtcagcgcaggggcgcccggttcttttttgtcaagac
cgacctgtccggtgccctgaatgaactgcaagacgaggcagcgcggctat
cgtggctggccacgacgggcgttccttgcgcagctgtgctcgacgttgtc
actgaagcgggaagggactggctgctattgggcgaagtgccggggcagga
tctcctgtcatctcaccttgctcctgccgagaaagtatccatcatggctg
atgcaatgcggcggctgcatacgcttgatccggctacctgcccattcgac
caccaagcgaaacatcgcatcgagcgagcacgtactcggatggaagccgg
tcttgtcgatcaggatgatctggacgaagagcatcaggggctcgcgccag
ccgaactgttcgccaggctcaaggcgagcatgcccgacggcgaggatctc
gtcgtgacccatggcgatgcctgcttgccgaatatcatggtggaaaatgg
ccgcttttctggattcatcgactgtggccggctgggtgtggcggaccgct -continued

```
atcaggacatagcgttggctacccgtgatattgctgaagagcttggcggc gaatgggctgaccgcttcctcgtgctttacggtatcgccgctcccgattc gcagcgcatcgccttctatcgccttcttgacgagttcttctgaattttgt taaaattttgttaaatcagctcattttttaaccaataggccgaaatcgg caccatcccttataaatcaaaagaatagaccgagatagggttgagtgttg ttccagtttggaacaagagtccactattaaagaacgtggactccaacgtc aaagggcgaaaaaccgtctatcagggcgatggcccactacgtgaaccatc accctaatcaagttttttgtggtcgaggtgccgtaaagcactaaatcgga accctaaagggagccccgatttagagcttgacggggaaagccggcgaac gtggcgagaaaggaagggaagaaagcgaaaggagcgggcgctagggcgct ggcaagtgtagcggtcacgctgcgcgtaaccaccacacccgcgcgcttaa tgcgccgctacagggcgcgtccattcgccattcaggatcgaattaattct taattaa
```

To produce the replication-defective adenovirus vector encoding both Gag and F, the plasmid pShuttle-dPR-TO-FL-rev was linearized with PmeI then electroporated into the bacterial strain BJ5183-AD-1 in order for it to be recombined into the E1-deleted adenovirus type 5 genome. These methods of adenovirus vector generation are common to those skilled in the art. Small colonies (indicative of plasmid recombination into the adenovirus genome) were selected for expansion and isolation of the recombinant adenovirus DNA containing the inserted pShuttle-dPR-TO-FL-rev sequences. A recombinant adenovirus DNA clone containing the inserted Gag and F genes was then digested with PacI to separate the adenovirus DNA from bacterial plasmid sequences and this DNA was transfected into T-Rex 293 cells in order to generate a replication-defective adenovirus strain. T-Rex 293 cells are HEK293 cells containing the Tet repressor gene. The E1 gene contained within all 293 cell lines allows for the replication of replication-defective adenovirus vectors and the Tet repressor in the T-Rex 293 line prevents F gene expression during virus propagation.

After successful isolation and expansion of the adenovirus vector encoding Gag and F on T-Rex 293 cells, this vector was used to transduce Vero cells for VLP production. Vero cells growing in T175 culture flasks in DMEM medium containing 10% fetal bovine serum were washed with serum-free VP-SFM medium then established in VP-SFM medium and then transduced with the Gag+F double adenovirus vector at a multiplicity of infection of 70:1. Within 24 hours the transduced Vero cells began to show cytopathic effects (CPE) consisting mainly of massive syncytia formation. By 72 hours extensive CPE were present with many large, floating syncytia observed. Medium was harvested at this time and clarified of cellular debris by centrifugation at 2000 rpm for 10 min. VLPs present in the medium were purified by centrifugation over a 2-step sucrose step gradient (30% and 60% sucrose in tris-buffered saline, pH 7.4) for 2 hours at 100,000×g at 10° C. A visible band at the junction of the 30% and 60% sucrose layers was observed and collected (FIG. 38(*a*)).

VLPs purified in this manner from several T175 flasks were diluted 2-fold in tris-buffered saline then subjected to 3 Joules of long wave UV radiation in the presence of 50 mcg/ml aminomethyl-trimethyl psoralen in order to inactivate any residual adenovirus vector not taken up into the Vero cells. Following residual vector inactivation, VLPs were rebanded on 30-60% sucrose step gradients as a final purification step.

Results

FIG. 38(*b*) shows a silver-stained SDS-PAGE analysis of the final purified VLP preparation and FIG. 39 shows an RSV-specific Western blot demonstrating the presence of the F1 fragment (reducing conditions). Finally, an electron micrograph (FIG. 40) shows the presence of enveloped VLPs in the final preparation. The adenoviral expression produced at least a ten-fold higher yield than the previous examples, showing that the viral expression is superior.

Example 14

Immunogenicity of Pseudotyped ALV Gag+RSV F VLPs

This example further demonstrates the immunogenic and protective properties of RSV F-pseudotyped ALV Gag VLPs.

Materials and Methods

To further demonstrate that RSV F-pseudotyped VLPs are both immunogenic and protective, VLPs were prepared as described in the previous example using the adenovirus expression system and were employed in a cotton rat vaccination and challenge model. In addition to the RSV F-pseudotyped Gag VLPs produced as described above, a sample of Gag-only VLPs was also produced using an adenovirus vector containing only the ALV Gag gene. This latter batch of "naked" VLPs lacking the RSV F antigen was produced and purified in a manner similar to that for the F-pseudotyped Gag VLPs and they served as a negative control vaccine.

An immunization trial employing five immunization groups consisting of twelve animals each was designed using specific pathogen-free female cotton rats. The five immunization groups were assigned the following vaccines, respectively:

1. VLP (3 μg F antigen, 30 μg total VLP protein per dose)
2. VLP+MPL adjuvant (3 μg F antigen, 30 μg total VLP protein, 50 μg monophosphoryl lipid A adjuvant per dose)
3. Gag-only VLP (60 μg total VLP protein per dose)
4. Live RSV (positive control—$1\times10^5$ pfu live RSV A per dose)
5. Naive (negative control group—no vaccination)

Vaccination groups 1-3 received primary and booster vaccination on days 0 and 21 as described above. Group 4 animals only received a single live RSV vaccination of day 0 and were not boosted on day 21. Naïve animals in group 5 received no vaccine administrations.

Serum samples were collected 2 weeks following the booster immunization (day 35) to analyze RSV-specific neutralizing antibody responses in a standard virus microneutralization assay.

All animals were challenged with $1\times10^5$ pfu of live RSV A on day 49. On day 54 (5 days following challenge), six animals from each group were sacrificed for determination of RSV virus titers in lung homogenates. Virus in lung homogenates was quantified by titration of virus infectivity in cell culture using standard techniques known to those skilled in the art.

Six animals were also sacrificed for lung histopathology measurements. Lung samples were formalin fixed, paraffin-embedded and H&E stained using methods known to those skilled in the art and slides were examined for alveolitis and interstitial pneumonia by a trained pathologist.

Results

Serum Antibody Response

Figure 41:
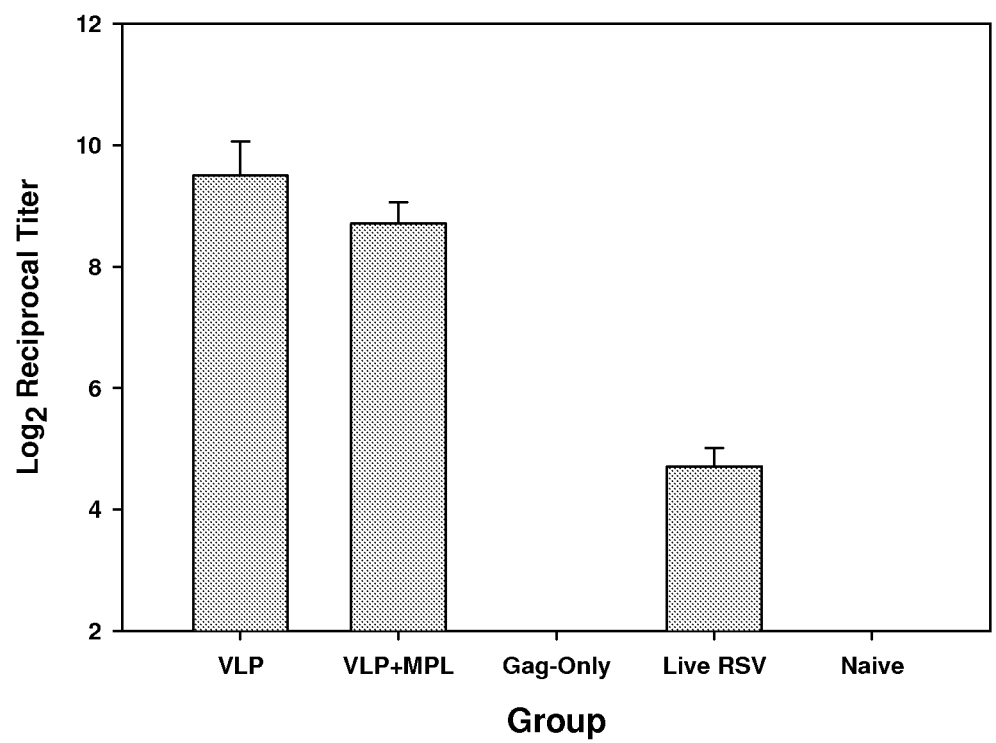
FIG. 41 shows RSV neutralization titers in cotton rats immunized with RSV VLPs.

Results demonstrating the serum antibody response are shown in FIG. 41. Strong neutralizing antibody titers were observed in the RSV F-pseudotyped VLP immunization groups with and without MPL adjuvant. No neutralizing responses were detected in the Gag-only VLP immunization group demonstrating the importance of the RSV F antigen for induction of specific immune responses. Finally, the live RSV positive control vaccination group exhibited modest virus neutralizing titers.

Virus Titer in Lung Tissue

Figure 42:
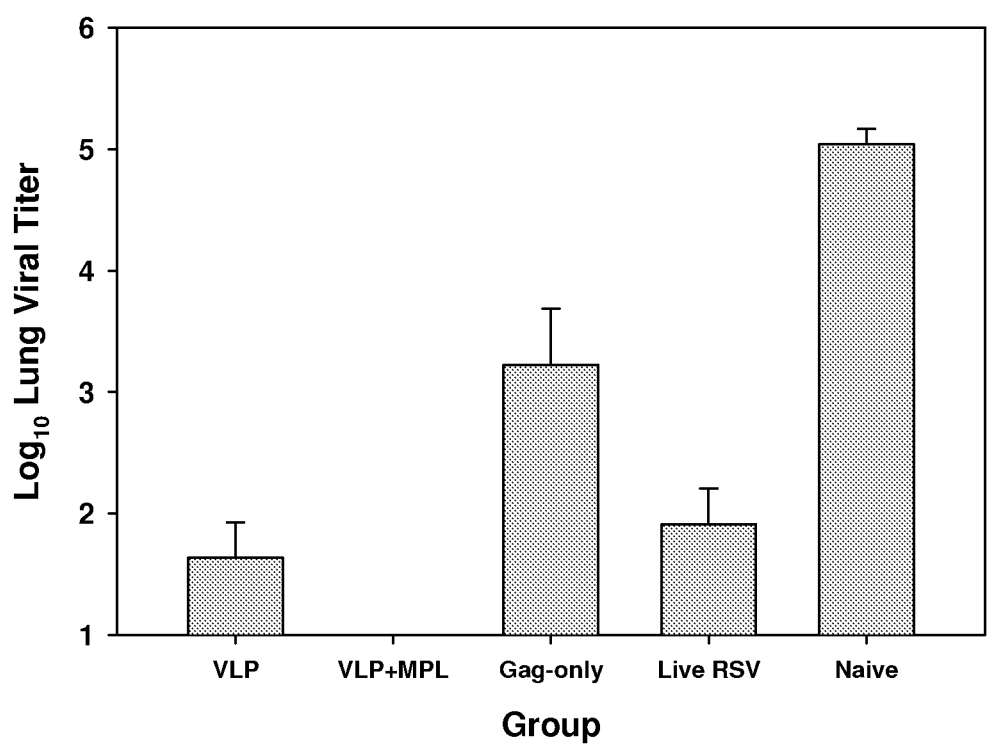
FIG. 42 shows virus titers in the lungs of immunized and challenged cotton rats.

Results demonstrating the virus titer in lung homogenates are shown in FIG. 42 in which naïve, non-vaccinated animals exhibited high levels of virus replication while VLP and live RSV-vaccinated animals showed significant protection from challenge. No virus was detected at all in the group immunized with VLP+MPL. A modest amount of protection was observed in the Gag-only-immunized animals and this may have been the result of innate immune activation via Gag-only VLP immunization since there were no RSV-specific neutralizing immune responses in this group (FIG. 41). The combined virus challenge and virus neutralization data demonstrate the ability of RSV F-pseudotyped VLPs to induce strong neutralizing immune responses that are protective against virus challenge.

Lung Histopathology Measurements

Figure 43:
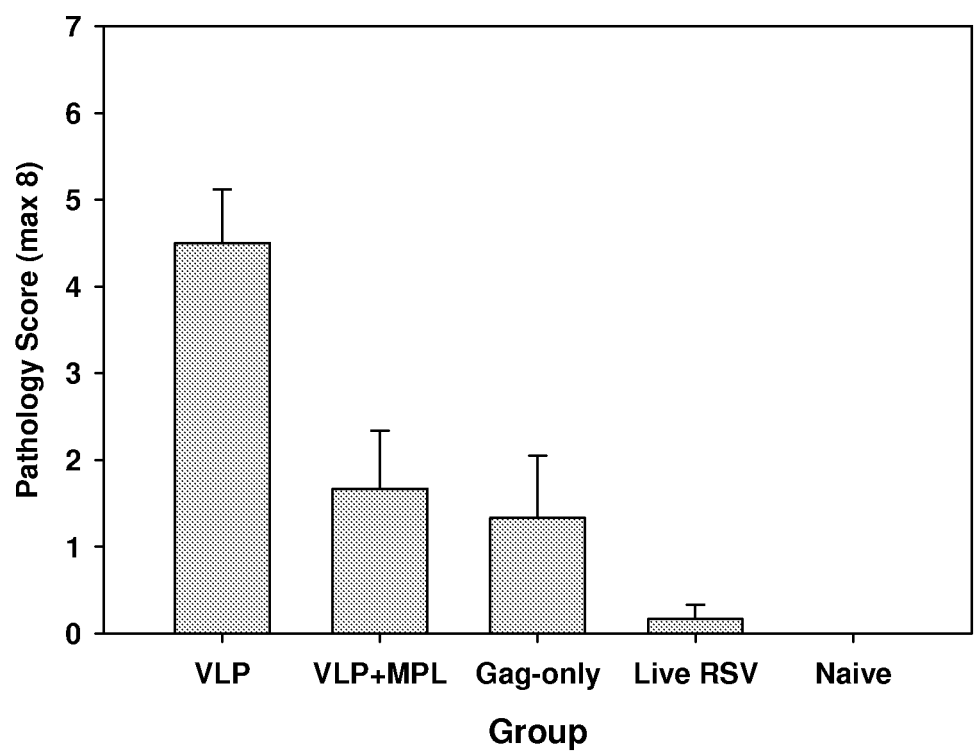
FIG. 43 shows lung histopathology scores (alveolitis and interstitial pneumonia) in VLP-immunized and challenged cotton rats.

Scores of the lung histopathology measurements are shown in FIG. 43 and demonstrate low pathology scores for the VLP+MPL and live RSV vaccination groups. Moderate pathology was observed in the VLP immunization group in the absence of the MPL adjuvant. The VLP+MPL vaccine formulation is therefore able to elicit strong neutralizing antibody titers resulting in complete vaccine protection against challenge in the absence of significant pathological reactions.

ADDITIONAL REFERENCES

1. Katz, J. M., W. Lim, C. B. Bridges, T. Rowe, J. Hu-Primmer, X. Lu, R. A. Abernathy, M. Clarke, L. Conn, H. Kwong, M. Lee, G. Au, Y. Y. Ho, K. H. Mak, N. J. Cox, and K. Fukuda. 1999. Antibody response in individuals infected with avian influenza A (H5N1) viruses and detection of anti-H5 antibody among household and social contacts. J Infect Dis 180:1763.
2. Peiris, J. S., W. C. Yu, C. W. Leung, C. Y. Cheung, W. F. Ng, J. M. Nicholls, T. K. Ng, K. H. Chan, S. T. Lai, W. L. Lim, K. Y. Yuen, and Y. Guan. 2004. Re-emergence of fatal human influenza A subtype H5N1 disease. Lancet 363:617.
3. Horimoto, T., N. Fukuda, K. Iwatsuki-Horimoto, Y. Guan, W. Lim, M. Peiris, S. Sugii, T. Odagiri, M. Tashiro, and Y. Kawaoka. 2004. Antigenic differences between H5N1 human influenza viruses isolated in 1997 and 2003. J Vet Med Sci 66:303.
4. Tran, T. H., T. L. Nguyen, T. D. Nguyen, T. S. Luong, P. M. Pham, V. C. Nguyen, T. S. Pham, C. D. Vo, T. Q. Le, T. T. Ngo, B. K. Dao, P. P. Le, T. T. Nguyen, T. L. Hoang, V. T. Cao, T. G. Le, D. T. Nguyen, H. N. Le, K. T. Nguyen, H. S. Le, V. T. Le, D. Christiane, T. T. Tran, J. Menno de, C. Schultsz, P. Cheng, W. Lim, P. Horby, and J. Farrar. 2004. Avian influenza A (H5N1) in 10 patients in Vietnam. N Engl J Med 350:1179.
5. Li, K. S., Y. Guan, J. Wang, G. J. Smith, K. M. Xu, L. Duan, A. P. Rahardjo, P. Puthavathana, C. Buranathai, T. D. Nguyen, A. T. Estoepangestie, A. Chaisingh, P. Auewarakul, H. T. Long, N. T. Hanh, R. J. Webby, L. L. Poon, H. Chen, K. F. Shortridge, K. Y. Yuen, R. G. Webster, and J. S. Peiris. 2004. Genesis of a highly pathogenic and potentially pandemic H5N1 influenza virus in eastern Asia. Nature 430:209.
6. Lipatov, A. S., E. A. Govorkova, R. J. Webby, H. Ozaki, M. Peiris, Y. Guan, L. Poon, and R. G. Webster. 2004. Influenza: emergence and control. J Virol 78:8951.
7. Lipatov, A. S., R. J. Webby, E. A. Govorkova, S. Krauss, and R. G. Webster. 2005. Efficacy of H5 influenza vaccines produced by reverse genetics in a lethal mouse model. J Infect Dis 191:1216.
8. Stephenson, I., K. G. Nicholson, J. M. Wood, M. C. Zambon, and J. M. Katz. 2004. Confronting the avian influenza threat: vaccine development for a potential pandemic. Lancet Infect Dis 4:499.
9. Liu, M., J. M. Wood, T. Ellis, S. Krauss, P. Seiler, C. Johnson, E. Hoffmann, J. Humberd, D. Hulse, Y. Zhang, R. G. Webster, and D. R. Perez. 2003. Preparation of a standardized, efficacious agricultural H5N3 vaccine by reverse genetics. Virology 314:580.
10. Subbarao, K., H. Chen, D. Swayne, L. Mingay, E. Fodor, G. Brownlee, X. Xu, X. Lu, J. Katz, N. Cox, and Y. Matsuoka. 2003. Evaluation of a genetically modified reassortant H5N1 influenza A virus vaccine candidate generated by plasmid-based reverse genetics. Virology 305:192.
11. Webby, R. J., D. R. Perez, J. S. Coleman, Y. Guan, J. H. Knight, E. A. Govorkova, L. R. McClain-Moss, J. S. Peiris, J. E. Rehg, E. I. Tuomanen, and R. G. Webster. 2004. Responsiveness to a pandemic alert: use of reverse genetics for rapid development of influenza vaccines. Lancet 363:1099.
12. Treanor, J. J., B. E. Wilkinson, F. Masseoud, J. Hu-Primmer, R. Battaglia, D. O'Brien, M. Wolff, G. Rabinovich, W. Blackwelder, and J. M. Katz. 2001. Safety and immunogenicity of a recombinant hemagglutinin vaccine for H5 influenza in humans. Vaccine 19:1732.
13. Stephenson, I., R. Bugarini, K. G. Nicholson, A. Podda, J. M. Wood, M. C. Zambon, and J. M. Katz. 2005. Cross-reactivity to highly pathogenic avian influenza H5N1 viruses after vaccination with nonadjuvanted and MF59-adjuvanted influenza A/Duck/Singapore/97 (H5N3) vaccine: a potential priming strategy. J Infect Dis 191:1210.
14. Nicholson, K. G., A. E. Colegate, A. Podda, I. Stephenson, J. Wood, E. Ypma, and M. C. Zambon. 2001. Safety and antigenicity of non-adjuvanted and MF59-adjuvanted influenza A/Duck/Singapore/97 (H5N3) vaccine: a randomised trial of two potential vaccines against H5N1 influenza. Lancet 357:1937.
15. Subbarao, K., B. R. Murphy, and A. S. Fauci. 2006. Development of effective vaccines against pandemic influenza. Immunity 24:5.
16. Kuper, C. F., P. J. Koornstra, D. M. Hameleers, J. Biewenga, B. J. Spit, A. M. Duijvestijn, P. J. van Breda Vriesman, and T. 5 minia. 1992. The role of nasopharyngeal lymphoid tissue. Immunol Today 13:219.
17. Liang, B., L. Hyland, and S. Hou. 2001. Nasal-associated lymphoid tissue is a site of long-term virus-specific antibody production following respiratory virus infection of mice. J Virol 75:5416.
18. Zuercher, A. W., S. E. Coffin, M. C. Thurnheer, P. Fundova, and J. J. Cebra. 2002. Nasal-associated lymphoid tissue is a mucosal inductive site for virus-specific humoral and cellular immune responses. J Immunol 168:1796.
19. Brandtzaeg, P. 1989. Overview of the mucosal immune system. Curr Top Microbiol Immunol 146:13.
20. Takada, A., S. Matsushita, A. Ninomiya, Y. Kawaoka, and H. Kida. 2003. Intranasal immunization with formalin- 21. Tamura, S. I., H. Asanuma, Y. Ito, Y. Hirabayashi, Y. Suzuki, T. Nagamine, C. Aizawa, T. Kurata, and A. Oya. 1992. Superior cross-protective effect of nasal vaccination to subcutaneous inoculation with influenza hemagglutinin vaccine. Eur J Immunol 22:477.

22. Tumpey, T. M., M. Renshaw, J. D. Clements, and J. M. Katz. 2001. Mucosal delivery of inactivated influenza vaccine induces B-cell-dependent heterosubtypic cross-protection against lethal influenza A H5N1 virus infection. J Virol 75:5141.

23. Kang, S. M., L. Guo, Q. Yao, I. Skountzou, and R. W. Compans. 2004. Intranasal immunization with inactivated influenza virus enhances immune responses to coadministered simian-human immunodeficiency virus-like particle antigens. J Virol 78:9624.

24. Guo, L., X. Lu, S. M. Kang, C. Chen, R. W. Compans, and Q. Yao. 2003. Enhancement of mucosal immune responses by chimeric influenza HA/SHIV virus-like particles. Virology 313:502.

25. Yao, Q., R. Zhang, L. Guo, M. L1, and C. Chen. 2004. The cell-independent immune responses to chimeric hemagglutinin/simian human immunodeficiency virus-like particles vaccine. J Immunol 173:1951.

26. Latham, T., and J. M. Galarza. 2001. Formation of wild-type and chimeric influenza virus-like particles following simultaneous expression of only four structural proteins. J Virol 75:6154.

27. Galarza, J. M., T. Latham, and A. Cupo. 2005. Virus-like particle vaccine conferred complete protection against a lethal influenza virus challenge. Viral Immunol 18:365.

28. Fromantin, C., B. Jamot, J. Cohen, L. Piroth, P. Pothier, and E. Kohli. 2001. Rotavirus 2/6 virus-like particles administered intranasally in mice, with or without the mucosal adjuvants cholera toxin and *Escherichia coli* heat-labile toxin, induce a Th1/Th2-like immune response. Virol 75:11010.

29. Harrington, P. R., B. Yount, R. E. Johnston, N. Davis, C. Moe, and R. S. Baric. 2002. Systemic, mucosal, and heterotypic immune induction in mice inoculated with Venezuelan equine encephalitis replicons expressing Norwalk virus-like particles. J Virol 76:730.

30. Shi, W., J. Liu, Y. Huang, and L. Qiao. 2001. Papillomavirus pseudovirus: a novel vaccine to induce mucosal and systemic cytotoxic T-lymphocyte responses. J Virol 75:10139.

31. Han, M. G., S. Cheetham, M. Azevedo, C. Thomas, and L. J. Saif. 2006. Immune responses to bovine norovirus-like particles with various adjuvants and analysis of protection in gnotobiotic calves. Vaccine 24:317.

32. Ilium, L. 1998. Chitosan and its use as a pharmaceutical excipient. Pharm Res 15:1326.

33. Ilium, L., I. Jabbal-Gill, M. Hinchcliffe, A. N. Fisher, and S. S. Davis. 2001. Chitosan as a novel nasal delivery system for vaccines. Adv Drug Deliv Rev 51:81.

34. Soane, R. J., M. Hinchcliffe, S. S. Davis, and L. Ilium. 2001. Clearance characteristics of chitosan based formulations in the sheep nasal cavity. Int J Pharm 217:183.

35. Baudner, B. C., M. M. Giuliani, J. C. Verhoef, R. Rappuoli, H. E. Junginger, and G. D. Giudice. 2003. The concomitant use of the LTK63 mucosal adjuvant and of chitosan-based delivery system enhances the immunogenicity and efficacy of intranasally administered vaccines. Vaccine 21:3837.

36. Fujihashi, K., T. Koga, F. W. van Ginkel, Y. Hagiwara, and J. R. McGhee. 2002. A dilemma for mucosal vaccination: efficacy versus toxicity using enterotoxin-based adjuvants. Vaccine 20:2431.

37. Mutsch, M., W. Zhou, P. Rhodes, M. Bopp, R. T. Chen, T. Linder, C. Spyr, and R. Steffen. 2004. Use of the inactivated intranasal influenza vaccine and the risk of Bell's palsy in Switzerland. N Engl J Med 350:896.

38. Baldridge, J. R., Y. Yorgensen, J. R. Ward, and J. T. Ulrich. 2000. Monophosphoryl lipid A enhances mucosal and systemic immunity to vaccine antigens following intranasal administration. Vaccine 18:2416.

39. Baldrick, P., D. Richardson, G. Elliott, and A. W. Wheeler. 2002. Safety evaluation of monophosphoryl lipid A (MPL): an immunostimulatory adjuvant. Regul Toxicol Pharmacol 35:398.

40. Baldridge, J. R., P. McGowan, J. T. Evans, C. Cluff, S. Mossman, D. Johnson, and D. Persing. 2004. Taking a Toll on human disease: Toll-like receptor 4 agonists as vaccine adjuvants and monotherapeutic agents. Expert Opin Biol Ther 4:1129.

41. Baldridge, J. GlaxoSmithKline, Personal Communication.

42. Huang, J., R. J. Garmise, T. M. Crowder, K. Mar, C. R. Hwang, A. J. Hickey, J. A. Mikszta, and V. J. Sullivan. 2004. A novel dry powder influenza vaccine and intranasal delivery technology: induction of systemic and mucosal immune responses in rats. Vaccine 23:794.

43. Mills, K. H., C. Cosgrove, E. A. McNeela, A. Sexton, R. Giemza, I. Jabbal-Gill, A. Church, W. Lin, L. Ilium, A. Podda, R. Rappuoli, M. Pizza, G. E. Griffin, and D. J. Lewis. 2003. Protective levels of diphtheria-neutralizing antibody induced in healthy volunteers by unilateral priming-boosting intranasal immunization associated with restricted ipsilateral mucosal secretory immunoglobulin a. Infect Immun 71:726.

44. Wimer-Mackin, S., M. Hinchcliffe, C. R. Petrie, S. J. Warwood, W. T. Tino, M. S. Williams, J. P. Stenz, A. Cheff, and C. Richardson. 2006. An intranasal vaccine targeting both the *Bacillus anthracis* toxin and bacterium provides protection against aerosol spore challenge in rabbits. Vaccine in press.

45. Noad, R., and P. Roy. 2003. Virus-like particles as immunogens. Trends Microbiol 11:438.

46. Yao, Q., V. Vuong, M. Li, and R. W. Compans. 2002. Intranasal immunization with SIV virus-like particles (VLPs) elicits systemic and mucosal immunity. Vaccine 20:2537.

47. Pushko, P., T. M. Tumpey, F. Bu, J. Knell, R. Robinson, and G. Smith. 2005. Influenza virus-like particles comprised of the HA, NA, and M1 proteins of H9N2 influenza virus induce protective immune responses in BALB/c mice. Vaccine 23:5751.

48. Baumert, T. F., S. Ito, D. T. Wong, and T. J. Liang. 1998. Hepatitis C virus structural proteins assemble into virus-like particles in insect cells. J Virol 72:3827.

49. Yao, Q., Z. Bu, A. Vzorov, C. Yang, and R. W. Compans. 2003. Virus-like particle and DNA-based candidate AIDS vaccines. Vaccine 21:638.

50. Tacket, C. O., M. B. Sztein, G. A. Losonsky, S. S. Wasserman, and M. K. Estes. 2003. Humoral, mucosal, and cellular immune responses to oral Norwalk virus-like particles in volunteers. Clin Immunol 108:241.

51. Gomez-Puertas, P., C. Albo, E. Perez-Pastrana, A. Vivo, and A. Portela. 2000. Influenza virus matrix protein is the major driving force in virus budding. J Virol 74:11538.

52. Gheysen, D., E. Jacobs, F. de Foresta, C. Thiriart, M. Francotte, D. Thines, and M. De Wilde. 1989. Assembly and release of HIV-1 precursor Pr55gag virus-like particles from recombinant baculovirus-infected insect cells. Cell 59:103.
53. Johnson, M. C., H. M. Scobie, and V. M. Vogt. 2001. PR domain of rous sarcoma virus Gag causes an assembly/budding defect in insect cells. J Virol 75:4407.
54. Kakker, N. K., M. V. Mikhailov, M. V. Nermut, A. Burny, and P. Roy. 1999. Bovine leukemia virus Gag particle assembly in insect cells: formation of chimeric particles by domain-switched leukemia/lentivirus Gag polyprotein. Virology 265:308.
55. Luo, L., Y. Li, and C. Y. Kang. 1990. Expression of gag precursor protein and secretion of virus-like gag particles of HIV-2 from recombinant baculovirus-infected insect cells. Virology 179:874.
56. Morikawa, S., T. F. Booth, and D. H. Bishop. 1991. Analyses of the requirements for the synthesis of virus-like particles by feline immunodeficiency virus gag using baculovirus vectors. Virology 183:288.
57. Takahashi, R. H., K. Nagashima, T. Kurata, and H. Takahashi. 1999. Analysis of human lymphotropic T-cell virus type II-like particle production by recombinant baculovirus-infected insect cells. Virology 256:371.
58. Yamshchikov, G. V., G. D. Ritter, M. Vey, and R. W. Compans. 1995. Assembly of SIV virus-like particles containing envelope proteins using a baculovirus expression system. Virology 214:50.
59. Weldon, R. A., Jr., C. R. Erdie, M. G. Oliver, and J. W. Wills. 1990. Incorporation of chimeric gag protein into retroviral particles. J Virol 64:4169.
60. Andrawiss, M., Y. Takeuchi, L. Hewlett, and M. Collins. 2003. Murine leukemia virus particle assembly quantitated by fluorescence microscopy: role of Gag-Gag interactions and membrane association. J Virol 77:11651.
61. Leser, G. P., and R. A. Lamb. 2005. Influenza virus assembly and budding in raft-derived microdomains: a quantitative analysis of the surface distribution of HA, NA and M2 proteins. Virology 342:215.
62. Takeda, M., G. P. Leser, C. J. Russell, and R. A. Lamb. 2003. Influenza virus hemagglutinin concentrates in lipid raft microdomains for efficient viral fusion. Proc Natl Acad Sci USA 100:14610.
63. Campbell, S. M., S. M. Crowe, and J. Mak. 2001. Lipid rafts and HIV-1: from viral entry to assembly of progeny virions. J Clin Virol 22:217.
64. Sandrin, V., and F. L. Cosset. 2006. Intracellular versus cell surface assembly of retroviral pseudotypes is determined by the cellular localization of the viral glycoprotein, its capacity to interact with Gag, and the expression of the Nef protein. J Biol Chem 281:528.
65. Salazar-Gonzalez, R. M., and S. J. McSorley. 2005. *Salmonella* flagellin, a microbial target of the innate and adaptive immune system. Immunol Lett 101:117.
66. Cuadros, C., F. J. Lopez-Hernandez, A. L. Dominguez, M. McClelland, and J. Lustgarten. 2004. Flagellin fusion proteins as adjuvants or vaccines induce specific immune responses. Infect Immun 72:2810.
67. Didierlaurent, A., I. Ferrero, L. A. Otten, B. Dubois, M. Reinhardt, H. Carlsen, R. Blomhoff, S. Akira, J. P. Kraehenbuhl, and J. C. Sirard. 2004. Flagellin promotes myeloid differentiation factor 88-dependent development of Th2-type response. J Immunol 172:6922.
68. Tsujimoto, H., T. Uchida, P. A. Efron, P. O, Scumpia, A. Verma, T. Matsumoto, S. K. Tschoeke, R. F. Ungaro, S. Ono, S. Seki, M. J. Clare-Salzler, H. V. Baker, H. Mochizuki, R. Ramphal, and L. L. Moldawer. 2005. Flagellin enhances NK cell proliferation and activation directly and through dendritic cell-NK cell interactions. J Leukoc Biol 78:888.
69. Hayashi, F., T. K. Means, and A. D. Luster. 2003. Toll-like receptors stimulate human neutrophil function. Blood 102: 2660.
70. Hayashi, F., K. D. Smith, A. Ozinsky, T. R. Hawn, E. C. Yi, D. R. Goodlett, J. K. Eng, S. Akira, D. M. Underhill, and A. Aderem. 2001. The innate immune response to bacterial flagellin is mediated by Toll-like receptor 5. Nature 410: 1099.
71. Gewirtz, A. T., P. O, Simon, Jr., C. K. Schmitt, L. J. Taylor, C. H. Hagedorn, A. D. O'Brien, A. S. Neish, and J. L. Madara. 2001. *Salmonella typhimurium* translocates flagellin across intestinal epithelia, inducing a proinflammatory response. J Clin Invest 107:99.
72. Means, T. K., F. Hayashi, K. D. Smith, A. Aderem, and A. D. Luster. 2003. The Toll-like receptor 5 stimulus bacterial flagellin induces maturation and chemokine production in human dendritic cells. J Immunol 170:5165.
73. Smith, K. D., E. Andersen-Nissen, F. Hayashi, K. Strobe, M. A. Bergman, S. L. Barrett, B. T. Cookson, and A. Aderem. 2003. Toll-like receptor 5 recognizes a conserved site on flagellin required for protofilament formation and bacterial motility. Nat Immunol 4:1247.
74. Honko, A. N., N. Sriranganathan, C. J. Lees, and S. B. Mizel. 2006. Flagellin is an effective adjuvant for immunization against lethal respiratory challenge with *Yersinia pestis*. Infect Immun 74:1113.
75. Jeon, S. H., T. Ben-Yedidia, and R. Arnon. 2002. Intranasal immunization with synthetic recombinant vaccine containing multiple epitopes of influenza virus. Vaccine 20:2772.
76. Levi, R., and R. Arnon. 1996. Synthetic recombinant influenza vaccine induces efficient long-term immunity and cross-strain protection. Vaccine 14:85.
77. Lee, S. E., S. Y. Kim, B. C. Jeong, Y. R. Kim, S. J. Bae, O, S. Ahn, J. J. Lee, H. C. Song, J. M. Kim, H. E. Choy, S. S. Chung, M. N. Kweon, and J. H. Rhee. 2006. A bacterial flagellin, *Vibrio vulnificus* FlaB, has a strong mucosal adjuvant activity to induce protective immunity. Infect Immun 74:694.
78. Applequist, S. E., E. Rollman, M. D. Wareing, M. Liden, B. Rozell, J. Hinkula, and H. G. Ljunggren. 2005. Activation of innate immunity, inflammation, and potentiation of DNA vaccination through mammalian expression of the TLR5 agonist flagellin. J Immunol 175:3882.
79. Ramos, H. C., M. Rumbo, and J. C. Sirard. 2004. Bacterial flagellins: mediators of pathogenicity and host immune responses in mucosa. Trends Microbiol 12:509.
80. Holsinger, L. J., and R. A. Lamb. 1991. Influenza virus M2 integral membrane protein is a homotetramer stabilized by formation of disulfide bonds. Virology 183:32.
81. Lamb, R. A., S. L. Zebedee, and C. D. Richardson. 1985. Influenza virus M2 protein is an integral membrane protein expressed on the infected-cell surface. Cell 40:627.
82. Holsinger, L. J., D. Nichani, L. H. Pinto, and R. A. Lamb. 1994. Influenza A virus M2 ion channel protein: a structure-function analysis. J Virol 68:1551.
83. Takeda, M., A. Pekosz, K. Shuck, L. H. Pinto, and R. A. Lamb. 2002. Influenza a virus M2 ion channel activity is essential for efficient replication in tissue culture. J Virol 76:1391.
84. Frace, A. M., A. I. Klimov, T. Rowe, R. A. Black, and J. M. Katz. 1999. Modified M2 proteins produce heterotypic immunity against influenza A virus. Vaccine 17:2237.

85. Neirynck, S., T. Deroo, X. Saelens, P. Vanlandschoot, W. M. Jou, and W. Fiers. 1999. A universal influenza A vaccine based on the extracellular domain of the M2 protein. Nat Med 5:1157.
86. Slepushkin, V. A., J. M. Katz, R. A. Black, W. C. Gamble, P. A. Rota, and N. J. Cox. 1995. Protection of mice against influenza A virus challenge by vaccination with baculovirus-expressed M2 protein. Vaccine 13:1399.
87. Treanor, J. J., E. L. Tierney, S. L. Zebedee, R. A. Lamb, and B. R. Murphy. 1990. Passively transferred monoclonal antibody to the M2 protein inhibits influenza A virus replication in mice. J Virol 64:1375.
88. De Filette, M., W. Min Jou, A. Birkett, K. Lyons, B. Schultz, A. Tonkyro, S. Resch, and W. Fiers. 2005. Universal influenza A vaccine: optimization of M2-based constructs. Virology 337:149.
89. De Filette, M., A. Ramne, A. Birkett, N. Lycke, B. Lowenadler, W. Min Jou, X. Saelens, and W. Fiers. 2006. The universal influenza vaccine M2e-HBc administered intranasally in combination with the adjuvant CTA1-DD provides complete protection. Vaccine 24:544.
90. Fiers, W., M. De Filette, A. Birkett, S. Neirynck, and W. Min Jou. 2004. A "universal" human influenza A vaccine. Virus Res 103:173.
91. Liu, W., Z. Peng, Z. Liu, Y. Lu, J. Ding, and Y. H. Chen. 2004. High epitope density in a single recombinant protein molecule of the extracellular domain of influenza A virus M2 protein significantly enhances protective immunity. Vaccine 23:366.
92. Fan, J., X. Liang, M. S. Horton, H. C. Perry, M. P. Citron, G. J. Heidecker, T. M. Fu, J. Joyce, C. T. Przysiecki, P. M. Keller, V. M. Garsky, R. Ionescu, Y. Rippeon, L. Shi, M. A. Chastain, J. H. Condra, M. E. Davies, J. Liao, E. A. Emini, and J. W. Shiver. 2004. Preclinical study of influenza virus A M2 peptide conjugate vaccines in mice, ferrets, and rhesus monkeys. Vaccine 22:2993.
93. Ionescu, R. M., C. T. Przysiecki, X. Liang, V. M. Garsky, J. Fan, B. Wang, R. Troutman, Y. Rippeon, E. Flanagan, J. Shiver, and L. Shi. 2006. Pharmaceutical and immunological evaluation of human papillomavirus viruslike particle as an antigen carrier. J Pharm Sci 95:70.
94. Hatziioannou, T., E. Delahaye, F. Martin, S. J. Russell, and F. L. Cosset. 1999. Retroviral display of functional binding domains fused to the amino terminus of influenza hemagglutinin. Hum Gene Ther 10:1533.
95. Li, Z. N., S, N. Mueller, L. Ye, Z. Bu, C. Yang, R. Ahmed, and D. A. Steinhauer. 2005. Chimeric influenza virus hemagglutinin proteins containing large domains of the *Bacillus anthracis* protective antigen: protein characterization, incorporation into infectious influenza viruses, and antigenicity. J Virol 79:10003.
96. Haynes, J. R., S. X. Cao, B. Rovinski, C. Sia, O. James, G. A. Dekaban, and M. H. Klein. 1991. Production of immunogenic HIV-1 viruslike particles in stably engineered monkey cell lines. AIDS Res Hum Retroviruses 7:17.
97. Rovinski, B., J. R. Haynes, S. X. Cao, O. James, C. Sia, S. Zolla-Pazner, T. J. Matthews, and M. H. Klein. 1992. Expression and characterization of genetically engineered human immunodeficiency virus-like particles containing modified envelope glycoproteins: implications for development of a cross-protective AIDS vaccine. J Virol 66:4003.
98. Fynan, E. F., R. G. Webster, D. H. Fuller, J. R. Haynes, J. C. Santoro, and H. L. Robinson. 1995. DNA vaccines: a novel approach to immunization. Int J Immunopharmacol 17:79.
99. Fynan, E. F., R. G. Webster, D. H. Fuller, J. R. Haynes, J. C. Santoro, and H. L. Robinson. 1993. DNA vaccines: protective immunizations by parenteral, mucosal, and gene-gun inoculations. Proc Natl Acad Sci USA 90:11478.
100. Kodihalli, S., J. R. Haynes, H. L. Robinson, and R. G. Webster. 1997. Cross-protection among lethal H5N2 influenza viruses induced by DNA vaccine to the hemagglutinin. J Virol 71:3391.
101. Robinson, H. L., S. Lu, D. M. Feltquate, C. T. Torres, J. Richmond, C. M. Boyle, M. J. Morin, J. C. Santoro, R. G. Webster, D. Montefiori, Y. Yasutomi, N. L. Letvin, K. Manson, M. Wyand, and J. R. Haynes. 1996. DNA vaccines. AIDS Res Hum Retroviruses 12:455.
102. Drape, R. J., M. D. Macklin, L. J. Barr, S. Jones, J. R. Haynes, and H. J. Dean. 2006. Epidermal DNA vaccine for influenza is immunogenic in humans. Vaccine in press.
103. Kretzchmar, E., R. Geyer, and H. D. Klenk. 1994. Baculovirus infection does not alter N-glycosylation in *Spodoptera frugiperda* cells. Biol Chem Hoppe Seyler 375:23.
104. Lu, D., and A. J. Hickey. 2005. Liposomal dry powders as aerosols for pulmonary delivery of proteins. AAPS PharmSciTech 6:E641.
105. Cowdery, S., M. Frey, S. Orlowski, and A. Gray. 1976. Stability characteristics of freeze-dried human live virus vaccines. Dev Biol Stand 36:297.
106. Peetermans, J., G. Colinet, A. Bouillet, E. D'Hondt, and J. Stephenne. 1976. Stability of live, freeze-dried virus vaccines. Dev Biol Stand 36:291.
107. Yannarell, D. A., K. M. Goldberg, and R. N. Hjorth. 2002. Stabilizing cold-adapted influenza virus vaccine under various storage conditions. J Virol Methods 102:15.
108. Sampson, H. A., J. Bernhisel-Broadbent, E. Yang, and S. M. Scanlon. 1991. Safety of casein hydrolysate formula in children with cow milk allergy. J Pediatr 118:520.
109. Gambaryan, A. A. Tuzikov, G. Pazynina, N. Bovin, A. Balish, and A. Klimov. 2005. Evolution of the receptor binding phenotype of influenza A (H5) viruses. Virology (electronic publication ahead of print version).
110. Suzuki, Y, 2005. Sialobiology of Influenza: Molecular Mechanism of Host Range Variation of Influenza Viruses. Biological and Pharmaceutical Bulletin 28:399-408.
111. Latham, T., and J. M. Galarza. 2001. Formation of wild-type and chimeric influenza virus-like particles following simultaneous expression of only four structural proteins. J. Virol. 75(13):6154-65.
112. Galarza, J. M., T. Latham, and A. Cupo. 2005. Virus-like particle (VLP) vaccine conferred complete protection against a lethal influenza virus challenge. Viral Immunol. 18(1):244-51.

SEQUENCE LISTING

<160> NUMBER OF SEQ ID NOS: 31

<210> SEQ ID NO 1
<211> LENGTH: 20
<212> TYPE: DNA

<213> ORGANISM: Artificial Sequence
<220> FEATURE:
<223> OTHER INFORMATION: Synthetic Construct

<400> SEQUENCE: 1
tccatgacgt tcctgacgtt                                              20

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
tctcccagcg tgcgccat                                                18

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
accgatgacg tcgccggtga cggcaccacg                                   30

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
tcgtcgtttt gtcgttttgt cgtt                                         24

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
tccatgacgt tcctgatgct                                              20

<210> SEQ ID NO 6
<211> LENGTH: 1650
<212> TYPE: DNA
<213> ORGANISM: Artificial Sequence
<220> FEATURE:
<223> OTHER INFORMATION: Synthetic Construct

<400> SEQUENCE: 6
atggaactgc tgatcctgaa ggctaacgct atcaccacca tcctgaccgc tgtcaccttc      60
tgcttcgcct ccggccagaa catcaccgag gaattctacc agtccacctg ctccgctgtc     120
tccaagggtt acctgtccgc tctgcgcacc ggctggtaca cctccgtcat caccatcgag     180
ctgtccaaca tcaaggaaaa caagtgcaac ggcaccgacg ctaaggtcaa gctgatcaag     240
caggaactgg acaagtacaa gaacgctgtc accgagctgc agctgctgat gcagtccacc     300
cccgctacca caaccgcgc tcgccgtgag ctgccccgct tcatgaacta cacccctgaac     360 aacgccaaga aaaccaacgt cacccctgtcc aagaagcgca agcgccgctt cctgggtttc     420

```
ctgctgggtg tcggttccgc tatcgcttcc ggtgtcgctg tctctaaggt cctgcacctg    480
gaaggcgagg tcaacaagat caagtccgcc ctgctgtcca ccaacaaggc tgtcgtgtcc    540
ctgtccaacg gtgtctccgt cctgacctcc aaggtgctgg acctgaagaa ctacatcgac    600
aagcagctgc tgcccatcgt caacaagcag tcctgctcca tctccaacat cgagactgtc    660
atcgagttcc agcagaagaa caaccgcctg ctggaaatca cccgcgagtt ctccgtcaac    720
gctggtgtca ccaccctgt ctccacctac atgctgacca ctccgagct gctgtccctg     780 atcaacgaca tgcccatcac caacgaccaa agaaactga tgtccaacaa cgtccagatc    840
gtccgccagc agtcctactc tatcatgagc atcatcaagg aagaggtcct ggcttacgtc    900
gtccagctgc ccctgtacgg tgtcatcgac accccctgct ggaagctgca cacctccccc    960
ctgtgcacca ccaacaccaa ggaaggttcc aacatctgcc tgacccgcac cgaccgcggc   1020
tggttctgcg acaacgctgg ctctgtctcc ttcttccccc aagctgagac ttgcaaggtc   1080
cagtccaacc gcgtgttctg cgacaccatg aactccctga ccctgccctc cgaggtcaac   1140
ctgtgcaacg tcgacatctt caaccccaag tacgactgca agatcatgac ctctaagacc   1200
gacgtgtcct cctctgtcat cacctccctg ggtgctatcg tgtcctgcta cggcaagacc   1260
aagtgcaccg cttccaacaa gaaccgcggt atcatcaaga ccttctccaa cggttgcgac   1320
tacgtgtcca caagggcgt cgacaccgtg tccgtcggca cacctgta ctacgtgaac      1380 aagcaggaag gcaagtccct gtacgtcaag ggcgagccca tcatcaactt ctacgacccc   1440
ctggtgttcc cctccgacga gttcgacgct tccatcagcc aggtcaacga gaagatcaac   1500
cagtccctgg ctttcatccg caagtccgac gagctgctgc acaacgtgaa cgctggcaag   1560
tctaccacca acatcatgat caccactatc atcatcgtga tcatcgtcat cctgctgtct   1620
ctgatcgctg tcggtctgct gctgtactaa                                    1650
```

<210> SEQ ID NO 7
<211> LENGTH: 549
<212> TYPE: PRT
<213> ORGANISM: Artificial Sequence
<220> FEATURE:
<223> OTHER INFORMATION: Synthetic Construct

<400> SEQUENCE: 7

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

```
Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Phe Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
        530                 535                 540

Gly Leu Leu Leu Tyr
545
```

<210> SEQ ID NO 8
<211> LENGTH: 1689
<212> TYPE: DNA
<213> ORGANISM: Artificial Sequence
<220> FEATURE:
<223> OTHER INFORMATION: Synthetic Construct

<400> SEQUENCE: 8

```
atggaactgc tgatcctgaa ggctaacgct atcaccacca tcctgaccgc tgtgaccttc      60
tgcttcgctt ccggccagaa catcaccgag gaattctacc agtccacctg ctccgctgtg     120
tccaagggtt acctgtccgc tctgcgtacc ggttggtaca cctccgtgat caccatcgag     180
ctgtccaaca tcaaagagaa caagtgcaac ggcaccgacg ctaaggtcaa gctgatcaag     240
caggaactgg acaagtacaa gaacgctgtg accgagctgc agctgctgat gcagtccacc     300
cccgctacca caaccgtgc tcgtcgtgag ctgccccgtt tcatgaacta caccctgaac     360
aacgccaaga aaccaacgt caccctgtcc aagaagcgta agcgtcgttt cctgggtttc     420
ctgctgggtg tgggtagcgc tatcgcctcc ggtgtcgctg tctccaaggt gctgcacctc     480
gagggcgagg tgaacaagat caagtccgcc ctgctgtcca ccaacaaggc tgtggtgtcc     540
ctgtccaacg gtgtctccgt tctgaccagc aaggtcttgg acctgaagaa ctacatcgac     600
aagcagctgc tgcccatcgt gaacaagcag tcctgctcca tctccaacat cgagactgtg     660
atcgagttcc agcagaagaa caaccgtctg ctcgagatca cccgtgagtt ctccgtgaac     720
gctggtgtca ccaccccgt gtccacctac atgctgacca actccgagct gctgtccctg     780
atcaacgaca tgcccatcac caacgaccag aaaaagctga tgtccaacaa cgtgcagatc     840
gtgcgtcagc agtcctactc tatcatgagc atcatcaaag aggaagtcct ggcttacgtg     900
gtgcagctgc ccctgtacgg tgtcatcgac accccctgct ggaagctgca cacctccccc     960
ctgtgcacca ccaacaccaa agagggttcc aacatctgcc tgacccgtac cgatcgtggt    1020
tggttctgtg acaacgctgg ttccgtgtcc ttcttccccc aagctgagac ttgcaaggtg    1080
cagtccaacc gtgtgttctg cgacaccatg aactccctga ccctgccctc cgaggtgaac    1140
ctgtgcaacg tggacatctt caaccccaag tacgactgca gatcatgac ctctaagacc    1200
gacgtgtcct cctccgtcat cacctcccctg ggtgctatcg tgtcctgcta cggcaagacc    1260
aagtgcaccg cttccaacaa gaaccgcggt atcatcaaga ccttctccaa cggttgcgac    1320
tacgtgtcca caagggtgt cgataccgtg tccgtcggta cacccctgta ctacgtcaac    1380
aagcaggaag gcaagtctct gtacgtgaag ggcgagccca tcatcaactt ctacgacccc    1440
ctggtgttcc cctccgacga gttcgacgct tccatcagcc aggtcaacga aagatcaac    1500
cagtccctgg cttttcatccg taagtccgac gagctgctgc acaacgtcaa cgctggcaag    1560
tccaccacca catcctgtc catctactcc accgtggctt cctccctggc tctggctatc    1620
atgatggctg tctgtccct gtggatgtgc tccaacggct ccctgcagtg ccgtatctgc    1680
atctaataa                                                           1689
```

<210> SEQ ID NO 9
<211> LENGTH: 561
<212> TYPE: PRT
<213> ORGANISM: Artificial Sequence
<220> FEATURE:
<223> OTHER INFORMATION: Synthetic Construct

<400> SEQUENCE: 9

Met Glu Leu Leu Ile Leu Lys Ala Asn Ala Ile Thr Thr Ile Leu Thr

-continued

```
1               5                   10                  15
Ala Val Thr Phe Cys Phe Ala Ser Gly Gln Asn Ile Thr Glu Glu Phe
                20                  25                  30
Tyr Gln Ser Thr Cys Ser Ala Val Ser Lys Gly Tyr Leu Ser Ala Leu
                35                  40                  45
Arg Thr Gly Trp Tyr Thr Ser Val Ile Thr Ile Glu Leu Ser Asn Ile
                50                  55                  60
Lys Glu Asn Lys Cys Asn Gly Thr Asp Ala Lys Val Lys Leu Ile Lys
 65                 70                  75                  80
Gln Glu Leu Asp Lys Tyr Lys Asn Ala Val Thr Glu Leu Gln Leu Leu
                    85                  90                  95
Met Gln Ser Thr Pro Ala Thr Asn Asn Arg Ala Arg Arg Glu Leu Pro
                100                 105                 110
Arg Phe Met Asn Tyr Thr Leu Asn Asn Ala Lys Lys Thr Asn Val Thr
                115                 120                 125
Leu Ser Lys Lys Arg Lys Arg Arg Phe Leu Gly Phe Leu Leu Gly Val
130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                    165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Gln Leu Leu Pro Ile Val Asn
                    195                 200                 205
Lys Gln Ser Cys Ser Ile Ser Asn Ile Glu Thr Val Ile Glu Phe Gln
210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                    245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
                275                 280                 285
Met Ser Ile Ile Lys Glu Glu Val Leu Ala Tyr Val Val Gln Leu Pro
                290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                    325                 330                 335
Thr Asp Arg Gly Trp Phe Cys Asp Asn Ala Gly Ser Val Ser Phe Phe
                340                 345                 350
Pro Gln Ala Glu Thr Cys Lys Val Gln Ser Asn Arg Val Phe Cys Asp
                355                 360                 365
Thr Met Asn Ser Leu Thr Leu Pro Ser Glu Val Asn Leu Cys Asn Val
                370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                    405                 410                 415
Tyr Gly Lys Thr Lys Cys Thr Ala Ser Asn Lys Asn Arg Gly Ile Ile
                420                 425                 430
```

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Leu Ser Ile
        515                 520                 525

Tyr Ser Thr Val Ala Ser Ser Leu Ala Leu Ala Ile Met Met Ala Gly
    530                 535                 540

Leu Ser Leu Trp Met Cys Ser Asn Gly Ser Leu Gln Cys Arg Ile Cys
545                 550                 555                 560

Ile

<210> SEQ ID NO 10
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 10

| | |
|---|---|
| atggaactgc tgatcctgaa ggctaacgct atcaccacca tcctgaccgc tgtgaccttc | 60 |
| tgcttcgctt ccggccagaa catcaccgag gaattctacc agtccacctg ctccgctgtg | 120 |
| tccaagggtt acctgtccgc tctgcgtacc ggttggtaca cctccgtgat caccatcgag | 180 |
| ctgtccaaca tcaaagagaa caagtgcaac ggcaccgacg ctaaggtcaa gctgatcaag | 240 |
| caggaactgg acaagtacaa gaacgctgtg accgagctgc agctgctgat gcagtccacc | 300 |
| cccgctacca caaccgtgc tcgtcgtgag ctgccccgtt tcatgaacta cacccctgaac | 360 |
| aacgccaaga aaaccaacgt caccctgtcc aagaagcgta agcgtcgttt cctgggtttc | 420 |
| ctgctgggtg tgggtagcgc tatcgcctcc ggtgtcgctg tctccaaggt gctgcacctc | 480 |
| gagggcgagt gaacaagat caagtccgcc ctgctgtcca ccaacaaggc tgtggtgtcc | 540 |
| ctgtccaacg tgtctccgt tctgaccagc aaggtcttgg acctgaagaa ctacatcgac | 600 |
| aagcagctgc tgcccatcgt gaacaagcag tcctgctcca tctccaacat cgagactgtg | 660 |
| atcgagttcc agcagaagaa caaccgtctg ctcgagatca cccgtgagtt ctccgtgaac | 720 |
| gctggtgtca ccaccccgt gtccacctac atgctgacca ctccgagct gctgtccctg | 780 |
| atcaacgaca tgcccatcac caacgaccag aaaaagctga tgtccaacaa cgtgcagatc | 840 |
| gtgcgtcagc agtcctactc tatcatgagc atcatcaaag aggaagtcct ggcttacgtg | 900 |
| gtgcagctgc ccctgtacgg tgtcatcgac acccccctgct ggaagctgca cacctccccc | 960 |
| ctgtgcacca ccaacaccaa agagggttcc aacatctgcc tgacccgtac cgatcgtggt | 1020 |
| tggttctgtg acaacgctgg ttccgtgtcc ttcttccccc aagctgagac ttgcaaggtg | 1080 |
| cagtccaacc gtgtgttctg cgacaccatg aactccctga ccctgccctc cgaggtgaac | 1140 |
| ctgtgcaacg tggacatctt caacccccaag tacgactgca agatcatgac ctctaagacc | 1200 |
| gacgtgtcct cctccgtcat cacctcccctg ggtgctatcg tgtcctgcta cggcaagacc | 1260 |

```
aagtgcaccg cttccaacaa gaaccgcggt atcatcaaga ccttctccaa cggttgcgac   1320
tacgtgtcca acaagggtgt cgataccgtg tccgtcggta acaccctgta ctacgtcaac   1380
aagcaggaag gcaagtctct gtacgtgaag ggcgagccca tcatcaactt ctacgacccc   1440
ctggtgttcc cctccgacga gttcgacgct tccatcagcc aggtcaacga gaagatcaac   1500
cagtccctgg ctttcatccg taagtccgac gagctgctgc acaacgtcaa cgctggcaag   1560
tccaccacca acggcaccta ccagatcctg tccatctact ccaccgtggc ttcctccctg   1620
gctctggcta tcatgatggc tggtctgtcc ctgtggatgt gctccaacgg ctccctgcag   1680
tgccgtatct gcatctaata a                                             1701
```

<210> SEQ ID NO 11
<211> LENGTH: 565
<212> TYPE: PRT
<213> ORGANISM: Artificial Sequence
<220> FEATURE:
<223> OTHER INFORMATION: Synthetic Construct

<400> SEQUENCE: 11

```
Met Glu Leu Leu Ile Leu Lys Ala Asn Ala Ile Thr Thr Ile Leu Thr
 1               5                  10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285
```

```
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Phe Cys Asp Asn Ala Gly Ser Val Ser Phe Phe
                340                 345                 350
Pro Gln Ala Glu Thr Cys Lys Val Gln Ser Asn Arg Val Phe Cys Asp
                355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
                435                 440                 445
Thr Val Ser Val Gly Asn Thr Leu Tyr Tyr Val Asn Lys Gln Glu Gly
450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
                500                 505                 510
Leu His Asn Val Asn Ala Gly Lys Ser Thr Thr Asn Gly Thr Tyr Gln
                515                 520                 525
Ile Leu Ser Ile Tyr Ser Thr Val Ala Ser Ser Leu Ala Leu Ala Ile
                530                 535                 540
Met Met Ala Gly Leu Ser Leu Trp Met Cys Ser Asn Gly Ser Leu Gln
545                 550                 555                 560
Cys Arg Ile Cys Ile
                565

<210> SEQ ID NO 12
<211> LENGTH: 1620
<212> TYPE: DNA
<213> ORGANISM: Artificial Sequence
<220> FEATURE:
<223> OTHER INFORMATION: Synthetic Construct

<400> SEQUENCE: 12
atgggccaga ctgttaccac tcccttaagt ttgaccttag gtcactggaa agatgtcgag      60
cggatcgctc acaaccagtc ggtagatgtc aagaagagac gttgggttac cttctgctct     120
gcagaatggc caacctttaa cgtcggatgg ccgcgagacg gcacctttaa ccgagacctc     180
atcacccagg ttaagatcaa ggtctttttca cctggcccgc atggacaccc agaccaggtc     240
ccctacatcg tgacctggga agccttggct tttgaccccc ctccctgggt caagcccttt     300
gtacacccta gcctccgcc tcctcttcct ccatccgccc cgtctctccc ccttgaacct     360
cctcgttcga ccccgcctcg atcctccctt tatccagccc tcactccttc tctaggcgcc     420
```

```
aaacctaaac ctcaagttct ttctgacagt ggggggccgc tcatcgacct acttacagaa    480
gaccccccgc cttatagggg cccaagacca ccccttccg acagggacgg aaatggtgga     540
gaagcgaccc ctgcgggaga ggcaccggac ccctccccaa tggcatctcg cctacgtggg    600
agacgggagc cccctgtggc cgactccact acctcgcagg cattccccct ccgcgcagga    660
ggaaacggac agcttcaata ctggccgttc tcctcttctg acctttacaa ctggaaaaat    720
aataaccctt ctttttctga agatccaggt aaactgacag ctctgatcga gtctgttctc    780
atcacccatc agcccacctg ggacgactgt cagcagctgt tggggactct gctgaccgga    840
gaagaaaaac aacgggtgct cttagaggct agaaaggcgg tgcggggcga tgatgggcgc    900
cccactcaac tgcccaatga agtcgatgcc gcttttcccc tcgagcgccc agactgggat    960
tacaccaccc aggcaggtag gaaccaccta gtccactatc gccagttgct cctagcgggt   1020
ctccaaaacg cgggcagaag ccccaccaat ttggccaagg taaaaggaat aacacaaggg   1080
cccaatgagt ctccctcggc cttcctagag agacttaagg aagcctatcg caggtacact   1140
ccttatgacc ctgaggaccc agggcaagaa actaatgtgt ctatgtcttt catttggcag   1200
tctgccccag acattgggag aaagttagag aggttagaag atttaaaaaa caagacgctt   1260
ggagatttgg ttagagaggc agaaaagatc tttaataaac gagaaccccc ggaagaagaa   1320
gaggaacgta tcaggagaga aacagaggaa aagaagaac gccgtaggac agaggatgag    1380
cagaaagaga agaaagaga tcgtaggaga catagagaga tgagcaagct attggccact    1440
gtcgttagtg gacagaaaca ggatagacag ggaggagaac gaaggaggtc ccaactcgat   1500
cgcgaccagt gtgcctactg caaagaaaag gggcactggg ctaaagattg tcccaagaaa   1560
ccacgaggac ctcggggacc aagaccccag acctccctcc tgaccctaga tgactagtag   1620
```

<210> SEQ ID NO 13
<211> LENGTH: 538
<212> TYPE: PRT
<213> ORGANISM: Artificial Sequence
<220> FEATURE:
<223> OTHER INFORMATION: Synthetic Construct

<400> SEQUENCE: 13

```
Met Gly Gln Thr Val Thr Thr Pro Leu Ser Leu Thr Leu Gly His Trp
 1               5                  10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Trp
                85                  90                  95

Val Lys Pro Phe Val His Pro Lys Pro Pro Pro Leu Pro Pro Ser
               100                 105                 110

Ala Pro Ser Leu Pro Leu Glu Pro Pro Arg Ser Thr Pro Pro Arg Ser
               115                 120                 125

Ser Leu Tyr Pro Ala Leu Thr Pro Ser Leu Gly Ala Lys Pro Lys Pro
           130                 135                 140

Gln Val Leu Ser Asp Ser Gly Gly Pro Leu Ile Asp Leu Leu Thr Glu
145                 150                 155                 160
```

```
Asp Pro Pro Tyr Arg Asp Pro Arg Pro Pro Ser Asp Arg Asp
            165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
    290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
    370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Arg Ile Arg Arg Glu Thr
        435                 440                 445

Glu Glu Lys Glu Glu Arg Arg Arg Thr Glu Asp Glu Gln Lys Glu Lys
    450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg Arg
                485                 490                 495

Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
        515                 520                 525

Pro Gln Thr Ser Leu Leu Thr Leu Asp Asp
    530                 535
```

<210> SEQ ID NO 14
<211> LENGTH: 1539
<212> TYPE: DNA
<213> ORGANISM: Artificial Sequence
<220> FEATURE:

<223> OTHER INFORMATION: Synthetic Construct

<400> SEQUENCE: 14

```
atgggagcca gagccagcgt gctgtctggc ggcgagctgg acagatggga gaagatccgg      60
ctgcggccag gcggcaagaa gaagtacaag ctgaagcaca tcgtgtgggc tagccgggag     120
ctggaaagat cgccgtgaa ccccggactg ctggaaacca gcgagggctg cagacagatc     180
ctgggccagc tgcagccatc tctgcagacc ggcagcgagg aactgcggag cctgtacaac     240
accgtggcca ccctgtactg cgtgcaccag cggatcgaga tcaaggacac caaagaggcc     300
ctggacaaga tcgaggaaga cagaacaag tccaagaaga aggcccagca ggccgctgcc     360
gataccggcc acagcagcca ggtgtcccag aactacccca tcgtgcagaa catccagggc     420
cagatggtgc accaggccat ctctcccaga accctgaacg cctgggtgaa agtggtggag     480
gaaaaggcct tcagccccga agtgatcccc atgttcagcg ccctgagcga aggcgccacc     540
cccaggacc tgaacaccat gctgaacacc gtgggaggac accaggccgc catgcagatg     600
ctgaaagaga caatcaacga gaggccgcc gagtgggaca gagtgcaccc tgtgcacgcc     660
ggacctatcg cccctggcca gatgagagag cccagaggca gcgatatcgc cggcaccaca     720
agcaccctgc aggaacagat cggctggatg acaaacaacc ccccatccc gtgggcgag     780
atctacaagc ggtggatcat cctgggcctg aacaagatcg tgcggatgta cagccccacc     840
tccatcctgg acatccggca gggccccaaa gagccctcc gggactacgt ggaccggttc     900
tacaagaccc tgcgggccga gcaggccagc caggaagtga gaactggat gaccgagaca     960
ctgctggtgc agaacgccaa ccccgactgc aagaccatcc tgaaggccct gggaccagc    1020
gccacctgg aagagatgat gaccgcctgt cagggcgtgg gcggacctgg acacaaagcc    1080
agagtgctgg ccgaggccat gagccaggtg accaacagcg ccaccatcat gatgcagcgg    1140
ggcaacttcc ggaaccagcg gaagatcgtg aagtgcttca ctgcggcaa ggaaggccac    1200
attgcccgga actgcagagc ccccagaaag aaaggctgct ggaagtgcgg aaagagggg    1260
caccagatga aggactgcac cgagcggcag gccaacttcc tcggcaaaat ctggcccagc    1320
tacaagggca gacccggcaa cttcctgcag agcagaccg agcctaccgc ccctcccttc    1380
ctgcagtcca ggcctgaacc taccgctccc ccgaggaaa gcttcagatc cggcgtggag    1440
acaaccaccc ctagccagaa gcaggaaccc atcgacaaag agctgtaccc cctgaccagc    1500
ctgagaagcc tgttcggcaa cgaccccagc agccagtga                           1539
```

<210> SEQ ID NO 15
<211> LENGTH: 512
<212> TYPE: PRT
<213> ORGANISM: Artificial Sequence
<220> FEATURE:
<223> OTHER INFORMATION: Synthetic Construct

<400> SEQUENCE: 15

```
Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Tyr Lys Leu Lys
             20                  25                  30

His Ile Val Trp Ala Ser Arg Glu Leu Glu Arg Phe Ala Val Asn Pro
         35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
```

-continued

```
                65                  70                  75                  80
            Thr Val Ala Thr Leu Tyr Cys Val His Gln Arg Ile Glu Ile Lys Asp
                            85                  90                  95
            Thr Lys Glu Ala Leu Asp Lys Ile Glu Glu Gln Asn Lys Ser Lys
                        100                 105                 110
            Lys Lys Ala Gln Gln Ala Ala Asp Thr Gly His Ser Ser Gln Val
                        115                 120                 125
            Ser Gln Asn Tyr Pro Ile Val Gln Asn Ile Gln Gly Gln Met Val His
                        130                 135                 140
            Gln Ala Ile Ser Pro Arg Thr Leu Asn Ala Trp Val Lys Val Val Glu
            145                 150                 155                 160
            Glu Lys Ala Phe Ser Pro Glu Val Ile Pro Met Phe Ser Ala Leu Ser
                                165                 170                 175
            Glu Gly Ala Thr Pro Gln Asp Leu Asn Thr Met Leu Asn Thr Val Gly
                        180                 185                 190
            Gly His Gln Ala Ala Met Gln Met Leu Lys Glu Thr Ile Asn Glu Glu
                        195                 200                 205
            Ala Ala Glu Trp Asp Arg Val His Pro Val His Ala Gly Pro Ile Ala
            210                 215                 220
            Pro Gly Gln Met Arg Glu Pro Arg Gly Ser Asp Ile Ala Gly Thr Thr
            225                 230                 235                 240
            Ser Thr Leu Gln Glu Gln Ile Gly Trp Met Thr Asn Asn Pro Pro Ile
                                245                 250                 255
            Pro Val Gly Glu Ile Tyr Lys Arg Trp Ile Ile Leu Gly Leu Asn Lys
                        260                 265                 270
            Ile Val Arg Met Tyr Ser Pro Thr Ser Ile Leu Asp Ile Arg Gln Gly
                        275                 280                 285
            Pro Lys Glu Pro Phe Arg Asp Tyr Val Asp Arg Phe Tyr Lys Thr Leu
                        290                 295                 300
            Arg Ala Glu Gln Ala Ser Gln Glu Val Lys Asn Trp Met Thr Glu Thr
            305                 310                 315                 320
            Leu Leu Val Gln Asn Ala Asn Pro Asp Cys Lys Thr Ile Leu Lys Ala
                                325                 330                 335
            Leu Gly Pro Ala Ala Thr Leu Glu Glu Met Met Thr Ala Cys Gln Gly
                        340                 345                 350
            Val Gly Gly Pro Gly His Lys Ala Arg Val Leu Ala Glu Ala Met Ser
                        355                 360                 365
            Gln Val Thr Asn Ser Ala Thr Ile Met Met Gln Arg Gly Asn Phe Arg
                        370                 375                 380
            Asn Gln Arg Lys Ile Val Lys Cys Phe Asn Cys Gly Lys Glu Gly His
            385                 390                 395                 400
            Ile Ala Arg Asn Cys Arg Ala Pro Arg Lys Lys Gly Cys Trp Lys Cys
                                405                 410                 415
            Gly Lys Glu Gly His Gln Met Lys Asp Cys Thr Glu Arg Gln Ala Asn
                        420                 425                 430
            Phe Leu Gly Lys Ile Trp Pro Ser Tyr Lys Gly Arg Pro Gly Asn Phe
                        435                 440                 445
            Leu Gln Ser Arg Pro Glu Pro Thr Ala Pro Pro Phe Leu Gln Ser Arg
                        450                 455                 460
            Pro Glu Pro Thr Ala Pro Pro Glu Glu Ser Phe Arg Ser Gly Val Glu
            465                 470                 475                 480
            Thr Thr Thr Pro Ser Gln Lys Gln Glu Pro Ile Asp Lys Glu Leu Tyr
                                485                 490                 495
```

Pro Leu Thr Ser Leu Arg Ser Leu Phe Gly Asn Asp Pro Ser Ser Gln
            500                 505                 510

<210> SEQ ID NO 16
<211> LENGTH: 1650
<212> TYPE: DNA
<213> ORGANISM: Artificial Sequence
<220> FEATURE:
<223> OTHER INFORMATION: Synthetic Construct

<400> SEQUENCE: 16

| | | | | | |
|---|---|---|---|---|---|
| atggagctgc | tgatcctgaa | ggccaacgcc | atcaccacca | tcctgaccgc | cgtgaccttc | 60 |
| tgcttcgcct | ccggccagaa | catcaccgag | gagttctacc | agtccacctg | ctccgccgtg | 120 |
| tccaagggct | acctgtccgc | cctgcggacc | ggctggtaca | cctccgtgat | caccatcgag | 180 |
| ctgtccaaca | tcaaagaaaa | caagtgcaac | ggcaccgacg | ccaaggtgaa | gctgatcaag | 240 |
| caggagctgg | acaagtacaa | gaacgccgtg | accgagctgc | agctgctgat | gcagtccacc | 300 |
| cctgccacca | caaccgggc | caggcggag | ctgcctcggt | tcatgaacta | caccctgaac | 360 |
| aacgccaaga | aaaccaacgt | caccctgtcc | aagaagcgga | agcggcggtt | cctgggcttc | 420 |
| ctgctgggcg | tgggctccgc | tatcgcctct | ggcgtggccg | tgtctaaggt | gctgcacctg | 480 |
| gagggcgagg | tgaacaagat | caagtctgcc | ctgctgtcca | ccaacaaggc | cgtggtgtcc | 540 |
| ctgtccaacg | gcgtgtccgt | gctgaccctc | aaggtgctgg | atctgaagaa | ctacatcgac | 600 |
| aagcagctgc | tgcctatcgt | gaacaagcag | tcctgctcca | tctccaacat | cgagacagtg | 660 |
| atcgagttcc | agcagaagaa | caccggctg | ctggaaatca | agagagagtt | ctccgtcaac | 720 |
| gctggtgtga | ccactcctgt | ctctacttat | atgctgacca | actccgagct | gctgtccctg | 780 |
| atcaacgaca | tgcctatcac | caacgaccag | aaaaagctga | tgtccaacaa | cgtgcagatc | 840 |
| gtgcggcagc | agtcctactc | tatcatgagc | atcatcaagg | aggaggtcct | ggcctacgtg | 900 |
| gtgcagctgc | ctctgtacgg | cgtgatcgac | acccccttgct | ggaagctgca | cacctccccc | 960 |
| ctgtgcacca | ccaacaccaa | ggagggctcc | aacatctgcc | tgacccggac | cgaccggggc | 1020 |
| tggttctgcg | acaacgccgg | ctccgtgtcc | ttctttccac | aggccgagac | atgcaaggtg | 1080 |
| cagtccaacc | gggtgttctg | cgataccatg | aactccctga | ccctgccttc | cgaggtgaac | 1140 |
| ctgtgcaacg | tggacatctt | caaccctaag | tacgactgca | agatcatgac | ctctaagacc | 1200 |
| gacgtgtcct | cctctgtgat | cacctccctg | ggcgccatcg | tgtcctgcta | cggcaagacc | 1260 |
| aagtgcaccg | cctccaacaa | gaaccgggga | atcatcaaga | ccttctccaa | cggctgcgac | 1320 |
| tacgtgtcca | ataagggcgt | ggacaccgtg | tccgtgggca | acacactgta | ctacgtgaat | 1380 |
| aagcaggagg | gcaagtctct | gtacgtgaag | ggcgagccta | tcatcaactt | ctacgacccct | 1440 |
| ctggtgttcc | cttccgacga | gttcgacgcc | tccatcagcc | aggtgaacga | gaagatcaac | 1500 |
| cagtccctgg | ccttcatccg | gaagtccgac | gagctgctgc | acaacgtgaa | cgctggcaag | 1560 |
| tctaccacca | accccgacca | ctccgccgcc | accaagccct | ccctgttcct | gttcctggtg | 1620 |
| tccctgctgc | acatcttctt | caagtgataa | | | | 1650 |

<210> SEQ ID NO 17
<211> LENGTH: 548
<212> TYPE: PRT
<213> ORGANISM: Artificial Sequence
<220> FEATURE:
<223> OTHER INFORMATION: Synthetic Construct

<400> SEQUENCE: 17

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Phe Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415
```

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Pro Asp His Ser
        515                 520                 525

Ala Ala Thr Lys Pro Ser Leu Phe Leu Phe Leu Val Ser Leu Leu His
    530                 535                 540

Ile Phe Phe Lys
545
```

<210> SEQ ID NO 18
<211> LENGTH: 1650
<212> TYPE: DNA
<213> ORGANISM: Artificial Sequence
<220> FEATURE:
<223> OTHER INFORMATION: Synthetic Construct

<400> SEQUENCE: 18

| | | |
|---|---|---|
| atggaactgc tgatcctgaa ggctaacgct atcaccacca tcctgaccgc tgtcaccttc | 60 |
| tgcttcgcct ccggccagaa catcaccgag gaattctacc agtccacctg ctccgctgtc | 120 |
| tccaagggtt acctgtccgc tctgcgcacc ggctggtaca cctccgtcat caccatcgag | 180 |
| ctgtccaaca tcaaggaaaa caagtgcaac ggcaccgacg ctaaggtcaa gctgatcaag | 240 |
| caggaactgg acaagtacaa gaacgctgtc accgagctgc agctgctgat gcagtccacc | 300 |
| cccgctacca caaccgcgc tcgccgtgag ctgccccgct tcatgaacta cacccctgaac | 360 |
| aacgccaaga aaaccaacgt caccctgtcc aagaagcgca agcgccgctt cctgggtttc | 420 |
| ctgctgggtg tcggttccgc tatcgcttcc ggtgtcgctg tctctaaggt cctgcacctg | 480 |
| gaaggcgagg tcaacaagat caagtccgcc tgctgtcca ccaacaaggc tgtcgtgtcc | 540 |
| ctgtccaacg tgtctccgt cctgacctcc aaggtgctgg acctgaagaa ctacatcgac | 600 |
| aagcagctgc tgcccatcgt caacaagcag tcctgctcca tctccaacat cgagactgtc | 660 |
| atcgagttcc agcagaagaa caaccgcctg ctggaaatca cccgcgagtt ctccgtcaac | 720 |
| gctggtgtca ccacccctgt ctccacctac atgctgacca ctccgagct gctgtccctg | 780 |
| atcaacgaca tgcccatcac caacgaccaa agaaaactga tgtccaacaa cgtccagatc | 840 |
| gtccgccagc agtcctactc tatcatgagc atcatcaagg aagaggtcct ggcttacgtc | 900 |
| gtccagctgc ccctgtacgg tgtcatcgac acccccctgct ggaagctgca cacctccccc | 960 |
| ctgtgcacca ccaacaccaa ggaaggttcc aacatctgcc tgacccgcac cgaccgcggc | 1020 |
| tggttctgcg acaacgctgg ctctgtctcc ttcttccccc aagctgagac ttgcaaggtc | 1080 |
| cagtccaacc gcgtgttctg cgacaccatg aactccctga ccctgccctc cgaggtcaac | 1140 |
| ctgtgcaacg tcgacatctt caaccccaag tacgactgca agatcatgac ctctaagacc | 1200 |
| gacgtgtcct cctctgtcat cacctccctg ggtgctatcg tgtcctgcta cggcaagacc | 1260 |

```
aagtgcaccg cttccaacaa gaaccgcggt atcatcaaga ccttctccaa cggttgcgac    1320
tacgtgtcca acaagggcgt cgacaccgtg tccgtcggca acaccctgta ctacgtgaac    1380
aagcaggaag gcaagtccct gtacgtcaag ggcgagccca tcatcaactt ctacgacccc    1440
ctggtgttcc cctccgacga gttcgacgct tccatcagcc aggtcaacga gaagatcaac    1500
cagtccctgg ctttcatccg caagtccgac gagctgctgc acaacgtgaa cgctggcaag    1560
tctaccacca acatcatgat caccactatc atcatcgtga tcatcgtcat cctgctgtct    1620
ctgatcgctg tcggtctgct gctgtactaa                                    1650
```

<210> SEQ ID NO 19
<211> LENGTH: 549
<212> TYPE: PRT
<213> ORGANISM: Artificial Sequence
<220> FEATURE:
<223> OTHER INFORMATION: Synthetic Construct

<400> SEQUENCE: 19

```
Met Glu Leu Leu Ile Leu Lys Ala Asn Ala Ile Thr Thr Ile Leu Thr
 1               5                  10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
```

```
         290                 295                 300
Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Phe Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
        530                 535                 540

Gly Leu Leu Leu Tyr
545

<210> SEQ ID NO 20
<211> LENGTH: 1734
<212> TYPE: DNA
<213> ORGANISM: Artificial Sequence
<220> FEATURE:
<223> OTHER INFORMATION: Synthetic Construct

<400> SEQUENCE: 20
atggaagctg tgatcaaggt catctcctcc gcttgcaaga cctactgcgg caagacctcc      60
ccctccaaga aagaaatcgg tgctatgctg tccctgctgc agaaagaggg cctgctgatg     120 tcccctccg acctgtactc ccccggttcc tgggaccctc tcaccgctgc tctgtcccag      180
cgtgctatga tcctgggcaa gtccggcgaa ctcaagacct ggggcctggt gctgggtgct     240
ctgaaggctg ctcgcgagga caagtgacc tccgagcagg ctaagttctg ctgggtctg       300 ggtggtggtc gtgtgtcccc ccctggtccc gagtgcatcg agaagcccgc taccgagcgt     360
cgtatcgaca agggcgagga agtgggcgag actaccgtgc agcgtgacgc taagatggct     420
cccgaggaaa ccgctacccc caagaccgtg ggcacctcct gctaccactg cggcaccgct     480
atcggttgca actgcgctac cgcttccgct cccccccctc cttacgtggg ctccggcctg     540
tacccttccc tggctggtgt cggcgagcag caaggacagg gtggagacac ccctcccggt     600
```

-continued

```
gctgaacagt cccgtgccga gcctggtcac gctggtcaag ctcccggtcc cgctctgact    660
gactgggctc gtgtgcgtga ggaactggct tccaccggtc ccctgtggt ggctatgccc     720
gtggtcatca agaccgaggg tcccgcttgg accccctgg aacccaagct gatcacccgt     780
ctggctgaca ccgtgcgtac caagggcctg cgttccccaa tcaccatggc tgaggtggag    840
gctctgatgt cctccccct gctgcctcac gacgtgacca acctgatgcg tgtgatcctg     900
ggtcccgctc cctacgctct gtggatggac gcttggggcg tgcagctgca gaccgtgatc    960
gctgctgcta cccgtgaccc ccgtcaccct gctaacggac agggtcgtgg cgagcgtacc   1020
aacctgaacc gtctgaaggg cctggctgac ggcatggtcg gcaaccctca gggacaggct   1080
gctctgctgc gtcctggcga gctggtcgct atcaccgcca gcgctctgca ggctttccgt   1140
gaggtggccc gtttggccga accagctggt ccctgggctg acatcatgca gggcccctcc   1200
gagtccttcg tggacttcgc taaccgtctg atcaaggctg tggagggctc cgacctccct   1260
ccttccgctc gtgctcccgt gatcatcgac tgcttccgtc agaagtccca gcccgacatc   1320
cagcagctga tccgtaccgc tccctccacc ctgactaccc ctggcgagat catcaagtac   1380
gtgctggacc gtcaaaagac cgctcccctg accaccaag gtatcgctgc cgctatgtcc    1440
tccgctatcc agcccctgat catggctgtc gtgaaccgcg agagggacgg acagaccggt   1500
tccggtggtc gtgctcgtgg cctgtgctac acttgcggtt ccccggtca ctaccaggct     1560
cagtgcccca agaagcgcaa gtccggaaac tcccgcgagc gctgccagct ctgcaacggc   1620
atgggtcaca cgccaagca gtgccgcaag cgcgacggaa accagggcca gcgtcccgga   1680
aagggactgt cctccggtcc ttggcctggt cctgagcccc tgctgtgtc ctaa          1734
```

<210> SEQ ID NO 21
<211> LENGTH: 577
<212> TYPE: PRT
<213> ORGANISM: Artificial Sequence
<220> FEATURE:
<223> OTHER INFORMATION: Synthetic Construct

<400> SEQUENCE: 21

```
Met Glu Ala Val Ile Lys Val Ile Ser Ser Ala Cys Lys Thr Tyr Cys
 1               5                   10                  15

Gly Lys Thr Ser Pro Ser Lys Lys Glu Ile Gly Ala Met Leu Ser Leu
            20                  25                  30

Leu Gln Lys Glu Gly Leu Leu Met Ser Pro Ser Asp Leu Tyr Ser Pro
        35                  40                  45

Gly Ser Trp Asp Pro Ile Thr Ala Ala Leu Ser Gln Arg Ala Met Ile
    50                  55                  60

Leu Gly Lys Ser Gly Glu Leu Lys Thr Trp Gly Leu Val Leu Gly Ala
65                  70                  75                  80

Leu Lys Ala Ala Arg Glu Glu Gln Val Thr Ser Glu Gln Ala Lys Phe
                85                  90                  95

Trp Leu Gly Leu Gly Gly Arg Val Ser Pro Gly Pro Glu Cys
            100                 105                 110

Ile Glu Lys Pro Ala Thr Glu Arg Arg Ile Asp Lys Gly Glu Glu Val
        115                 120                 125

Gly Glu Thr Thr Val Gln Arg Asp Ala Lys Met Ala Pro Glu Glu Thr
    130                 135                 140

Ala Thr Pro Lys Thr Val Gly Thr Ser Cys Tyr His Cys Gly Thr Ala
145                 150                 155                 160
```

```
Ile Gly Cys Asn Cys Ala Thr Ala Ser Ala Pro Pro Pro Tyr Val
            165                 170                 175
Gly Ser Gly Leu Tyr Pro Ser Leu Ala Gly Val Gly Glu Gln Gln Gly
            180                 185                 190
Gln Gly Gly Asp Thr Pro Pro Gly Ala Glu Gln Ser Arg Ala Glu Pro
            195                 200                 205
Gly His Ala Gly Gln Ala Pro Gly Pro Ala Leu Thr Asp Trp Ala Arg
            210                 215                 220
Val Arg Glu Glu Leu Ala Ser Thr Gly Pro Pro Val Val Ala Met Pro
225                 230                 235                 240
Val Val Ile Lys Thr Glu Gly Pro Ala Trp Thr Pro Leu Glu Pro Lys
            245                 250                 255
Leu Ile Thr Arg Leu Ala Asp Thr Val Arg Thr Lys Gly Leu Arg Ser
            260                 265                 270
Pro Ile Thr Met Ala Glu Val Glu Ala Leu Met Ser Ser Pro Leu Leu
            275                 280                 285
Pro His Asp Val Thr Asn Leu Met Arg Val Ile Leu Gly Pro Ala Pro
            290                 295                 300
Tyr Ala Leu Trp Met Asp Ala Trp Gly Val Gln Leu Gln Thr Val Ile
305                 310                 315                 320
Ala Ala Ala Thr Arg Asp Pro Arg His Pro Ala Asn Gly Gln Gly Arg
            325                 330                 335
Gly Glu Arg Thr Asn Leu Asn Arg Leu Lys Gly Leu Ala Asp Gly Met
            340                 345                 350
Val Gly Asn Pro Gln Gly Gln Ala Ala Leu Leu Arg Pro Gly Glu Leu
            355                 360                 365
Val Ala Ile Thr Ala Ser Ala Leu Gln Ala Phe Arg Glu Val Ala Arg
            370                 375                 380
Leu Ala Glu Pro Ala Gly Pro Trp Ala Asp Ile Met Gln Gly Pro Ser
385                 390                 395                 400
Glu Ser Phe Val Asp Phe Ala Asn Arg Leu Ile Lys Ala Val Glu Gly
            405                 410                 415
Ser Asp Leu Pro Pro Ser Ala Arg Ala Pro Val Ile Ile Asp Cys Phe
            420                 425                 430
Arg Gln Lys Ser Gln Pro Asp Ile Gln Gln Leu Ile Arg Thr Ala Pro
            435                 440                 445
Ser Thr Leu Thr Thr Pro Gly Glu Ile Ile Lys Tyr Val Leu Asp Arg
            450                 455                 460
Gln Lys Thr Ala Pro Leu Thr Asp Gln Gly Ile Ala Ala Ala Met Ser
465                 470                 475                 480
Ser Ala Ile Gln Pro Leu Ile Met Ala Val Val Asn Arg Glu Arg Asp
            485                 490                 495
Gly Gln Thr Gly Ser Gly Gly Arg Ala Arg Gly Leu Cys Tyr Thr Cys
            500                 505                 510
Gly Ser Pro Gly His Tyr Gln Ala Gln Cys Pro Lys Lys Arg Lys Ser
            515                 520                 525
Gly Asn Ser Arg Glu Arg Cys Gln Leu Cys Asn Gly Met Gly His Asn
            530                 535                 540
Ala Lys Gln Cys Arg Lys Arg Asp Gly Asn Gln Gly Gln Arg Pro Gly
545                 550                 555                 560
Lys Gly Leu Ser Ser Gly Pro Trp Pro Gly Pro Glu Pro Pro Ala Val
            565                 570                 575
Ser
```

<210> SEQ ID NO 22
<211> LENGTH: 2109
<212> TYPE: DNA
<213> ORGANISM: Artificial Sequence
<220> FEATURE:
<223> OTHER INFORMATION: Synthetic Construct

<400> SEQUENCE: 22

| | |
|---|---:|
| atggaagccg tgatcaaagt gatcagcagc gcctgcaaga cctactgcgg caagaccagc | 60 |
| cccagcaaga agaaattgg cgccatgctg tctctgctgc agaaggaagg cctgctgatg | 120 |
| agccccagcg acctgtacag ccccggcagc tgggatccta tcacagctgc cctgagccag | 180 |
| agagccatga tcctgggcaa gagcggcgag ctgaaaacct ggggcctggt gctgggagcc | 240 |
| ctgaaggccg ccagagaaga acaggtcacc agcgagcagg ccaagttttg gctgggcctg | 300 |
| ggcggaggaa gagtgtctcc ccctggcccc gagtgtatcg agaagcccgc caccgagcgg | 360 |
| agaatcgaca agggcgagga agtgggcgag acaaccgtgc agcgggacgc caagatggcc | 420 |
| cctgaggaaa ccgccacccc caagaccgtg gcaccagct gctaccactg tggcaccgcc | 480 |
| atcggctgca attgtgccac cgccagcgcc cctccacctc cttacgtggg cagcggcctc | 540 |
| tatccttcac tggccggcgt gggcgaacag cagggacagg gcggcgatac acctcctggc | 600 |
| gccgagcaga gcagagccga acctggacat gccggacagg ccctggaccc tgctctgacc | 660 |
| gattgggcca gagtgcggga ggaactggcc tctaccggac cccctgtggt ggctatgccc | 720 |
| gtggtgatta agacagaggg ccctgcctgg acccctctgg aacccaagct gatcacccgg | 780 |
| ctggccgata cagtgcggac caagggcctg agaagcccca tcaccatggc cgaggtggag | 840 |
| gccctgatga gcagccccct gctgcccac gacgtgacca acctgatgag agtgatcctg | 900 |
| ggacccgctc cctacgccct gtggatggat gcctggggcg tgcagctgca gacagtgatc | 960 |
| gccgctgcca cagagatcc cagacacccc gccaatggcc agggcagagg cgagagaacc | 1020 |
| aacctgaacc ggctgaaggg cctggccgac ggcatggtcg gcaatcctca gggacaggcc | 1080 |
| gctctgctga ggcctggcga actggtggcc atcacagcca gcgccctgca ggccttcaga | 1140 |
| gaagtggcta actggccga acctgccggc ccttgggccg atatcatgca gggccccagc | 1200 |
| gagagcttcg tggacttcgc caaccggctg atcaaggccg tggagggcag cgatctgcct | 1260 |
| cctagcgcca gagcccccgt gatcatcgac tgcttccggc agaagtccca gcccgacatc | 1320 |
| cagcagctga tcagaaccgc ccccagcacc ctgaccaccc ctggcgagat catcaaatac | 1380 |
| gtgctggacc ggcagaaaac cgcccctctg accgatcagg cattgccgc cgctatgagc | 1440 |
| agcgccatcc agcccctgat tatggccgtg gtgaaccggg agagggatgg ccagacagga | 1500 |
| agcggcggca gagctagagg actgtgctac acctgtggca gccctggcca ctaccaggct | 1560 |
| cagtgcccca gaagcggaa gtccggcaac agccgggaga gatgccagct gtgcaacggc | 1620 |
| atgggccaca cgccaagca gtgcagaaag agggacggca atcagggcca gaggcccggc | 1680 |
| aaaggcctgt ctagcggacc ttggcctgga cctgagcctc ctgccgtgag cctggccatg | 1740 |
| accatggaac acaaggaccg gcccctggtc cgcgtgatcc tgaccaacac cggcagccac | 1800 |
| cccgtgaagc agcggagcgt gtacatcacc ggccctgctgg actctggcgc cgacatcacc | 1860 |
| atcatcagcg aagaggactg gcccaccgac tggcctgtga tggaagccgc caacccccag | 1920 |
| atccacggca tcgcggagg catccccatg cggaagtcca gagacatgat cgagctgggc | 1980 |
| gtgatcaacc gggacggcag cctggaaaga cccctgctgc tgttcccagc tgtggccatg | 2040 |

```
gtccggggca gcatcctggg cagagactgt ctgcaggac tgggcctgcg gctgaccaat    2100
ctgtgatga                                                            2109
```

<210> SEQ ID NO 23
<211> LENGTH: 701
<212> TYPE: PRT
<213> ORGANISM: Artificial Sequence
<220> FEATURE:
<223> OTHER INFORMATION: Synthetic Construct

<400> SEQUENCE: 23

```
Met Glu Ala Val Ile Lys Val Ile Ser Ala Cys Lys Thr Tyr Cys
 1               5                  10                  15

Gly Lys Thr Ser Pro Ser Lys Lys Glu Ile Gly Ala Met Leu Ser Leu
             20                  25                  30

Leu Gln Lys Glu Gly Leu Leu Met Ser Pro Ser Asp Leu Tyr Ser Pro
         35                  40                  45

Gly Ser Trp Asp Pro Ile Thr Ala Ala Leu Ser Gln Arg Ala Met Ile
     50                  55                  60

Leu Gly Lys Ser Gly Glu Leu Lys Thr Trp Gly Leu Val Leu Gly Ala
 65                  70                  75                  80

Leu Lys Ala Ala Arg Glu Glu Gln Val Thr Ser Glu Gln Ala Lys Phe
                 85                  90                  95

Trp Leu Gly Leu Gly Gly Gly Arg Val Ser Pro Pro Gly Pro Glu Cys
            100                 105                 110

Ile Glu Lys Pro Ala Thr Glu Arg Arg Ile Asp Lys Gly Glu Glu Val
        115                 120                 125

Gly Glu Thr Thr Val Gln Arg Asp Ala Lys Met Ala Pro Glu Glu Thr
    130                 135                 140

Ala Thr Pro Lys Thr Val Gly Thr Ser Cys Tyr His Cys Gly Thr Ala
145                 150                 155                 160

Ile Gly Cys Asn Cys Ala Thr Ala Ser Ala Pro Pro Pro Tyr Val
                165                 170                 175

Gly Ser Gly Leu Tyr Pro Ser Leu Ala Gly Val Gly Glu Gln Gln Gly
            180                 185                 190

Gln Gly Gly Asp Thr Pro Pro Gly Ala Glu Gln Ser Arg Ala Glu Pro
        195                 200                 205

Gly His Ala Gly Gln Ala Pro Gly Pro Ala Leu Thr Asp Trp Ala Arg
    210                 215                 220

Val Arg Glu Glu Leu Ala Ser Thr Gly Pro Pro Val Val Ala Met Pro
225                 230                 235                 240

Val Val Ile Lys Thr Glu Gly Pro Ala Trp Thr Pro Leu Glu Pro Lys
                245                 250                 255

Leu Ile Thr Arg Leu Ala Asp Thr Val Arg Thr Lys Gly Leu Arg Ser
            260                 265                 270

Pro Ile Thr Met Ala Glu Val Glu Ala Leu Met Ser Ser Pro Leu Leu
        275                 280                 285

Pro His Asp Val Thr Asn Leu Met Arg Val Ile Leu Gly Pro Ala Pro
    290                 295                 300

Tyr Ala Leu Trp Met Asp Ala Trp Gly Val Gln Leu Gln Thr Val Ile
305                 310                 315                 320

Ala Ala Ala Thr Arg Asp Pro Arg His Pro Ala Asn Gly Gln Gly Arg
                325                 330                 335

Gly Glu Arg Thr Asn Leu Asn Arg Leu Lys Gly Leu Ala Asp Gly Met
            340                 345                 350
```

```
Val Gly Asn Pro Gln Gly Gln Ala Ala Leu Leu Arg Pro Gly Glu Leu
        355                 360                 365

Val Ala Ile Thr Ala Ser Ala Leu Gln Ala Phe Arg Glu Val Ala Arg
    370                 375                 380

Leu Ala Glu Pro Ala Gly Pro Trp Ala Asp Ile Met Gln Gly Pro Ser
385                 390                 395                 400

Glu Ser Phe Val Asp Phe Ala Asn Arg Leu Ile Lys Ala Val Glu Gly
                405                 410                 415

Ser Asp Leu Pro Pro Ser Ala Arg Ala Pro Val Ile Ile Asp Cys Phe
            420                 425                 430

Arg Gln Lys Ser Gln Pro Asp Ile Gln Gln Leu Ile Arg Thr Ala Pro
        435                 440                 445

Ser Thr Leu Thr Thr Pro Gly Glu Ile Ile Lys Tyr Val Leu Asp Arg
    450                 455                 460

Gln Lys Thr Ala Pro Leu Thr Asp Gln Gly Ile Ala Ala Ala Met Ser
465                 470                 475                 480

Ser Ala Ile Gln Pro Leu Ile Met Ala Val Val Asn Arg Glu Arg Asp
                485                 490                 495

Gly Gln Thr Gly Ser Gly Gly Arg Ala Arg Gly Leu Cys Tyr Thr Cys
            500                 505                 510

Gly Ser Pro Gly His Tyr Gln Ala Gln Cys Pro Lys Lys Arg Lys Ser
        515                 520                 525

Gly Asn Ser Arg Glu Arg Cys Gln Leu Cys Asn Gly Met Gly His Asn
    530                 535                 540

Ala Lys Gln Cys Arg Lys Arg Asp Gly Asn Gln Gly Gln Arg Pro Gly
545                 550                 555                 560

Lys Gly Leu Ser Ser Gly Pro Trp Pro Gly Pro Glu Pro Pro Ala Val
                565                 570                 575

Ser Leu Ala Met Thr Met Glu His Lys Asp Arg Pro Leu Val Arg Val
            580                 585                 590

Ile Leu Thr Asn Thr Gly Ser His Pro Val Lys Gln Arg Ser Val Tyr
        595                 600                 605

Ile Thr Ala Leu Leu Asp Ser Gly Ala Asp Ile Thr Ile Ile Ser Glu
    610                 615                 620

Glu Asp Trp Pro Thr Asp Trp Pro Val Met Glu Ala Ala Asn Pro Gln
625                 630                 635                 640

Ile His Gly Ile Gly Gly Gly Ile Pro Met Arg Lys Ser Arg Asp Met
                645                 650                 655

Ile Glu Leu Gly Val Ile Asn Arg Asp Gly Ser Leu Glu Arg Pro Leu
            660                 665                 670

Leu Leu Phe Pro Ala Val Ala Met Val Arg Gly Ser Ile Leu Gly Arg
        675                 680                 685

Asp Cys Leu Gln Gly Leu Gly Leu Arg Leu Thr Asn Leu
    690                 695                 700

<210> SEQ ID NO 24
<211> LENGTH: 1179
<212> TYPE: DNA
<213> ORGANISM: Artificial Sequence
<220> FEATURE:
<223> OTHER INFORMATION: Synthetic Construct

<400> SEQUENCE: 24
atgggtagac tgacttccgg agtgggcacc gccgctctgc tggtcgtggc tgtgggcctg    60
```

```
cgcgtcgtgt gcgccaagta cgcactggcc gatccctccc tgaagatggc cgaccctaac      120
cgcttccgcg gcaagaacct ccccgtgctg gaccagctga ccgacccccc tggcgtgaag      180
cgcgtgtacc acatccagcc ttccctggaa gatcccttcc agccccctc catccccatc      240 accgtgtact acgcagtgct ggaacgcgcc tgccgctccg tgctgctgca tgctcccttcc     300 gaggcccctc agatcgtgcg cggagcctcc gacgaggccc gcaagcacac ctacaacctg      360
actatcgcct ggtacaggat gggcgacaac tgcgccatcc ctatcactgt gatggaatac      420
accgagtgcc cctacaacaa gtccctgggc gtgtgcccca tccgcaccca gccccgctgg      480
tcctactacg actccttctc cgccgtgtcc gaggacaacc tgggcttcct gatgcacgcc      540
cctgccttcg aaaccgccgg cacctacctg aggctggtca agatcaacga ctggaccgag      600
atcacccagt tcatcctgga acaccgcgcc agggcctctt gcaagtacgc tctgcccctg      660
cgcatccccc ctgccgcctg cctgacctct aaggcctacc agcagggcgt gaccgtggac      720
tccatcggca tgctgcctcg cttcatcccc gagaaccagc gcaccgtggc cctgtacagc      780
ctgaagatcg ccggctggca cggccccaag ccaccctaca cctccaccct gctgcccccc      840
gagctgtccg acaccaccaa cgccacccag cccgagctgg tgcccgagga ccctgaggac      900
tccgccctgc tcgaagatcc cgccggaacc gtgtcctccc agatcccccc caactggcac      960
atcccttcca tccaggacgt ggccccccac cacgctccag ccgcaccttc aacccaggc     1020 ctgatcatcg gagccctggc cggctccacc ctggccgtcc tggtcatcgg cggaatcgct    1080
ttctgggtca ggagaagggc ccagatggct ccaaagcgcc tgcgcctgcc ccacatccgc    1140
gacgacgacg cccctccctc tcaccagccc ctgttctac                            1179
```

<210> SEQ ID NO 25
<211> LENGTH: 393
<212> TYPE: PRT
<213> ORGANISM: Artificial Sequence
<220> FEATURE:
<223> OTHER INFORMATION: Synthetic Construct

<400> SEQUENCE: 25

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
    50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
```

165					170					175
Leu Met His Ala Pro Ala Phe Glu Thr Ala Gly Thr Tyr Leu Arg Leu
		180					185					190

Val Lys Ile Asn Asp Trp Thr Glu Ile Thr Gln Phe Ile Leu Glu His
		195					200					205

Arg Ala Arg Ala Ser Cys Lys Tyr Ala Leu Pro Leu Arg Ile Pro Pro
		210					215					220

Ala Ala Cys Leu Thr Ser Lys Ala Tyr Gln Gln Gly Val Thr Val Asp
225					230					235					240

Ser Ile Gly Met Leu Pro Arg Phe Ile Pro Glu Asn Gln Arg Thr Val
			245					250					255

Ala Leu Tyr Ser Leu Lys Ile Ala Gly Trp His Gly Pro Lys Pro Pro
			260					265					270

Tyr Thr Ser Thr Leu Leu Pro Pro Glu Leu Ser Asp Thr Thr Asn Ala
			275					280					285

Thr Gln Pro Glu Leu Val Pro Glu Asp Pro Glu Asp Ser Ala Leu Leu
			290					295					300

Glu Asp Pro Ala Gly Thr Val Ser Ser Gln Ile Pro Pro Asn Trp His
305					310					315					320

Ile Pro Ser Ile Gln Asp Val Ala Pro His Ala Pro Ala Ala Pro
			325					330					335

Ser Asn Pro Gly Leu Ile Ile Gly Ala Leu Ala Gly Ser Thr Leu Ala
			340					345					350

Val Leu Val Ile Gly Gly Ile Ala Phe Trp Val Arg Arg Arg Ala Gln
			355					360					365

Met Ala Pro Lys Arg Leu Arg Leu Pro His Ile Arg Asp Asp Asp Ala
			370					375					380

Pro Pro Ser His Gln Pro Leu Phe Tyr
385					390

<210> SEQ ID NO 26
<211> LENGTH: 1560
<212> TYPE: DNA
<213> ORGANISM: Artificial Sequence
<220> FEATURE:
<223> OTHER INFORMATION: Synthetic Construct

<400> SEQUENCE: 26
atgggtgctg ctacctccgc tctgaaccgt cgtcagctgg accagttcga agatccgt      60 ctgcgtccca acggcaagaa gaagtaccag atcaagcacc tgatctgggc tggcaaggaa     120
atggaacgtt tcggtctgca cgagcgtctg ctggaaaccg aggaaggttg caagcgtatc     180
atcgaggtgc tgtaccccct ggaacccacc ggttccgagg gcctgaagtc cctgttcaac     240
ctcgtgtgcg tgctgtactg cctgcacaag gaacagaagg tcaaggacac cgaggaagct     300
gtggctaccg tccgtcagca ctgccacctg gtggagaagg aaaagtccgc taccgagact     360
tcctccggcc agaagaagaa cgacaagggt atcgctgctc cccctggtgg ttcccagaac     420
ttccccgccc agcagcaggg aaaacgcttg gtgcacgtgc ctctgtcccc cgtactctg      480 aacgcctggg tcaaggctgt ggaggaaaag aagttcggcg ctgagatcgt gcccatgttc     540
caggctctgt ccgagggttg cactccctac gacatcaacc agatgctgaa cgtgctgggt     600
gaccaccagg gtgctctgca gatcgtgaag gaaatcatca cgaagaggc tgctcagtgg     660 gacgtgaccc accctctgcc tgctggtcct ctgccagccg ccagctgcg tgaccctcgt     720 ggttccgaca tcgctggcac cacctcttcc gtgcaagagc agctggaatg gatctacacc     780

```
gctaacccccc gtgtggacgt gggcgctatc taccgtcgtt ggatcatcct gggtctgcaa      840
aagtgcgtga agatgtacaa ccctgtgtcc gtgctggaca tccgtcaggg tcccaaggaa      900
cccttcaagg actacgtgga ccgcttctac aaggctatcc gtgccgagca ggcttccggc      960
gaggtcaagc agtggatgac cgagtccctg ctgatccaga cgctaacccc cgactgcaag     1020
gtcatcctga agggcctggg catgcacccc accctggaag agatgctgac cgcttgccag     1080
ggtgtcggtg gtccctccta caaggccaag gtcatggctg agatgatgca gaccatgcag     1140
aaccagaaca tggtgcagca gggtggtccc aagcgtcagc gtccccctct gcgttgctac     1200
aactgcggca agttcggtca catgcagcgc cagtgccctg agcctcgcaa gaccaagtgc     1260
ctgaagtgcg gaaagctggg tcacctggct aaggactgcc gtggtcaagt gaacttcctg     1320
ggttacggtc gttggatggg tgccaagccc cgtaacttcc ctgctgctac cctgggtgcc     1380
gagccttctg ctccccctcc ccctccggt actacccct acgacccgc taagaagctg      1440 ctccagcagt acgctgagaa gggcaagcag ctgcgcgagc agaagcgtaa cccccctgct     1500
atgaaccctg actggaccga gggttacagc ctgaactctc tgttcggcga ggaccagtaa     1560
```

<210> SEQ ID NO 27
<211> LENGTH: 519
<212> TYPE: PRT
<213> ORGANISM: Artificial Sequence
<220> FEATURE:
<223> OTHER INFORMATION: Synthetic Construct

<400> SEQUENCE: 27

```
Met Gly Ala Ala Thr Ser Ala Leu Asn Arg Arg Gln Leu Asp Gln Phe
  1               5                  10                  15

Glu Lys Ile Arg Leu Arg Pro Asn Gly Lys Lys Lys Tyr Gln Ile Lys
             20                  25                  30

His Leu Ile Trp Ala Gly Lys Glu Met Glu Arg Phe Gly Leu His Glu
         35                  40                  45

Arg Leu Leu Glu Thr Glu Glu Gly Cys Lys Arg Ile Ile Glu Val Leu
     50                  55                  60

Tyr Pro Leu Glu Pro Thr Gly Ser Glu Gly Leu Lys Ser Leu Phe Asn
 65                  70                  75                  80

Leu Val Cys Val Leu Tyr Cys Leu His Lys Glu Gln Lys Val Lys Asp
                 85                  90                  95

Thr Glu Glu Ala Val Ala Thr Val Arg Gln His Cys His Leu Val Glu
            100                 105                 110

Lys Glu Lys Ser Ala Thr Glu Thr Ser Ser Gly Gln Lys Lys Asn Asp
        115                 120                 125

Lys Gly Ile Ala Ala Pro Pro Gly Gly Ser Gln Asn Phe Pro Ala Gln
    130                 135                 140

Gln Gln Gly Asn Ala Trp Val His Val Pro Leu Ser Pro Arg Thr Leu
145                 150                 155                 160

Asn Ala Trp Val Lys Ala Val Glu Glu Lys Phe Gly Ala Glu Ile
                165                 170                 175

Val Pro Met Phe Gln Ala Leu Ser Glu Gly Cys Thr Pro Tyr Asp Ile
            180                 185                 190

Asn Gln Met Leu Asn Val Leu Gly Asp His Gln Gly Ala Leu Gln Ile
        195                 200                 205

Val Lys Glu Ile Ile Asn Glu Glu Ala Ala Gln Trp Asp Val Thr His
    210                 215                 220
```

```
Pro Leu Pro Ala Gly Pro Leu Pro Ala Gly Gln Leu Arg Asp Pro Arg
225                 230                 235                 240

Gly Ser Asp Ile Ala Gly Thr Thr Ser Ser Val Gln Glu Gln Leu Glu
            245                 250                 255

Trp Ile Tyr Thr Ala Asn Pro Arg Val Asp Val Gly Ala Ile Tyr Arg
        260                 265                 270

Arg Trp Ile Ile Leu Gly Leu Gln Lys Cys Val Lys Met Tyr Asn Pro
    275                 280                 285

Val Ser Val Leu Asp Ile Arg Gln Gly Pro Lys Glu Pro Phe Lys Asp
290                 295                 300

Tyr Val Asp Arg Phe Tyr Lys Ala Ile Arg Ala Glu Gln Ala Ser Gly
305                 310                 315                 320

Glu Val Lys Gln Trp Met Thr Glu Ser Leu Leu Ile Gln Asn Ala Asn
            325                 330                 335

Pro Asp Cys Lys Val Ile Leu Lys Gly Leu Gly Met His Pro Thr Leu
        340                 345                 350

Glu Glu Met Leu Thr Ala Cys Gln Gly Val Gly Pro Ser Tyr Lys
    355                 360                 365

Ala Lys Val Met Ala Glu Met Met Gln Thr Met Gln Asn Gln Asn Met
370                 375                 380

Val Gln Gln Gly Gly Pro Lys Arg Gln Arg Pro Pro Leu Arg Cys Tyr
385                 390                 395                 400

Asn Cys Gly Lys Phe Gly His Met Gln Arg Gln Cys Pro Glu Pro Arg
            405                 410                 415

Lys Thr Lys Cys Leu Lys Cys Gly Lys Leu Gly His Leu Ala Lys Asp
        420                 425                 430

Cys Arg Gly Gln Val Asn Phe Leu Gly Tyr Gly Arg Trp Met Gly Ala
    435                 440                 445

Lys Pro Arg Asn Phe Pro Ala Ala Thr Leu Gly Ala Glu Pro Ser Ala
450                 455                 460

Pro Pro Pro Pro Ser Gly Thr Thr Pro Tyr Asp Pro Ala Lys Lys Leu
465                 470                 475                 480

Leu Gln Gln Tyr Ala Glu Lys Gly Lys Gln Leu Arg Glu Gln Lys Arg
            485                 490                 495

Asn Pro Pro Ala Met Asn Pro Asp Trp Thr Glu Gly Tyr Ser Leu Asn
        500                 505                 510

Ser Leu Phe Gly Glu Asp Gln
    515

<210> SEQ ID NO 28
<211> LENGTH: 7583
<212> TYPE: DNA
<213> ORGANISM: Artificial Sequence
<220> FEATURE:
<223> OTHER INFORMATION: Synthetic Construct

<400> SEQUENCE: 28
catcatcaat aatataccct attttggatt gaagccaata tgataatgag ggggtggagt        60
ttgtgacgtg gcgcggggcg tgggaacggg gcgggtgacg tagtagtgtg gcggaagtgt       120
gatgttgcaa gtgtggcgga acacatgtaa gcgacggatg tggcaaaagt gacgtttttg       180
gtgtgcgccg gtgtacacag gaagtgacaa ttttcgcgcg gttttaggcg gatgttgtag       240
taaatttggg cgtaaccgag taagatttgg ccattttcgc gggaaaactg aataagagga       300
agtgaaatct gaataatttt gtgttactca tagcgcgtaa tactgtaata gtaatcaatt       360
```

```
acggggtcat tagttcatag cccatatatg gagttccgcg ttacataact tacggtaaat    420
ggcccgcctg gctgaccgcc caacgacccc cgcccattga cgtcaataat gacgtatgtt    480
cccatagtaa cgccaatagg gactttccat tgacgtcaat gggtggagta tttacggtaa    540
actgcccact tggcagtaca tcaagtgtat catatgccaa gtacgccccc tattgacgtc    600
aatgacggta aatggcccgc ctggcattat gcccagtaca tgaccttatg gactttcct    660 acttggcagt acatctagta ttagtcatcg ctattaccat ggtgatgcgg ttttggcagt    720
acatcaatgg gcgtggatag cggtttgact cacggggatt ccaagtctc cacccattg    780 acgtcaatgg gagtttgttt tggcaccaaa atcaacggga cttttccaaaa tgtcgtaaca    840 actccgcccc attgacgcaa atgggcggta ggcgtgtacg gtgggaggtc tatataagca    900
gagctctccc tatcagtgat agagatctcc ctatcagtga tagagatcgt cgacgagctc    960
gtttagtgaa ccgtcagatc gcctggagac gccatccacg ctgttttgac ctccatagaa   1020
gacaccggga ccgatccagc ctccggactc tagcgtttcg tcgacgcggc cgctcgagcc   1080
taagcttcta gataagatat ccgatccacc ggatctagat aactgatcat aatcagccat   1140
accacatttg tagaggtttt acttgcttta aaaaacctcc cacacctccc cctgaacctg   1200
aaacataaaa tgaatgcaat tgttgttgtt aacttgttta ttgcagctta taatggttac   1260
aaataaagca atagcatcac aaatttcaca aataaagcat ttttttcact gcattctagt   1320
tgtggtttgt ccaaactcat caatgtatct taacgcggat ctgggcgtgg ttaagggtgg   1380
gaaagaatat ataaggtggg ggtcttatgt agttttgtat ctgttttgca gcagccgccg   1440
ccgccatgag caccaactcg tttgatggaa gcattgtgag ctcatatttg acaacgcgca   1500
tgcccccatg ggccggggtg cgtcagaatg tgatgggctc cagcattgat ggtcgccccg   1560
tcctgcccgc aaactctact accttgacct acgagaccgt gtctggaacg ccgttggaga   1620
ctgcagcctc cgccgccgct tcagccgctg cagccaccgc ccgcgggatt gtgactgact   1680
ttgctttcct gagcccgctt gcaagcagtg cagcttcccg ttcatccgcc cgcgatgaca   1740
agttgacggc tcttttggca caattggatt ctttgacccg ggaacttaat gtcgtttctc   1800
agcagctgtt ggatctgcgc cagcaggttt ctgccctgaa ggcttcctcc cctcccaatg   1860
cggtttaaaa cataaataaa aaaccagact ctgtttggat ttggatcaag caagtgtctt   1920 gctgtctttta tttaggggtt ttgcgcgcgc ggtaggcccg ggaccagcgg tctcggtcgt   1980
tgagggtcct gtgtattttt tccaggacgt ggtaaaggtg actctggatg ttcagataca   2040
tgggcataag cccgtctctg ggtggaggt agcaccactg cagagcttca tgctgcgggg   2100
tggtgttgta gatgatccag tcgtagcagg agcgctgggc gtggtgccta aaaatgtctt   2160
tcagtagcaa gctgattgcc aggggcaggc ccttggtgta agtgtttaca aagcggttaa   2220
gctgggatgg gtgcatacgt ggggatatga gatgcatctt ggactgtatt tttaggttgg   2280
ctatgttccc agccatatcc ctccggggat tcatgttgtg cagaaccacc agcacagtgt   2340
atccggtgca cttgggaaat tgtcatgta gcttagaagg aaatgcgtgg aagaacttgg   2400
agacgccctt gtgacctcca agattttcca tgcattcgtc cataatgatg gcaatgggcc   2460
cacgggcggc ggcctgggcg aagatatttc tgggatcact aacgtcatag ttgtgttcca   2520
ggatgagatc gtcataggcc atttttacaa agcgcgggcg gagggtgcca gactgcggta   2580
taatggttcc atccggccca ggggcgtagt taccctcaca gatttgcatt tcccacgctt   2640
tgagttcaga tggggggatc atgtctacct gcggggcgat gaagaaaacg gtttccgggg   2700
taggggagat cagctgggaa gaaagcaggt tcctgagcag ctgcgactta ccgcagccgg   2760
```

-continued

```
tgggcccgta aatcacacct attaccggct gcaactggta gttaagagag ctgcagctgc    2820
cgtcatccct gagcaggggg gccacttcgt taagcatgtc cctgactcgc atgttttccc    2880
tgaccaaatc cgccagaagg cgctcgccgc ccagcgatag cagttcttgc aaggaagcaa    2940
agttttcaa cggtttgaga ccgtccgccg taggcatgct tttgagcgtt tgaccaagca     3000
gttccaggcg gtcccacagc tcggtcacct gctctacggc atctcgatcc agcatatctc    3060
ctcgtttcgc gggttggggc ggctttcgct gtacggcagt agtcggtgct cgtccagacg    3120
ggccagggtc atgtctttcc acgggcgcag ggtcctcgtc agcgtagtct gggtcacggt    3180
gaaggggtgc gctccgggct gcgcgctggc caggtgcgc ttgaggctgg tcctgctggt     3240
gctgaagcgc tgccggtctt cgccctgcgc gtcggccagg tagcatttga ccatggtgtc    3300
atagtccagc cctccgcgg cgtggccctt ggcgcgcagc ttgcccttgg aggaggcgcc     3360
gcacgagggg cagtgcagac ttttgagggc gtagagcttg ggcgcgagaa ataccgattc    3420
cggggagtag gcatccgcgc cgcaggcccc gcagacggtc tcgcattcca cgagccaggt    3480
gagctctggc cgttcggggt caaaaaccag gtttccccca tgcttttga tgcgtttctt     3540
acctctggtt tccatgagcc ggtgtccacg ctcggtgacg aaaaggctgt ccgtgtcccc    3600
gtatacagac ttgagaggga gttaaacga attcaatagc ttgttgcatg ggcggcgata     3660
taaaatgcaa ggtgctgctc aaaaaatcag gcaaagcctc gcgcaaaaaa gaaagcacat    3720
cgtagtcatg ctcatgcaga taaaggcagg taagctccgg aaccaccaca gaaaaagaca    3780
ccatttttct ctcaaacatg tctgcgggtt tctgcataaa cacaaaataa aataacaaaa    3840
aaacatttaa acattagaag cctgtcttac aacaggaaaa acaaccctta taagcataag    3900
acggactacg gccatgccgg cgtgaccgta aaaaaactgg tcaccgtgat taaaaagcac    3960
caccgacagc tcctcggtca tgtccggagt cataatgtaa gactcggtaa acacatcagg    4020
ttgattcaca tcggtcagtg ctaaaaagcg accgaaatag cccggggaa tacatacccg      4080
caggcgtaga gacaacatta cagcccccat aggaggtata acaaaattaa taggagagaa    4140
aaacacataa acacctgaaa aaccctcctg cctaggcaaa atagcaccct cccgctccag    4200
aacaacatac agcgcttcca cagcggcagc cataacagtc agccttacca gtaaaaaga     4260
aaacctatta aaaaacacc actcgacacg gcaccagctc aatcagtcac agtgtaaaaa     4320
agggccaagt gcagagcgag tatatatagg actaaaaat gacgtaacgg ttaaagtcca     4380
caaaaacac ccagaaaacc gcacgcgaac ctacgcccag aaacgaaagc caaaaaaccc     4440
acaacttcct caaatcgtca cttccgtttt cccacgttac gtcacttccc atttaagaa     4500
aactacaatt cccaacacat acaagttact ccgccctaaa acctacgtca cccgccccgt    4560
tcccacgccc cgccgccacgt cacaaactcc accccctcat tatcatattg gcttcaatcc   4620
aaaataaggt atattattga tgatgttaat taacatgcat ggatccatat gcggtgtgaa    4680
ataccgcaca gatgcgtaag gagaaaatac cgcatcaggc gctcttccgc ttcctcgctc    4740
actgactcgc tgcgctcggt cgttcggctg cggcgagcgg tatcagctca ctcaaaggcg    4800
gtaatacggt tatccacaga atcagggggat aacgcaggaa agaacatgtg agcaaaaggc    4860
cagcaaaagg ccaggaaccg taaaaaggcc gcgttgctgg cgttttccca taggctccgc    4920
ccccctgacg agcatcacaa aaatcgacgc tcaagtcaga ggtggcgaaa cccgacagga    4980
ctataaagat accaggcgtt tccccctgga agctccctcg tgcgctctcc tgttccgacc    5040
ctgccgctta ccggatacct gtccgccttt ctcccttcgg gaagcgtggc gctttctcat    5100
```

```
agctcacgct gtaggtatct cagttcggtg taggtcgttc gctccaagct gggctgtgtg    5160 cacgaaccccc ccgttcagcc cgaccgctgc gccttatccg gtaactatcg tcttgagtcc    5220
aacccggtaa gacacgactt atcgccactg gcagcagcca ctggtaacag gattagcaga    5280
gcgaggtatg taggcggtgc tacagagttc ttgaagtggt ggcctaacta cggctacact    5340
agaaggacag tatttggtat ctgcgctctg ctgaagccag ttaccttcgg aaaaagagtt    5400
ggtagctctt gatccggcaa acaaaccacc gctggtagcg gtggtttttt tgtttgcaag    5460
cagcagatta cgcgcagaaa aaaggatct caagaagatc ctttgatctt ttctacgggg    5520
tctgacgctc agtggaacga aaactcacgt taagggattt tggtcatgag attatcaaaa    5580
aggatcttca cctagatcct tttaaattaa aaatgaagtt ttaaatcaat ctaaagtata    5640
tatgagtaaa cttggtctga cagttaccaa tgcttaatca gtgaggcacc tatctcagcg    5700
atctgtctat ttcgttcatc catagttgcc tgactccccg tcgtgtagat aactacgata    5760
cgggagggct taccatctgg ccccagtgct gcaatgatac cgcgagaccc acgctcaccg    5820
gctccagatt tatcagcaat aaaccagcca gccggaaggg ccgagcgcag aagtggtcct    5880
gcaactttat ccgcctccat ccagtctatt aattgttgcc gggaagctag agtaagtagt    5940
tcgccagtta atagtttgcg caacgttgtt gccattgctg cagccatgag attatcaaaa    6000
aggatcttca cctagatcct tttcacgtag aaagccagtc cgcagaaacg gtgctgaccc    6060
cggatgaatg tcagctactg ggctatctgg acaagggaaa acgcaagcgc aaagagaaag    6120
caggtagctt gcagtgggct tacatggcga tagctagact gggcggtttt atggacagca    6180
agcgaaccgg aattgccagc tggggcgccc tctggtaagg ttgggaagcc ctgcaaagta    6240
aactggatgg ctttcttgcc gccaaggatc tgatggcgca ggggatcaag ctctgatcaa    6300
gagacaggat gaggatcgtt tcgcatgatt gaacaagatg gattgcacgc aggttctccg    6360
gccgcttggg tggagaggct attcggctat gactgggcac aacagacaat cggctgctct    6420
gatgccgccg tgttccggct gtcagcgcag gggcgcccgg ttcttttttgt caagaccgac    6480 ctgtccggtg ccctgaatga actgcaagac gaggcagcgc ggctatcgtg gctggccacg    6540
acgggcgttc cttgcgcagc tgtgctcgac gttgtcactg aagcgggaag ggactggctg    6600
ctattgggcg aagtgccggg gcaggatctc ctgtcatctc accttgctcc tgccgagaaa    6660
gtatccatca tggctgatgc aatgcggcgg ctgcatacgc ttgatccggc tacctgccca    6720
ttcgaccacc aagcgaaaca tcgcatcgag cgagcacgta ctcggatgga agccggtctt    6780
gtcgatcagg atgatctgga cgaagagcat caggggctcg cgccagccga actgttcgcc    6840
aggctcaagg cgagcatgcc cgacggcgag gatctcgtcg tgacccatgg cgatgcctgc    6900
ttgccgaata tcatggtgga aaatggccgc ttttctggat tcatcgactg tggccggctg    6960
ggtgtggcgg accgctatca ggacatagcg ttggctaccc gtgatattgc tgaagagctt    7020
ggcggcgaat gggctgaccg cttcctcgtg ctttacggta tcgccgctcc cgattcgcag    7080
cgcatcgcct tctatcgcct tcttgacgag ttcttctgaa ttttgttaaa attttttgtta    7140 aatcagctca ttttttaacc aataggccga atcggcacc atcccttata aatcaaaaga    7200
atagaccgag atagggttga gtgttgttcc agtttggaac aagagtccac tattaaagaa    7260
cgtggactcc aacgtcaaag ggcgaaaaac cgtctatcag ggcgatggcc cactacgtga    7320
accatcaccc taatcaagtt ttttgtggtc gaggtgccgt aaagcactaa atcggaaccc    7380
taaagggagc ccccgattta gagcttgacg gggaaagccg cgaacgtggc gagaaagga    7440 agggaagaaa gcgaaaggag cgggcgctag ggcgctggca agtgtagcgg tcacgctgcg    7500
```

-continued

```
cgtaaccacc acacccgcgc gcttaatgcg ccgctacagg gcgcgtccat tcgccattca    7560
ggatcgaatt aattcttaat taa                                           7583

<210> SEQ ID NO 29
<211> LENGTH: 9198
<212> TYPE: DNA
<213> ORGANISM: Artificial Sequence
<220> FEATURE:
<223> OTHER INFORMATION: Synthetic Construct

<400> SEQUENCE: 29
catcatcaat aatataccct attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataaggaga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gactttccat tgacgtcaat gggtggagta tttacgtaa      540 actgcccact tggcagtaca tcaagtgtat catatgccaa gtacgccccc tattgacgtc     600
aatgacggta atggcccgcc tggcattat gcccagtaca tgaccttatg gactttcct      660 acttggcagt acatctacgt attagtcatc gctattacca tggtgatgcg gttttggcag     720
tacatcaatg ggcgtggata gcggtttgac tcacggggat ttccaagtct ccaccccatt     780
gacgtcaatg ggagtttgtt ttggcaccaa aatcaacggg actttccaaa atgtcgtaac     840
aactccgccc cattgacgca aatgggcggt aggcgtgtac ggtgggaggt ctatataagc     900
agagctggtt tagtgaaccg tcagatccgc tagagatctg gtaccgtcga cgcggccgcc     960
cccttcacca tggaagctgt gatcaaggtc atctcctccg cttgcaagac ctactgcggc    1020
aagacctccc cctccaagaa agaaatcggt gctatgctgt ccctgctgca gaaagagggc    1080
ctgctgatgt cccccctccga cctgtactcc cccggttcct gggaccctat caccgctgct   1140 (sic)

ctgtcccagc gtgctatgat cctgggcaag tccggcgaac tcaagacctg ggcctggtg     1200 ctgggtgctc tgaaggctgc tcgcgaggaa caagtgacct ccgagcaggc taagttctgg    1260
ctgggtctgg tgtggtgtcg tgtgtccccc cctggtcccg agtgcatcga agcccgct      1320 accgagcgtc gtatcgacaa gggcgaggaa gtgggcgaga ctaccgtgca gcgtgacgct    1380
aagatggctc ccgaggaaac cgctaccccc aagaccgtgg gcacctcctg ctaccactgc   1440
ggcaccgcta tcggttgcaa ctgcgctacc gcttccgctc cccccctcc ttacgtgggc    1500 (sic)

tccggcctgt accttccct ggctggtgtc ggcgagcagc aaggacaggg tggagacacc     1560
cctcccggtg ctgaacagtc ccgtgccgag cctggtcacg ctggtcaagc tcccggtccc    1620
gctctgactg actgggctcg tgtgcgtgag gaactggctt ccaccggtcc ccctgtggtg    1680
gctatgcccg tggtcatcaa gaccgaggt cccgcttgga ccccctgga acccaagctg     1740 (sic)

atcacccgtc tggctgacac cgtgcgtacc aagggcctgc gttccccaat caccatggct    1800
gaggtggagg ctctgatgtc ctcccccctg ctgcctcacg acgtgaccaa cctgatgcgt    1860
gtgatcctgg gtcccgctcc ctacgctctg tggatggacg cttggggcgt gcagctgcag    1920
```

```
accgtgatcg ctgctgctac ccgtgacccc cgtcaccctg ctaacggaca gggtcgtggc    1980
gagcgtacca acctgaaccg tctgaagggc ctggctgacg gcatggtcgg caaccctcag    2040
ggacaggctg ctctgctgcg tcctggcgag ctggtcgcta tcaccgccag cgctctgcag    2100
gctttccgtg aggtggcccg ttttggccgaa ccagctggtc cctgggctga catcatgcag    2160
ggcccctccg agtccttcgt ggacttcgct aaccgtctga tcaaggctgt ggagggctcc    2220
gacctccctc cttccgctcg tgctcccgtg atcatcgact gcttccgtca gaagtcccag    2280
cccgacatcc agcagctgat ccgtaccgct ccctccaccc tgactacccc tggcgagatc    2340
atcaagtacg tgctggaccg tcaaaagacc gctccctga ccgaccaagg tatcgctgcc    2400
gctatgtcct ccgctatcca gcccctgatc atggctgtcg tgaaccgcga gagggacgga    2460
cagaccggtt ccgtggtcg tgctcgtggc ctgtgctaca cttgcggttc ccccggtcac    2520
taccaggctc agtgccccaa gaagcgcaag tccggaaact cccgcgagcg ctgccagctc    2580
tgcaacggca tgggtcacaa cgccaagcag tgccgcaagc gcgacggaaa ccagggccag    2640
cgtcccggaa agggactgtc ctccggtcct tggcctggtc ctgagccccc tgctgtgtcc    2700
taataagcgc gcgatccgat ccaccggatc tagataactg atcataatca gccataccac    2760
atttgtagag gttttacttg cttaaaaaa cctcccacac ctcccctga acctgaaaca    2820 taaaatgaat gcaattgttg ttgttaactt gtttattgca gcttataatg gttacaaata    2880
aagcaatagc atcacaaatt tcacaaataa agcatttttt tcactgcatt ctagttgtgg    2940
tttgtccaaa ctcatcaatg tatcttaacg cggatctggg cgtggttaag ggtgggaaag    3000
aatatataag gtgggggtct tatgtagttt tgtatctgtt ttgcagcagc cgccgccgcc    3060
atgagcacca actcgtttga tggaagcatt gtgagctcat atttgacaac gcgcatgccc    3120
ccatgggccg gggtgcgtca gaatgtgatg ggctccagca ttgatggtcg ccccgtcctg    3180 cccgcaaaact ctactacctt gacctacgag accgtgtctg gaacgccgtt ggagactgca    3240
gcctccgccg ccgcttcagc cgctgcagcc accgccgcg ggattgtgac tgactttgct    3300
ttcctgagcc cgcttgcaag cagtgcagct tcccgttcat ccgcccgcga tgacaagttg    3360
acggctcttt tggcacaatt ggattctttg acccgggaac ttaatgtcgt ttctcagcag    3420
ctgttggatc tgcgccagca ggtttctgcc ctgaaggctt cctcccctcc caatgcggtt    3480
taaaacataa ataaaaaacc agactctgtt tggatttgga tcaagcaagt gtcttgctgt    3540
ctttatttag gggttttgcg cgcgcggtag gcccgggacc agcggtctcg gtcgttgagg    3600
gtcctgtgta ttttttccag gacgtggtaa aggtgactct ggatgttcag atacatgggc    3660
ataagcccgt ctctggggtg gaggtagcac cactgcagag cttcatgctg cggggtggtg    3720
ttgtagatga tccagtcgta gcaggagcgc tgggcgtggt gcctaaaaat gtctttcagt    3780
agcaagctga ttgccagggg caggcccttg gtgtaagtgt ttacaaagcg gttaagctgg    3840
gatgggtgca tacgtgggga tatgagatgc atcttggact gtattttag gttggctatg    3900 ttcccagcca tatccctccg gggattcatg ttgtgcagaa ccaccagcac agtgtatccg    3960
gtgcacttgg gaaatttgtc atgtagctta gaaggaaatg cgtggaagaa cttggagacg    4020
cccttgtgac ctccaagatt ttccatgcat tcgtccataa tgatggcaat gggcccacgg    4080
gcggcggcct gggcgaagat atttctggga tcactaacgt catagttgtg ttccaggatg    4140
agatcgtcat aggccatttt tacaaagcgc gggcggaggg tgccagactg cggtataatg    4200
gttccatccg gcccagggc gtagttaccc tcacagattt gcatttccca cgctttgagt    4260
tcagatgggg ggatcatgtc tacctgcggg gcgatgaaga aaacggtttc cggggtaggg    4320
```

```
gagatcagct gggaagaaag caggttcctg agcagctgcg acttaccgca gccggtgggc   4380
ccgtaaatca cacctattac cggctgcaac tggtagttaa gagagctgca gctgccgtca   4440
tccctgagca gggggggccac ttcgttaagc atgtccctga ctcgcatgtt ttccctgacc   4500
aaatccgcca gaaggcgctc gccgcccagc gatagcagtt cttgcaagga agcaaagttt   4560
ttcaacggtt tgagaccgtc cgccgtaggc atgcttttga gcgtttgacc aagcagttcc   4620
aggcggtccc acagctcggt cacctgctct acggcatctc gatccagcat atctcctcgt   4680
ttcgcgggtt ggggcggctt tcgctgtacg gcagtagtcg gtgctcgtcc agacgggcca   4740
gggtcatgtc tttccacggg cgcagggtcc tcgtcagcgt agtctgggtc acggtgaagg   4800
ggtgcgctcc gggctgcgcg ctggccaggg tgcgcttgag gctggtcctg ctggtgctga   4860
agcgctgccg gtcttcgccc tgcgcgtcgg ccaggtagca tttgaccatg gtgtcatagt   4920
ccagcccctc cgcggcgtgg cccttggcgc gcagcttgcc cttggaggag gcgccgcacg   4980
aggggcagtg cagacttttg agggcgtaga gcttgggcgc gagaaatacc gattccgggg   5040
agtaggcatc cgcgccgcag gccccgcaga cggtctcgca ttccacgagc aggtgagct    5100 ctggccgttc ggggtcaaaa accaggtttc ccccatgctt tttgatgcgt ttcttacctc   5160
tggtttccat gagccggtgt ccacgctcgg tgacgaaaag gctgtccgtg tccccgtata   5220
cagacttgag agggagttta acgaattca atagcttgtt gcatgggcgg cgatataaaa   5280
tgcaaggtgc tgctcaaaaa atcaggcaaa gcctcgcgca aaaagaaag cacatcgtag    5340 tcatgctcat gcagataaag gcaggtaagc tccggaacca ccacagaaaa agacaccatt   5400
tttctctcaa acatgtctgc gggtttctgc ataaacacaa aataaaataa caaaaaaaca   5460
tttaaacatt agaagcctgt cttacaacag gaaaaacaac ccttataagc ataagacgga   5520
ctacggccat gccggcgtga ccgtaaaaaa actggtcacc gtgattaaaa agcaccaccg   5580
acagctcctc ggtcatgtcc ggagtcataa tgtaagactc ggtaaacaca tcaggttgat   5640
tcacatcggt cagtgctaaa aagcgaccga aatagcccgg gggaatacat acccgcaggc   5700
gtagagacaa cattcagcc cccataggag gtataacaaa attaatagga gagaaaaaca    5760
cataaacacc tgaaaaaccc tcctgcctag gcaaaatagc accctcccgc tccagaacaa   5820
catacagcgc ttccacagcg gcagccataa cagtcagcct taccagtaaa aagaaaacc    5880 tattaaaaaa acaccactcg acacggcacc agctcaatca gtcacagtgt aaaaaagggc   5940
caagtgcaga gcgagtatat ataggactaa aaaatgacgt aacggttaaa gtccacaaaa   6000
aacacccaga aaaccgcacg cgaacctacg cccagaaacg aaagccaaaa acccacaac    6060 ttcctcaaat cgtcacttcc gttttcccac gttacgtcac ttcccatttt aagaaaacta   6120
caattcccaa cacatacaag ttactccgcc ctaaaaccta cgtcaccgc cccgttccca    6180 cgccccgcgc cacgtcacaa actccacccc ctcattatca tattggcttc aatccaaaat   6240
aaggtatatt attgatgatg ttaattaaca tgcatggatc catatgcggt gtgaaatacc   6300
gcacagatgc gtaaggagaa ataccgcat caggcgctct tccgcttcct cgctcactga    6360
ctcgctgcgc tcggtcgttc ggctgcggcg agcggtatca gctcactcaa aggcggtaat   6420
acggttatcc acagaatcag gggataacgc aggaaagaac atgtgagcaa aaggccagca   6480
aaaggccagg aaccgtaaaa aggccgcgtt gctggcgttt ttccataggc tccgccccc    6540 tgacgagcat cacaaaaatc gacgctcaag tcagaggtgg cgaaacccga caggactata   6600
aagataccag gcgtttcccc ctggaagctc cctcgtgcgc tctcctgttc cgaccctgcc   6660
```

```
gcttaccgga tacctgtccg cctttctccc ttcgggaagc gtggcgcttt ctcatagctc   6720
acgctgtagg tatctcagtt cggtgtaggt cgttcgctcc aagctgggct gtgtgcacga   6780
accccccgtt cagcccgacc gctgcgcctt atccggtaac tatcgtcttg agtccaaccc   6840
ggtaagacac gacttatcgc cactggcagc agccactggt aacaggatta gcagagcgag   6900
gtatgtaggc ggtgctacag agttcttgaa gtggtggcct aactacggct acactagaag   6960
gacagtattt ggtatctgcg ctctgctgaa gccagttacc ttcggaaaaa gagttggtag   7020
ctcttgatcc ggcaaacaaa ccaccgctgg tagcggtggt ttttttgttt gcaagcagca   7080
gattacgcgc agaaaaaaag gatctcaaga agatcctttg atcttttcta cggggtctga   7140
cgctcagtgg aacgaaaact cacgttaagg gattttggtc atgagattat caaaaaggat   7200
cttcacctag atccttttaa attaaaaatg aagttttaaa tcaatctaaa gtatatatga   7260
gtaaacttgg tctgacagtt accaatgctt aatcagtgag gcacctatct cagcgatctg   7320
tctatttcgt tcatccatag ttgcctgact ccccgtcgtg tagataacta cgatacggga   7380
gggcttacca tctggcccca gtgctgcaat gataccgcga cccacgct caccggctcc   7440
agatttatca gcaataaacc agccagccgg aagggccgag cgcagaagtg gtcctgcaac   7500
tttatccgcc tccatccagt ctattaattg ttgccgggaa gctagagtaa gtagttcgcc   7560
agttaatagt ttgcgcaacg ttgttgccat tgctgcagcc atgagattat caaaaaggat   7620
cttcacctag atccttttca cgtagaaagc cagtccgcag aaacggtgct gaccccggat   7680
gaatgtcagc tactgggcta tctggacaag ggaaaacgca agcgcaaaga gaaagcaggt   7740
agcttgcagt gggcttacat ggcgatagct agactgggcg gttttatgga cagcaagcga   7800
accggaattg ccagctgggg cgccctctgg taaggttggg aagccctgca agtaaactg    7860
gatggctttc ttgccgccaa ggatctgatg gcgcagggga tcaagctctg atcaagagac   7920
aggatgagga tcgtttcgca tgattgaaca agatggattg cacgcaggtt ctccggccgc   7980
ttgggtggag aggctattcg gctatgactg gcacaacag acaatcggct gctctgatgc    8040
cgccgtgttc cggctgtcag cgcaggggcg cccggttctt tttgtcaaga ccgacctgtc   8100
cggtgccctg aatgaactgc aagacgagg agcgcggcta tcgtggctgg ccacgacggg   8160
cgttccttgc gcagctgtgc tcgacgttgt cactgaagcg ggaagggact ggctgctatt   8220
gggcgaagtg ccggggcagg atctcctgtc atctcacctt gctcctgccg agaaagtatc   8280
catcatggct gatgcaatgc ggcggctgca tacgcttgat ccggctacct gcccattcga   8340
ccaccaagcg aaacatcgca tcgagcgagc acgtactcgg atggaagccg gtcttgtcga   8400
tcaggatgat ctggacgaag agcatcaggg gctcgcgcca gccgaactgt tcgccaggct   8460
caaggcgagc atgcccgacg cgaggatct cgtcgtgacc catggcgatg cctgcttgcc   8520
gaatatcatg gtggaaaatg gccgcttttc tggattcatc gactgtggcc ggctgggtgt   8580
ggcggaccgc tatcaggaca tagcgttggc tacccgtgat attgctgaag agcttggcgg   8640
cgaatgggct gaccgcttcc tcgtgcttta cggtatcgcc gctcccgatt cgcagcgcat   8700
cgccttctat cgccttcttg acgagttctt ctgaattttg ttaaattttt tgttaaatca   8760
gctcattttt taaccaatag gccgaaatcg gcaccatccc ttataaatca aaagaataga   8820
ccgagatagg gttgagtgtt gttccagttt ggaacaagag tccactatta agaacgtgg    8880
actccaacgt caagggcgga aaaccgtctc atcagggcga tggcccacta cgtgaaccat   8940
caccctaatc aagttttttg tggtcgaggt gccgtaaagc actaaatcgg aaccctaaag   9000
ggagcccccg atttagagct tgacggggaa agccggcgaa cgtggcgaga aggaaggga   9060
```

```
agaaagcgaa aggagcgggc gctagggcgc tggcaagtgt agcggtcacg ctgcgcgtaa    9120
ccaccacacc cgcgcgctta atgcgccgct acagggcgcg tccattcgcc attcaggatc    9180
gaattaattc ttaattaa                                                  9198

<210> SEQ ID NO 30
<211> LENGTH: 9303
<212> TYPE: DNA
<213> ORGANISM: Artificial Sequence
<220> FEATURE:
<223> OTHER INFORMATION: Synthetic Construct

<400> SEQUENCE: 30
catcatcaat aatataccttt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tactgtaata gtaatcaatt    360
acggggtcat tagttcatag cccatatatg gagttccgcg ttacataact tacggtaaat    420
ggcccgcctg gctgaccgcc caacgacccc cgcccattga cgtcaataat gacgtatgtt    480
cccatagtaa cgccaatagg gactttccat tgacgtcaat gggtggagta tttacggtaa    540
actgcccact tggcagtaca tcaagtgtat catatgccaa gtacgccccc tattgacgtc    600
aatgacggta aatggcccgc ctggcattat gcccagtaca tgaccttatg ggactttcct    660
acttggcagt acatctagta ttagtcatcg ctattaccat ggtgatgcgg ttttggcagt    720
acatcaatgg gcgtggatag cggtttgact cacggggatt tccaagtctc cacccccattg   780 acgtcaatgg gagtttgttt tggcaccaaa atcaacggga cttttccaaaa tgtcgtaaca    840 actccgcccc attgacgcaa atgggcggta ggcgtgtacg gtgggaggtc tatataagca    900
gagctctccc tatcagtgat agagatctcc ctatcagtga tagagatcgt cgacgagctc    960
gtttagtgaa ccgtcagatc gcctggagac gccatccacg ctgttttgac ctccatagaa   1020
gacaccggga ccgatccagc ctccggactc tagcgtttcg tcgacgcggc cgccccccttc   1080 accatggagc tgctgatcct gaaggccaac gccatcacca ccatcctgac cgccgtgacc   1140
ttctgcttcg cctccggcca gaacatcacc gaggagttct accagtccac tgctccgcc    1200 gtgtccaagg gctacctgtc cgccctgcgg accggctggt acacctccgt gatcaccatc   1260
gagctgtcca acatcaaaga aaacaagtgc aacggcaccg acgccaaggt gaagctgatc   1320
aagcaggagc tggacaagta caagaacgcc gtgaccgagc tgcagctgct gatgcagtcc   1380 accccctgcca ccaacaaccg ggccaggcgg agctgcctc ggttcatgaa ctacaccctg    1440
aacaacgcca agaaaccaa cgtcaccctg tccaagaagc ggaagcggcg gttcctgggc    1500
ttcctgctgg gcgtgggctc cgctatcgcc tctggcgtgg ccgtgtctaa ggtgctgcac    1560
ctggagggcg aggtgaacaa gatcaagtct gccctgctgt ccaccaacaa ggccgtggtg   1620
tccctgtcca acggcgtgtc cgtgctgacc tccaaggtgc tggatctgaa gaactacatc   1680
gacaagcagc tgctgcctat cgtgaacaag cagtcctgct ccatctccaa catcgagaca    1740
gtgatcgagt tccagcagaa gaacaaccgg ctgctggaaa tcacaagaga gttctccgtc   1800
aacgctggtg tgaccactcc tgtctctact tatatgctga ccaactccga gctgctgtcc    1860
```

```
ctgatcaacg acatgcctat caccaacgac cagaaaaagc tgatgtccaa caacgtgcag   1920
atcgtgcggc agcagtccta ctctatcatg agcatcatca aggaggaggt cctggcctac   1980
gtggtgcagc tgcctctgta cggcgtgatc gacacccctt gctggaagct gcacacctcc   2040
cccctgtgca ccaccaacac caaggagggc tccaacatct gcctgacccg gaccgaccgg   2100
ggctggttct gcgacaacgc cggctccgtg tccttctttc cacaggccga gacatgcaag   2160
gtgcagtcca accgggtgtt ctgcgatacc atgaactccc tgacccctgcc ttccgaggtg   2220
aacctgtgca acgtggacat cttcaaccct aagtacgact gcaagatcat gacctctaag   2280
accgacgtgt cctcctctgt gatcacctcc ctgggcgcca tcgtgtcctg ctacggcaag   2340
accaagtgca ccgcctccaa caagaaccgg ggaatcatca agaccttctc caacggctgc   2400
gactacgtgt ccaataaggg cgtggacacc gtgtccgtgg caacacact gtactacgtg    2460
aataagcagg agggcaagtc tctgtacgtg aagggcgagc ctatcatcaa cttctacgac   2520
cctctggtgt tcccttccga cgagttcgac gcctccatca gccaggtgaa cgagaagatc   2580
aaccagtccc tggccttcat ccggaagtcc gacgagctgc tgcacaacgt gaacgctggc   2640
aagtctacca ccaacatcat gatcaccaca atcatcattg tcatcatcgt catcctgctg   2700
tctctgatcg ccgtgggcct gctgctgtac tgcaaggccc ggtccacccc cgtgaccctg   2760
agcaaggacc agctgtccgg catcaacaat atcgccttca gcaactgatg agcgcgcgat   2820
ccgatccacc ggatctagat aactgatcat aatcagccat accacatttg tagaggtttt   2880
acttgcttta aaaaacctcc cacacctccc cctgaacctg aaacataaaa tgaatgcaat   2940
tgttgttgtt aacttgttta ttgcagctta taatggttac aaataaagca atagcatcac   3000
aaatttcaca aataaagcat ttttttcact gcattctagt tgtggtttgt ccaaactcat   3060
caatgtatct taacgcggat ctgggcgtgg ttaagggtgg gaaagaatat ataaggtggg   3120
ggtcttatgt agttttgtat ctgttttgca gcagccgccg ccgccatgag caccaactcg   3180
tttgatggaa gcattgtgag ctcatatttg acaacgcgca tgcccccatg ggccggggtg   3240
cgtcagaatg tgatgggctc cagcattgat ggtcgccccg tcctgcccgc aaactctact   3300
accttgacct acgagaccgt gtctggaacg ccgttggaga ctgcagcctc cgccgccgct   3360
tcagccgctg cagccaccgc ccgcgggatt gtgactgact ttgctttcct gagcccgctt   3420
gcaagcagtg cagcttcccg ttcatccgcc cgcgatgaca agttgacggc tcttttggca   3480
caattggatt ctttgacccg ggaacttaat gtcgtttctc agcagctgtt ggatctgcgc   3540
cagcaggttt ctgccctgaa ggcttcctcc cctcccaatg cggtttaaaa cataaataaa   3600
aaaccagact ctgtttggat ttggatcaag caagtgtctt gctgtctttta tttaggggtt   3660
ttgcgcgcgc ggtaggcccg ggaccagcgg tctcggtcgt tgagggtcct gtgtattttt   3720
tccaggacgt ggtaaaggtg actctggatg ttcagataca tgggcataag cccgtctctg   3780
gggtggaggt agcaccactg cagagcttca tgctgcgggg tggtgttgta gatgatccag   3840
tcgtagcagg agcgctgggc gtggtgccta aaaatgtctt tcagtagcaa gctgattgcc   3900
aggggcaggc ccttggtgta agtgtttaca aagcggttaa gctgggatgg gtgcatacgt   3960
ggggatatga gatgcatctt ggactgtatt tttaggttgg ctatgttccc agccatatcc   4020
ctccggggat tcatgttgtg cagaaccacc agcacagtgt atccggtgca cttgggaaat   4080
ttgtcatgta gcttagaagg aaatgcgtgg aagaacttgg agacgccctt gtgacctcca   4140
agatttccca tgcattcgtc cataatgatg gcaatgggcc cacgggcggc ggcctgggcg   4200
aagatatttc tgggatcact aacgtcatag ttgtgttcca ggatgagatc gtcataggcc   4260
```

```
attttttacaa agcgcgggcg gagggtgcca gactgcggta taatggttcc atccggccca   4320
ggggcgtagt taccctcaca gatttgcatt tcccacgctt tgagttcaga tgggggggatc   4380
atgtctacct gcggggcgat gaagaaaacg gtttccgggg tagggagat cagctgggaa    4440
gaaagcaggt tcctgagcag ctgcgactta ccgcagccgg tgggcccgta aatcacacct   4500
attaccggct gcaactggta gttaagagag ctgcagctgc cgtcatccct gagcagggg    4560
gccacttcgt taagcatgtc cctgactcgc atgttttccc tgaccaaatc cgccagaagg   4620
cgctcgccgc ccagcgatag cagttcttgc aaggaagcaa agttttttcaa cggtttgaga  4680
ccgtccgccg taggcatgct tttgagcgtt tgaccaagca gttccaggcg gtcccacagc   4740
tcggtcacct gctctacggc atctcgatcc agcatatctc ctcgtttcgc gggttggggc   4800
ggctttcgct gtacggcagt agtcggtgct cgtccagacg ggccagggtc atgtctttcc   4860
acgggcgcag ggtcctcgtc agcgtagtct gggtcacggt gaagggtgc gctccgggct   4920
gcgcgctggc cagggtgcgc ttgaggctgg tcctgctggt gctgaagcgc tgccggtctt   4980
cgccctgcgc gtcggccagg tagcatttga ccatggtgtc atagtccagc ccctccgcgg   5040
cgtgcccctt ggcgcgcagc ttgcccttgg aggaggcgcc gcacgagggg cagtgcagac   5100
ttttgagggc gtagagcttg ggcgcgagaa ataccgattc cggggagtag gcatccgcgc   5160
cgcaggcccc gcagacggtc tcgcattcca cgagccaggt gagctctggc cgttcggggt   5220
caaaaaccag gtttcccca tgcttttga tgcgtttctt acctctggtt tccatgagcc    5280
ggtgtccacg ctcggtgacg aaaaggctgt ccgtgtcccc gtatacagac ttgagaggga   5340
gtttaaacga attcaatagc ttgttgcatg ggcggcgata taaaatgcaa ggtgctgctc   5400
aaaaaatcag gcaaagcctc gcgcaaaaaa gaaagcacat cgtagtcatg ctcatgcaga   5460
taaaggcagg taagctccgg aaccaccaca gaaaagaca ccatttttct ctcaaacatg    5520
tctgcgggtt tctgcataaa cacaaaataa aataacaaaa aaacatttaa acattagaag   5580
cctgtcttac aacaggaaaa acaaccctta taagcataag acggactacg gccatgccgg   5640
cgtgaccgta aaaaaactgg tcaccgtgat taaaaagcac caccgacagc tcctcggtca   5700
tgtccggagt cataatgtaa gactcggtaa acacatcagg ttgattcaca tcggtcagtg   5760
ctaaaaagcg accgaaatag cccgggggaa tacatacccg caggcgtaga gacaacatta   5820
cagcccccat aggaggtata acaaaattaa taggagagaa aaacacataa acacctgaaa   5880
aacccctcctg cctaggcaaa atagcacccct cccgctccag aacaacatac agcgcttcca  5940
cagcggcagc cataacagtc agccttacca gtaaaaaaga aaacctatta aaaaaacacc   6000
actcgacacg gcaccagctc aatcagtcac agtgtaaaaa agggccaagt gcagagcgag   6060
tatatatagg actaaaaaat gacgtaacgg ttaaagtcca caaaaaacac ccagaaaacc   6120
gcacgcgaac ctacgcccag aaacgaaagc caaaaaaccc acaacttcct caaatcgtca   6180
cttccgtttt cccacgttac gtcacttccc attttaagaa aactacaatt cccaacacat   6240
acaagttact ccgccctaaa acctacgtca cccgccccgt tcccacgccc cgcgccacgt   6300
cacaaactcc accccctcat tatcatattg gcttcaatcc aaaataaggt atattattga   6360
tgatgttaat taacatgcat ggatccatat gcggtgtgaa ataccgcaca gatgcgtaag   6420
gagaaaatac cgcatcaggc gctcttccgc ttcctcgctc actgactcgc tgcgctcgt    6480
cgttcggctg cggcgagcgg tatcagctca ctcaaaggcg gtaatacggt tatccacaga   6540
atcaggggat aacgcaggaa agaacatgtg agcaaaaggc cagcaaaagg ccaggaaccg   6600
```

```
taaaaaggcc gcgttgctgg cgttttccca taggctccgc ccccctgacg agcatcacaa    6660
aaatcgacgc tcaagtcaga ggtggcgaaa cccgacagga ctataaagat accaggcgtt    6720
tccccctgga agctccctcg tgcgctctcc tgttccgacc ctgccgctta ccggatacct    6780
gtccgccttt ctcccttcgg aagcgtggc gctttctcat agctcacgct gtaggtatct    6840
cagttcggtg taggtcgttc gctccaagct gggctgtgtg cacgaacccc ccgttcagcc    6900
cgaccgctgc gccttatccg gtaactatcg tcttgagtcc aacccggtaa gacacgactt    6960
atcgccactg gcagcagcca ctggtaacag gattagcaga gcgaggtatg taggcggtgc    7020
tacagagttc ttgaagtggt ggcctaacta cggctacact agaaggacag tatttggtat    7080
ctgcgctctg ctgaagccag ttaccttcgg aaaaagagtt ggtagctctt gatccggcaa    7140
acaaaccacc gctggtagcg gtggtttttt tgtttgcaag cagcagatta cgcgcagaaa    7200
aaaaggatct caagaagatc ctttgatctt ttctacgggg tctgacgctc agtggaacga    7260
aaactcacgt taagggattt tggtcatgag attatcaaaa aggatcttca cctagatcct    7320
tttaaattaa aaatgaagtt ttaaatcaat ctaaagtata tatgagtaaa cttggtctga    7380
cagttaccaa tgcttaatca gtgaggcacc tatctcagcg atctgtctat ttcgttcatc    7440
catagttgcc tgactccccg tcgtgtagat aactacgata cgggagggct taccatctgg    7500
ccccagtgct gcaatgatac cgcgagaccc acgctcaccg gctccagatt tatcagcaat    7560
aaaccagcca gccggaaggg ccgagcgcag aagtggtcct gcaactttat ccgcctccat    7620
ccagtctatt aattgttgcc gggaagctag agtaagtagt tcgccagtta atagtttgcg    7680
caacgttgtt gccattgctg cagccatgag attatcaaaa aggatcttca cctagatcct    7740
tttcacgtag aaagccagtc cgcagaaacg gtgctgaccc cggatgaatg tcagctactg    7800
ggctatctgg acaagggaaa acgcaagcgc aaagagaaag caggtagctt gcagtgggct    7860
tacatggcga tagctagact gggcggtttt atggacagca agcgaaccgg aattgccagc    7920
tggggcgccc tctggtaagg ttgggaagcc ctgcaaagta aactggatgg ctttcttgcc    7980
gccaaggatc tgatggcgca ggggatcaag ctctgatcaa gagacaggat gaggatcgtt    8040
tcgcatgatt gaacaagatg gattgcacgc aggttctccg ccgcttgggt ggagaggct    8100
attcggctat gactgggcac aacagacaat cggctgctct gatgccgccg tgttccggct    8160
gtcagcgcag gggcgcccgg ttcttttttgt caagaccgac ctgtccggtg ccctgaatga    8220
actgcaagac gaggcagcgc ggctatcgtg gctggccacg acgggcgttc cttgcgcagc    8280
tgtgctcgac gttgtcactg aagcgggaag ggactggctg ctattgggcg aagtgccggg    8340
gcaggatctc ctgtcatctc accttgctcc tgccgagaaa gtatccatca tggctgatgc    8400
aatgcggcgg ctgcatacgc ttgatccggc tacctgccca ttcgaccacc aagcgaaaca    8460
tcgcatcgag cgagcacgta ctcggatgga agccggtctt gtcgatcagg atgatctgga    8520
cgaagagcat caggggctcg cgccagccga actgttcgcc aggctcaagg cgagcatgcc    8580
cgacggcgag gatctcgtcg tgacccatgg cgatgcctgc ttgccgaata tcatggtgga    8640
aaatggccgc ttttctggat tcatcgactg tggccggctg ggtgtggcgg accgctatca    8700
ggacatagcg ttggctaccc gtgatattgc tgaagagctt ggcggcgaat gggctgaccg    8760
cttcctcgtg ctttacggta tcgccgctcc cgattcgcag cgcatcgcct tctatcgcct    8820
tcttgacgag ttcttctgaa ttttgttaaa attttttgtta aatcagctca tttttaacc    8880
aataggccga atcggcacc atcccttata aatcaaaaga atagaccgag ataggggttga    8940
gtgttgttcc agtttggaac aagagtccac tattaaagaa cgtggactcc aacgtcaaag    9000
```

```
ggcgaaaaac cgtctatcag ggcgatggcc cactacgtga accatcaccc taatcaagtt      9060
ttttgtggtc gaggtgccgt aaagcactaa atcggaaccc taaagggagc ccccgattta      9120
gagcttgacg gggaaagccg gcgaacgtgg cgagaaagga agggaagaaa gcgaaaggag      9180
cgggcgctag ggcgctggca agtgtagcgg tcacgctgcg cgtaaccacc acacccgcgc      9240
gcttaatgcg ccgctacagg gcgcgtccat tcgccattca ggatcgaatt aattcttaat      9300
taa                                                                   9303

<210> SEQ ID NO 31
<211> LENGTH: 11807
<212> TYPE: DNA
<213> ORGANISM: Artificial Sequence
<220> FEATURE:
<223> OTHER INFORMATION: Synthetic Construct

<400> SEQUENCE: 31
catcatcaat aatataccttt attttggatt gaagccaata tgataatgag ggggtggagt       60
ttgtgacgtg gcgcggggcg tgggaacggg gcgggtgacg tagtagtgtg gcggaagtgt      120
gatgttgcaa gtgtggcgga acacatgtaa gcgacggatg tggcaaaagt gacgttttttg     180 gtgtgcgccg gtgtacacag gaagtgacaa ttttcgcgcg gttttaggcg gatgttgtag      240
taaatttggg cgtaaccgag taagatttgg ccattttcgc gggaaaactg aataagagga      300
agtgaaatct gaataatttt gtgttactca tagcgcgtaa tactgtaata gtaatcaatt      360
acggggtcat tagttcatag cccatatatg gagttccgcg ttacataact tacggtaaat      420
ggcccgcctg gctgaccgcc caacgacccc cgcccattga cgtcaataat gacgtatgtt      480
cccatagtaa cgccaatagg gactttccat tgacgtcaat gggtggagta tttacggtaa      540
actgcccact tggcagtaca tcaagtgtat catatgccaa gtacgccccc tattgacgtc      600
aatgacggta aatggcccgc ctggcattat gcccagtaca tgaccttatg gactttcct       660 acttggcagt acatctacgt attagtcatc gctattacca tggtgatgcg gttttggcag      720
tacatcaatg ggcgtggata gcggtttgac tcacggggat ttccaagtct ccaccccatt      780
gacgtcaatg ggagtttgtt ttggcaccaa aatcaacggg actttccaaa atgtcgtaac      840
aactccgccc cattgacgca aatgggcggt aggcgtgtac ggtgggaggt ctatataagc      900
agagctggtt tagtgaaccg tcagatccgc tagagatctg gtaccgtcga cgcggccgcc      960
cccttcacca tggaagctgt gatcaaggtc atctcctccg cttgcaagac ctactgcggc     1020
aagacctccc cctccaagaa agaaatcggt gctatgctgt ccctgctgca gaagagggc      1080 ctgctgatgt cccccctccga cctgtactcc cccggttcct gggaccctat caccgctgct     1140
ctgtcccagc gtgctatgat cctgggcaag tccggcgaac tcaagacctg ggcctggtg      1200 ctgggtgctc tgaaggctgc tcgcgaggaa caagtgacct ccgagcaggc taagttctgg     1260
ctgggtctgg tggtggtcg tgtgtccccc cctggtcccg agtgcatcga gaagcccgct     1320
accgagcgtc gtatcgacaa gggcgaggaa gtgggcgaga ctaccgtgca gcgtgacgct     1380
aagatggctc ccgaggaaac cgctaccccc aagaccgtgg gcacctcctg ctaccactgc     1440
ggcaccgcta tcggttgcaa ctgcgctacc gcttccgctc ccccccctcc ttacgtgggc     1500
tccggcctgt accctttcct ggctggtgtc ggcgagcagc aaggacaggg tggagacacc     1560
cctcccggtg ctgaacagtc ccgtgccgag cctggtcacg ctggtcaagc tcccggtccc     1620
gctctgactg actgggctcg tgtgcgtgag gaactggctt ccaccggtcc ccctgtggtg     1680
```

```
gctatgcccg tggtcatcaa gaccgagggt cccgcttgga cccccctgga acccaagctg    1740
atcacccgtc tggctgacac cgtgcgtacc aagggcctgc gttccccaat caccatggct    1800
gaggtggagg ctctgatgtc ctccccctg ctgcctcacg acgtgaccaa cctgatgcgt     1860
gtgatcctgg gtcccgctcc ctacgctctg tggatggacg cttggggcgt gcagctgcag    1920
accgtgatcg ctgctgctac ccgtgacccc cgtcaccctg ctaacggaca gggtcgtggc    1980
gagcgtacca acctgaaccg tctgaagggc ctggctgacg gcatggtcgg caaccctcag    2040
ggacaggctg ctctgctgcg tcctggcgag ctggtcgcta tcaccgccag cgctctgcag    2100
gctttccgtg aggtggcccg tttggccgaa ccagctggtc cctgggctga catcatgcag    2160
ggcccctccg agtccttcgt ggacttcgct aaccgtctga tcaaggctgt ggagggctcc    2220
gacctccctc cttccgctcg tgctcccgtg atcatcgact gcttccgtca gaagtcccag    2280
cccgacatcc agcagctgat ccgtaccgct ccctccaccc tgactacccc tggcgagatc    2340
atcaagtacg tgctggaccg tcaaaagacc gctcccctga ccgaccaagg tatcgctgcc    2400
gctatgtcct ccgctatcca gccctgatc atggctgtcg tgaaccgcga gagggacgga    2460
cagaccggtt ccggtggtcg tgctcgtggc ctgtgctaca cttgcggttc ccccggtcac    2520
taccaggctc agtgccccaa gaagcgcaag tccggaaact cccgcgagcg ctgccagctc    2580
tgcaacggca tgggtcacaa cgccaagcag tgccgcaagc gcgacggaaa ccagggccag    2640
cgtcccggaa agggactgtc ctccggtcct tggcctggtc ctgagccccc tgctgtgtcc    2700
taataagcgc gcgatccgat ccaccggatc tagataactg atcataatca gccataccac    2760
atttgtagag gttttacttg ctttaaaaaa cctcccacac ctcccctga acctgaaaca     2820
taaaatgaat gcaattgttg ttgttaactt gtttattgca gcttataatg gttacaaata    2880
aagcaatagc atcacaaatt tcacaaataa agcatttttt tcactgcatt ctagttgtgg    2940
tttgtccaaa ctcatcaatg tatcttaacg cggcgcgccc tcatcagttg ctgaaggcga    3000
tattgttgat gccggacagc tggtccttgc tcagggtcac gggggtggac cgggccttgc    3060
agtacagcag caggcccacg gcgatcagag acagcaggat gacgatgatg acaatgatga    3120
ttgtggtgat catgatgttg gtggtagact tgccagcgtt cacgttgtgc agcagctcgt    3180
cggacttccg gatgaaggcc agggactggt tgatcttctc gttcacctgg ctgatggagg    3240
cgtcgaactc gtcggaaggg aacaccgagg gtcgtagaa gttgatgata ggctcgccct     3300
tcacgtacag agacttgccc tcctgcttat tcacgtagta cagtgtgttg cccacggaca    3360
cggtgtccac gcccttattg gacacgtagt cgcagccgtt ggagaaggtc ttgatgattc    3420
cccggttctt gttggaggcg gtgcacttgg tcttgccgta gcaggacacg atggcgccca    3480
gggaggtgat cacagaggag gacacgtcgg tcttagaggt catgatcttg cagtcgtact    3540
tagggttgaa gatgtccacg ttgcacaggt tcacctcgga aggcagggtc agggagttca    3600
tggtatcgca gaacacccgg ttggactgca ccttgcatgt ctcggcctgt ggaaagaagg    3660
acacggagcc ggcgttgtcg cagaaccagc ccggtcggt ccgggtcagg cagatgttgg     3720
agccctcctt ggtgttggtg gtgcacaggg gggaggtgtg cagcttccag caagggtgt     3780
cgatcacgcc gtacagaggc agctgcacca cgtaggccag gacctcctcc ttgatgatgc    3840
tcatgataga gtaggactgc tgccgcacga tctgcacgtt gttggacatc agcttttttct   3900
ggtcgttggt gataggcatg tcgttgatca gggacagcag ctcggagttg gtcagcatat    3960
aagtagagac aggagtggtc acaccagcgt tgacggagaa ctctcttgtg atttccagca    4020
gccggttgtt cttctgctgg aactcgatca ctgtctcgat gttggagatg gagcaggact    4080
```

```
gcttgttcac gataggcagc agctgcttgt cgatgtagtt cttcagatcc agcaccttgg   4140
aggtcagcac ggacacgccg ttggacaggg acaccacggc cttgttggtg gacagcaggg   4200
cagacttgat cttgttcacc tcgccctcca ggtgcagcac cttagacacg gccacgccag   4260
aggcgatagc ggagcccacg cccagcagga agcccaggaa ccgccgcttc cgcttcttgg   4320
acagggtgac gttggttttc ttggcgttgt tcagggtgta gttcatgaac cgaggcagct   4380
cccgcctggc ccggttgttg gtggcagggg tggactgcat cagcagctgc agctcggtca   4440
cggcgttctt gtacttgtcc agctcctgct tgatcagctt caccttggcg tcggtgccgt   4500
tgcacttgtt ttctttgatg ttggacagct cgatggtgat cacggaggtg taccagccgg   4560
tccgcagggc ggacaggtag cccttggaca cggcggagca ggtggactgg tagaactcct   4620
cggtgatgtt ctggccggag gcgaagcaga aggtcacggc ggtcaggatg gtggtgatgg   4680
cgttggcctt caggatcagc agctccatgg tgaagggggc ggccgcgtcg acgaaacgct   4740
agagtccgga ggctggatcg gtcccggtgt cttctatgga ggtcaaaaca gcgtggatgg   4800
cgtctccagg cgatctgacg gttcactaaa cgagctcgtc gacgatctct atcactgata   4860
gggagatctc tatcactgat agggagagct ctgcttatat agacctccca ccgtacacgc   4920
ctaccgccca tttgcgtcaa tggggcggag ttgttacgac attttggaaa gtcccgttga   4980
ttttggtgcc aaaacaaact cccattgacg tcaatgggt ggagacttgg aaatccccgt    5040
gagtcaaacc gctatccacg cccattgatg tactgccaaa accgcatcac catggtaata   5100
gcgatgacta atactagatg tactgccaag taggaaagtc ccataaggtc atgtactggg   5160
cataatgcca ggcgggccat ttaccgtcat tgacgtcaat aggggggcgta cttggcatat   5220 gatacacttg atgtactgcc aagtgggcag tttaccgtaa atactccacc cattgacgtc   5280
aatggaaagt ccctattggc gttactatgg gaacatacgt cattattgac gtcaatgggc   5340
gggggtcgtt gggcggtcag ccaggcgggc catttaccgt aagttatgta acgcggaact   5400
ccatatatgg gctatgaact aatgaccccg taattgatta ctattacagt agttaacttg   5460
tttattgcag cttataatgg ttacaaataa agcaatagca tcacaaattt cacaaataaa   5520 gcatttttt cactgcattc tagttgtggt ttgtccaaac tcatcaatgt atcttaacgc   5580
ggatctgggc gtggttaagg gtgggaaaga atatataagg tgggggtctt atgtagtttt   5640
gtatctgttt tgcagcagcc gccgccgcca tgagcaccaa ctcgtttgat ggaagcattg   5700
tgagctcata tttgacaacg cgcatgcccc catgggccgg ggtgcgtcag aatgtgatgg   5760
gctccagcat tgatggtcgc cccgtcctgc ccgcaaactc tactaccttg acctacgaga   5820
ccgtgtctgg aacgccgttg gagactgcag cctccgccgc cgcttcagcc gctgcagcca   5880
ccgcccgcgg gattgtgact gactttgctt tcctgagccc gcttgcaagc agtgcagctt   5940
cccgttcatc cgcccgcgat gacaagttga cggctctttt ggcacaattg gattctttga   6000
cccgggaact taatgtcgtt ctcagcagc tgttggatct cgccagcag gtttctgccc    6060 tgaaggcttc ctcccctccc aatgcggttt aaaacataaa taaaaaacca gactctgttt   6120
ggatttggat caagcaagtg tcttgctgtc tttatttagg ggttttgcgc gcgcggtagg   6180
cccgggacca gcggtctcgg tcgttgaggg tcctgtgtat ttttccagg acgtggtaaa    6240 ggtgactctg gatgttcaga tacatgggca taagcccgtc tctggggtgg aggtagcacc   6300
actgcagagc ttcatgctgc ggggtggtgt tgtagatgat ccagtcgtag caggagcgct   6360
gggcgtggtg cctaaaaatg tctttcagta gcaagctgat tgccaggggc aggcccttgg   6420
```

```
tgtaagtgtt tacaaagcgg ttaagctggg atgggtgcat acgtggggat atgagatgca    6480
tcttggactg tattttagg ttggctatgt tcccagccat atccctccgg ggattcatgt    6540
tgtgcagaac caccagcaca gtgtatccgg tgcacttggg aaatttgtca tgtagcttag    6600
aaggaaatgc gtggaagaac ttggagacgc ccttgtgacc tccaagattt tccatgcatt    6660
cgtccataat gatggcaatg ggcccacggg cggcggcctg ggcgaagata tttctgggat    6720
cactaacgtc atagttgtgt tccaggatga gatcgtcata ggccatttt acaaagcgcg    6780 ggcggagggt gccagactgc ggtataatgg ttccatccgg cccaggggcg tagttaccct    6840
cacagatttg catttcccac gctttgagtt cagatggggg gatcatgtct acctgcgggg    6900
cgatgaagaa aacggtttcc ggggtagggg agatcagctg ggaagaaagc aggttcctga    6960
gcagctgcga cttaccgcag ccggtgggcc cgtaaatcac acctattacc ggctgcaact    7020
ggtagttaag agagctgcag ctgccgtcat ccctgagcag ggggccact tcgttaagca    7080 tgtccctgac tcgcatgttt tccctgacca atccgccag aaggcgctcg ccgcccagcg    7140
atagcagttc ttgcaaggaa gcaaagtttt tcaacggttt gagaccgtcc gccgtaggca    7200
tgcttttgag cgtttgacca agcagttcca ggcggtccca cagctcggtc acctgctcta    7260
cggcatctcg atccagcata tctcctcgtt tcgcggttg gggcggcttt cgctgtacgg    7320
cagtagtcgg tgctcgtcca gacgggccag ggtcatgtct ttccacgggc gcagggtcct    7380
cgtcagcgta gtctgggtca cggtgaaggg gtgcgctccg ggctgcgcgc tggccagggt    7440
gcgcttgagg ctggtcctgc tggtgctgaa gcgctgccgg tcttcgccct gcgcgtcggc    7500
caggtagcat ttgaccatgg tgtcatagtc cagcccctcc gcggcgtggc ccttggcgcg    7560
cagcttgccc ttggaggagg cgccgcacga ggggcagtgc agacttttga gggcgtagag    7620
cttgggcgcg agaaataccg attccgggga gtaggcatcc gcgccgcagg ccccgcagac    7680
ggtctcgcat tccacgagcc aggtgagctc tggccgttcg gggtcaaaaa ccaggtttcc    7740
cccatgcttt ttgatgcgtt tcttacctct ggtttccatg agccggtgtc cacgctcggt    7800
gacgaaaagg ctgtccgtgt ccccgtatac agacttgaga gggagtttaa acgaattcaa    7860
tagcttgttg catgggcggc gatataaaat gcaaggtgct gctcaaaaaa tcaggcaaag    7920
cctcgcgcaa aaagaaagc acatcgtagt catgctcatg cagataaagg caggtaagct    7980
ccggaaccac cacagaaaaa gacaccattt ttctctcaaa catgtctgcg ggtttctgca    8040
taaacacaaa ataaaataac aaaaaaacat ttaaacatta gaagcctgtc ttacaacagg    8100
aaaaacaacc cttataagca taagacggac tacggccatg ccggcgtgac cgtaaaaaaa    8160
ctggtcaccg tgattaaaaa gcaccaccga cagctcctcg gtcatgtccg gagtcataat    8220
gtaagactcg gtaaacacat caggttgatt cacatcggtc agtgctaaaa agcgaccgaa    8280
atagcccggg ggaatacata cccgcaggcg tagagacaac attacagccc ccataggagg    8340
tataacaaaa ttaataggag agaaaaacac ataaacacct gaaaaccct cctgcctagg    8400 caaaatagca ccctcccgct ccagaacaac atacagcgct tccacagcgg cagccataac    8460
agtcagcctt accagtaaaa aagaaaacct attaaaaaaa caccactcga cacggcacca    8520
gctcaatcag tcacagtgta aaaagggcc aagtgcagag cgagtatata taggactaaa    8580
aaatgacgta acggttaaag tccacaaaaa acacccagaa aaccgcacgc gaacctacgc    8640
ccagaaacga aagccaaaaa acccacaact tcctcaaatc gtcacttccg ttttcccacg    8700
ttacgtcact tccattttta agaaaactac aattcccaac acatcaagt tactccgccc    8760 taaaacctac gtcacccgcc ccgttcccac gccccgcgcc acgtcacaaa ctccaccccc    8820
```

```
tcattatcat attggcttca atccaaaata aggtatatta ttgatgatgt taattaacat   8880
gcatggatcc atatgcggtg tgaaataccg cacagatgcg taaggagaaa ataccgcatc   8940
aggcgctctt ccgcttcctc gctcactgac tcgctgcgct cggtcgttcg gctgcggcga   9000
gcggtatcag ctcactcaaa ggcggtaata cggttatcca cagaatcagg ggataacgca   9060
ggaaagaaca tgtgagcaaa aggccagcaa aaggccagga accgtaaaaa ggccgcgttg   9120
ctggcgtttt tccataggct ccgcccccct gacgagcatc acaaaaatcg acgctcaagt   9180
cagaggtggc gaaacccgac aggactataa agataccagg cgtttccccc tggaagctcc   9240
ctcgtgcgct ctcctgttcc gaccctgccg cttaccggat acctgtccgc ctttctccct   9300
tcgggaagcg tggcgctttc tcatagctca cgctgtaggt atctcagttc ggtgtaggtc   9360
gttcgctcca agctgggctg tgtgcacgaa ccccccgttc agcccgaccg ctgcgcctta   9420
tccggtaact atcgtcttga gtccaacccg gtaagacacg acttatcgcc actggcagca   9480
gccactggta acaggattag cagagcgagg tatgtaggcg gtgctacaga gttcttgaag   9540
tggtggccta actacggcta cactagaagg acagtatttg gtatctgcgc tctgctgaag   9600
ccagttacct tcggaaaaag agttggtagc tcttgatccg gcaaacaaac caccgctggt   9660
agcggtggtt tttttgtttg caagcagcag attacgcgca gaaaaaaagg atctcaagaa   9720
gatcctttga tcttttctac ggggtctgac gctcagtgga acgaaaactc acgttaaggg   9780
attttggtca tgagattatc aaaaaggatc ttcacctaga tccttttaaa ttaaaaatga   9840
agttttaaat caatctaaag tatatatgag taaacttggt ctgacagtta ccaatgctta   9900
atcagtgagg cacctatctc agcgatctgt ctatttcgtt catccatagt tgcctgactc   9960
cccgtcgtgt agataactac gatacgggag ggcttaccat ctggccccag tgctgcaatg  10020
ataccgcgag acccacgctc accggctcca gatttatcag caataaacca gccagccgga  10080
agggccgagc gcagaagtgg tcctgcaact ttatccgcct ccatccagtc tattaattgt  10140
tgccgggaag ctagagtaag tagttcgcca gttaatagtt tgcgcaacgt tgttgccatt  10200
gctgcagcca tgagattatc aaaaaggatc ttcacctaga tccttttcac gtagaaagcc  10260
agtccgcaga aacggtgctg accccggatg aatgtcagct actgggctat ctggacaagg  10320
gaaaacgcaa gcgcaaagag aaagcaggta gcttgcagtg gcttacatg gcgatagcta  10380 gactgggcgg ttttatggac agcaagcgaa ccggaattgc cagctggggc gccctctggt  10440
aaggttggga agccctgcaa agtaaactgg atggctttct tgccgccaag gatctgatgg  10500
cgcaggggat caagctctga tcaagagaca ggatgaggat cgtttcgcat gattgaacaa  10560
gatggattgc acgcaggttc tccggccgct tgggtggaga ggctattcgg ctatgactgg  10620
gcacaacaga caatcggctg ctctgatgcc gccgtgttcc ggctgtcagc gcaggggcgc  10680
ccggttcttt ttgtcaagac cgacctgtcc ggtgccctga tgaactgca agacgaggca  10740 gcgcggctat cgtggctggc cacgacgggc gttccttgcg cagctgtgct cgacgttgtc  10800
actgaagcgg gaagggactg gctgctattg ggcgaagtgc cggggcagga tctcctgtca  10860
tctcaccttg ctcctgccga gaaagtatcc atcatggctg atgcaatgcg gcggctgcat  10920
acgcttgatc cggctacctg cccattcgac caccaagcga aacatcgcat cgagcgagca  10980
cgtactcgga tggaagccgg tcttgtcgat caggatgatc tggacgaaga gcatcagggg  11040
ctcgcgccag ccgaactgtt cgccaggctc aaggcgagca tgcccgacgg cgaggatctc  11100
gtcgtgaccc atggcgatgc ctgcttgccg aatatcatgg tggaaaatgg ccgcttttct  11160
```

```
ggattcatcg actgtggccg gctgggtgtg gcggaccgct atcaggacat agcgttggct  11220
acccgtgata ttgctgaaga gcttggcggc gaatgggctg accgcttcct cgtgctttac  11280
ggtatcgccg ctcccgattc gcagcgcatc gccttctatc gccttcttga cgagttcttc  11340
tgaattttgt taaaatttt gttaaatcag ctcatttttt aaccaatagg ccgaaatcgg  11400
caccatccct tataaatcaa aagaatagac cgagataggg ttgagtgttg ttccagtttg  11460
gaacaagagt ccactattaa agaacgtgga ctccaacgtc aaagggcgaa aaaccgtcta  11520
tcagggcgat ggcccactac gtgaaccatc accctaatca agttttttgt ggtcgaggtg  11580
ccgtaaagca ctaaatcgga accctaaagg gagcccccga tttagagctt gacggggaaa  11640
gccggcgaac gtggcgagaa aggaagggaa gaaagcgaaa ggagcgggcg ctagggcgct  11700
ggcaagtgta gcggtcacgc tgcgcgtaac caccacaccc gcgcgcttaa tgcgccgcta  11760
cagggcgcgt ccattcgcca ttcaggatcg aattaattct taattaa                11807
```

What is claimed is:

1. A chimeric virus-like particle comprising a lentivirus or an alpha-retrovirus Gag polypeptide and a respiratory syncytial virus F polypeptide.

2. The virus-like particle of claim 1, wherein the Gag polypeptide is from a simian immunodeficiency virus or a human immunodeficiency virus.

3. The virus-like particle of claim 1, wherein the Gag polypeptide is from an avian leukosis virus or rous sarcoma virus.

4. The virus-like particle of claim 1, further comprising mammalian glycosylation.

5. The virus-like particle of claim 1, further comprising an adjuvant in admixture with the virus-like particle.

6. The virus-like particle of claim 5, wherein the adjuvant is located outside the virus-like particle.

7. The virus-like particle of claim 5, wherein the adjuvant is located inside the virus-like particle.

8. The virus-like particle of claim 5, wherein the adjuvant is covalently linked to the respiratory syncytial virus F polypeptide to form a covalent linkage.

9. The virus-like particle of claim 1, wherein a neutralizing anti-RSV-F antibody binds to the respiratory syncytial virus F polypeptide.

10. The virus-like particle of claim 9, wherein the neutralizing anti-RSV-F antibody is Palivizumab.

11. The virus-like particle of claim 1, further comprising an additional VLP-associating antigen.

12. The virus-like particle of claim 1, further comprising an additional VLP-associating polypeptide linked to a second antigen.

13. A method for producing a chimeric virus-like particle, comprising:
   (a) providing one or more expression vectors together which express a lentivirus or an alpha-retrovirus Gag polypeptide and a respiratory syncytial virus F polypeptide;
   (b) introducing the one or more expression vectors into a eukaryotic cell in a media; and
   (c) expressing the Gag polypeptide and the respiratory syncytial virus F polypeptide to produce the chimeric virus-like particle.

14. The method of claim 13, wherein the eukaryotic cell is a yeast cell, a mammalian cell, or an insect cell.

15. The method of claim 13, wherein the eukaryotic cell is a mammalian cell.

16. The method of claim 13, further comprising the step of recovering the virus-like particle from the media in which the eukaryotic cell is cultured.

17. The method of claim 13, wherein the expression vector is a viral vector.

18. The method of claim 17, wherein the viral vector is selected from the group consisting of: an adenovirus, a herpesvirus, a poxvirus and a retrovirus.

19. The method of claim 17, wherein the viral vector further includes a transcriptional regulator that down-regulates expression of the respiratory syncytial virus F polypeptide when the viral vector is propagated in a helper cell or up-regulates expression of the respiratory syncytial virus F polypeptide in the eukaryotic cell.

20. The method of claim 19, wherein the transcriptional regulator is a tet repressor or a metallothionine inducible enhancer.

21. The method of claim 13, wherein the eukaryotic cell is selected from the group consisting of a BHK cell, a VERO cell, an HT1080 cell, an MRC-5 cell, a WI 38 cell, an MDCK cell, an MDBK cell, an HEK293 cell, a 293T cell, an RD cell, a COS-7 cell, a CHO cell, a PER.C6 (TM) cell, a Jurkat cell, a HUT cell, a SUPT cell, a C8166cell, a MOLT4/clone8 cell, an MT-2 cell, an MT-4 cell, an H9 cell, a PM1 cell, a CEM cell, a myeloma cell, SB20 cell, a LtK cell, a HeLa cell, a WI-38 cell, an L2 cell, a CMT-93, and a CEMX174 cell.

22. A method for treating or preventing respiratory syncytial virus infection comprising administering to a subject an immunogenic amount of the virus-like particle of claim 1.

23. A pharmaceutical composition comprising an immunogenic amount of the virus-like particle of claim 1.

24. A method for providing protection against respiratory syncytial virus infection comprising administering to a subject an immunogenic amount of the virus-like particle of claim 1.

* * * * *